US011445921B2

(12) United States Patent
Yoshizawa et al.

(10) Patent No.: US 11,445,921 B2
(45) Date of Patent: Sep. 20, 2022

(54) BIOLOGICAL INFORMATION MEASURING APPARATUS AND BIOLOGICAL INFORMATION MEASURING METHOD, AND COMPUTER PROGRAM PRODUCT

(71) Applicant: TOHOKU UNIVERSITY, Sendai (JP)

(72) Inventors: Makoto Yoshizawa, Miyagi (JP); Norihiro Sugita, Miyagi (JP); Makoto Abe, Miyagi (JP); Tomoyuki Yambe, Miyagi (JP); Noriyasu Homma, Miyagi (JP); Kazuma Obara, Miyagi (JP); Akira Tanaka, Fukushima (JP); Yuki Horihata, Miyagi (JP)

(73) Assignee: TOHOKU UNIVERSITY, Sendai (JP)

( * ) Notice: Subject to any disclaimer, the term of this patent is extended or adjusted under 35 U.S.C. 154(b) by 1285 days.

(21) Appl. No.: 15/720,863

(22) Filed: Sep. 29, 2017

(65) Prior Publication Data
US 2018/0042486 A1 Feb. 15, 2018

Related U.S. Application Data

(63) Continuation of application No. PCT/JP2016/059253, filed on Mar. 23, 2016.

(30) Foreign Application Priority Data

Mar. 30, 2015 (JP) .............................. JP2015-070270
Feb. 23, 2016 (JP) .............................. JP2016-032467

(51) Int. Cl.
*A61B 5/0205* (2006.01)
*A61B 5/024* (2006.01)
(Continued)

(52) U.S. Cl.
CPC ........ *A61B 5/02055* (2013.01); *A61B 5/0077* (2013.01); *A61B 5/02125* (2013.01);
(Continued)

(58) Field of Classification Search
None
See application file for complete search history.

(56) References Cited

U.S. PATENT DOCUMENTS 5,941,837 A 8/1999 Amano et al.
8,428,699 B2 * 4/2013 Pinter .................... A61B 5/318
600/509
(Continued)

FOREIGN PATENT DOCUMENTS

CN 103908236 A 7/2014
JP 2-213323 8/1990
(Continued)

OTHER PUBLICATIONS

Sugita et al. "Techniques for estimating blood pressure variation using video images." Annu Int Conf IEEE Eng Med Biol Soc. 2015; 2015:4218-21. (Year: 2015).*
(Continued)

*Primary Examiner* — Luther Behringer
(74) *Attorney, Agent, or Firm* — Oblon, McClelland, Maier & Neustadt, L.L.P.

(57) ABSTRACT

A biological information measuring apparatus according to an embodiment includes a calculating unit and a measuring unit. The calculating unit is configured to calculate information related to a pulse wave of a subject, on the basis of luminance information of a picture signal of the subject. The measuring unit is configured to measure a fluctuation of blood pressure of the subject based on an increase or a decrease in the information related to the pulse wave, in accordance with a site of the subject from which the picture signal was obtained.

6 Claims, 65 Drawing Sheets

(51) Int. Cl.
| | |
|---|---|
| *G06V 40/40* | (2022.01) |
| *A61B 5/00* | (2006.01) |
| *A61B 5/021* | (2006.01) |
| *A61B 5/103* | (2006.01) |
| *G06T 7/00* | (2017.01) |
| *A61B 5/02* | (2006.01) |
| *G16H 30/20* | (2018.01) |
| *G16H 30/40* | (2018.01) |
| *G06V 40/10* | (2022.01) |

(52) U.S. Cl.
CPC ........ *A61B 5/02416* (2013.01); *A61B 5/1032* (2013.01); *A61B 5/4035* (2013.01); *A61B 5/7278* (2013.01); *G06T 7/0012* (2013.01); *G06V 40/45* (2022.01); *A61B 5/0013* (2013.01); *A61B 5/02007* (2013.01); *A61B 5/486* (2013.01); *A61B 5/7246* (2013.01); *A61B 5/743* (2013.01); *A61B 5/746* (2013.01); *A61B 5/7425* (2013.01); *A61B 2503/22* (2013.01); *A61B 2560/0252* (2013.01); *A61B 2562/029* (2013.01); *A61B 2576/00* (2013.01); *G06T 2207/10024* (2013.01); *G06T 2207/30088* (2013.01); *G06V 40/15* (2022.01); *G16H 30/20* (2018.01); *G16H 30/40* (2018.01)

(56) References Cited

U.S. PATENT DOCUMENTS

| | | | |
|---|---|---|---|
| 2010/0305460 A1* | 12/2010 | Pinter | A61B 5/318 600/509 |
| 2011/0251493 A1 | 10/2011 | Poh et al. | |
| 2013/0127980 A1 | 5/2013 | Haddick et al. | |
| 2013/0218028 A1 | 8/2013 | Mestha | |
| 2014/0012142 A1 | 1/2014 | Mestha et al. | |
| 2014/0240668 A1 | 8/2014 | Uji et al. | |
| 2014/0330132 A1 | 11/2014 | Raskin | |
| 2015/0042774 A1 | 2/2015 | Sugano et al. | |
| 2017/0164904 A1* | 6/2017 | Kirenko | G06T 7/20 |

FOREIGN PATENT DOCUMENTS

| | | |
|---|---|---|
| JP | 9-135819 | 5/1997 |
| JP | 9-299339 | 11/1997 |
| JP | 2007-319246 | 12/2007 |
| JP | 2010-264095 | 11/2010 |
| JP | 2013-027633 | 2/2013 |
| JP | 2013-169464 | 9/2013 |
| JP | 2013-208140 | 10/2013 |
| JP | 2014-036801 | 2/2014 |
| JP | 2014-036901 | 2/2014 |
| JP | 2014-166269 A | 9/2014 |
| JP | 2014-188237 | 10/2014 |
| JP | 2014-198198 | 10/2014 |
| JP | 2015-029841 | 2/2015 |
| JP | 2015-504616 | 2/2015 |
| JP | 2015-054223 | 3/2015 |
| WO | 2015/045554 | 4/2015 |

OTHER PUBLICATIONS

J. Muehlsteff, X. L. Aubert and M. Schuett, "Cuffless Estimation of Systolic Blood Pressure for Short Effort Bicycle Tests: The Prominent Role of the Pre-Ejection Period," 2006 International Conference of the IEEE Engineering in Medicine and Biology Society, 2006, pp. 5088-5092 (Year: 2006).*

International Search Report dated Jun. 28, 2016 in PCT/JP2016/059253 filed Mar. 23, 2016 (with English Translation).

Written Opinion dated Jun. 28, 2016 in PCT/JP2016/059253 filed Mar. 23, 2016.

Japanese Office Action dated Mar. 3, 2020 in Patent Application No. 2020-011157 (with English translation), 5 pages.

Yoshizawa et al.—"A Great Impact of Green Video Signals on Tele-Healthcare in Daily Life, Especially for Rural or Disaster Areas", Transactions of Japanese Society for Medical and Biological Engineering, vol. 51 (2013) Issue Supplement Overview 1 page.

Yoshizawa et al.—"Easy Extraction of Blood Pressure Variability from Body Video Images Using Simulink", $37^{th}$ Annual International Conference of IEEE Engineering in Medicine and Biology Society (IEEE EMBC2015) Aug. 25-29, 2015, 1 page.

Sugita et al.—"Techniques for estimating blood pressure variation using video images", 37th Annual Conference of IEEE Engineering in Medicine Biology Society 2015, pp. 4218-4221, (Aug. 2015).

Yoshizawa et al.—"Remote Monitoring of Autonomic Nervous System Indices Using Video Cameras", 2015 IEEE $4^{th}$ Global Conference on Consumer Electronics (GCCE), Oct. 2015, pp. 670-671.

* cited by examiner

FIG.4A

| MEASUREMENT DATE/TIME | MEASURED RESULTS | | | | |
| --- | --- | --- | --- | --- | --- |
| | FLUCTUATION FROM REFERENCE VALUE | DIFFERENCE FROM REFERENCE VALUE | | TIME PERIOD TO REACH REFERENCE VALUE (sec) | ... |
| | | MAXIMUM VALUE | MINIMUM VALUE | | |
| 201501010715 | DECREASE | - | 0.1 | 50 | ... |
| 201501011026 | INCREASE | 0.16 | - | 63 | ... |
| ⋮ | ⋮ | ⋮ | ⋮ | ⋮ | ⋮ |

FIG.4B

| REFERENCE INFORMATION | | dPTT | PD |
| --- | --- | --- | --- |
| BLOOD PRESSURE VALUE CONVERSION INFORMATION (UPDATED ON 20150101) | | | |
| CORRECTION INFORMATION (TEMPERATURE) | 5 | | |
| | 10 | | |
| | 15 | | |
| | 20 | | |
| | 25 | | |
| | 30 | | |
| CORRECTION INFORMATION (HUMIDITY) | 20 | | |
| | 40 | | |
| | 60 | | |
| | 80 | | |
| | 100 | | |

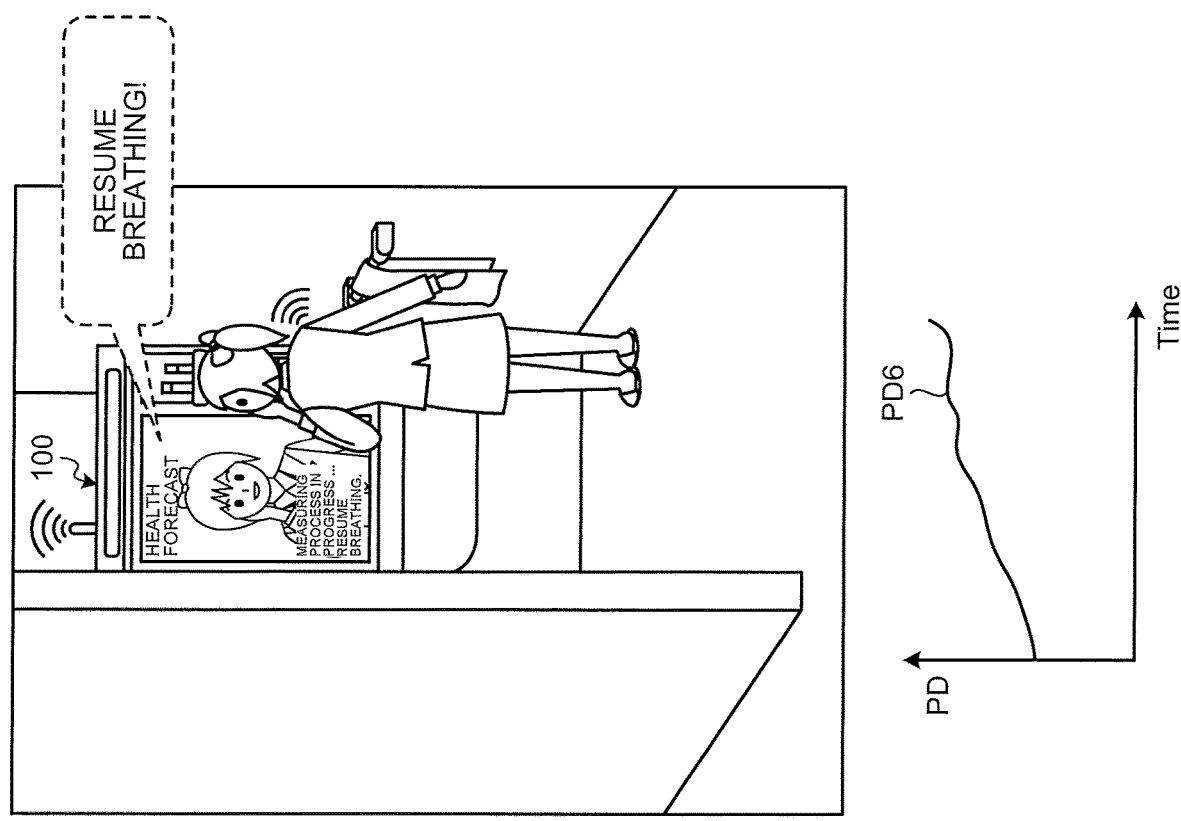
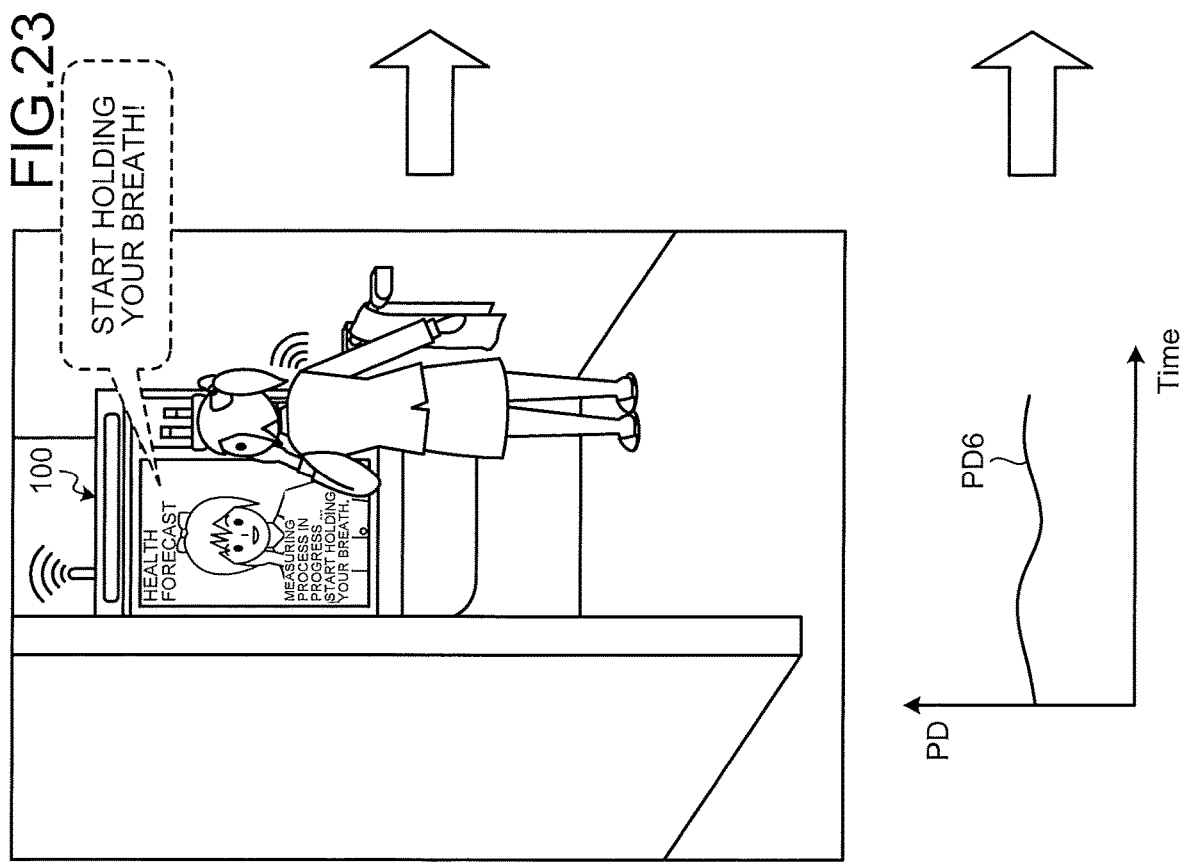
FIG.23

FIG.34A

INPUT SOURCE OF PICTURE SIGNALS
○ FROM CAMERA
◉ FROM FILE

TYPE OF FILTER
◉ BAND-PASS FILTER
○ COMB FILTER

MOSAIC DISPLAY
◉ YES
○ NO

SETTING ANALYSIS TARGET REGIONS
◉ TOP AND BOTTOM
○ LEFT AND RIGHT
○ MANUAL

SKIN COLOR REGION TRACKING
◉ YES
○ NO

[CANCEL]
[OK]

FIG.34B

FRAME FREQUENCY [fps]:

40

CALCULATION DISPLAY CYCLE [s]:

10

LENGTH [s] OF INPUT DATA WINDOW:

10

LENGTH [s] OF OUTPUT DISPLAY:

100

LENGTH [s] OF DATA TO BE STORED ON DISK:

120

CYCLE [s] FOR TRACKING SKIN COLOR REGION:

1

[LOWER LIMIT FREQUENCY AND UPPER LIMIT FREQUENCY] [Hz] OF BAND-PASS FILTER:

[0.5, 2]

THE NUMBER [QTY.] OF SECTIONS INTO WHICH SCREEN IS DIVIDED [COLUMNS, ROWS]:

[10, 10]

DEGREE (3 OR LARGER FOR APPLICATIONS) OF MEDIAN FILTER FOR LUMINANCE SIGNALS:

0

THRESHOLD VALUE [%] FOR TRIMMED MEAN VALUES (0-50%):

30

OK    CANCEL

FIG.42A

| CALCULATION DATE/TIME | CALCULATION RESULTS | | | |
| --- | --- | --- | --- | --- |
| | FIRST BLOOD FLOW INFORMATION | SECOND BLOOD FLOW INFORMATION | DIFFERENCE | ... |
| 201501010715 | FV11 | SV11 | ΔV11 | ... |
| 201501011026 | FV12 | SV12 | ΔV12 | ... |
| ⋮ | ⋮ | ⋮ | ⋮ | ⋮ |

FIG.42B

| REFERENCE INFORMATION | | dPTT | PD |
| --- | --- | --- | --- |
| BLOOD FLOW VALUE CONVERSION INFORMATION (UPDATED ON 20150101) | | | |
| CORRECTION INFORMATION (TEMPERATURE) | 5 | | |
| | 10 | | |
| | 15 | | |
| | 20 | | |
| | 25 | | |
| | 30 | | |
| CORRECTION INFORMATION (HUMIDITY) | 20 | | |
| | 40 | | |
| | 60 | | |
| | 80 | | |
| | 100 | | |

FIG.44
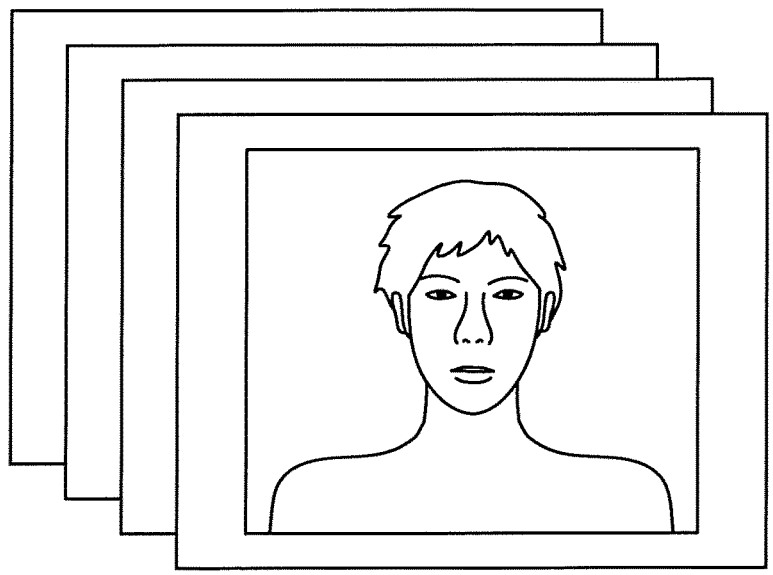
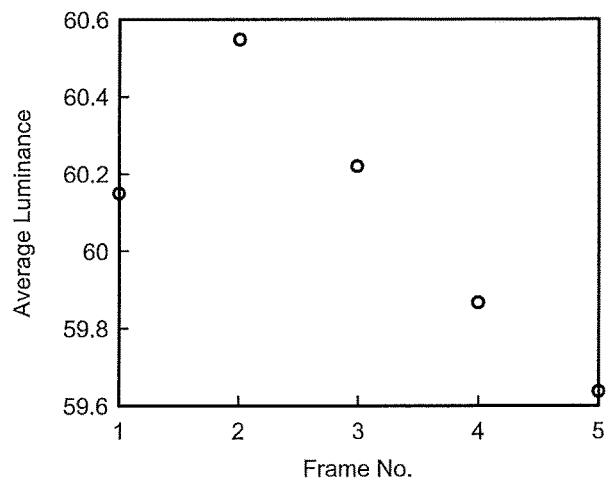
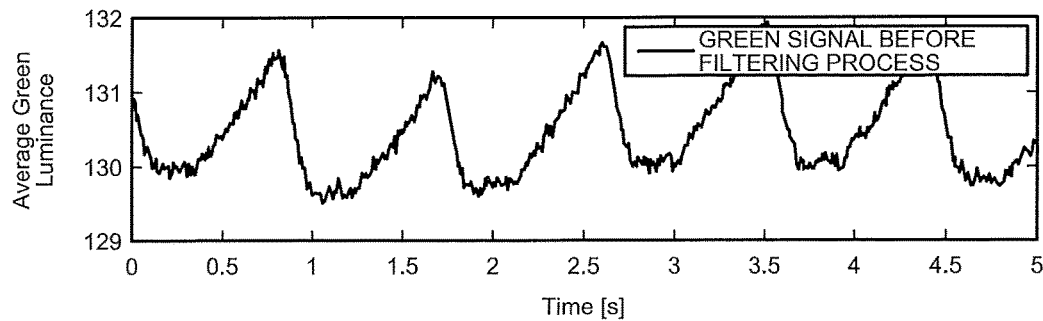

BIOLOGICAL INFORMATION MEASURING APPARATUS AND BIOLOGICAL INFORMATION MEASURING METHOD, AND COMPUTER PROGRAM PRODUCT

CROSS-REFERENCE TO RELATED APPLICATIONS

This application is a continuation of International Application No. PCT/JP2016/059253, filed on Mar. 23, 2016 which claims the benefit of priority of the prior Japanese Patent Application No. 2015-070270, filed on Mar. 30, 2015; and No. 2016-032467, filed on Feb. 23, 2016; the entire contents of which are incorporated herein by reference.

FIELD

Embodiments described herein relate generally to a biological information measuring apparatus and a biological information measuring method.

BACKGROUND

In recent years, due to an increase in the rate of incidence of lifestyle diseases caused by dietary habits and lifestyles, the demand for a "health monitoring process" is growing where people try to detect diseases at a stage before an onset and to address the problems earlier, instead of addressing the diseases after the onset. In other words, it is in demand to construct an environment where, by using the "health monitoring process", we are able to detect abnormalities in our health condition in our daily life and to have access to early-stage treatments, in addition to simply having medical examinations at medical institutions and having diagnoses.

To meet such needs, attempts have been made to install a health management function in a wearable terminal which people are able to wear and carry around. Terminals in various forms such as wristwatches, rings, and clothing items have already been made public. By using such a terminal, it is possible to obtain a pulse wave, an electrocardiogram, an acceleration activity amount, a temperature, and the like, and it is possible to obtain information such as a heart rate, a breathing rate, the number of walking steps, consumed calories, a sleep state, the body temperature, and the like, from obtained signals. In the current state, however, not very much attention is paid to blood pressure information, which is one of important biological indices for daily-basis health management.

At present, blood pressure information can be obtained by using an oscillometric sphygmomanometer, a volume-compensating continuous sphygmomanometer, or a photoplethysmograph. Oscillometric sphygmomanometers are configured to measure a blood pressure value while a cuff wrapped around the upper arm and are popularly used also in general households. The sphygmomanometers of this type are capable of measuring an average of blood pressure values during a number of heart beats. Measuring blood pressure values multiple times a day so as to measure fluctuations of the blood pressure in each day can be used for diagnosing high blood pressure or the like. Volume-compensating continuous sphygmomanometers are configured to be able to measure a blood pressure value for each heartbeat and can be used not only for evaluating autonomic nervous functions, but also for diagnosing sick sinus syndrome. Photoplethysmographs are configured to irradiate a fingertip or an earlobe with constant light to measure changes in the volume of the blood contained in blood vessels on the basis of changes in the amount of light that has passed therethrough or been reflected thereby and can be used for estimating fluctuations of blood pressure.

Further, volume-compensating continuous sphygmomanometers and photoplethysmographs are capable of measuring a drastic fluctuation of blood pressure occurring in a short period of time which oscillometric sphygmomanometers are unable to measure. Such a drastic fluctuation of blood pressure is caused by straining oneself during exercise, excessive stress, or a sudden change in the environment temperature. Because, in some situations, drastic fluctuations of blood pressure can drastically change one's physiological state and have a possibility of putting human bodies in dangerous situations, a method for estimating fluctuations of blood pressure in our daily life is in demand. However, volume-compensating continuous sphygmomanometers have disadvantages of being large in size, being expensive, and making user feel restrained. Photoplethysmographs also have a disadvantage of pressing the skin while being in contact therewith. Thus, according to the conventional methods, because the use of the apparatuses is limited by issues related to apparatuses causing trouble or costs of the apparatuses, it is difficult to use the apparatuses for health management on a daily basis.

Incidentally, in recent years, attentions are paid to an analysis performed on a video picture obtained by imaging the skin of a human being, as a method for acquiring biological information on a daily basis in a contactless manner. For example, by analyzing a video picture obtained by imaging the skin of a human being, it is possible to estimate Heart Rate Variability (HRV) or a breathing rate. Such a method by which the biological information is acquired by analyzing the video picture is highly advantageous because the devices (e.g., web cameras, smartphones) that can take video pictures are familiar things in our life and because the method is completely contactless due to the use of the pictures. Thus, people are expecting this method to be used for health management on a daily basis.

BRIEF DESCRIPTION OF THE DRAWINGS

FIG. 4A is a table illustrating examples of measured results according to the first embodiment.

FIG. 4B is a table illustrating examples of reference information according to the first embodiment.

FIG. 23 is a drawing of an example of measuring guidance provided by the biological information measuring apparatus according to the first embodiment.

FIG. 34A is a drawing for explaining an example of an image-based photoplethysmogram analysis performed by the biological information measuring apparatus according to the second embodiment.

FIG. 34B is a drawing for explaining another example of the image-based photoplethysmogram analysis performed by the biological information measuring apparatus according to the second embodiment.

FIG. 42A is a table of examples of calculation results according to the fourth embodiment.

FIG. 42B is a table of examples of reference information according to the fourth embodiment.

FIG. 44 is a drawing for explaining an extraction of a green signal according to the fourth embodiment.

DETAILED DESCRIPTION

Exemplary embodiments of a biological information measuring apparatus, a biological information measuring method, a biological information displaying apparatus, and a biological information displaying method of the present disclosure will be explained, with reference to the accompanying drawings. In the following sections, at first, a biological information measuring apparatus and a biological information measuring method of the present disclosure will be explained in the first to the third embodiments. In the exemplary embodiments described below, details of the biological information measuring apparatus will be explained by using an example of a "daily-basis medical checkup system" realized by a "health monitoring process" that utilizes the biological information measuring apparatus according to the present disclosure. The exemplary embodiments described below are merely examples, and possible embodiments are not limited to the contents of the explanations below.

(A Daily-Basis Medical Checkup System Realized by the Present Disclosure)

Figure 1:
FIG. 1 a drawing for explaining a daily-basis medical checkup system realized by the present disclosure.

FIG. 1 is a drawing for explaining a daily-basis medical checkup system realized by the present disclosure. In a modern society that has a declining birthrate and aging population, people are threatened and prevented from having a peaceful life by the anxiety for potential illnesses in the future, dementia, depression, a sense of isolation, worrying about distant family members, and the like. In a "modern society" like this, it would be ideal for everyone to be able to live a healthy and active life while working or enjoying hobbies with his/her family in the society. A means for realizing the ideal is the "daily-basis medical checkup system" illustrated in FIG. 1. While using the "daily-basis medical checkup system", blood pressure information is acquired by using unconscious sensing technology so that the condition of health on each day is fed back to the subject, on the basis of acquired blood pressure information.

More specifically, the biological information measuring apparatus used for the "daily-basis medical checkup system" according to the present disclosure is configured to acquire the blood pressure information of the subject by analyzing a picture signal of the subject from whom the blood pressure information is acquired and to provide the subject with information about his/her health condition on the basis of the acquired blood pressure information. More specifically, the biological information measuring apparatus is configured to estimate a fluctuation of the blood pressure of the subject by analyzing the picture signal that changes in accordance with the fluctuation of the blood pressure and to provide the subject with the information about his/her health condition on the basis of the estimated result. Even more specifically, the biological information measuring apparatus is configured to extract pulse wave information from each of the picture signals obtained by imaging the face and another site other than the face of the subject and to estimate the fluctuation of the blood pressure on the basis of a fluctuation of the difference between the extracted pieces of pulse wave information.

In this situation, a pulse wave denotes a propagation of arterial pressure wave motion generated by a pump action of the heart. Further, it is known that Pulse Transit Time (PTT) values defined as a time period it takes for a pulse wave to propagate through blood vessels are correlated with fluctuations of blood pressure. Accordingly, the biological information measuring apparatus of the present disclosure estimates a fluctuation of the blood pressure of the subject, by using the principle where PTT values are correlated with fluctuations of blood pressure. More specifically, the biological information measuring apparatus of the present disclosure calculates information related to the pulse wave of the subject, on the basis of luminance information of the picture signal of the subject. Further, the biological information measuring apparatus of the present disclosure measures the fluctuation of the blood pressure of the subject based on an increase or a decrease in the information related to the pulse wave, in accordance with each of the sites from which the picture signals were obtained.

First Embodiment

First, a biological information measuring apparatus according to a first embodiment will be explained. The biological information measuring apparatus according to the first embodiment is configured to estimate a fluctuation of the blood pressure of the subject by using a picture obtained by imaging the face and another site other than the face of the subject. More specifically, the biological information measuring apparatus according to the first embodiment calculates an index value corresponding to a PTT, by extracting pulse wave information from the picture signals of the face and the site other than the face of the subject and estimates the fluctuation of the blood pressure on the basis of a fluctuation of the calculated index value.

In this situation, at first, a principle used for extracting the pulse wave information from the picture signals will be explained. For example, image taking apparatuses such as video cameras are configured to record the light reflected by a subject as a picture that has passed through filters corresponding to different wavelengths while using the light in the three colors of red (R), green (G), and blue (B) as primary colors and to express various colors in accordance with luminance values thereof. As a focus is placed on the optical absorption characteristics of bloodstream hemoglobin for visible light, a high peak is exhibited at the wavelength band of 520 nm to 600 nm and substantially overlaps the wavelength band of 500 nm to 570 nm where a green filter of a camera is highly sensitive. While the pulse wave propagates through the whole body due to the pulsation of the heart, the blood flow volume in the whole body including the body surface cyclically increases and decreases. When the blood flow volume in peripheral sites increases as the heart contracts, because a relative amount of bloodstream hemoglobin also increases, the absorption amount for green light on the surface of the skin also increases. Because the camera receives the light reflected by the surface of the skin, the luminance value of the green in the picture becomes smaller when the relative amount of bloodstream hemoglobin increases. On the contrary, when the heart expands, because the blood flow volume in peripheral sites decreases, a relative amount of bloodstream hemoglobin also decreases. Thus, the absorption amount for green light on the surface of the skin also decreases. The fluctuation in the luminance values of the green light is extremely small and not visually recognizable for human eyes. However, it is possible to detect the fluctuation by using a commercially-available video camera or the like.

The biological information measuring apparatus extracts the aforementioned luminance values of the green light as the pulse wave information and estimates the fluctuation of the blood pressure. As mentioned above, at present, blood pressure information is acquired by using an oscillometric sphygmomanometer, a volume-compensating continuous sphygmomanometer, or a photoplethysmograph. In other words, when the subject consciously attaches a device to his/her own body and starts a blood pressure measuring process, the blood pressure information is acquired. Thus, according to conventional blood pressure acquiring methods, it is not easy to continuously acquire the blood pressure information on a daily basis, due to the trouble of attaching the device and the cost of the device.

In contrast, when the daily-basis medical checkup system realized in the first embodiment is used, the blood pressure information is acquired by analyzing the picture signals of the subject. Accordingly, as illustrated in FIG. 1, for example, the subject simply standing in front of a mirror makes it possible to feedback a "health forecast" that indicates the condition of health of the day to the subject, by acquiring the blood pressure information of the subject in a contactless manner and analyzing the acquired blood pressure information. In other words, without the subject being particularly conscious about the process, it is possible to acquire the blood pressure information in his/her daily life unconsciously and to feedback the condition of health to the subject. In this situation, the "health forecast" illustrated in FIG. 1 is configured to provide information about the condition of health analyzed on the basis of the fluctuation of the blood pressure of the subject. For example, analyses are made as to how the current blood pressure of the subject is (e.g., higher or lower) in comparison to a blood pressure reference value, how much fluctuation from the reference value is exhibited by the current blood pressure of the subject, and how long, if a significant fluctuation is exhibited by the current blood pressure of the subject, it takes for the blood pressure of the subject to return to the reference value, so that the "health forecast" is provided on the basis of the results of the analyses.

With this arrangement, it is possible to casually carry out the health monitoring process regarding the blood pressure in the subject's daily life so as to make it possible for the subject to understand his/her own health condition on a daily basis. For example, as illustrated in FIG. 1, the subject is able to understand the current condition of his/her own, by being provided with the "health forecast" indicating "body temperature: 36.5° C., blood pressure: slightly low; lack of sleep; iron intake is recommended". In this situation, the information about the condition of the subject's health can not only be fed back the subject, but also be offered to his/her family member or primary medical doctor via a network. For example, every time blood pressure information of the subject is acquired, an analysis result may be transmitted to a mobile phone, a smartphone, or a tablet terminal of the family member or to a terminal operated by the primary medical doctor. With this arrangement, not only the subject himself/herself, but also the family member and the primary medical doctor are able to understand the condition of the subject's health.

Figure 2:
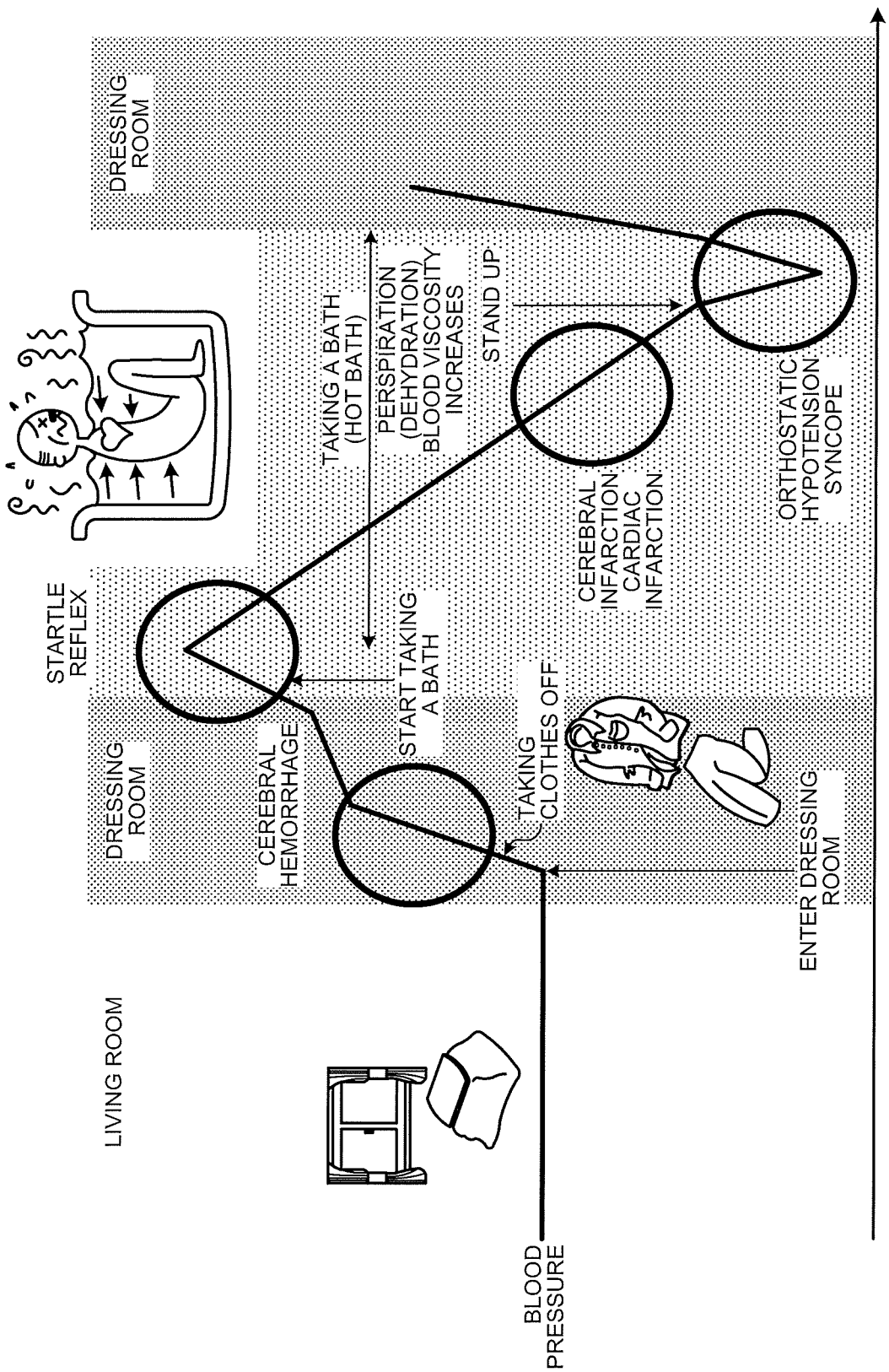
FIG. 2 is a drawing for explaining impacts on a human body made by changes in an environment temperature when a person takes a bath.

As mentioned above, a drastic fluctuation of blood pressure is caused by straining oneself during exercise, excessive stress, or a sudden change in the environment temperature. In some situations, drastic fluctuations of blood pressure can drastically change one's physiological state and have a possibility of putting human bodies in dangerous situations. In particular, when a focus is placed on the sudden changes in the environment temperature, impacts on human bodies made by changes in the environment temperature when people take a bath (which may be referred to as a heat shock) have been recognized as a major problem. FIG. 2 is a drawing for explaining the impacts on a human body made by changes in the environment temperature when a person takes a bath. FIG. 2 illustrates a chart of a fluctuation of the blood pressure value before and after taking a bath, while the vertical axis expresses the blood pressure, and the horizontal axis expresses time. Further, FIG. 2 illustrates actions of the person taking a bath and the impacts on the human body caused by the fluctuations of the blood pressure.

For example, as for the blood pressure values before and after the person takes a bath, as illustrated in FIG. 2, the blood pressure increases when he moves from the living room to the dressing room in order to take a bath. The blood pressure further increases when he moves to the bathroom. Further, the blood pressure value rapidly decreases after starting to take a bath. When he stands up to finish taking a bath, the blood pressure further decreases once, and subsequently, the blood pressure gradually increases. The fluctuations are caused by the sudden increase of the blood pressure caused by a cold stimulation due to the temperature difference between the living room and the dressing room and the sudden decrease of the blood pressure caused by the temperature rise caused when he takes a bath. When the blood pressure rapidly fluctuates in this manner, for example, cerebral hemorrhage may be caused by the sudden increase of the blood pressure when he enters the dressing room and takes off his clothes, and cerebral infarction or cardiac infarction may be caused by the sudden decrease of the blood pressure after he takes a bath. Furthermore, when he stands up to finish taking a bath, syncope may be caused by orthostatic hypotension.

The number of people who die during a bath related to such a heat shock is approximately 17,000 per year. Among those, it is reported that approximately 14,000 people are elderly people. The reasons why elderly people account for a large part are that the sensitivity to coldness is lowered as people become older and that the increase of the blood pressure caused by a cold stimulation is more significant in elderly people than in younger people. Accordingly, the biological information measuring apparatus according to the first embodiment also makes it possible to detect dangerous situations for elderly people, which keep increasing in number also in the future, by monitoring the blood pressure information in various points in time in their daily life and providing the feedback of a health forecast every time, based on the results of the monitoring process.

As explained above, by using the biological information measuring apparatus according to the first embodiment, it is possible to measure the fluctuation of the blood pressure in the simple and contactless manner. In this situation, not only the biological information measuring apparatus according to the first embodiment can be installed in a residence, but also the same process may be performed in a server apparatus provided in a network outside the residence. For example, a picture signal taken by a camera installed in the residence may be transmitted to the server apparatus via a network, so that the server apparatus receives the picture signal and measures a fluctuation of the blood pressure of the subject corresponding to the picture signal. Further, the server apparatus provided in a network may acquire pieces of blood pressure information of individual people from biological information measuring apparatuses installed in the residences thereof and may manage the acquired pieces of blood pressure information in a centrally-controlled manner. In that situation, the server apparatus may acquire and store, as life log information, the blood pressure information of the individual people so as to be kept in association with action information. Further, the server apparatus may manage big data in a cloud in a centrally-controller manner, the big data integrating together a large volume of biological information and life log information that are acquired in a time series with respect to a plurality of users.

Further, by analyzing the big data, the server apparatus may analyze potential risks of illnesses in the future and responsive reactions of the human bodies to amounts of food, amounts of exercise, or exercise loads in a sophisticated and detailed manner. Accordingly, the users become able to plan day-to-day life while pursuing the ideals, by selecting meals, exercises, life styles, medications, and supplements that are suitable for the potential risks of illnesses, signs of seizures, their own physical tendencies, and life styles. Further, the server apparatus is able to feedback the information not only to the users, but also to medical institutions. Medical doctors are able to, for example, recognize a group of people having a high risk of developing illnesses on the basis of the results of the analyses provided by the server apparatus as a feedback and to proactively contact those people, if necessary. In addition, the blood pressure information transmitted from each of the subjects is also useful in detecting abnormalities in the body of the subject. For example, the server apparatus may constantly monitor the blood pressure information transmitted daily from the subjects who are in the group having a high risk of developing illnesses, and when an abnormality is detected, the server apparatus may immediately feedback the detection result to a medical institution or the like. By configuring the server apparatus to provide medical institutions and various corporations with results of the analyses performed on the big data, the system may be used in various services and may contribute to creation of new industries.

Next, details of the biological information measuring apparatus according to the first embodiment will be explained. In the embodiment below, an example will be explained in which the biological information measuring apparatus installed in a residence is connected via a network to a Personal Health Record (PHR) apparatus, which serves as the server apparatus described above; however possible embodiments are not limited to this example. The biological information measuring apparatus may be used without being connected to any network.

(A Configuration of the Biological Information Measuring Apparatus According to the First Embodiment)

Figure 3:
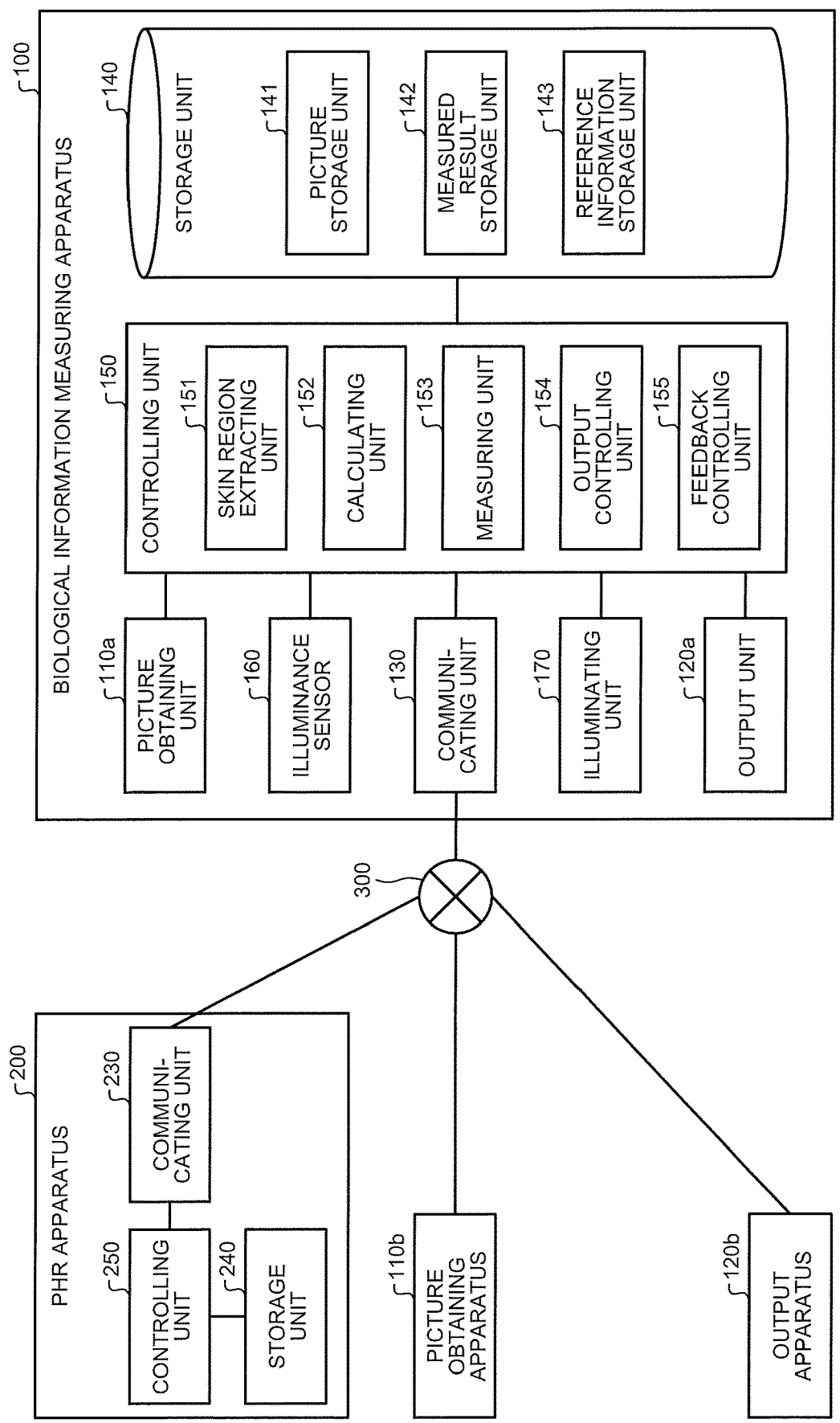
FIG. 3 is a functional block diagram of an exemplary configuration of a biological information measuring apparatus according to a first embodiment.

The biological information measuring apparatus according to the first embodiment used for realizing the "daily-basis medical checkup system" described above will be explained. FIG. 3 is a functional block diagram of an exemplary configuration of a biological information measuring apparatus 100 according to the first embodiment. As illustrated in FIG. 3, the biological information measuring apparatus 100 includes a picture obtaining unit 110*a*, an output unit 120*a*, a communicating unit 130, a storage unit 140, a controlling unit 150, an illuminance sensor 160, and an illuminating unit 170. The biological information measuring apparatus 100 is connected to a PHR apparatus 200, a picture obtaining apparatus 110*b*, and an output apparatus 120*b*, via a network 300. In FIG. 3, one biological information measuring apparatus 100, one PHR apparatus 200, one picture obtaining apparatus 110*b*, and one output apparatus 120*b* are provided; however, two or more of each type of apparatus may be connected together.

The network 300 is a Local Area Network (LAN), a Wide Area Network (WAN), or the like. As illustrated in FIG. 3, the PHR apparatus 200 is a server apparatus that includes a communicating unit 230, a storage unit 240, and a controlling unit 250 and is configured to manage PHR data (e.g., the blood pressure information) unconsciously acquired on a daily basis, in a health care cloud in a centrally-controlled manner. In this situation, the PHR data is information in which sensing data (e.g., the blood pressure information) acquired from each individual person is kept in correspondence with the individual person. In other words, the PHR apparatus 200 obtains and manages the blood pressure information of the individual people from a plurality of biological information measuring apparatuses 100 via the network 300. Further, the health care cloud is a cloud that is structured by the one or more PHR apparatuses 200, the one or more biological information measuring apparatuses 100, the network 300, and the like and is configured to provide various users with the service of the "daily-basis medical checkup system".

The communicating unit 230 included in the PHR apparatus 200 is configured to communicate, via the network 300, with the biological information measuring apparatus 100, the picture obtaining apparatus 110*b*, and the output apparatus 120*b* in a wired or wireless manner, to receive blood pressure information acquired by the biological information measuring apparatus 100, to receive picture signals obtained by the picture obtaining apparatus 110*b*, and to transmit output information to the output apparatus 120*b*. The storage unit 240 is configured to store therein various types of information such as the PHR data. For example, the storage unit 240 stores therein the blood pressure information acquired by the biological information measuring apparatus 100 so as to be kept in correspondence with the subject. Further, the storage unit 240 stores therein the picture signals taken by the biological information measuring apparatus 100 so as to be kept in correspondence with the subject. In other words, the storage unit 240 stores the big data therein and is also able to store therein the same information as stored in the storage unit 140 of the biological information measuring apparatus 100.

In this situation, the PHR apparatus 200 is able to not only manage the information acquired by the biological information measuring apparatus 100, but also perform the same processes as those performed by the biological information measuring apparatus 100 described below. In other words, the PHR apparatus 200 is able to measure the blood pressure information of the subject by receiving the picture signals of the subject obtained by either the biological information measuring apparatus 100 or the picture obtaining apparatus 110*b* and analyzing the received picture signals. More specifically, the controlling unit 250 included in the PHR apparatus 200 measures the fluctuation of the blood pressure on the basis of the picture signals by performing the same processes as those performed by the controlling unit 150 included in the biological information measuring apparatus 100 described below. The storage unit 240 stores therein the blood pressure information or the like measured by the controlling unit 250 so as to be kept in correspondence with the subject. Further, in response to a request from the biological information measuring apparatus 100 or the output apparatus 120*b* for output information, the controlling unit 250 exercises control so that information is read from the storage unit 240 and the read information is transmitted to the biological information measuring apparatus 100 or the output apparatus 120*b*.

The picture obtaining apparatus 110*b* is a camera that has installed therein an imaging device such as a Charge Coupled Device (CCD) or a Complementary Metal Oxide Semiconductor (CMOS) and may have installed therein three or more types of light receiving elements corresponding to, for example, red (R), green (G), and blue (B). Further, the picture obtaining apparatus 110*b* may be, for example, a reflective photo sensor that has installed therein a green Light Emitting Diode (LED). Further, the picture obtaining apparatus 110*b* can be provided in any of various places where the subject spends time in life and is configured to obtain picture signals of the subject and to transmit the obtained picture signals to the biological information measuring apparatus 100 or the PHR apparatus 200 via the network 300. For example, the picture obtaining apparatus 110*b* obtains a picture signal of the face of the subject and a picture signal of a site other than the face taken at the same time as the picture signal of the face of the subject is taken and transmits the obtained picture signals to the biological information measuring apparatus 100 or the PHR apparatus 200. In this situation, the site other than the face is a site in which, when the blood pressure increases, peripheral arterioles raise a peripheral blood vessel resistance under the control of sympathetic nerves. Further, the picture obtaining apparatus 110*b* may be a camera configured to image the face and the site other than the face of the subject in a single picture. Alternatively, the picture obtaining apparatus 110*b* may be configured with two separate cameras that image the face and the site other than the face of the subject, respectively.

The output apparatus 120*b* is a display device such as a monitor and/or an audio output device such as a speaker. Further, the output apparatus 120*b* may be installed in any of various places where the subject spends time in life or a place where information can be output for the subject's family member or primary medical doctor who observes the blood pressure information of the subject. The output apparatus 120*b* is configured to receive the output information such as picture information and/or audio information from the biological information measuring apparatus 100 or the PHR apparatus 200 and to output the received output information. Alternatively, the output unit 120*b* may be configured by using a display device such as a liquid crystal panel and may be configured by being combined with an input unit so as to be able to display a Graphical User Interface (GUI) to receive an input operation through the input unit. The output information will be explained in detail later.

The biological information measuring apparatus 100 may be configured by using a camera-equipped mobile phone, a smartphone, a tablet terminal, a camera-equipped Personal Computer (PC), or the like and is configured to measure the fluctuation of the blood pressure by analyzing the picture signals of the subject. Although FIG. 3 illustrates the example in which the biological information measuring apparatus 100 includes the picture obtaining unit 110*a*, possible embodiments are not limited to this example. For instance, the biological information measuring apparatus 100 may be configured to analyze the picture signals received from the picture obtaining apparatus 110*b*, without including the picture obtaining unit 110a. In that situation, the biological information measuring apparatus 100 may be configured by using a mobile phone or a PC that is not equipped with a camera. Further although FIG. 3 illustrates the example in which the biological information measuring apparatus 100 includes the output unit 120a, possible embodiments are not limited to this example. For instance, the biological information measuring apparatus 100 may be configured to control the output apparatus 120b so as to output the output information, without including the output unit 120a. In that situation, the biological information measuring apparatus 100 may be an information processing apparatus that is not provided with a monitor or a speaker.

The picture obtaining unit 110a may be configured by using a camera that has installed therein an imaging device such as a CCD or a CMOS and may have installed therein three or more types of light receiving elements corresponding to, for example, red (R), green (G), and blue (B). For example, the picture obtaining unit 110a may be a camera installed in a mobile phone, a smartphone, a tablet terminal, a PC, or the like. In this situation, the picture obtaining unit 110a does not necessarily have to be a camera installed in a mobile phone, a smartphone, a tablet terminal, a PC, or the like before being shipped from the factory. The picture obtaining unit 110a may be a camera attached to the device afterward. Further, the picture obtaining unit 110a is configured to obtain the picture signals of the subject and to transmit the obtained picture signals to the controlling unit 150. For example, the picture obtaining unit 110a obtains the picture signal of the face of the subject and the picture signal of the site other than the face taken at the same time as the picture signal of the face of the subject is taken and transmits the obtained picture signals to the controlling unit 150. In this situation, the site other than the face is a site in which, when the blood pressure increases, peripheral arterioles raise the peripheral blood vessel resistance under the control of sympathetic nerves. Further, the picture obtaining unit 110a may be a camera configured to image the face and the site other than the face of the subject in a single picture. Alternatively, the picture obtaining unit 110a may be configured with two separate cameras that image the face and the site other than the face of the subject, respectively.

The output unit 120a is a display device such as a monitor and/or an audio output device such as a speaker. For example, the output unit 120a may be a monitor and/or a speaker of a mobile phone, a smartphone, a tablet terminal, a PC, or the like. Further, the output unit 120a is configured to output the output information such as picture information and/or audio information. Alternatively, the output unit 120a may be configured by using a display device such as a liquid crystal panel and may be configured by being combined with an input unit so as to be able to display a GUI to receive an input operation through the input unit. The output information will be explained in detail later.

The communicating unit 130 is configured to communicate, via the network 300, with the picture obtaining apparatus 110b, the output apparatus 120b, and the PHR apparatus 200 in a wired or wireless manner. For example, the communicating unit 130 receives the picture signals of the subject from the picture obtaining apparatus 110b and transmits the received picture signals to the controlling unit 150. Further, the communicating unit 130 transmits the output information to the output apparatus 120b. Further, the communicating unit 130 transmits the picture signals and measured results to the PHR apparatus 200, and also, transmits and receives the output information to and from the PHR apparatus 200.

The illuminance sensor 160 is a sensor configured to measure illuminance in the vicinity of the skin of the subject. For example, the illuminance sensor measures levels of illuminance of the face and the site other than the face of the subject from which the picture signals are obtained and transmits the measured results to the controlling unit 150. The illuminating unit 170 is configured to irradiate the subject with light. For example, the illuminating unit 170 may be an illumination device employing one or more light emitting diodes (LEDs) and is configured to irradiate the subject with the light under the control of the controlling unit 150. The irradiation of the subject with the light will be explained in detail later.

As illustrated in FIG. 3, the storage unit 140 includes a picture storage unit 141, a measured result storage unit 142, and a reference information storage unit 143. The storage unit 140 may be, for example, a storage device such as a hard disk, an optical disk, or the like or a semiconductor memory device such as a Random Access Memory (RAM), a flash memory, or the like. The storage unit 140 is configured to store therein various types of computer programs executed by the biological information measuring apparatus 100, and the like.

The picture storage unit 141 is configured to store therein the picture signals of the subject. More specifically, the picture storage unit 141 stores therein the picture signals of the subject obtained by the picture obtaining unit 110a and the picture obtaining apparatus 110b. For example, the picture storage unit 141 stores therein the picture signal of the face of the subject and the picture signal of a site other than the face taken at the same time as the picture signal of the face of the subject is taken. In this situation, the picture storage unit 141 may store therein a picture containing the picture signals of the face and the site other than the face in the single picture. Alternatively, the picture storage unit 141 may store therein a picture of the face and a picture of the site other than the face, as separate pictures. When the picture of the face and the picture of the site other than the face are separate from each other, in order to make it possible to compare pieces of luminance information belonging to the separate pictures and corresponding to mutually the same time, the picture storage unit 141 stores the pictures therein so as to be kept in correspondence with time information.

The measured result storage unit 142 is configured to store therein a measured result from a measuring process performed by the controlling unit 150 (explained later). More specifically, the measured result storage unit 142 stores therein information related to the fluctuation of the blood pressure of the subject measured by a measuring unit 153 included in the controlling unit 150. For example, the measured result storage unit 142 stores therein a measured result about the fluctuation of the blood pressure measured by using an index value corresponding to a PTT and being calculated from the picture signals. FIG. 4A is a table illustrating examples of measured results according to the first embodiment. For example, as illustrated in FIG. 4A, the measured result storage unit 142 stores therein, for each subject, measurement information in which measurement dates/times are kept in correspondence with measured results. In this situation, each of the "measurement dates/times" illustrated in FIG. 4A denotes a date/time at which the face and the site other than the face of the subject were imaged and the fluctuation of the blood pressure was measured on the basis of the picture signals taken. Further, each of the "measured results" illustrated in FIG. 4A denotes the result of the items measured on the corresponding measurement date/time.

In this situation, examples of the measured items include, as illustrated in FIG. 4A, a "fluctuation from the reference value", a "difference from the reference value: maximum value", a "difference from the reference value: minimum value", and a "time period (sec) to reach the reference value". The "fluctuation from the reference value" indicates whether a certain index value has increased or decreased at the current point in time, compared to a predetermined reference value. Further, when a certain calculated index value exhibits an increase from the predetermined reference value at the current point in time, the "difference from the reference value: maximum value" indicates the difference between the maximum value of the value that has increased and the predetermined reference value. Further, when a certain calculated index value exhibits a decrease from the predetermined reference value at the current point in time, the "difference from the reference value: minimum value" indicates the difference between the minimum value of the value that has decreased and the predetermined reference value. Further, the "time period (sec) to reach the reference value" denotes a time period it takes for a certain index value to return to the predetermined reference value, when the calculated value exhibits a fluctuation at the current point in time. The predetermined reference value in this situation may be a value that is set for each of the subjects or may be a general value. When the predetermined reference value is set for each of the subjects, for example, an index value may be calculated from the picture signals while measuring a blood pressure value by employing an apparatus for each subject, so as to use an average value of index values while the blood pressure is stable as the reference value.

The predetermined reference value and the index value described above are not represented by absolute values of blood pressure but are represented by index values corresponding to PTT values, which are correlated with fluctuations of the blood pressure. In other words, the predetermined reference value described above is an index value corresponding to a blood pressure value used as a reference. For example, as illustrated in FIG. 4A, the measured result storage unit 142 stores therein "fluctuation from the reference value: decrease; difference from the reference value: minimum value: 0.1; and time period (sec) to reach the reference value: 50" as a measured result corresponding to the "measurement date/time: 201501010715". In other words, the information indicates that the index value calculated at "7:15 a.m. on the first of January in the year 2015" indicates that the blood pressure exhibits a "decrease" from the predetermined reference value, that the difference between the reference value and the minimum value is "0.1", and that the time period it took for the decreased value to return to the reference value was "50 (sec)".

Similarly, the measured result storage unit 142 stores therein "fluctuation from the reference value: increase; difference from the reference value: maximum value: 0.16; and time period (sec) to reach the reference value: 63" as a measured result of the same subject corresponding to the "measurement date/time: 201501011026". In this manner, the measured result storage unit 142 stores therein the results of the calculated index value every time a fluctuation of the blood pressure is measured. Although FIG. 4A illustrates the example in which the results are stored with respect to the single index value, possible embodiments are not limited to this example. For instance, a plurality of index values may be calculated from the same picture signal, so that results are stored for each of the plurality of index values.

Returning to the description of FIG. 3, the reference information storage unit 143 is configured to store therein reference information referenced during a measuring process performed by the controlling unit 150 (explained later). More specifically, the reference information storage unit 143 stores therein the reference information referenced when the measuring unit 153 measures the information related to the fluctuation of the blood pressure of the subject. FIG. 4B is a table illustrating examples of the reference information according to the first embodiment. For example, as illustrated in FIG. 4B, the reference information storage unit 143 stores therein information in which "reference information" is kept in correspondence with "dPTT" values and "PD" values. In this situation, the "reference information" denotes the information referenced when the measuring unit 153 measures the fluctuation of the blood pressure. For example, as illustrated in FIG. 4B, the "reference information" includes "blood pressure value conversion information (updated on 20150101)", "correction information (temperature)", and "correction information (humidity)". Further, the "dPTT" denotes a difference of pulse transit time, which is the time difference between predetermined feature points in the luminance values of the green light in the picture signals of the face and the site other than the face. Further, the "PD" denotes an instantaneous phase difference (or simply, "phase difference") indicating a phase difference between the luminance values of the green light in the picture signals of the face and the site other than the face. The "blood pressure value conversion information" is information used for converting an index value into an absolute value of blood pressure. Further, the "correction information (temperature)" is information used for correcting a calculated index value or the reference value in accordance with temperatures. The "correction information (humidity)" is information used for correcting a calculated index value or the reference value in accordance with humidity levels.

As explained above, the measured results of the fluctuation of the blood pressure measured by the measuring unit 153 are not based on absolute values of blood pressure, but are based on index values. For this reason, because the reference information storage unit 143 stores therein the conversion information used for converting any index value into an absolute value of blood pressure, the measuring unit 153 is able to convert the index value into a blood pressure value by using the conversion information. For example, a blood pressure value corresponding to the point in time when picture signals are obtained is measured by using an oscillometric sphygmomanometer or a continuous sphygmomanometer, so that the conversion information (e.g., a conversion coefficient) is calculated on the basis of a correspondence relationship between the index value calculated from the picture signals and the blood pressure value and is stored into the reference information storage unit 143. In this situation, the conversion information may be updated periodically.

Further, the "dPTT" and the "PD" illustrated in FIG. 4B each denote an index value corresponding to a PTT and being calculated from the picture signals. The biological information measuring apparatus 100 according to the first embodiment measures the fluctuation of the blood pressure of the subject by using either the "dPTT" or the "PD" described above. In this situation, by referencing the reference information corresponding to each index value, the biological information measuring apparatus 100 is able to calculate an absolute value of blood pressure and to make corrections in accordance with temperatures and humidity levels. The process of measuring the fluctuation of the blood pressure of the subject by using the "dPTT" or the "PD" will be explained in detail later.

Returning to the description of FIG. 3, the controlling unit 150 includes a skin region extracting unit 151, a calculating unit 152, the measuring unit 153, an output controlling unit 154, and a feedback controlling unit 155. The controlling unit 150 may be, for example, an electronic circuit such as a Central Processing Unit (CPU), a Micro Processing Unit (MPU), or the like, or an integrated circuit such as an Application Specific Integrated Circuit (ASIC), a Field Programmable Gate Array (FPGA), or the like and is configured to exercise overall control of the biological information measuring apparatus 100.

Figure 5:
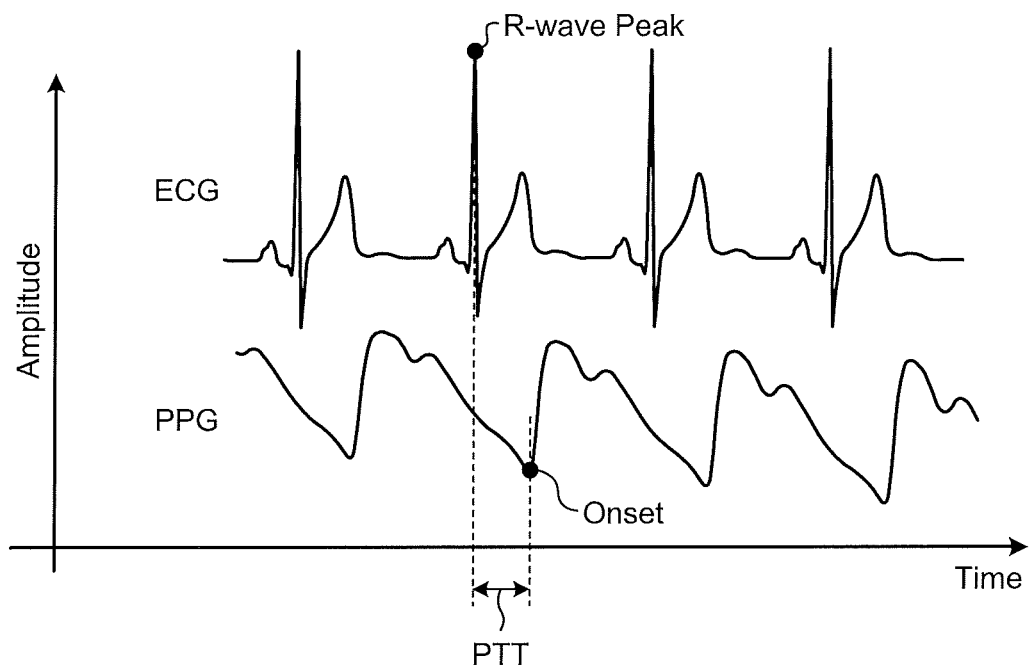
FIG. 5 is a chart for explaining a definition of a pulse transit time according to the first embodiment.

As a result of the processes performed by the functional units described above, the controlling unit 150 is configured to calculate the index value corresponding to a PTT by extracting the pulse wave information from the picture signals of the face and the site other than the face of the subject and to estimate the fluctuation of the blood pressure on the basis of a fluctuation of the calculated index value. Next, at first, a principle and a definition of the estimation of the fluctuation of the blood pressure that uses a pulse transit time (PTT) will be explained. A PTT value denotes the time period it takes for a pulse wave propagating from an aorta toward peripheral regions to travel from a certain reference point and reach a separate measurement point. FIG. 5 is a chart for explaining the definition of the pulse transit time according to the first embodiment. In this situation, in the chart illustrated in FIG. 5, the vertical axis expresses "amplitude", whereas the horizontal axis expresses "time", so as to indicate waveforms of an electrocardiogram (ECG) and photoplethysmography (PPG) data.

For example, as illustrated in FIG. 5, a PTT is defined, in general, as the time difference up to a feature point in a pulse wave waveform measured on the peripheral side while using an "R-wave Peak" in an electrocardiogram as a reference point. Further, it is known that PTT values have a negative correlation with blood pressure values. For example, the velocity "v" with which a pulse wave propagates through a blood vessel is dependent on the inside diameter of the blood vessel and stiffness of the vascular wall. An analytical relational expression may be a "Moens-Korteweg" equation presented below as Expression (1).

$$v = \sqrt{g\frac{hE}{\rho d}} \quad (1)$$

In Expression (1), "g" denotes a gravity constant; "E" denotes a Young's modulus of the blood vessel; "ρ" denotes the specific gravity of the blood vessel; "h" denotes the thickness of the vascular wall; and "d" denotes the diameter of the blood vessel. When the blood pressure increases, because the thickness "h" of the vascular wall decreases, whereas the diameter "d" of the blood vessel increases in Expression (1), it may be suspected that the velocity "v" should decrease; however, as indicated in Expression (2) below, the Young's modulus "E" of the blood vessel exponentially changes with respect to the blood pressure "P", and the impact of this change exceeds the impact of changes in the shape. For this reason, when the blood pressure increases, the velocity "v" with which the pulse wave propagates increases in actuality. In other words, when the blood pressure increases, the time period it takes for a pulse wave to propagate becomes shorter. In Expression (2), "$E_0$" denotes the Young's modulus corresponding to "P=0". Further, "γ" in Expression (2) denotes a constant dependent on the blood vessel and the value thereof ranges from "0.016 mmHg$^{-1}$" to "0.018 mmHg$^{-1}$".

$$E = E_0 e^{\gamma P} \quad (2)$$

When the pulse transit time is expressed as "T", whereas the length of the vascular path is expressed as "L", it is possible to express the pulse transit time as indicated in Expression (3) below.

$$T = \frac{L}{v} \quad (3)$$

In this situation, Expressions (4) and (5) below are obtained by assigning Expressions (1) and (2) to Expression (3) and squaring both sides of the equation.

$$g\frac{hE_0 e^{\gamma P}}{\rho d} = \frac{L^2}{T^2} \quad (4)$$

$$\therefore e^{\gamma P} = \frac{\rho d L^2}{g h E_0}\frac{1}{T^2} \quad (5)$$

Further, by calculating the logarithm of Expression (5), it is possible to obtain Expression (6) below indicating the blood pressure "P".

$$P = \frac{1}{\gamma}\left[\ln\left(\frac{\rho d L^2}{g h E_0}\right) - 2\ln T\right] \quad (6)$$

With respect to changes in the blood pressure "P" expressed by Expression (6), when it is assumed that changes in the thickness "h" of the vascular wall and the diameter "d" of the blood vessel are small while changes in "$E_0$" are sufficiently slow, the first term on the right-hand side of Expression (6) is negligible. Thus, by taking the derivative of Expression (6) with respect to the pulse transit time "T", Expression (7) presented below is obtained.

$$\Delta P = -\frac{2}{\gamma T}\Delta T \quad (7)$$

In other words, Expression (7) is obtained in which the fluctuation amount "ΔP" of the blood pressure "P" is expressed by using the fluctuation amount "ΔT" of the pulse transit time. Because the fluctuation amount "ΔP" of the blood pressure "P" is expressed by using the fluctuation amount "ΔT" of the pulse transit time in this manner, it is understood that it is possible to estimate the fluctuation of the blood pressure by using the pulse transit time "T".

According to the principle explained above, the biological information measuring apparatus 100 according to the first embodiment measures the fluctuation of the blood pressure by considering the luminance value of the green light in the picture signal as the pulse wave and measuring the fluctuation of the pulse transit time "PTT". In this situation, as explained above, the "PTT" denotes the time period it takes to travel from a certain reference point and reach a separate measurement point. In general, a "PTT" value is defined as the time difference up to a feature point in a pulse wave waveform measured on the peripheral side while using an "R-wave" in an electrocardiogram as a reference point. However, because it is necessary to use an apparatus to obtain the electrocardiogram, if the fluctuation of the blood pressure were to be measured on the basis of a "PTT" value using an electrocardiogram, it would be impossible to measure the fluctuation of the blood pressure in a contactless manner. To cope with this situation, according to the first embodiment, the fluctuation of the blood pressure is measured by using the aforementioned index value corresponding to a "PTT" without using any electrocardiograms, so that it is possible to measure the fluctuation of the blood pressure in a simple and contactless manner.

More specifically, the biological information measuring apparatus 100 according to the first embodiment measures the fluctuation of the blood pressure by measuring a fluctuation of either the "PD" indicating the phase difference between the luminance values of the green light in the picture signals of the face and the site other than the face of the subject or the "dPTT" indicating the time difference between the predetermined feature points in the luminance values of the green light in the picture signals of the face and the site other than the face of the subject. In the following sections, processes performed by the biological information measuring apparatus 100 will sequentially be explained in the order of: a process of extracting pulse wave information from the picture signals and a process of calculating a "PD" and a "dPTT" from the extracted pulse wave information.

Returning to the description of FIG. 3, the skin region extracting unit 151 included in the controlling unit 150 is configured to extract one or more skin regions of the subject contained in the picture obtained by either the picture obtaining unit 110a or the picture obtaining apparatus 110b. More specifically, the skin region extracting unit 151 automatically extracts the skin regions on the basis of color information in the picture. Alternatively, the skin region extracting unit 151 may extract one or more regions designated by an operator via an input unit (not illustrated) as the skin regions. In the following sections, these processes will sequentially be explained in detail. In this situation, the picture serving as a processing target of the skin region extracting unit 151 may be a real-time picture obtained by either the picture obtaining unit 110a or the picture obtaining apparatus 110b or may be a picture from the past stored in the picture storage unit 141.

Figure 6A:
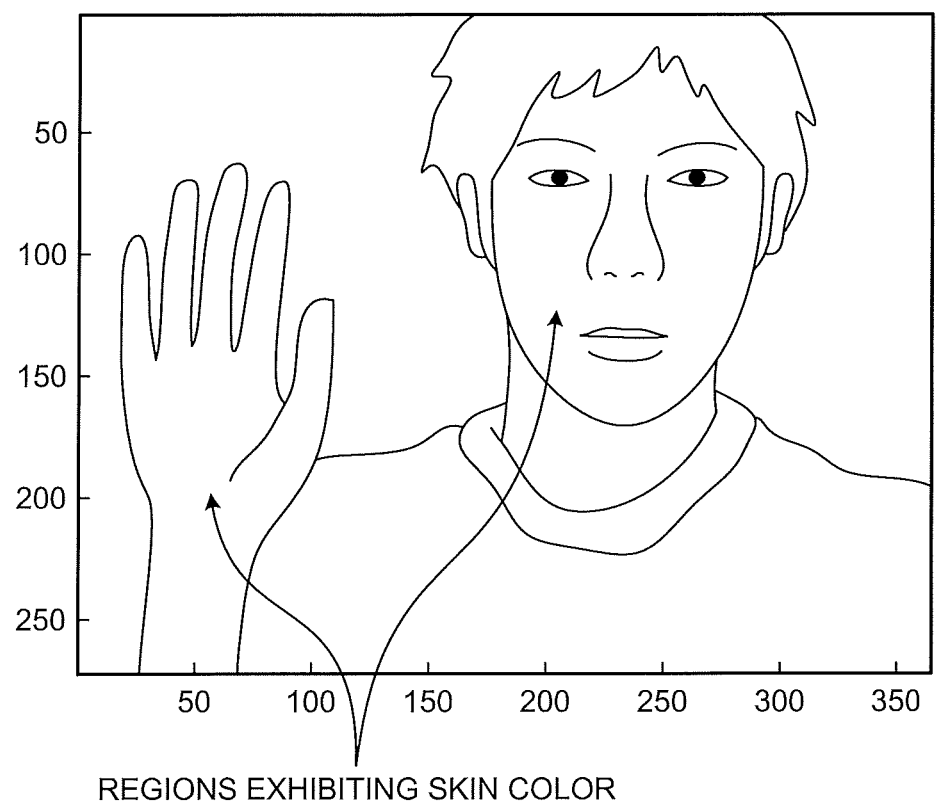
FIG. 6A is a drawing for explaining an automatic extracting process of skin regions according to the first embodiment.

First, an example in which the skin regions are automatically extracted on the basis of the color information in the picture will be explained, with reference to FIG. 6A. FIG. 6A is a drawing for explaining the automatic extracting process of the skin regions according to the first embodiment. For example, as illustrated in FIG. 6A, the skin region extracting unit 151 extracts the skin regions of the subject by extracting regions exhibiting a skin color from the picture. In other words, the skin region extracting unit 151 extracts all the coordinates (coordinates of the pixels) exhibiting colors (luminance values) corresponding to the skin color from the two-dimensional coordinates of the picture and extracts one or more regions obtained by putting together such pixels that have continuous coordinates among the extracted coordinates, as the skin regions. In this situation, by putting together such pixels of which the coordinates are not continuous, as the coordinates of mutually-different regions, the skin region extracting unit 151 is able to extract the skin regions corresponding to a plurality of sites.

In one example, the skin region extracting unit 151 extracts coordinates of a hand section and the coordinates of a face section exhibiting the skin color (luminance values) in the picture illustrated in FIG. 6A. Further, the skin region extracting unit 151 puts together such pixels that have continuous coordinates among the extracted coordinates, as skin regions. In this situation, because the coordinates of the hand section and the coordinates of the face section are not continuous with each other, the skin region extracting unit 151 puts together and extracts the coordinates extracted from the hand section separately from the coordinates extracted from the face section, as two sets of coordinates of the skin regions of the mutually-different sites. Further, by performing a face recognition process on the picture illustrated in FIG. 6A, for example, the skin region extracting unit 151 extracts the coordinates of the pixels of the face region of the subject. After that, the skin region extracting unit 151 determines the region containing the extracted coordinates of the face region within the extracted skin regions, as a face skin region.

As explained above, the skin region extracting unit 151 extracts the coordinates of the skin region of the face of the subject and the coordinates of the skin region of the site other than the face contained in the picture and transmits the extracted sets of coordinates of the skin regions to the calculating unit 152. In this situation, the colors (the luminance values) corresponding to the skin color may arbitrarily be set. For example, it is possible to set luminance values in a predetermined range for each of different human races, so that such coordinates that exhibit luminance values included in the set range in the picture are extracted as the coordinates corresponding to the skin color.

Figure 6B:
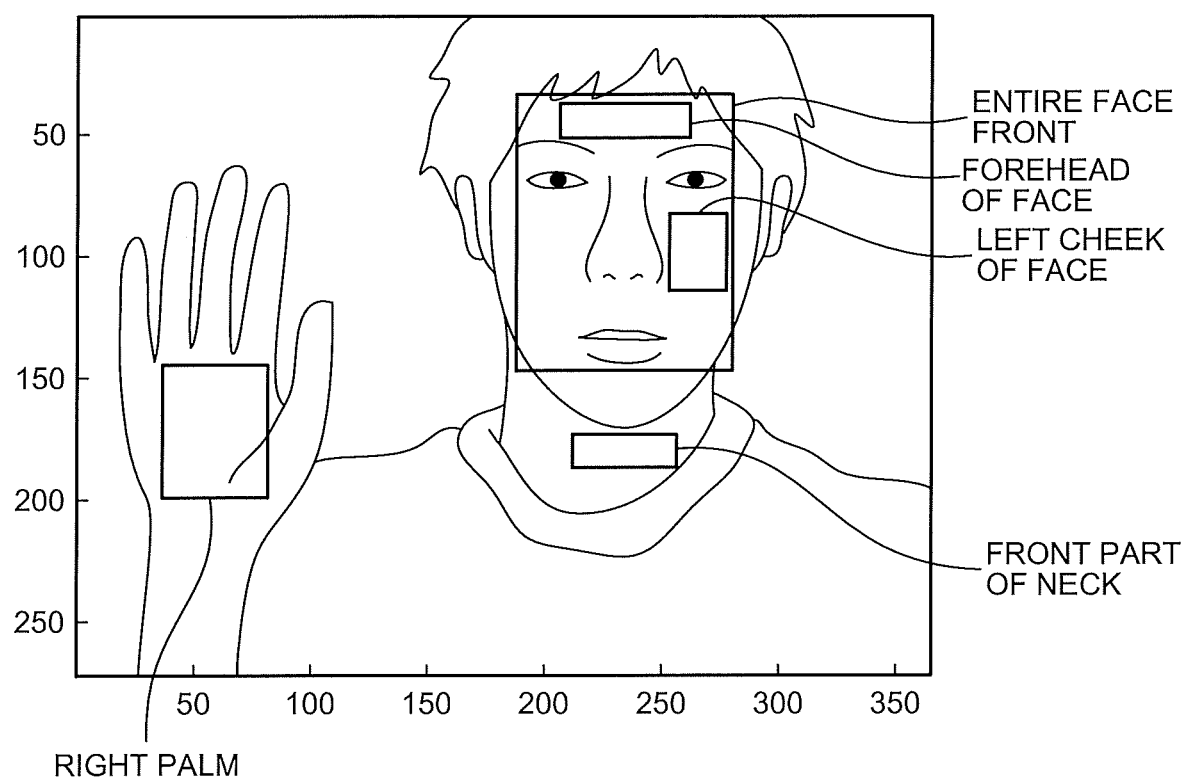
FIG. 6B is a drawing for explaining a manual extracting process of skin regions according to the first embodiment.

Next, an example in which regions designated by the operator are set as the skin regions will be explained, with reference to FIG. 6B. FIG. 6B is a drawing for explaining a manual extracting process of the skin regions according to the first embodiment. For example, as illustrated in FIG. 6B, by operating an input unit such as a mouse and/or a touch panel, the operator is able to set a region of the "right palm", a region of the "entire face front", a region of the "forehead of the face", a region of the "left cheek of the face", and a region of a "front part of the neck" in the picture as regions of interest (ROIs). As illustrated in FIG. 6B, when the regions of interest are set, the skin region extracting unit 151 extracts the coordinates of the set regions and transmits the coordinates of each of the regions to the calculating unit 152. In this situation, whether each of the regions corresponds to a region of the face (hereinafter "face region") or a region of a site other than the face may be designated by the operator or may be determined by performing the face recognition process described above.

In other words, from among the five regions of interest that were set, the operator designates the region of "the entire face front", the region of the "forehead of the face", and the region of the "left cheek of the face" as face regions and designates the region of "the right palm" and the region of the "front part of the neck" as regions of sites other than the face. As a result, the skin region extracting unit 151 is able to recognize whether each of the regions of interest is a face region or a region of a site other than the face. Alternatively, when the abovementioned designation is not made, the skin region extracting unit 151 extracts the coordinates of the face region of the subject by performing the face recognition process on the picture as described above and extracts such a region that contains the extracted coordinates of the face region from within the set regions of interest, as the skin region of the face.

The skin region extracting unit 151 performs the skin region extracting process described above on each of the frames structuring the picture and sequentially transmits the coordinates of the skin regions in each of the frames to the calculating unit 152. In this situation, when the regions of interest are set, the skin region extracting unit 151 tracks the coordinates of the regions of interest in each of the frames by performing a tracking process while using feature points in the picture, with respect to the frame in which the regions of interest are set and the frames following thereafter, so as to sequentially transmit the coordinates in the results of the tracking process to the calculating unit 152.

When the regions of interest are manually set, it is desirable to arrange the skin region to occupy a large area of each of the ROIs while including as little as possible of the eyes, the nose, and the hair and to avoid any part that has a shadow. Further, the skin region extracting unit 151 is able to extract such pixels that have luminance values corresponding to the skin color from each of the ROIs that are manually set and to set a region obtained by putting together the extracted pixels as a region of interest. In other words, when the ROIs are manually set, even if the set ROIs include the eyes or the hair, the skin region extracting unit 151 is able to set a region excluding the pixels corresponding to such parts, as a skin region.

Returning to the description of FIG. 3, the calculating unit 152 is configured to calculate the difference between luminance information of the picture signal of the face of the subject and luminance information of the picture signal of the site other than the face taken at the same time as the picture signal of the face of the subject is taken. More specifically, the calculating unit 152 extracts the luminance values of the green light contained in the picture signals of the face and the site other than the face of the subject and calculates either a time difference (dPTT) between predetermined feature points in the extracted luminance values of the green light in the picture signals or a phase difference (PD) between the luminance values of the green light in the picture signals.

In this situation, before extracting the green light from the picture signals, the calculating unit 152 at first eliminates artificial impulse noise occurring in the camera itself serving as the picture obtaining unit 110a or the picture obtaining apparatus 110b, by performing an image smoothing process. For example, the calculating unit 152 applies a median filter of 5-by-5 pixels to the entire image in each of the frames. After that, the calculating unit 152 extracts the green light in the skin regions extracted by the skin region extracting unit 151, with respect to each of the frames to which the median filter has been applied.

Figure 7:
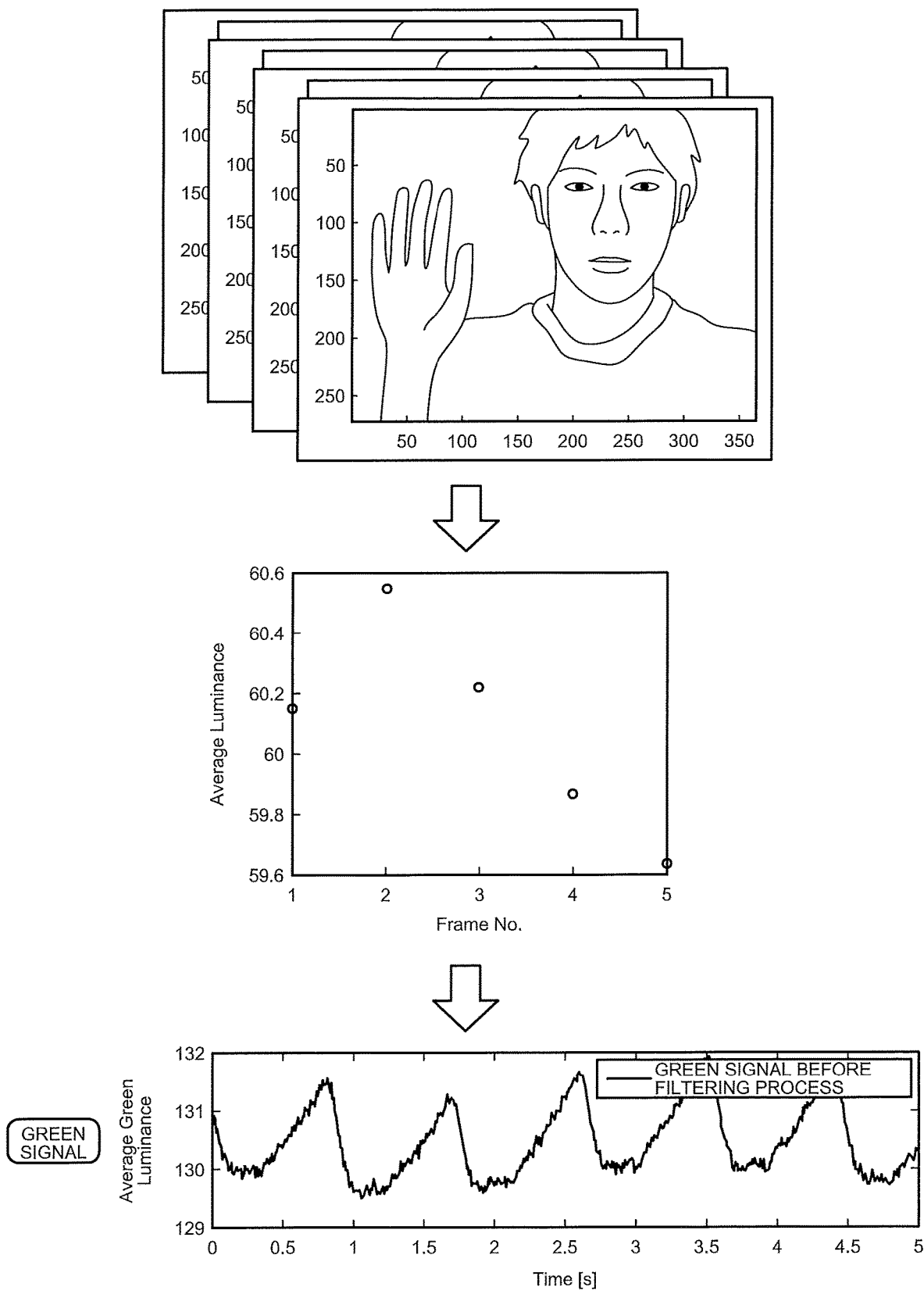
FIG. 7 is a drawing for explaining an extraction of a green signal according to the first embodiment.

As explained above, each of the pixels in each of the frames of the picture stores therein luminance values corresponding to the three colors of "red (R)", "green (G)" and "blue (B)". The color of each pixel is expressed by a combination of such luminance values. Accordingly, the calculating unit 152 extracts only the luminance value of green light having strong optical absorption characteristics for bloodstream hemoglobin, either by applying a green filter to the skin regions (i.e., the skin region of the face and the skin region of the site other than the face) in each of the frames or by utilizing luminance values of green (G). After that, the calculating unit 152 extracts a green signal expressed in a temporal-change curve obtained by calculating an average luminance value of the green light for each of the frames, with respect to the skin region of the face and the skin region of the site other than the face. FIG. 7 is a drawing for explaining the extraction of the green signal according to the first embodiment. In FIG. 7, the upper section illustrates a schematic drawing of a plurality of frames contained in the picture; the middle section illustrates a chart of the average luminance value of the green light in which the vertical axis expresses "average luminance value (Average Luminance)", whereas the horizontal axis expresses "frame numbers (Frame No.)". Further, the lower section of FIG. 7 illustrates an example of the green signal while the vertical axis expresses "average luminance value of green (Average Green Luminance)", whereas the horizontal axis expresses "time [s]".

For example, as illustrated in the upper section of FIG. 7, the calculating unit 152 extracts the luminance values of the green light in the skin regions, either by applying a green filter to each of the plurality of frames structuring the picture or by utilizing the luminance values of green (G). After that, the calculating unit 152 extracts a chart indicating the average luminance values of green as illustrated in the middle section of FIG. 7, by calculating an average value of the extracted luminance values of the green light for each of the frames. By performing the abovementioned process on each of the frames in the picture, the calculating unit 152 extracts a "green signal" as illustrated in the lower section of FIG. 7. The calculating unit 152 extracts a "green signal" for each of the skin regions extracted by the skin region extracting unit 151. More specifically, the calculating unit 152 extracts the "green signal" for the skin region of the face (i.e., the region of interest set in the face) and for the skin region of the site other than the face (i.e., the region of interest set in the site other than the face).

Subsequently, the calculating unit 152 extracts a pulse wave signal for each of the skin regions, by applying a band-pass filtering process to each of the extracted "green signals" of the skin regions, the band-pass filtering process passing only a heartbeat frequency band. In other words, because the green signals include body motions and respiratory fluctuations, the calculating unit 152 performs the filtering process to eliminate the body motions and the respiratory fluctuations. For example, the calculating unit 152 eliminates signal components other than heartbeat components by employing a fifth (5th)-degree Butterworth filter that passes the frequency band of "0.7 Hz to 2.0 Hz". This arrangement corresponds to the component of "40 bpm to 120 bpm", which is a range of fluctuations of a heart rate of a healthy person. In the first embodiment, the example is explained in which the Butterworth filter is used as the band-pass filter that passes only the heartbeat frequency band; however, possible embodiments are not limited to this example. It is acceptable to use any band-pass filter as long as the filter is capable of passing only the heartbeat frequency band.

Figure 8:
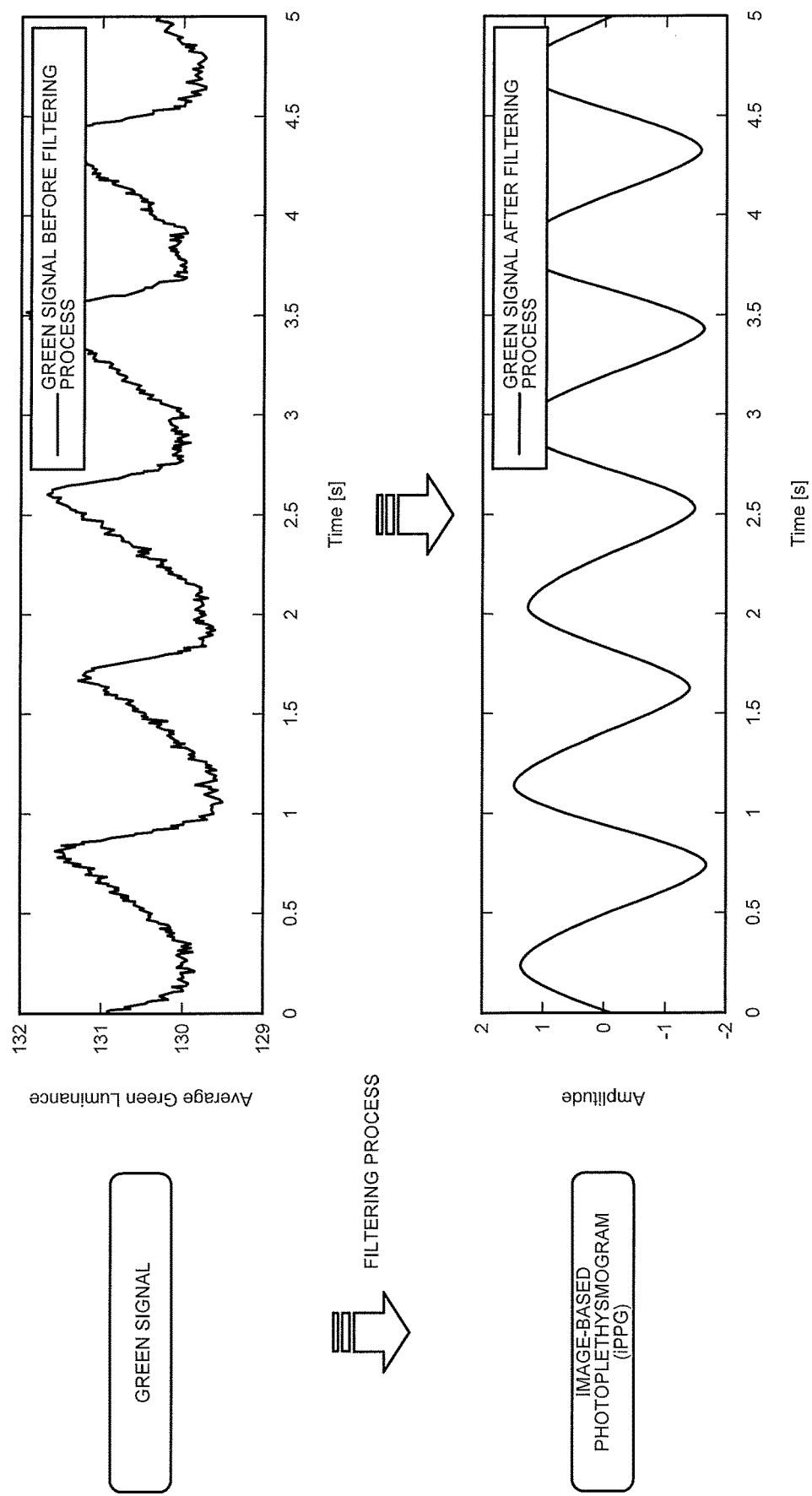
FIG. 8 is a drawing for explaining an extraction of a pulse wave signal according to the first embodiment.

FIG. 8 is a drawing for explaining the extraction of the pulse wave signal according to the first embodiment. FIG. 8 illustrates an example in which a pulse wave is extracted from the "green signal" indicated in the lower section of FIG. 7. The lower section of FIG. 8 illustrates a pulse wave signal, while the vertical axis expresses "amplitude", whereas the horizontal axis expresses "time [s]". In the first embodiment, to make a distinction from a pulse wave in a "photoplethysmogram (PPG)" measured by an apparatus such as a photoplethysmograph, the pulse wave extracted from the picture signal will be referred to as image-based photoplethysmography (iPPG), as indicated in FIG. 8. For example, as illustrated in FIG. 8, the calculating unit 152 extracts an "image-based photoplethysmogram (iPPG)" by applying the filtering process to the "green signal". As illustrated in FIG. 8, the extracted "image-based photoplethysmogram" exhibits a periodic sinusoidal waveform in which a pulse wave generated by one heartbeat corresponds to one crest in the waveform resulting from the filtering process.

In the first embodiment, in principle, the green signal decreases when the blood flow increases. For this reason, for the purpose of arranging an increase or a decrease of the blood flow to match an increase or a decrease of the green signal, the calculating unit 152 may perform the abovementioned filtering process after multiplying the green signal by "−1" so as to reverse the positive and negative signs. The image-based photoplethysmogram illustrated in FIG. 8 has a waveform obtained by reversing the positive and negative signs.

As explained above, the calculating unit 152 extracts an image-based photoplethysmogram of the face from the luminance information of the green light in the picture signal of the face and extracts an image-based photoplethysmogram of the site other than the face from the luminance information of the green light in the picture signal of the site other than the face. Further, by using the extracted image-based photoplethysmograms, the calculating unit 152 calculates the index values "dPTT" and "PD" corresponding to a "PTT" that uses an R-wave in an ECG. In the following sections, the calculation of the "dPTT" will be explained first, and subsequently, the calculation of the "PD" will be explained.

Generally speaking, a "PTT", which is correlated with fluctuations of blood pressure, can be defined as the time difference between an R-wave in an ECG and a feature point in a PPG. However, because a "PTT" is the propagation time period of a pulse wave pumped out from the heart, it is also possible to define a "PTT" by using a pulse wave waveform measured in two locations such as a site positioned close to the heart and a site positioned distant from the heart on a blood vessel serving as a propagation path. In other words, it is possible to define the difference in the propagation time period between the pulse wave waveform measured in the site positioned close to the heart and the pulse wave waveform measured in the site positioned distant from the heart, as the propagation time period of the pulse wave. Accordingly, in the first embodiment, the time difference between a feature point in a pulse wave waveform (iPPG) extracted from the picture signal of the face and a feature point in a pulse wave waveform (iPPG) extracted from the picture signal of the site other than the face will be used as an index value "dPTT: a difference of pulse transit time" corresponding to a "PTT".

As for the feature points in the pulse wave waveforms, there is no definite definitions and a plurality of determining methods are available. Examples of the determining methods include: a "bottom method" by which a point at which the "PPG" is at a minimum within a heartbeat is used as a feature point; a "top method" by which a point at which the "PPG" is at a maximum within a heartbeat is used as a feature point; a "first derivative method" by which a point at which a velocity pulse wave (a waveform from the first-order derivative of a PPG) is at a maximum within a heartbeat is used as a feature point; and a "second derivative method" by which a point at which an acceleration pulse wave (a waveform from the second-order derivative of a PPG) is at a maximum within a heartbeat is used as a feature point. The calculating unit 152 is able to determine the feature points by using any method arbitrarily selected from among various methods including these methods. Among the methods listed above, because the "second derivative method" tends to have a higher tolerance against noise than the other methods, the "second derivative method" may be set as a default method.

Figure 9:
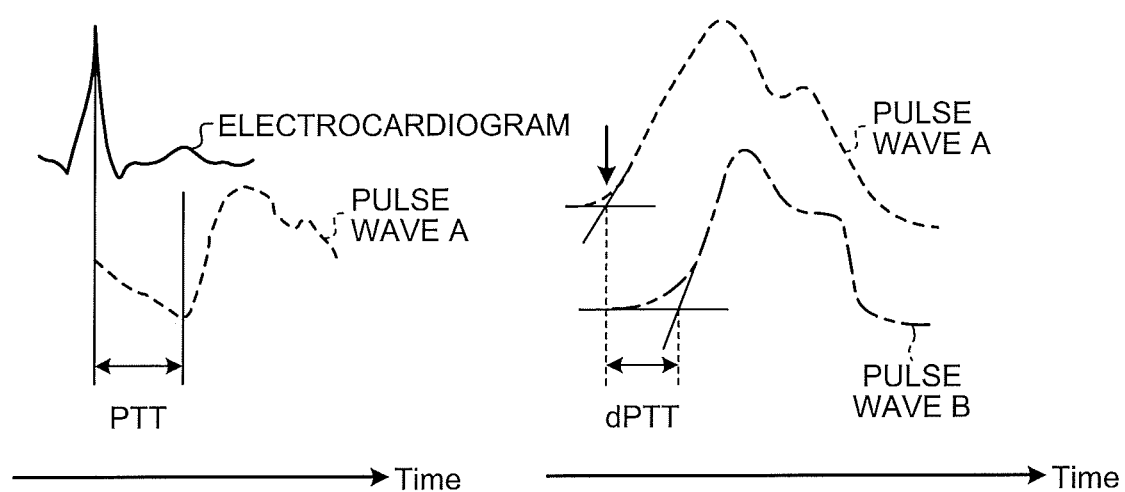
FIG. 9 presents charts illustrating a definition of a difference of pulse transit time according to the first embodiment.

By determining the feature points in the pulse wave waveforms by implementing the method described above, the calculating unit 152 is able to define a "dPTT" and to calculate the "dPTT" from the image-based photoplethysmograms extracted from the picture signals, as illustrated in FIG. 9. FIG. 9 presents charts illustrating the definition of a difference of pulse transit time according to the first embodiment. The left section of FIG. 9 illustrates the definition of a Pulse Transit Time (PTT), whereas the right section of FIG. 9 illustrates the definition of a difference of Pulse Transit Time (dPTT). In other words, in the first embodiment, as an index value corresponding to a "PTT" indicating the time period from an R-wave in an electrocardiogram to a feature point in a pulse wave A, the time difference between a feature point in the pulse wave A and the same feature point in a pulse wave B will be used as a "dPTT".

For example, by implementing the second derivative method, the calculating unit 152 detects feature points from the image-based photoplethysmogram "iPPG" extracted from the picture signal of the face and the image-based photoplethysmogram "iPPG" extracted from the picture signal of the site other than the face and further calculates the time difference "dPTT" between the detected feature points. The calculating unit 152 calculates "dPTT" values over time by calculating a "dPTT" value for each of the crests that each correspond to one heartbeat, by using the image-based photoplethysmograms each exhibiting a periodic sinusoidal waveform.

Next, the calculation of a "PD" will be explained. As explained above, in the first embodiment, the "dPTT" is calculated as an index value corresponding to a "PTT". When the "dPTT" values are used, the level of precision of detection times of the feature points has a large impact on the estimation of the fluctuation of the blood pressure. In particular, the frequency band of an "iPPG" is close to noise from body movements caused by heartbeats. In addition, because the changes in luminance on the skin are too small to be visually recognized by human eyes, the positions of the feature points significantly vary depending on the noise. Furthermore, no conclusion has been reached as to which method is most suitable for determining the feature points. Some methods for determining feature points require a high sampling frequency and may not be suitable for the application to "iPPG" data. For this reason, in the first embodiment, the "PD" corresponding to a "PTT" is calculated from a phase difference between "iPPGs" in two mutually-different ROIs.

In the present example, to calculate the phase difference between the two pulse wave signals (the image-based photoplethysmographic signal extracted from the picture signal of the face and the image-based photoplethysmographic signal extracted from the picture signal of the site other than the face), the calculating unit 152 first calculates an instantaneous phase by using a Hilbert transform explained below. A Hilbert transform on an "iPPG" at a time "t" (i.e., "H[iPPG(t)]") can be expressed on a time axis by using Expression (8) below.

$$H[iPPG(t)] = iPPG(t) * \left(\frac{1}{\pi t}\right) \qquad (8)$$

In Expression (8), "*" denotes a convolution operation. When "1/πt" in Expression (8) is Fourier-transformed, "−i sgn(f)" is obtained (where i is an imaginary number, and sgn(f) is a function). Thus, it is possible to express the result (i.e., "F[H[iPPG(t)]]") of a Fourier transform on "H[iPPG(t)]" by using Expression (9) below.

$$F[H[iPPG(t)]]=F[iPPG(t)]\times(-i\ sgn(f))$$

$$F[H[iPPG(t)]]=F[iPPG(t)]\times(-j\ sgn(f)) \quad (9)$$

In other words, the Hilbert transform is an operation to either delay or advance the positive and negative frequency components of "iPPG(t)" by "90 degree". As a result, a "cos" component becomes a "−sin" component, whereas a "sin component" becomes a "cos" component.

As for the result (i.e., "H[iPPG(t)]") of the Hilbert transform on "iPPG(t)", because the phase thereof is advanced from that of "iPPG(t)" by "90 degrees", it is possible to express the instantaneous phase "θ(t)" as indicated in Expression (10) below.

$$\theta(t) = \tan^{-1}\left(\frac{H[iPPG(t)]}{iPPG(t)}\right) \quad (10)$$

The calculating unit 152 calculates an instantaneous phase of each of the two pulse wave signals by performing the Hilbert transform described above and further calculates the difference between the two instantaneous phases as the index value "PD" corresponding to a "PTT". For example, when the "iPPGs" obtained from two mutually-different regions (a region of the face and a region of the site other than the face) are expressed as "iPPG$_1$(t)" and "iPPG$_2$(t)", it is possible to obtain instantaneous phases "θ$_1$(t)" and "θ$_2$(t)" of the "iPPGs" by using Expression (10) above. In this situation, when the iPPG measured from a position closer to the heart is assumed to be "iPPG$_1$(t), because the pulse wave sequentially propagates starting from positions close to the heart, the instantaneous phase "θ$_1$(t)" is considered to be more advanced than the instantaneous phase "θ$_2$(t)". Accordingly, because the difference "PD" between the two instantaneous phases is considered to reflect the time difference in the propagations of the pulse waves of the two mutually-different ROIs, it is possible to assume the "PD" to be substantially equivalent to a "PTT". It is possible to calculate the instantaneous phase difference by using Expression (11) below. By using the instantaneous phases of the pulse waves in this manner, the calculating unit 152 calculates the phase difference while using the information in the entirety of the waveform corresponding to one heartbeat, instead of using the phase information of one point per heartbeat.

$$PD(t)=\theta_1(t)-\theta_2(t) \quad (11)$$

Figure 10:
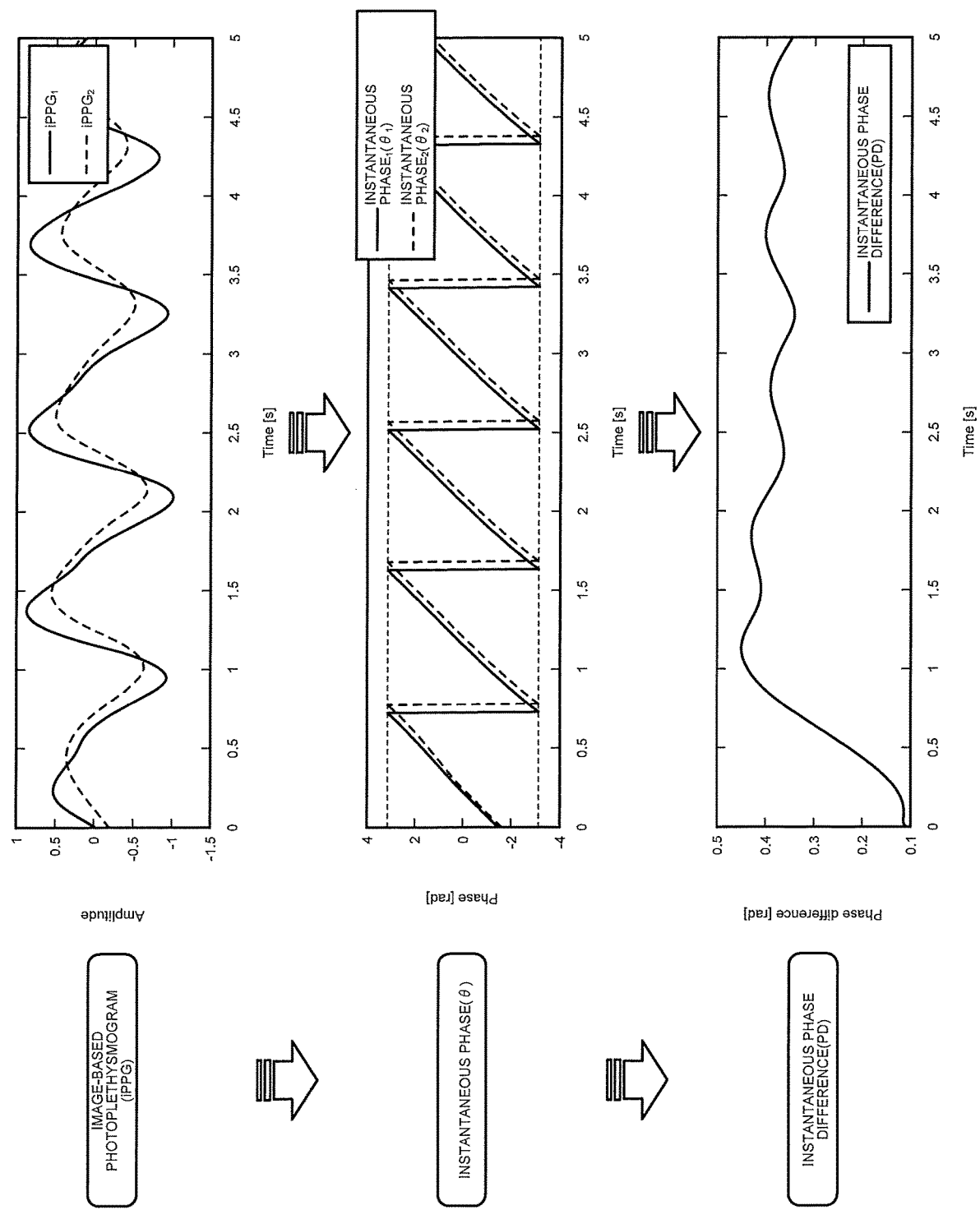
FIG. 10 presents charts for explaining an example of a calculation of an instantaneous phase difference according to the first embodiment.

FIG. 10 presents charts for explaining an example of the calculation of the instantaneous phase difference according to the first embodiment. FIG. 10 schematically illustrates a series of processes for calculating "instantaneous phases (θ)" from the "image-based photoplethysmograms (iPPGs)" and further calculating "instantaneous phase difference (PD)" from the instantaneous phases (θ)". In other words, the upper section of FIG. 10 illustrates image-based photoplethysmograms (iPPGs) while the vertical axis expresses "amplitude", whereas the horizontal axis expresses "time [s]". The middle section of FIG. 10 illustrates "instantaneous phases (θ)" while the vertical axis expresses "phase [rad]", whereas the horizontal axis expresses "time [s]". The lower section of FIG. 10 illustrates "instantaneous phase difference (PD)" while the vertical axis expresses "phase difference [rad]", whereas the horizontal axis expresses "time [s]".

For example, as illustrated in FIG. 10, the calculating unit 152 calculates instantaneous phase 1 "θ$_1$" and instantaneous phase 2 "θ$_2$" from the image-based photoplethysmogram "iPPG$_1$" extracted from the picture signal of the face and the image-based photoplethysmogram "iPPG$_2$" extracted from the picture signal of a site other than the face (e.g., a hand). The instantaneous phases illustrated in the middle section of FIG. 10 are results of folding back the data in the range of (−π,π). Further, the calculating unit 152 calculates the instantaneous phase difference "PD" as illustrated in FIG. 10, by calculating the difference between instantaneous phase 1 "θ$_1$" and instantaneous phase 2 "θ$_2$" while using Expression (11) presented above.

Returning to the description of FIG. 3, the measuring unit 153 is configured to measure the fluctuation of the blood pressure of the subject corresponding to an increase or a decrease in the difference calculated by the calculating unit 152. More specifically, the measuring unit 153 measures the fluctuation of the blood pressure of the subject corresponding to the increase or the decrease in either the difference of pulse transit time "dPTT" or the instantaneous phase difference "PD" calculated by the calculating unit 152. In this situation, the measuring unit 153 measures an increase in the difference (either the "dPTT" or the "PD") as an increasing fluctuation of the blood pressure and measures a decrease in the difference as a decreasing fluctuation of the blood pressure. In other words, when either the "dPTT" or the "PD" increases, the measuring unit 153 determines that the blood pressure has increased. When either the "dPTT" or the "PD" decreases, the measuring unit 153 determines that the blood pressure has decreased.

As explained above, from conventional findings, it is known that fluctuations of blood pressure have a negative correlation with fluctuations of the "PTT". In other words, when fluctuations of blood pressure are estimated by simply using the conventional findings, an increase in either the "dPTT" or the "PD" means a decrease of the blood pressure, whereas a decrease in either the "dPTT" or the "PD" means an increase of the blood pressure. In contrast, the biological information measuring apparatus 100 according to the first embodiment is configured to estimate the fluctuation of the blood pressure by using the opposite correlation (i.e., a positive correlation). In the following sections, results of actual experiments and a principle of the first embodiment will be explained.

(The Method of the Experiment)

Twenty healthy adult males in the age range of "22.8±1.1" years old participated as subjects. The experiment was performed once on each subject. The subjects were seated at rest, while the data was measured for five minutes. By using an electrocardiographic/photoplethysmographic amplifier and a sensor for biological signals, an ECG waveform was taken from electrodes (electrocardiography electrodes called 'Blue Sensor' manufactured by Mets) pasted on the chest of each subject and a PPG was measured from a photoplethysmograph sensor ('Nellcor DS-100A' manufactured by Envitec) attached to the index finger of the left hand of each subject. Further, blood pressure was measured by attaching a continuous sphygmomanometer ('Portapres' manufactured by Finapres Medical Systems) to the middle finger of the left hand of each subject. The measured signals were recorded at a sampling frequency of "1 kHz", by using a "16-bit" A/D converter ('MP150' manufactured by BIOPAC).

Pictures of the body were taken by using a video camera, at the same time as the biological signals were measured. An industrial video camera ('TGX02c' manufactured by Baumer) was used for the image taking process. This camera was selected for the advantages of being capable of taking images at a maximum framerate of "140 fps" and not requiring a compressing process in the time direction during the recording process. As illustrated in FIG. 6B, the angle of view was set so as to include the entire face, the neck, and the palm of the right hand. A frame stage for fixing the face and the right hand as well as a table to place the right elbow thereon were provided. Each subject was instructed to place the right hand to the right side of his face, while his right palm was facing the camera. The distance between the video camera and the face was approximately "100 cm". The settings of the video camera used in the present experiment are indicated below. Because the camera performed an automatic exposure adjusting process and the like immediately after the beginning of the image taking process, the first five seconds at the beginning were excluded from the analysis.

The settings of the video camera were as follows:
"The number of pixels: 440×440 pixels"
"The framerate: 120 fps"
"Colors: 24-bit RGB (3 channels×8 bits/channel)"
"Saving Format: uncompressed avi format"
"recording length: 305 secs (5 minutes and 5 seconds)"

To illuminate the face and the hand, a direct-current white LED light ('LWK-10' manufactured by Hataya Limited) was installed on a side of the camera. Because lighting driven by an alternating current power source such as a fluorescent lamp would have caused commercial frequency noise in the pictures, only the direct-current LED was used as the lighting in the experiment environment. The illuminance in the positions of the face and the hand was "1,000 lux".

In the present experiment, the blood pressure was intentionally fluctuated, so as to verify whether it was possible to extract the fluctuation from "iPPG" signals. In the present example, a breath-holding test was performed to create a load to raise the blood pressure. The experiment was continuously performed for a total of five minutes including one minute of being at rest, followed by one minute of holding the breath, and three minutes of being at rest. While the subject was at rest, breathing was not controlled, and he was allowed to breathe freely. However, the subject was instructed to refrain as much as possible from any action that would drastically change the intrapulmonary pressure or the respiratory pattern (e.g., coughing). Further, the method for holding the breath was standardized by instructing each subject to verbally count down ten seconds before starting to hold his breath and to hold his breath after inhaling fully. Naturally, some of the subjects were unable to hold the breath for one minute. Thus, each subject was instructed to change to the free breathing when he felt his limit for holding his breath, even before one minute elapsed.

(A Method of the Analysis)

To use a "PTT" value obtained by a conventional method as a comparison target, an R-wave was detected from the recorded ECG signal. Further, a fifth-order Butterworth low-pass filter having a passband of "10 Hz" or lower was applied to infrared photoplethysmography (irPPG) data measured by the sensor attached to the fingertip. A maximum point in the second-order derivative within each heartbeat was detected in the filter-processed "irPPG" waveform and in each of the "iPPG" waveforms obtained from the ROIs in the five locations illustrated in FIG. 6B, so that the detected maximum points were used as the feature points for calculating "PTT" and "dPTT" values. By using the R-wave and the feature points in the "irPPG" and the "iPPG", a pulse transit time "PTT" was calculated for each of the combinations. The combinations of "iPPGs" used for calculating the difference of pulse transit time "dPTT" and the instantaneous phase difference "PD" will be explained later.

From the continuous blood pressure waveform, the following values were calculated for each heartbeat: a maximum value (i.e., systolic blood pressure: SBP [mmHg]); a minimum value (i.e., diastolic blood pressure: DBP [mmHg]); and an average value (i.e., mean blood pressure: MBP [mmHg]). With respect to the "PTT", "dPTT", and "PD" values obtained from the "irPPG" and "iPPG" signals of each of the subjects, it was checked to see whether there was any correlation with the blood pressure value obtained by the continuous sphygmomanometer. The signals were re-sampled to "2 Hz" by performing a spline interpolation thereon, and subsequently, a correlation coefficient "r" was calculated so as to evaluate similarly between the two. It is possible to express the correlation coefficient "r" by using Expression (12) below.

$$r = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}} \quad (12)$$

In Expression (12), "n" denotes the number of samples; "$x_i$" denotes the blood pressure; "x-bar" denotes an average of "$x_i$" values; "$y_i$" denotes each "PTT" value; and "y-bar" denotes an average of "$y_i$" values. The purpose of the present experiment was not estimating an accurate blood pressure value for each heartbeat, but was detecting a short-period rapid fluctuation of the blood pressure caused by the load. Accordingly, to check to see if there was any correlation with the frequency components lower than those of vasomotor blood pressure fluctuations, a low-pass filtering process (fc=0.04 Hz) in the time direction was applied to each of the "SBP", "PTT", "dPTT", and "PD" signals.

(Results of the Experiments)

Figure 11A:
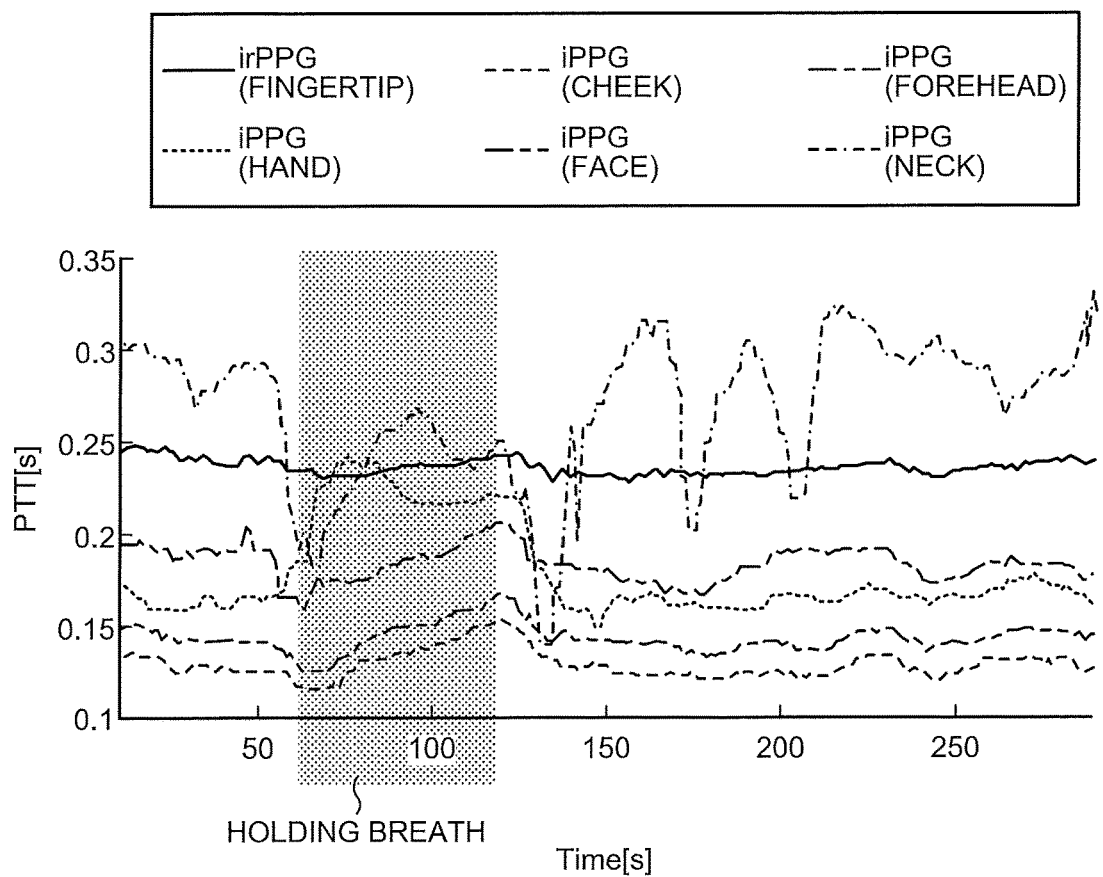
FIG. 11A is a chart of fluctuations of pulse transit time (PTT) values at different sites of a representative subject according to the first embodiment.

The following are the results of the experiment explained above. First, analysis results regarding the R-waves in the electrocardiograms and the pulse transit time values in the image-based photoplethysmograms of the ROIs will be explained, with reference to FIGS. 11A to 12B. FIG. 11A is a chart of fluctuations of PTT values at the different sites of a representative subject according to the first embodiment. FIG. 11A illustrates the chart of the fluctuations of the PTT values in which the vertical axis expresses PTT, whereas the horizontal axis expresses time. Further, FIG. 11A illustrates, while using the R-wave in the ECG as a reference, a fluctuation of PTT calculated from the feature point in the irPPG(fingertip) measured by the sensor attached to the fingertip; a fluctuation of PTT calculated from the feature point in the iPPG(cheek) extracted from the picture signal of the left cheek of the face illustrated in FIG. 6B ("CHEEK" in 11A); a fluctuation of PTT calculated from the feature point in the iPPG(forehead) extracted from the picture signal of the forehead of the face illustrated in FIG. 6B ("FOREHEAD" in 11A); a fluctuation of PTT calculated from the feature point in the iPPG(hand) extracted from the picture signal of the right palm illustrated in FIG. 6B ("HAND" in 11A); a fluctuation of PTT calculated from the feature point in the iPPG(face) extracted from the picture signal of the entire face front illustrated in FIG. 6B ("FACE" in 11A); and a fluctuation of PTT calculated from the feature point in the iPPG(neck) extracted from the picture signal of the front part of the neck illustrated in FIG. 6B ("NECK" in 11A).

As explained above, because each PTT value is calculated on the basis of the time period from the R-wave in the ECG to the feature point in the PPG, the later the pulsation arrives, the larger the PTT value is. In this situation, as illustrated in FIG. 11A, the iPPG waveforms of the different sites directly reflect the distances from the heart. It is observed that the values increase in the order of "cheek", "face", "forehead", and "fingertip". Consequently, it is considered possible to calculate the PTT values by obtaining the pulse waves propagating toward the peripheral regions while using the iPPG waveforms. It should be noted, however, that the PTT value from the iPPG(hand) exhibited a peculiar fluctuation, compared to the PTT values from the other regions. Further, because the iPPG(neck) contained a lot of noise from body movements and the like, it was difficult to detect the feature point used for calculating the PTT. In addition, because it was not possible to accurately calculate a PTT value from the iPPG(neck) for any of the subjects, the iPPG(neck) will be excluded from the analyses hereinafter.

Figure 11B:
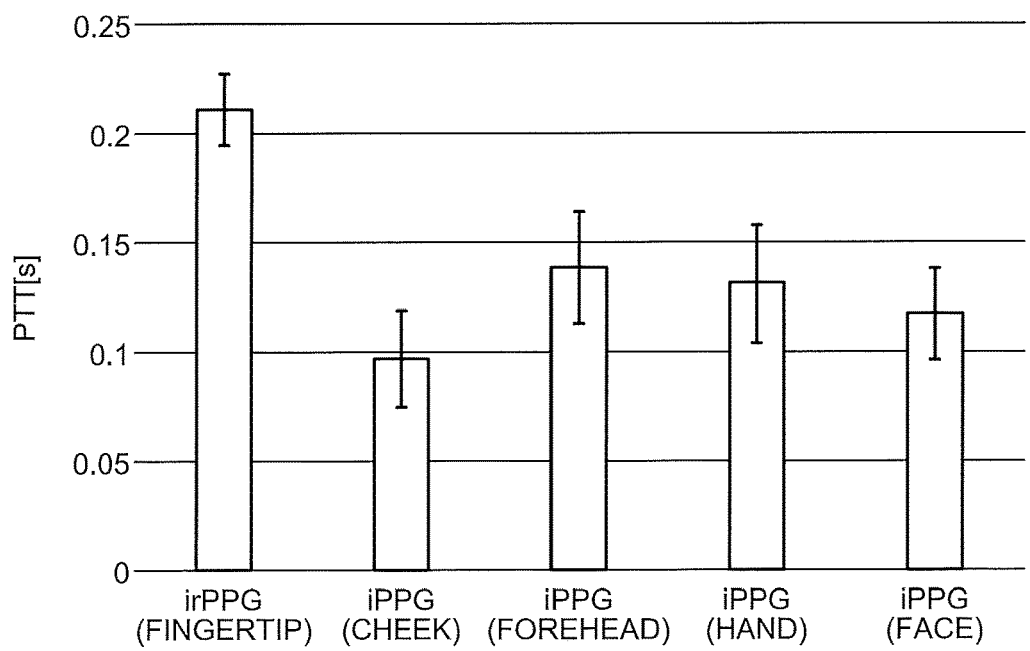
FIG. 11B is a chart of average values and standard deviations of PTT values at different sites of all the subjects according to the first embodiment.

FIG. 11B is a chart of average values and standard deviations of the PTT values at the different sites of all the subjects according to the first embodiment. In FIG. 11B, the vertical axis expresses PTT, while the charts of the average values and the standard deviations of the PTT values of the different sites are arranged in a row in the horizontal direction. The iPPG(neck) was excluded from the calculations because the noise was too large, as explained above. As for the average value of the PTT values for each of the site, the iPPG(cheek) was smallest, whereas irPPG(fingertip) was largest, as illustrated in FIG. 11B. Considering the distances from the heart, reasonable results were obtained. However, the PTT value calculated from the iPPG(hand) was approximately equal to the PTT of the face region, although the hand was positioned more distant from the heart than the face was.

Figure 12A:
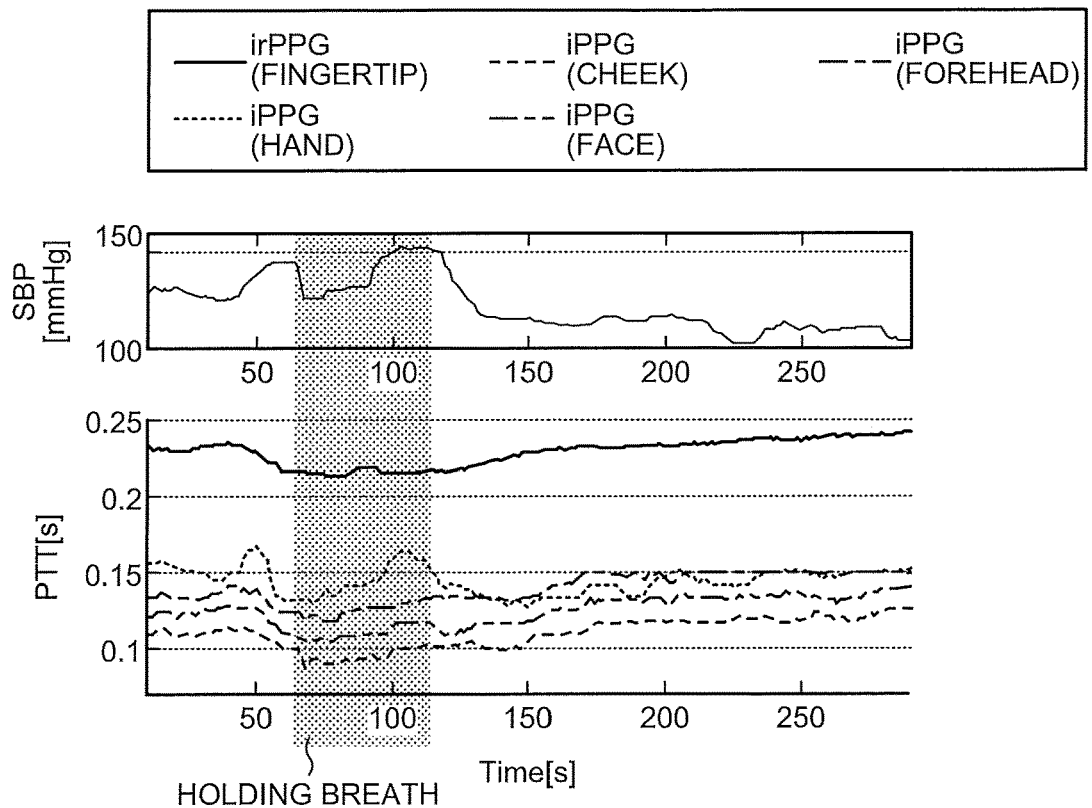
FIG. 12A presents charts of Systolic Blood Pressure (SBP) values and fluctuations of PTT values at different sites of a representative subject according to the first embodiment.
Figure 12B:
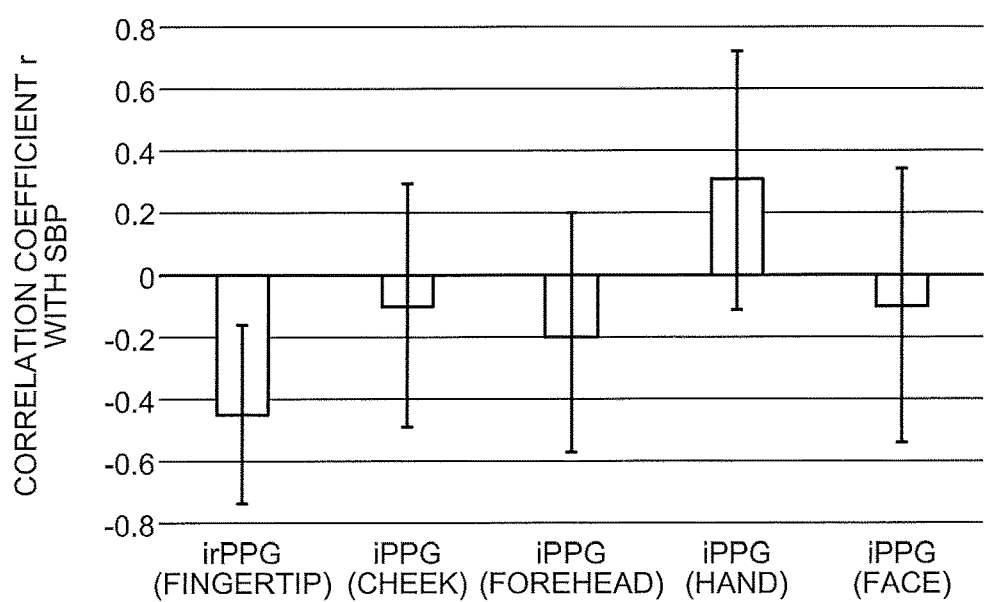
FIG. 12B is a chart of average values and standard deviations of correlation coefficients between SBP values and PTT values at different sites of all the subjects according to the first embodiment.

FIG. 12A presents charts of SBP values and fluctuations of PTT values at the different sites of a representative subject according to the first embodiment. FIG. 12A illustrates an example of a representative subject who is different from the subject illustrated in FIG. 11A. Further, the lower section of FIG. 12A illustrates a fluctuation chart of the PTT values at the different sites, while the vertical axis expresses PTT, whereas the horizontal axis expresses time. The upper section of FIG. 12B illustrates a fluctuation chart of SBP, while the vertical axis expresses SBP, whereas horizontal axis expresses time. In this situation, the fluctuation chart of SBP and the fluctuation chart of PTT use mutually-the-same horizontal axis, so that it is possible to compare the fluctuation of SBP with the fluctuation of PTT from the same time period. First, it is observed from FIG. 12A that SBP (systolic blood pressure) exhibited a rapid increase while the subject was holding the breath. Further, it is observed that as the SBP value increased, the PTT values from the irPPG (fingertip) and the iPPG(cheek, forehead, and face) decreased, although the PTT value from the iPPG(hand) increased.

FIG. 12B is a chart of average values and standard deviations of the correlation coefficients between SBP values and PTT values at the different sites of all the subjects according to the first embodiment. In FIG. 12B, the vertical axis expresses the correlation coefficients in relation to the SBP values, while the charts of the average values and the standard deviations of the correlation coefficients at the different sites are arranged in a row in the horizontal direction. As illustrated in FIG. 12B, it is observed that the correlation coefficients between the SBP values and the PTT values at the different sites exhibited large differences among the subjects (hereinafter, "individual differences") because the standard deviations were larger than the average values. In this situation, because it is known that PTT values have a negative correlation with blood pressure values, each of all the correlation coefficients had been expected to have a negative value. In actuality, however, as illustrated in FIG. 12B, the correlations with the PTT values from the iPPG (cheek, forehead, and face) were weak. The correlation with the PTT value from the iPPG(hand) exhibited a positive correlation.

Next, the analysis results related to the difference of pulse transit time "dPTT" between image-based photoplethysmograms of two ROIs will be explained, with reference to FIGS. 13A to 13C. In this situation, as for the combinations of two ROIs used for calculating the "dPTT" values, the following three combinations were selected: (1) the left cheek of the face and the forehead of the face (hereinafter, "cheek-forehead"); (2) the left cheek of the face and the right palm (hereinafter, "cheek-hand"); and (3) the forehead of the face and the right palm (hereinafter, "forehead-hand"). In this situation, because it was impossible to accurately calculate a PTT value from the iPPG(neck), the iPPG(neck) was not included in the candidates for the combinations.

Figure 13A:
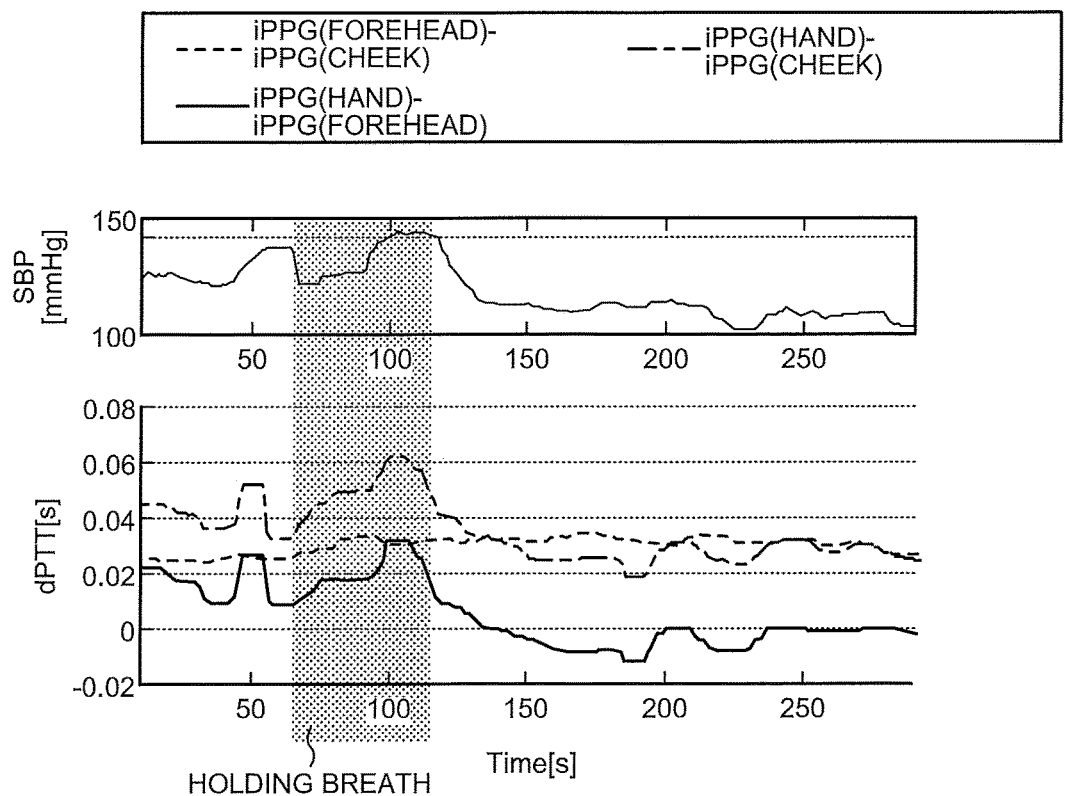
FIG. 13A presents charts of fluctuations of SBP values and difference of pulse transit time (dPTT) values of a representative subject according to the first embodiment.

FIG. 13A presents charts of fluctuations of SBP values and dPTT values of a representative subject according to the first embodiment. The lower section of FIG. 13A illustrates a fluctuation chart of the dPTT values of the different combinations while the vertical axis expresses dPTT, whereas the horizontal axis expresses time. The upper section of FIG. 13A illustrates a fluctuation chart of SBP, while the vertical axis expresses SBP, whereas the horizontal axis expresses time. In this situation, the fluctuation chart of SBP and the fluctuation chart of dPTT use mutually-the-same horizontal axis, so that it is possible to compare the fluctuation of SBP with the fluctuation of dPTT from the same time period. It is observed from FIG. 13A that the iPPG(hand)-iPPG(cheek) chart and the iPPG(hand)-iPPG (forehead) chart, which each indicate a dPTT obtained by calculating the time difference from the iPPG(hand), exhibited fluctuations similar to that of SBP as a whole by, for example, exhibiting an increase while the subject was holding the breath. In contrast, it is also observed from FIG. 13A that the iPPG(forehead)-iPPG(cheek) chart indicating a dPTT obtained by calculating the time difference between the regions that are both in the face exhibited a fluctuation that was not so similar to that of SBP, compared to the other two combinations. As for this subject, because there were times when the feature point in the iPPG(hand) appeared earlier than the feature point in the iPPG(forehead), the dPTT value from the iPPG(hand)-iPPG(forehead) chart in FIG. 13A exhibited negative values in some parts.

Figure 13B:
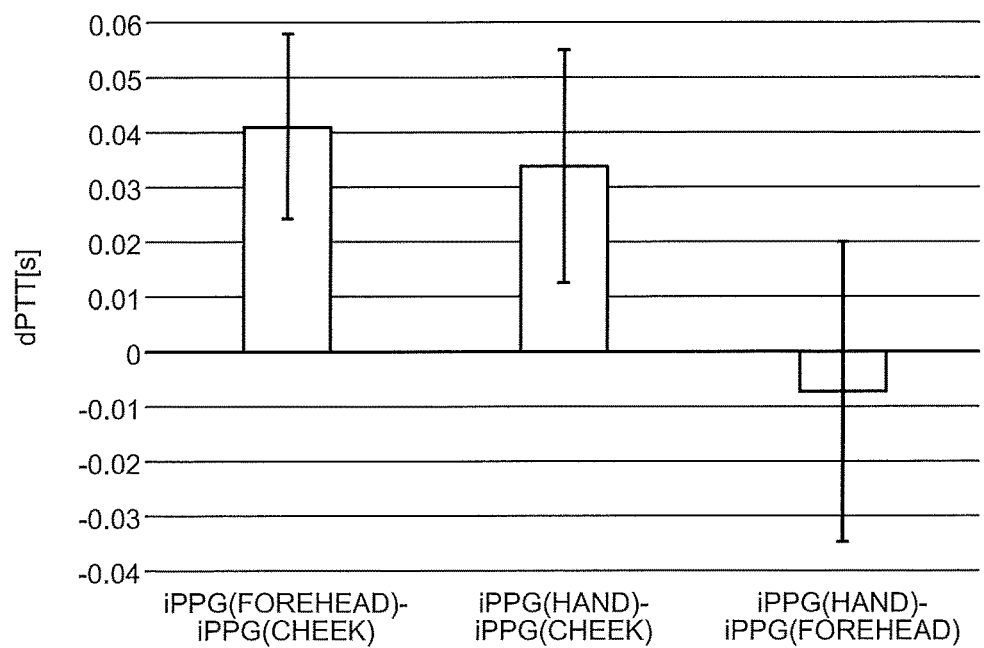
FIG. 13B is a chart of average values and standard deviations of dPTT values for different combinations with respect to all the subjects according to the first embodiment.

FIG. 13B is a chart of average values and standard deviations of dPTT values for the different combinations with respect to all the subjects according to the first embodiment. In FIG. 13B, the vertical axis expresses dPTT, while the charts of the average values and the standard deviations of the dPTT values for the different combinations are arranged in a row in the horizontal direction. As illustrated in FIG. 13B, even if there was a large difference in the distance from the heart between the two locations of measurement (e.g., iPPG(hand)-iPPG(forehead)), the results indicate that the dPTT value was approximately "0.01 s".

When the absolute value of dPTT is small like this, because the dynamic range of dPTT during the fluctuation of the blood pressure becomes small, it is considered desirable to adopt the dPTT values calculated from the iPPG(forehead)-iPPG(cheek) and the iPPG(hand)-iPPG(cheek), each of which has a larger absolute value of dPTT than the iPPG (hand)-iPPG(forehead).

Figure 13C:
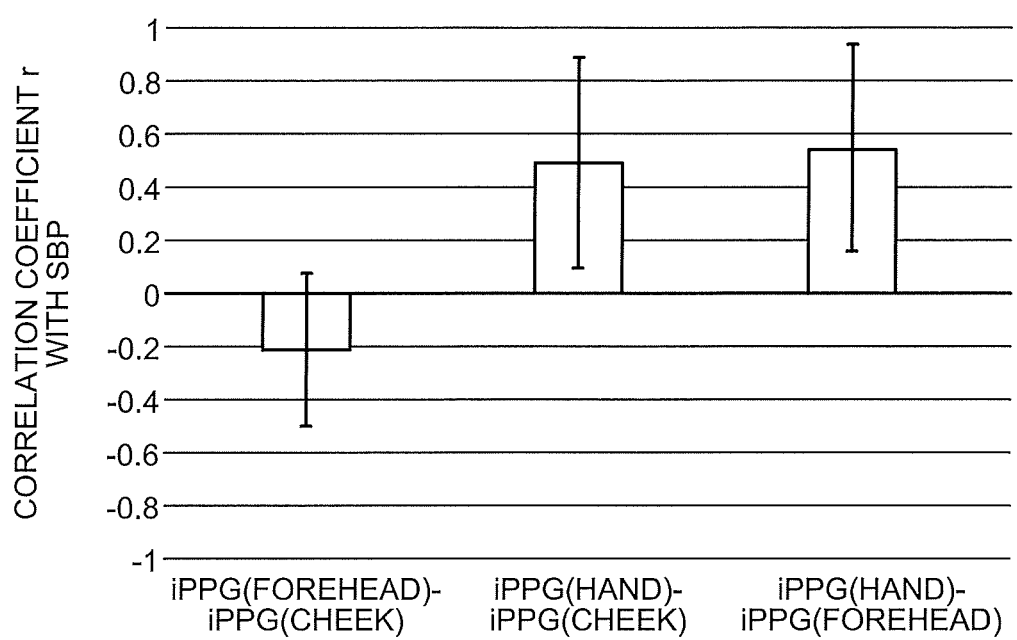
FIG. 13C is a chart of average values and standard deviations of correlation coefficients between dPTT values and SBP values of all the subjects according to the first embodiment.

FIG. 13C is a chart of average values and standard deviations of correlation coefficients between dPTT values and SBP values of all the subjects according to the first embodiment. In FIG. 13C, the vertical axis expresses the correlation coefficients in relation to SBP, while the charts of the average values and the standard deviations of the correlation coefficients for the different combinations are arranged in a row in the horizontal direction. It is observed from FIG. 13C that the correlation coefficients between the SBP values and the dPTT values for the different combinations exhibited large individual differences because the standard deviations were larger than the average values. Similarly to the analyses of the pulse transit time between the R-waves in the electrocardiograms and the image-based photoplethysmograms at the ROIs, although each of all the correlation coefficients had been expected to have a negative value, all of the iPPG(hand)-iPPG(cheek) chart and the iPPG(hand)-iPPG(forehead) chart, which each indicate a dPTT obtained by calculating the time different from the iPPG(hand), exhibited a positive correlation with SBP. It is considered that the reason was because the fluctuation of the PTT from the iPPG(hand) was larger than those from the iPPG(cheek, forehead), the impact of the iPPG(hand) significantly remained even after the difference between the two was calculated.

Figure 14A:
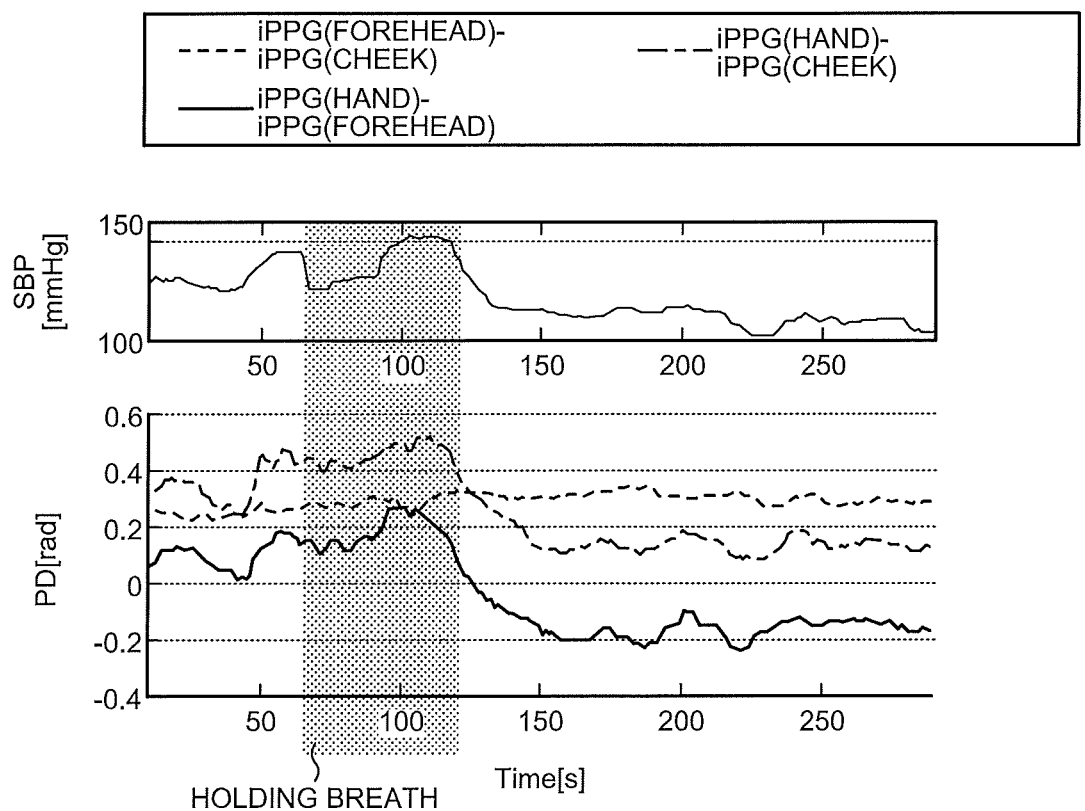
FIG. 14A presents charts of fluctuations of SBP values and PD values of a representative subject according to the first embodiment.

Next, analysis results regarding the instantaneous phase difference "PD" between image-based photoplethysmograms of two ROIs will be explained, with reference to FIGS. 14A and 14B. In this situation, as for the combinations of two ROIs used for calculating the "PD" values, the same combinations as those used for calculating the "dPTT" values were used. FIG. 14A presents charts of fluctuations of SBP values and PD values of a representative subject according to the first embodiment. The lower section of FIG. 14A illustrates a fluctuation chart of the PD values of the different combinations, while the vertical axis expresses SBP, whereas the horizontal axis expresses time. The upper section of FIG. 14A illustrates a fluctuation chart of SBP, while the vertical axis expresses SBP, whereas the horizontal axis expresses time. In this situation, the fluctuation chart of SBP and the fluctuation chart of PD use mutually-the-same horizontal axis, so that it is possible to compare the fluctuation of SBP with the fluctuation of PD from the same time period.

It is observed from FIG. 14A that, similarly to the results of the dPTT values, the iPPG(hand)-iPPG(cheek) chart and the iPPG(hand)-iPPG(forehead) chart, which each indicate a PD value obtained by calculating an instantaneous phase difference from the iPPG(hand), exhibited a fluctuation similar to that of SBP as a whole. In addition, it is also observed that, similarly to the results of the dPTT values, the iPPG(forehead)-iPPG(cheek) chart indicating a PD obtained by calculating the instantaneous phase difference between the regions that are both in the face exhibited a fluctuation that was not so similar to that of SBP, compared to the other two combinations. As for this subject, because there were times when the instantaneous phase of the iPPG(hand) appeared to be more advanced than the instantaneous phase of the iPPG(forehead), the PD value from the iPPG(hand)-iPPG(forehead) chart in FIG. 14A exhibited negative values in some parts.

Figure 14B:
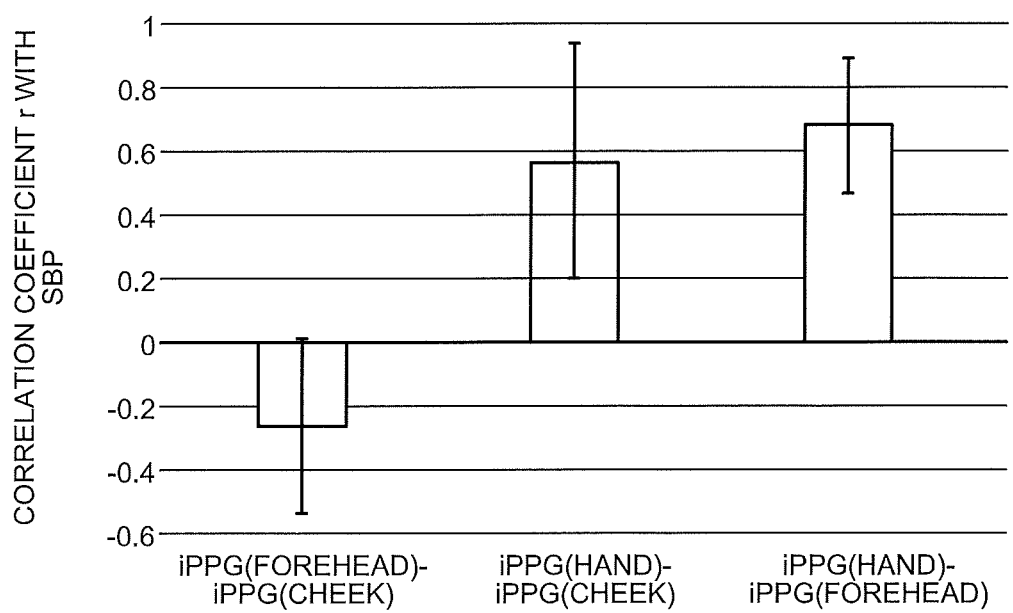
FIG. 14B is a chart of average values and standard deviations of correlation coefficients between SBP values and PD values of all the subjects according to the first embodiment.

FIG. 14B is a chart of average values and standard deviations of correlation coefficients between SBP values and PD values of all the subjects according to the first embodiment. In FIG. 14B, the vertical axis expresses the correlation coefficients in relation to SBP, while the charts of the average values and the standard deviations of the correlation coefficients for the different combinations are arranged in a row in the horizontal direction. It is observed from FIG. 14B that the correlation coefficients between the SBP values and the PD values for the different combinations exhibited large individual differences because the standard deviations were larger than the average values. The results indicate that the tendency of the correlation coefficients was the same as that of the correlation coefficients with the dPTT values. Accordingly, with regard to the relationship with SBP values, it is possible to assume that the dPTT values and the PD values obtained by using iPPGs from two mutually-different locations contain information similar to each other.

The results presented above indicate that the "dPTT" values and the "PD" values calculated from the image-based photoplethysmogram "iPPG" extracted from the picture signal of the face and the image-based photoplethysmogram "iPPG" extracted from the picture signal of the site other than the face (e.g., the hand) each have a positive correlation with the blood pressure values. However, it is considered that the results exhibited large individual differences because the standard deviations were large. It is considered that the main cause was that the low frequency components of the signals did not exhibit fluctuations for some of the subject whose blood pressure hardly increased when the load was applied by holding the breath. In addition, it is known that the degree of correlations among PTT values, dPTT values, and SBP values varies among individuals (i.e., individual differences). It means that, as understood from Expressions (1) to (7), depending on the characteristic of the blood vessels, the fluctuation of the blood pressure is easily reflected as a fluctuation of the pulse transit time for some people and is not so easily reflected for other people.

Although the large individual differences were exhibited as explained above, it is not that the correlation is not useful as an index. The reason is that it is reported that the individual differences above are caused by lifestyle (exercising habits) of younger people. Also, it is also reported that the correlation among PTT values, dPTT values, and SBP values becomes stronger for elderly people because the stretchability of arterial walls becomes lower. Furthermore, in view of the fact that the blood pressure values of elderly people are increased by the load more significantly than the blood pressure values of younger people, it is expected that the correlation will be stronger than that in the present experiment results when elderly people participate in the experiment as subjects. Because elderly people have a higher possibility of putting the human bodies in dangerous situations with fluctuations of blood pressure, further analyses were performed by narrowing down the subjects, even though they were young, to those whose fluctuations of blood pressure were easily reflected in the PTT values.

Figure 15A:
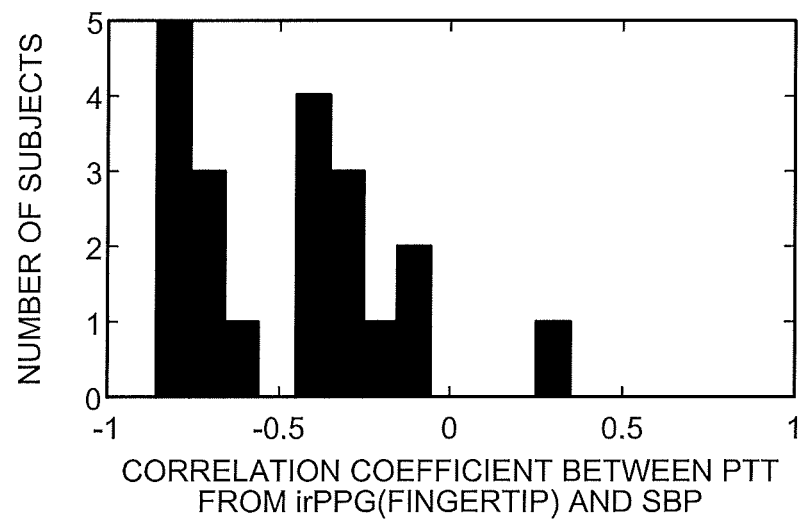
FIG. 15A is a histogram of correlation coefficients between PTT values from infrared photoplethysmogram on a fingertip (irPPG(fingertip)) and SBP values according to the first embodiment.

More specifically, a screening process to confirm the tendency was performed by selecting, from among the total of twenty subjects, such subjects whose fluctuations of blood pressure were easily reflected in the PTT values and the dPTT values. FIG. 15A is a histogram of correlation coefficients between PTT values from infrared photoplethysmograms(fingertip) and SBP values according to the first embodiment. FIG. 15A illustrates the histogram in which the vertical axis expresses the number of subjects, whereas the horizontal axis expresses the correlation coefficients. As illustrated in FIG. 15A, the correlation coefficients between the PTT values from the irPPG(fingertip) and the SBP values varied among the total of twenty subjects. In order to perform an analysis on such subjects, even though they were young, whose fluctuations of blood pressure were easily reflected in the PTT values, nine subjects (hereinafter, "screened group") whose correlation coefficients in the histogram illustrated in FIG. 15A were "−0.5" or smaller were selected, so as to check the level of precision in the estimation of the blood pressure based on iPPGs for the selected group of subjects.

Figure 15B:
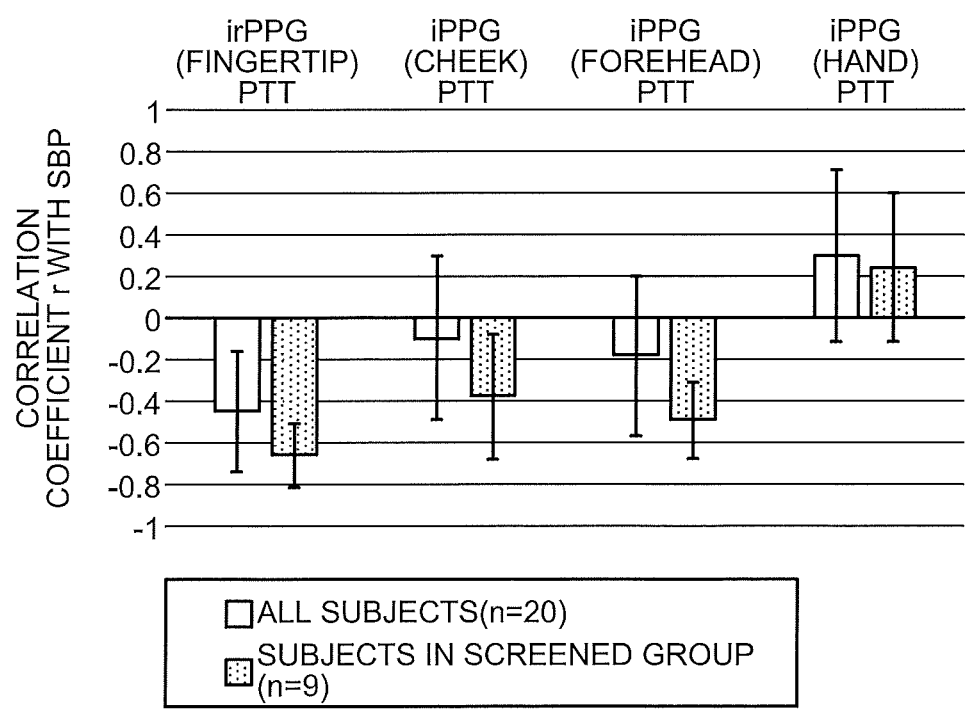
FIG. 15B is a chart to compare between before and after a screening process with respect to correlation coefficients between PTT values and SBP values according to the first embodiment.

First, a comparison was made with regard to PTT values between before and after the screening process. FIG. 15B is a chart to compare between before and after the screening process with respect to the correlation coefficients between PTT values and SBP values according to the first embodiment. FIG. 15B illustrates average values and standard deviations of the correlation coefficients between the SBP values and the PTT values from the iPPGs of the different sites for all the subjects (n=20) and for the subjects in the screened group (n=9). In FIG. 15B, the vertical axis expresses the correlation coefficient, while the charts of the average values and the standard deviations of the correlation coefficients of the different sites before and after the screening process are arranged in a row in the horizontal direction. It is observed from FIG. 15B that the selected subjects (i.e., the subjects in the screened group) exhibited a tendency for stronger correlations between the PTT values from the iPPG(cheek) and the iPPG(forehead) and the SBP values. In other words, it is considered that the subjects whose fluctuations of blood pressure were easily reflected in the fingertip PTT values had a tendency where the fluctuation of the blood pressure was reflected in the PTT values of the cheek and the forehead, too. In contrast, for the PTT values from the iPPG(hand), no change was found in the correlational relationship between before the screening process and after the screening process. The reason why the tendencies of the correlations with the fluctuation of the blood pressure were different between the fingertip and the palm, although the fingertip and the palm are positioned close to each other, may be related to the difference in the blood pressure information contained in the irPPG and the iPPG. The details will be explained later.

Figure 15C:
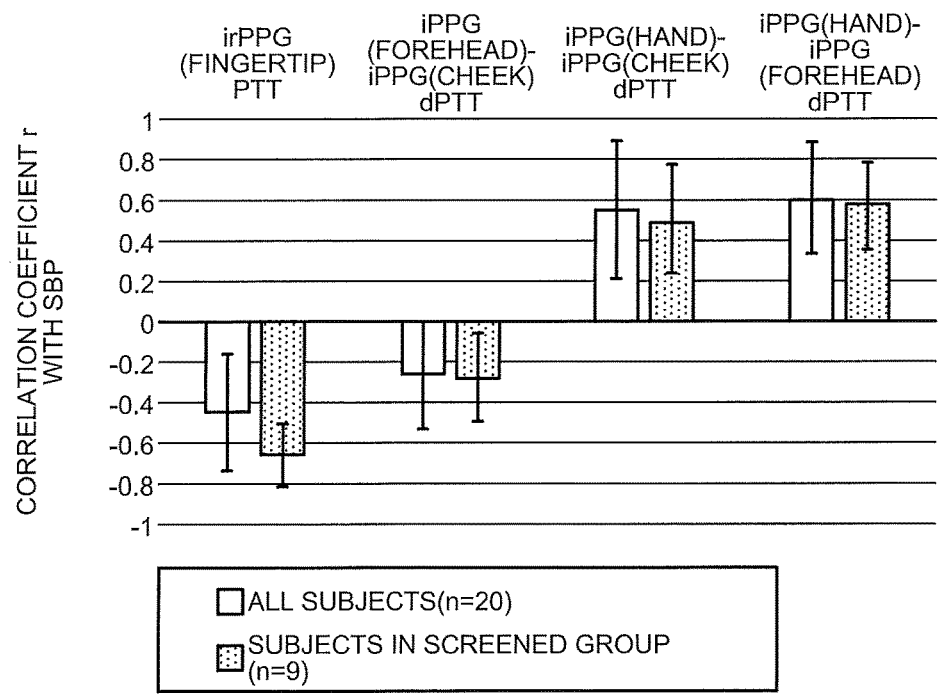
FIG. 15C is a chart to compare between before and after the screening process with respect to correlation coefficients between dPTT values and SBP values according to the first embodiment.

Subsequently, a comparison was made with regard to dPTT values between before and after the screening process. FIG. 15C is a chart to compare between before and after the screening process with respect to the correlation coefficients between dPTT values and SBP values according to the first embodiment. FIG. 15C illustrates the average values and the standard deviations of the correlation coefficients between the SBP values and the dPTT values from the iPPGs of the different sites for all the subjects (n=20) and for the subjects in the screened group (n=9). In FIG. 15C, the vertical axis expresses the correlation coefficient, while the charts of the average values and the standard deviations of the correlation coefficients for the different combinations before and after the screening process are arranged in a row in the horizontal direction. It is observed from FIG. 15C that, with any of the combinations, no significant difference in the average value was found between before the screening process and after the screening process and that, even with the selected subjects, no significant difference was found in the correlation coefficients between the dPTT values and the SBP values. Further, the correlation between the dPTT values from the iPPG(forehead)-iPPG(cheek) chart and the SBP values were particularly weak, and it seemed difficult to estimate a fluctuation of blood pressure on the basis of a body picture imaging only the face, according to the current method.

Figure 15D:
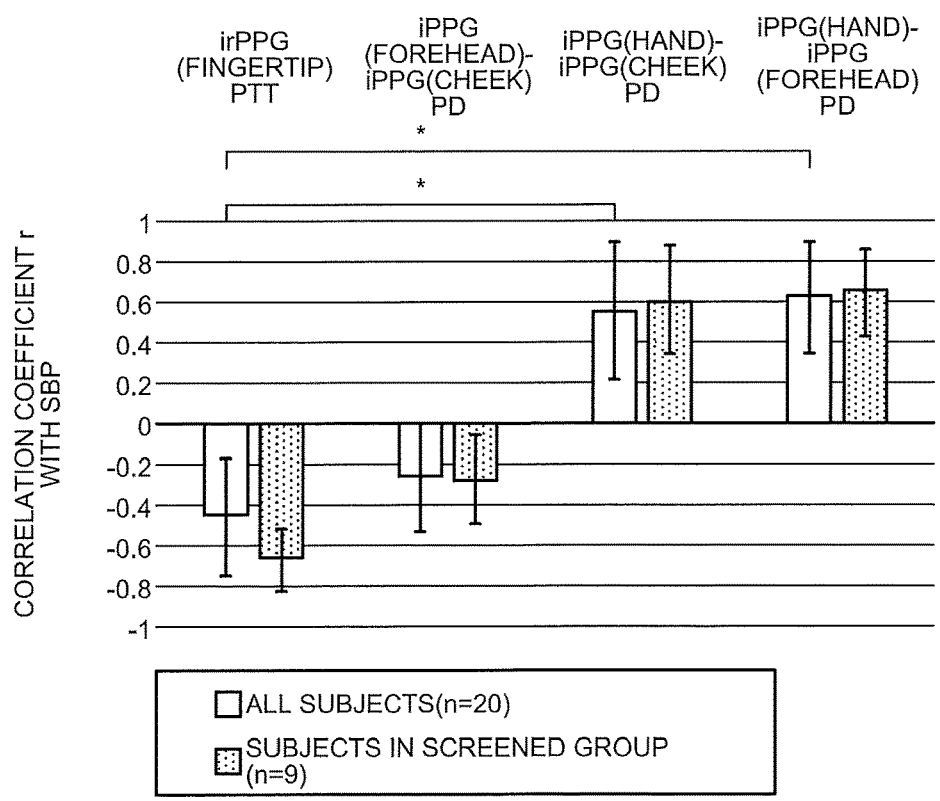
FIG. 15D is a chart to compare between before and after the screening process with respect to correlation coefficients between PD values and SBP values according to the first embodiment.

After that, a comparison was made with regard to PD values between before and after the screening process. FIG. 15D is a chart to compare between before and after the screening process with respect to the correlation coefficients between PD values and SBP values according to the first embodiment. FIG. 15D illustrates the average values and the standard deviations of the correlation coefficients between the SBP values and the PD values from the iPPGs of the different sites for all the subjects (n=20) and for the subjects in the screened group (n=9). In FIG. 15D, the vertical axis expresses the correlation coefficient, while the charts of the average values and the standard deviations of the correlation coefficients for the different combinations before and after the screening process are arranged in a row in the horizontal direction. It is observed from FIG. 15D that, with any of the combinations, no significant difference in the average value was found between before and after the screening process and that, even with the selected subjects, no significant difference was found in the correlation coefficients between the PD values and the SBP values. Further, a Student's t-test was performed by calculating the absolute values of the correlation coefficients of all the subjects. As a result, the correlation coefficients were significantly higher ($p<0.05$) with the method according to the first embodiment implemented on the PTT values from the irPPG(fingertip), the PD values from the combination of the iPPG(hand)-iPPG (cheek), and the PD values from the combination of the iPPG(hand)-iPPG(forehead). Further, with respect to the absolute values of the correlation coefficients in relation to the SBP values, the PD values from the iPPG(hand)-iPPG (cheek) and the iPPG(hand)-iPPG(forehead) after the screening process were substantially equal ($r=0.6$ approximately) to the PTT values from irPPG(fingertip) used as a reference. Accordingly, it was suggested that, when the subjects are limited, it might be possible to estimate a fluctuation of blood pressure only from body pictures by placing a focus on these ROIs.

Figure 15E:
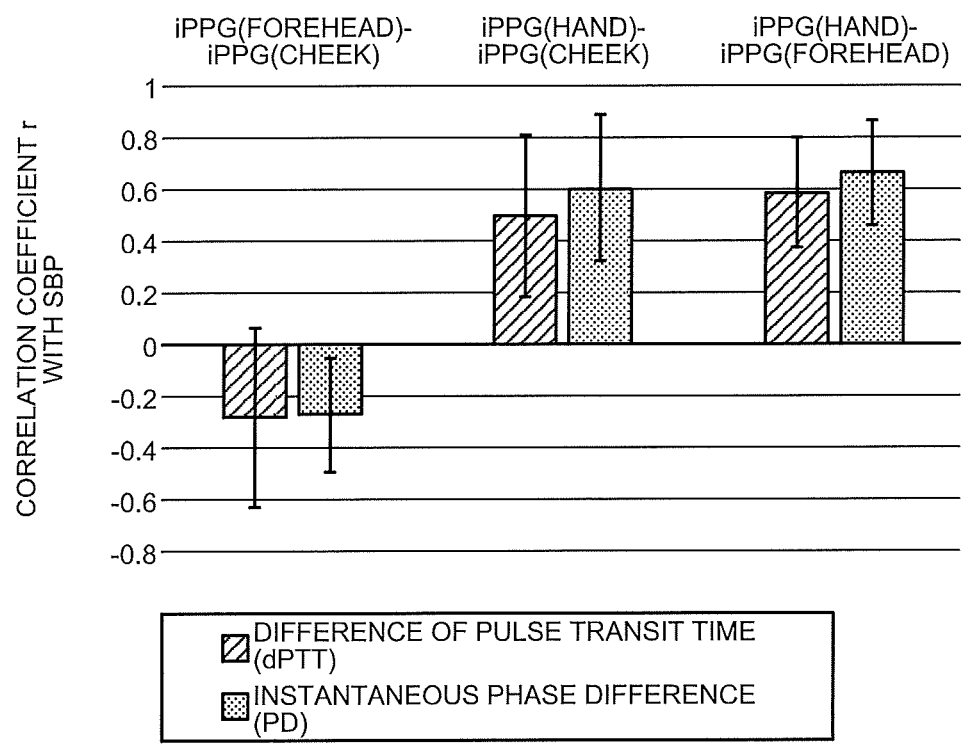
FIG. 15E is a chart to compare between dPTT values and PD values of subjects in a screened group according to the first embodiment.

Finally, a comparison was made between dPTT values and PD values only for the subjects in the screened group. FIG. 15E is a chart to compare between the dPTT values and the PD values of subjects in the screened group according to the first embodiment. FIG. 15E illustrates the average values and the standard deviations of the correlation coefficients between the SBP values and the dPTT and PD values from the iPPGs at the different sites for the subjects in the screened group (n=9). In FIG. 15E, the vertical axis expresses the correlation coefficient, while the charts of the average values and the standard deviations of the correlation coefficients between the dPTT and PD values and the SBP values for the different combinations are arranged in a row in the horizontal direction. It is understood from FIG. 15E that the PD values from the iPPG(hand)-iPPG(cheek) and the iPPG(hand)-iPPG(forehead) have a stronger correlation with the SBP values than the dPTT values do.

Figure 16:
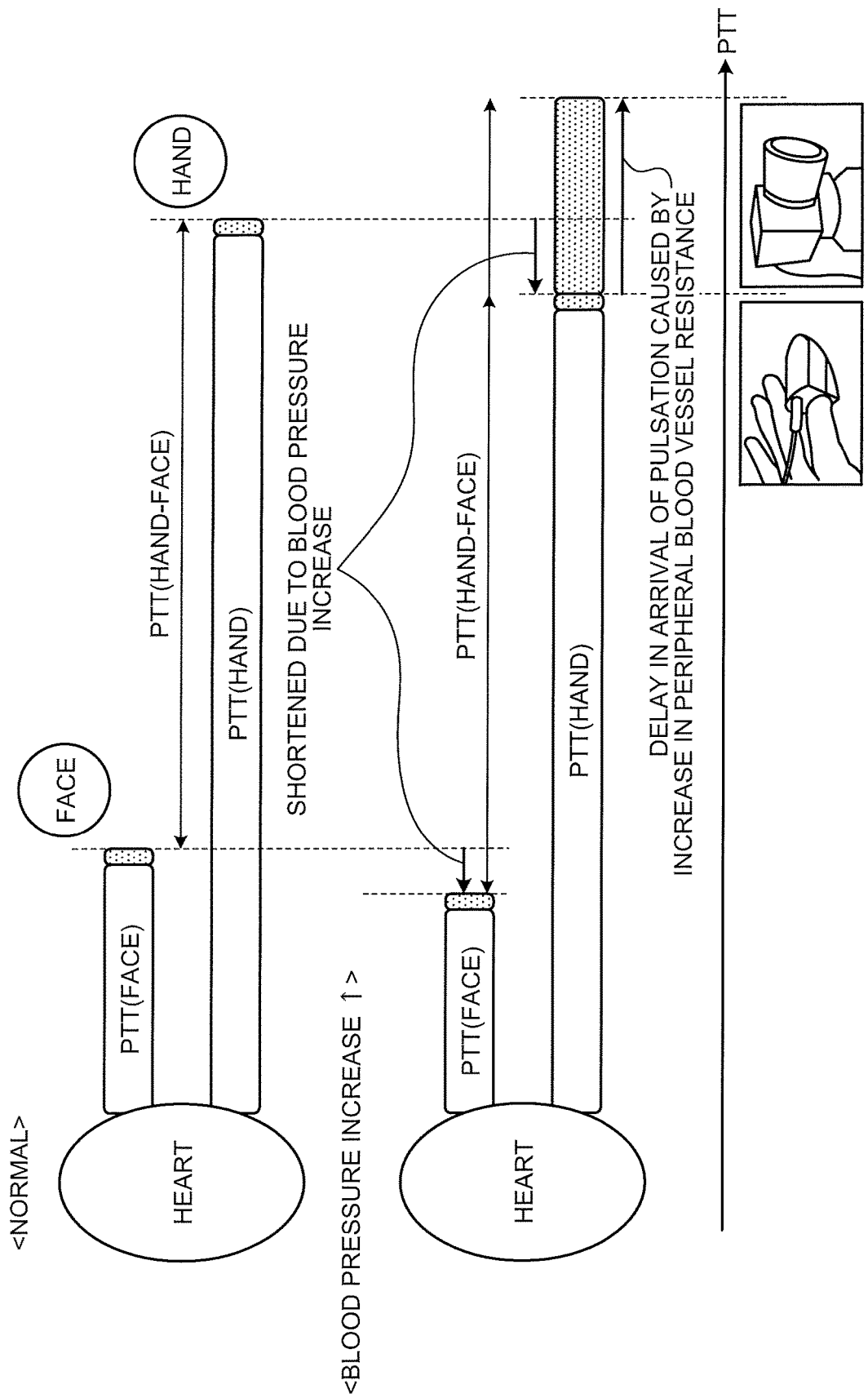
FIG. 16 is a schematic chart illustrating fluctuations of a pulse transit time according to the first embodiment.

As explained above, when the dPTT values and the PD values are calculated from the image-based photoplethysmograms of the two locations such as the face and the site other than the face (the hand), the result exhibited that the dPTT and PD values each have a positive correlation with the fluctuation of the blood pressure. This result is different from the finding that is hitherto known indicating that PTT values have a negative correlation with fluctuations of blood pressure. This point will be explained, with reference to FIG. 16. FIG. 16 is a schematic chart illustrating fluctuations of a pulse transit time according to the first embodiment. FIG. 16 illustrates the fluctuations of the pulse transit time observed when the blood pressure has increased from a level at normal times. For example, as illustrated in FIG. 16, the pulse transit time of the face "PTT(face)" is shorter than the pulse transit time of the hand "PTT(hand)". The PTT lengths correspond to the distances from the heart, which is the same for the normal times and when the blood pressure has increased.

When the blood pressure has increased from a level at normal times, the "PTT(face)" becomes shorter due to the increase of the blood pressure. In contrast, the "PTT(hand)" value may become shorter or longer, depending on the measuring method being used. In other words, as illustrated in FIG. 16, when the "PTT(hand)" value is calculated by using an irPPG measured with the use of a photoplethysmograph, if the blood pressure increases, the "PTT(hand)" value becomes shorter, similarly to the "PTT(face)" value. On the contrary, when the "PTT(hand)" value is calculated by using an iPPG extracted from the picture signal taken by the video camera, if the blood pressure increases, the "PTT (hand)" value becomes longer. In other words, as for the "PTT(hand-face)" indicating the difference in the pulse transit time between the two ROIs (the face and the hand), because the PTT(face) becomes shorter in the face region, while the PTT(hand) becomes longer in the hand region, a positive correlation is exhibited where the time difference increases as the blood pressure increases.

The reasons why the correlational relationship between the PTT values and blood vessels varies depending on the measuring method as explained above, even though both results are related to the hand region, are that the skin penetration depths are different between the light used for measuring the irPPG and the light used for measuring the iPPG due to the wavelengths thereof and that the arrival of the pulse wave is delayed in the hand region due to an increase in the peripheral blood vessel resistance. More specifically, the light used for measuring the irPPG and the light used for measuring the iPPG have mutually-different skin penetration depths due to the difference in the wavelengths thereof, and thus the blood flows being measured are different. Further, it is considered that the correlational relationship between the PTT values and the blood vessels varies depending on the measuring method because one of the blood flows that are measured is such a blood flow that is affected by the delay in the arrival of the pulse wave caused by the increase in the peripheral blood vessel resistance, whereas the other of the blood flows is such a blood flow that is not affected by the delay. The details will further be explained below.

Figure 17:
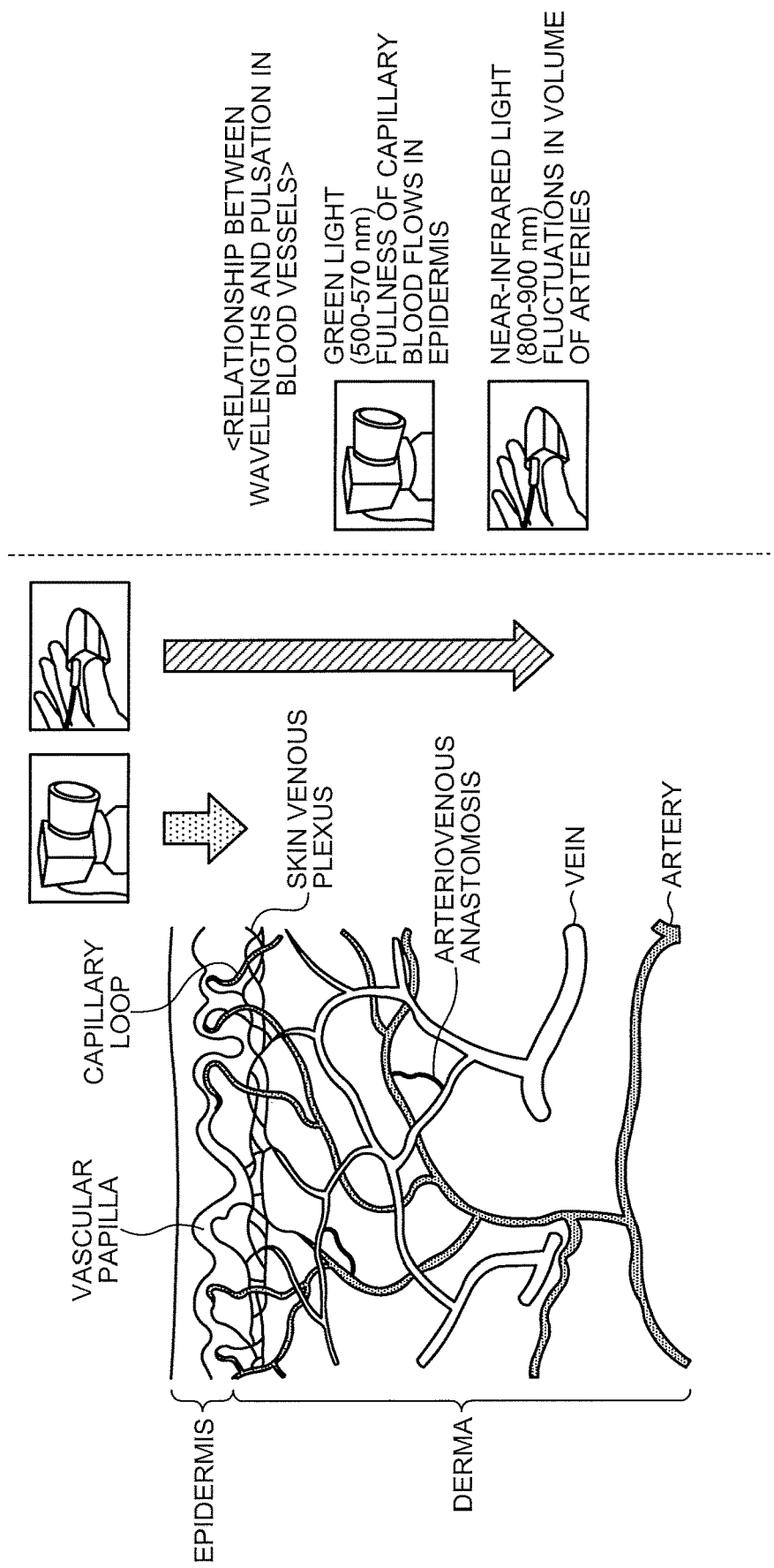
FIG. 17 is a drawing for explaining a difference in skin penetration depths between beams of light according to the first embodiment.

First, the difference in the skin penetration depths between the beams of light will be explained. FIG. 17 is a drawing for explaining the difference in the skin penetration depths between the beams of light according to the first embodiment. FIG. 17 presents a schematic drawing of the structure of human skin, a skin penetration depth of light, and a relationship between the wavelengths of the beams of light used for measuring the irPPG and the iPPG and pulsations in blood vessels. As illustrated in FIG. 17, the skin is structured with three layers that are called, from the surface side, the epidermis, the derma, and a subcutaneous tissue. The derma is structured with a papillary layer and a reticular layer. The thickness of each of the layers of the skin varies among different sites of the body. As for the thickness of the epidermis and the derma together excluding the subcutaneous tissue, the eyelid is thinnest (0.60 mm), while the back is thickest (2.30 mm). As for cutaneous blood flows in the derma, blood paths extend upward through arteries from the subcutaneous tissue to the derma, where a subcutaneous vascular plexus is formed first. Further, after the blood paths reach upward (toward the surface) through arteries, a subpapillary vascular plexus is formed. After that, the blood paths form loop-like blood vessels in the papillary dermis as capillary vessels, before returning to veins as a subpapillary vascular plexus.

When the skin structured as described above is optically analyzed, the elements of the skin are considered to have mutually-different characteristics. The epidermis contains melanin that powerfully absorbs ultraviolet (UV) rays of shorter than "240 nm". Light scattering is considered to be of no importance for the epidermis. The derma has papillary dermis capillary vessels therein, and absorbents such as bloodstream hemoglobin, beta carotene, bilirubin absorb light beams having wavelength components longer than "320 nm". Further, light scattering caused by collagen and blood corpuscles largely determines the depth by which the light beams having those wavelengths penetrate the derma. It is possible to define the penetration depth as a distance (the depth) at which the intensity of the light proceeding to the inside of the skin is reduced to 37% (=1/e) of the intensity on the surface of the skin. With the light source used in the first embodiment, the penetration depth of the green light (525 nm) is "300 µm", whereas the penetration depth of near-infrared light (800 nm) is "1200 µm". Accordingly, it is possible to conjecture that the iPPG captures the blood flows in the epidermal capillaries in a shallow part of the skin and that the irPPG captures the blood flows in the arteries. In other words, as illustrated in FIG. 17, according to the relationship between the wavelengths of the light and the pulsations in the blood vessels, the green light (500 nm to 570 nm) indicates fullness of capillary blood flows in the epidermis, whereas the near-infrared light (800 nm to 900 nm) indicate fluctuations of the volume of arteries.

Next, the delay in the arrival of the pulse wave in the hand region caused by an increase in the peripheral blood vessel resistance will be explained. One of the reasons why the PTT value from the iPPG including the hand region has a positive correlation with the fluctuation of blood pressure may be related to the difference in the blood vessel contractions between the hand and the face in response to a fluctuation of blood pressure. According to the present experiment method, sympathetic nerves were activated by the load of holding the breath. When the activities of sympathetic nerves are dominant, the blood pressure increases due to an increase in the contraction force of the heart, an increase in the peripheral blood vessel resistance, an increase in the viscosity of the blood, and the like. In that situation, because peripheral arterioles raise the peripheral blood vessel resistance under the control of sympathetic nerves, the blood flow volume entering the surface of the skin becomes relatively smaller. Accordingly, when the blood pressure increases, a delay is caused in the hand region in the arrival of the pulse wave at the surface layer of the skin from the arteries, and thus the PTT value measured at the surface layer of the skin is increased.

In contrast, in the face region, it is reported that expansions and contractions of the blood vessels are under the control of not only sympathetic nerves but also parasympathetic nerves. One familiar example is that one's cheeks become red in a cold environment. The reason is that, even when the peripheral blood vessels get narrower in the cold environment, the blood flows on the surface of the skin in the face region do not decrease excessively. Although the activities of the sympathetic nerves were dominant in the present experiment also, it is considered that no delay was caused in the arrival of the pulse wave at the surface layer of the skin from the arteries, because the blood vessels in the face did not contract because of being under the influence of the control of parasympathetic nerves.

In addition, it is also considered that the delay in the arrival of the pulse wave at the surface layer of the skin from the arteries is also dependent on the structure of the skin. Arteries cover from the depth of the subcutaneous tissue to the dermal layer, and delays caused in the arrival at the surface layer of the skin are dependent on the thickness of the epidermal layer. The thickness of the epidermal layer of the palm is approximately "600 μm", whereas the thickness of the epidermal layer of the cheek is approximately "100 μm". This can be one of the reasons why a large delay was caused in the arrival of the pulse wave at the surface layer of the skin from the arteries, in the hand region.

The results of the actual experiment and the principle of the first embodiment have thus been explained. As explained above, the "dPTT" values and the "PD" values calculated from the luminance information of the green light in the picture signals of the face and the hand have a positive correlation with the blood pressure. It is considered that any site and the face are in the same correlational relationship, as long as the site is where peripheral arterioles raise the peripheral blood vessel resistance under the control of sympathetic nerves, when the blood pressure increases. For example, it is considered that, with a combination of the face and a foot or a combination of the face and an arm, "dPTT" values and "PD" values each have a positive correlation with blood pressure values.

For this reason, the calculating unit 152 according to the first embodiment selects, as a site other than the face, such a site where peripheral arterioles raise the peripheral blood vessel resistance under the control of sympathetic nerves, when the blood pressure increases. The calculating unit 152 thus calculates the difference between the luminance information of the picture signal of the face and the luminance information of the picture signal of the site other than the face. In that situation, to calculate the difference on the basis of green light indicative of the fullness of the capillary blood flows in the epidermis, the calculating unit 152 calculates the difference between the luminance information of the picture signal based on the light reflected by the epidermis of the face of the subject and the luminance information of the picture signal based on the light reflected by the epidermis of the site other than the face. As a result, the measuring unit 153 is able to measure an increase in the difference as an increasing fluctuation of the blood pressure and to measure a decrease in the difference as a decreasing fluctuation of the blood pressure.

Figure 18A:
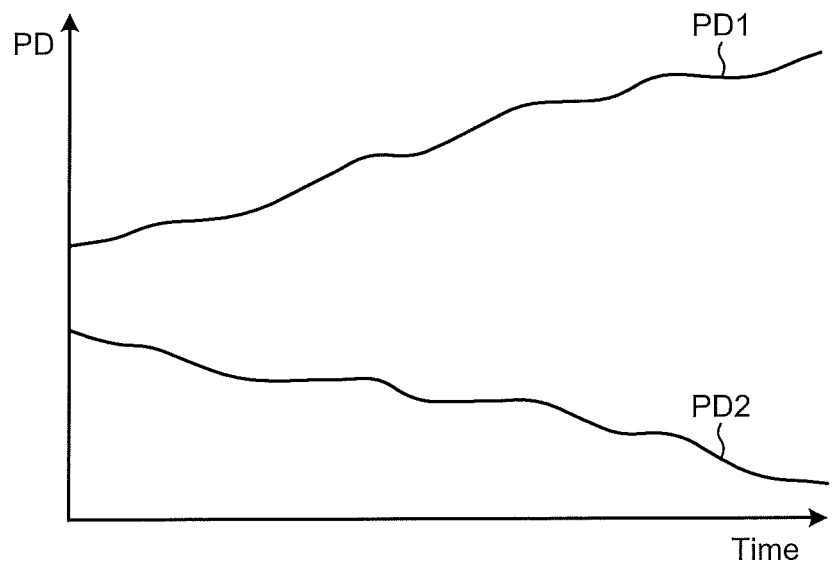
FIG. 18A is a drawing for explaining an example of a blood pressure fluctuation measuring process according to the first embodiment.
Figure 18B:
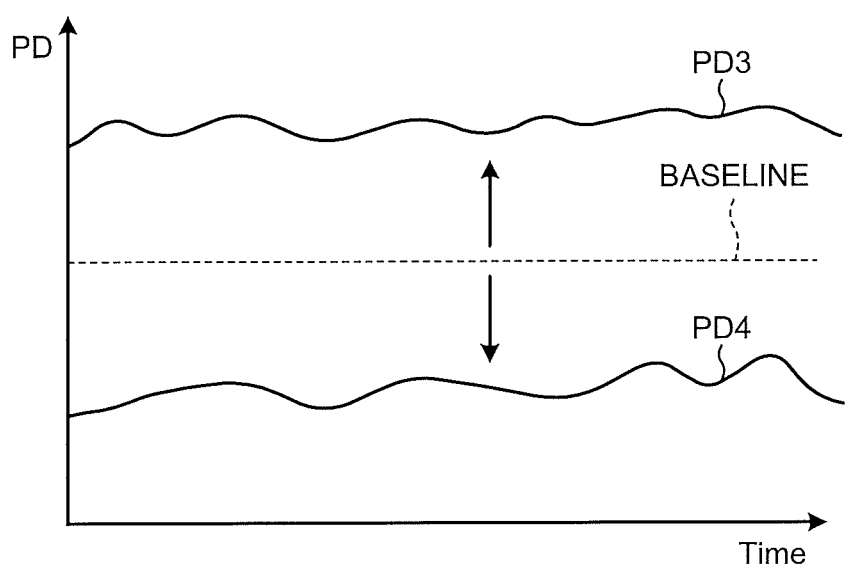
FIG. 18B is a drawing for explaining another example of the blood pressure fluctuation measuring process according to the first embodiment.
Figure 18C:
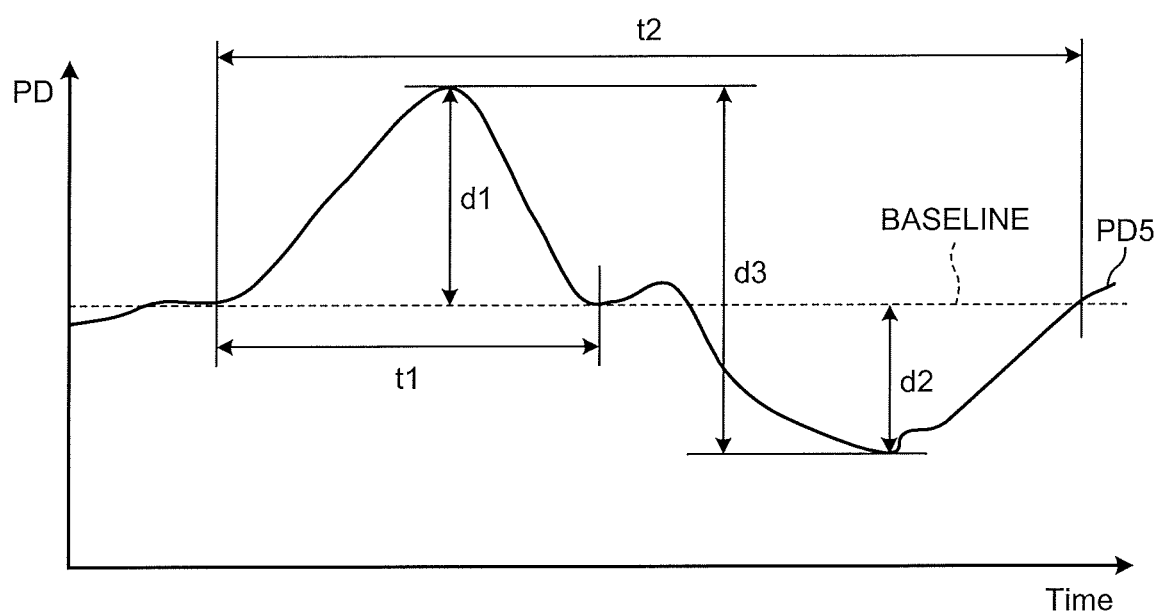
FIG. 18C is a drawing for explaining yet another example of the blood pressure fluctuation measuring process according to the first embodiment.

Next, an example of the blood pressure fluctuation measuring process performed by the measuring unit 153 will be explained. For example, on the basis of the difference (the dPTT or the PD) calculated by the calculating unit 152, the measuring unit 153 measures at least one selected from among the following: a fluctuation of the blood pressure of the subject from the reference value; the difference between the reference value and a maximum value observed when the blood pressure increases; the difference between a maximum value observed when the blood pressure increases and a minimum value observed when the blood pressure decreases; and the time period from when the blood pressure starts fluctuating and when the blood pressure returns to the reference value. FIGS. 18A to 18C are drawings for explaining examples of the blood pressure fluctuation measuring process according to the first embodiment. FIGS. 18A to 18C illustrate fluctuation charts of PD values in which the vertical axis expresses PD, whereas the horizontal axis expresses time.

For example, as indicated by PD1 in FIG. 18A, when the PD value calculated by the calculating unit 152 increases over time, the measuring unit 153 determines that the blood pressure of the subject is increasing in the time period. In contrast, as indicated by PD2 in FIG. 18A, for example, when the PD value calculated by the calculating unit 152 decreases over time, the measuring unit 153 determines that the blood pressure of the subject is decreasing in the time period. In this situation, the measuring unit 153 may determine that the blood pressure is increasing or decreasing when the amount of increase or the amount of decrease compared with the level at the start of the measuring process has reached a predetermined percentage.

In another example, as indicated by PD3 in FIG. 18B, when the PD value calculated by the calculating unit 152 is larger than a baseline, the measuring unit 153 determines that the blood pressure has increased and measures the amount of increase from the baseline. In this situation, the baseline illustrated in FIG. 18B is a reference value used for determining the state of the blood pressure and may be set arbitrarily. For example, a PD value corresponding to a standard blood pressure value that corresponds to the age and the gender of the subject may be set as the baseline. Alternatively, a reference value calculated from PD values of the subject from the past may be set as the baseline. In that situation, for example, the measuring unit 153 may calculate an average value of the PD values of the subject from the past and may set the calculated average value as the baseline.

In yet another example, as indicated by PD4 in FIG. 18B, when the PD value calculated by the calculating unit 152 is larger than a baseline, the measuring unit 153 determines that the blood pressure has decreased and measures the amount of decrease from the baseline. In this situation, as for the baseline illustrated in FIG. 18B, a single baseline may be set so as to be used for both when the blood pressure has increased and when the blood pressure has decreased. Alternatively, a baseline for the increase and a baseline for the decrease may be set separately from each other. In that situation, for example, a value calculated as an average PD value from the past "+5%" may be used as the baseline for the increase, whereas a value calculated as the average value "−5%" may be used as the baseline for the decrease. Conversely, a value calculated as the average value "+5%" may be used as the baseline for the decrease, whereas a value calculated as the average value "−5%" may be used as the baseline for the increase.

In yet another example, as illustrated in FIG. 18C, the measuring unit 153 is able to measure various types of values related to the fluctuation of the PD values. For example, with the chart PD5 in FIG. 18C, the measuring unit 153 measures a time period "t1" it takes for the PD value to return to the baseline after an increase. As another example, with the chart PD5 in FIG. 18C, the measuring unit 153 measures a time period "t2" it takes for the PD value to return to the baseline after increases and decreases. In this situation, by setting a judgment criterion for the time period it takes for the PD value to return to the baseline, it is also possible to judge whether or not the measured time periods represent a symptom that needs attention. For example, a predetermined threshold value may be set for the time period it takes for the PD value to return to the baseline after an increase. The measuring unit 153 compares the measured time period "t1" with the predetermined threshold value that was set. If the measured time period "t1" is longer than the predetermined threshold value, the measuring unit 153 determines that the time period represents a symptom that needs attention. On the contrary, if the measured time period "t1" is shorter than the predetermined threshold value, the measuring unit 153 determines that the time period does not represent a symptom that needs attention.

Further, for example, with the chart PD5 illustrated in FIG. 18C, the measuring unit 153 calculates the difference "d1" between an increase peak of the PD value and the baseline, the difference "d2" between a decrease bottom of the PD value and the baseline, and the difference "d3" between the increase peak and the decrease bottom of the PD value. In this situation, by setting judgment criteria also for these differences, it is also possible to judge whether or not the measured differences represent symptoms that need attention. For example, a predetermined threshold value can be set for the difference between an increase peak and the baseline. The measuring unit 153 compares the measured difference "d1" with the predetermined threshold value that was set. If the measured difference "d1" is larger than the predetermined threshold value, the measuring unit 153 determines that the difference represents a symptom that needs attention. On the contrary, if the measured difference "d1" is smaller than the predetermined threshold value, the measuring unit 153 determines that the difference does not represent a symptom that needs attention.

As explained above, the measuring unit 153 measures the fluctuation of the blood pressure by using the difference calculated by the calculating unit 152 and performs the judging process by using the measured results. After performing the blood pressure fluctuation measuring process and the judging process, the measuring unit 153 stores the measured results and the judgment results into the measured result storage unit 142. For example, the measuring unit 153 stores the measured results illustrated in FIG. 4A into the measured result storage unit 142. The examples explained above are merely examples, and possible embodiments are not limited to those examples. In other words, the items measured by the measuring unit 153 and the threshold values that are set may arbitrarily be set by the operator. Further, the measured data is not limited to "PD" values, and the measuring unit 153 may perform similar measuring and judging processes on "dPTT" values as well.

In this situation, the measuring unit 153 may perform the measuring and judging processes not only by using the "PD" and "dPTT" values, but also after converting the "PD" and "dPTT" values into blood pressure values. More specifically, the measuring unit 153 may convert the "PD" values or the "dPTT" values into blood pressure values by referring to the reference information stored in the reference information storage unit 143, so as to perform the measuring and judging process by using the blood pressure values resulting from the conversion. In one example, the measuring unit 153 converts the fluctuation chart of PD values illustrated in FIG. 18C into a fluctuation chart of absolute values of blood pressure, by referring to the blood pressure value conversion information for "PD" values contained in the reference information indicated in FIG. 4B, so as to calculate the differences "d1" to "d3". In this situation, one set each of blood pressure value conversion information may be stored for "PD" values and for "dPTT" values.

Alternatively, a plurality of sets of blood pressure value conversion information may be stored in correspondence with various environment factors. In that situation, for example, a set of blood pressure value conversion information may be stored for each of different measurement locations. In addition, one set of blood pressure value conversion information may be stored for each of different time spans.

In other words, because blood pressure values represent biological information that easily fluctuates in our normal life, one's blood pressure may vary depending on the time of the day or the location in some situations. Further, the correspondence relationship between "PD" values or "dPTT" values and blood pressure values may not necessarily be constant at all times. Accordingly, another arrangement is also acceptable in which a plurality of sets of blood pressure value conversion information are stored in correspondence with various environment factors, so that the measuring unit 153 reads a set of blood pressure value conversion information that corresponds to the environment at the current point in time and converts the "PD" values or the "dPTT" values into blood pressure values.

Further, the measuring unit 153 is capable of not only converting the "PD" values and the "dPTT" values into blood pressure values, but also performing a correcting process on the "PD" values and the "dPTT" values. For example, after correcting either the difference or the reference value calculated by the calculating unit 152 while using one or both of the temperature and the humidity of the location where the subject was imaged, the measuring unit 153 measures at least one selected from among the following: a fluctuation of the blood pressure of the subject from the reference value; the difference between the reference value and a maximum value observed when the blood pressure increases; the difference between a maximum value observed when the blood pressure increases and a minimum value observed when the blood pressure decreases; and the time period from when the blood pressure starts fluctuating and when the blood pressure returns to the reference value. In other words, the measuring unit 153 reads the correction information corresponding to the temperature and/or the humidity of the location where the subject is being imaged, from the reference information storage unit 143, and after correcting the "PD" or "dPTT" values or the baseline, the measuring unit 153 performs the measuring and judging processes described above. In one example, the measuring unit 153 obtains information about the temperature and the humidity of the location where the subject is being imaged, reads the correction information corresponding to the obtained temperature and humidity from the reference information illustrated in FIG. 4B, and performs the measuring and judging processes after performing a correcting process by using the read correction information.

As explained above, having performed the measuring process related to the fluctuation of the blood pressure, the measuring unit 153 stores the measured results into the measured result storage unit 142 and transmits the measured results to the output controlling unit 154. The output controlling unit 154 exercises control so that either the output unit 120a or the output apparatus 120b outputs the output information based on at least one selected from among the following: the luminance information of the picture signals of the face and a site other than the face; the difference calculated by the calculating unit 152; and the measured result obtained by the measuring unit 153. The output information output by the output unit 120a and the output apparatus 120b will be explained later in detail.

As explained above, the biological information measuring apparatus 100 measures the fluctuation of the blood pressure on the basis of the change in the luminance value (the change in the green signal) in the picture signals of the subject. In this situation, if the subject or the camera moves while the subject is being imaged, the skin regions of the subject in the picture may move (make a translation movement or a rotation movement). Further, while the subject is being imaged, the intensity of the ambient light with which the skin is irradiated may change. Such a change in the luminance value due to the movement of the skin regions and such a temporal change in the intensity of the ambient light have a possibility of causing a noise component that does not directly reflect an actual change in the volume of blood. To cope with this situation, the biological information measuring apparatus 100 of the present disclosure performs a process while the abovementioned circumstances are taken into consideration.

As for the noise caused by the translation movement and/or the rotation movement of the skin regions, the biological information measuring apparatus 100 makes a correction by performing a sequential tracking process on the skin color parts. For example, by sequentially tracking how each of the skin regions changes in the following frames, the skin region extracting unit 151 extracts the skin region from each of the frames. In one example, the skin region extracting unit 151 extracts the skin region from each of the frames by varying (updating) the positions of the feature points in the picture and the mutual positional relationship between the plurality of feature points. The sequential tracking process is not limited to the example explained herein. It is acceptable to use any other method to perform the sequential tracking process.

As for the temporal change in the intensity of the ambient light, the biological information measuring apparatus 100 adjusts the intensity of the light in the vicinity of the skin of the subject, by controlling the illuminating unit 170 in accordance with the level of illuminance measured by the illuminance sensor 160. More specifically, the feedback controlling unit 155 varies the intensity of the light radiated from the illuminating unit 170, on the basis of the level of illuminance received from the illuminance sensor 160. In other words, the feedback controlling unit 155 varies the intensity of the light radiated from the illuminating unit 170 in such a manner that the level of illuminance measured by the illuminance sensor 160 is kept at a certain value. With this arrangement, for example, even in an environment where there is a high possibility that the intensity of the ambient light may temporally change (e.g., inside an automobile), it is possible to measure the blood pressure with a high level of precision.

The feedback controlling unit 155 is also capable of exercising feedback control that is different from that in the process described above. For example, the feedback controlling unit 155 is capable of correcting temporal changes in the intensity of the ambient light, by exercising feedback control based on changes in the luminance values of the picture signals, without using measured result obtained by the illuminance sensor 160. In one example, the feedback controlling unit 155 varies the intensity of the light radiated by the illuminating unit 170 in such a manner that, with respect to an average luminance of the skin region, frequency components in direct-current components and alternating-current components that are lower than the heartbeat frequency band are kept at a certain value.

Although FIG. 3 illustrates the example in which the biological information measuring apparatus 100 includes the illuminance sensor 160 and the illuminating unit 170, possible embodiments are not limited to this example. The illuminance sensor 160 and the illuminating unit 170 provided on the outside of the biological information measuring apparatus 100 may be connected to the biological information measuring apparatus 100. Further, another arrangement is also acceptable in which the illuminance sensor 160 and the illuminating unit 170 are included in the picture obtaining apparatus 110b, so that the feedback controlling unit 155 included in the biological information measuring apparatus 100 controls the illuminating unit 170 via the network 300.

In the description above, the example is explained in which the correction is made by using the illuminating unit 170 in response to the temporal changes in the intensity of the ambient light. However, the biological information measuring apparatus 100 is also capable of making a correction in response to the temporal changes in the intensity of the ambient light, without using the illuminance sensor 160 or the illuminating unit 170. For example, the calculating unit 152 calculates the difference in the average luminance value in the skin region between frames, with respect to the frames contained in a time period of a predetermined length within the picture signals of the subject. After that, the calculating unit 152 compares the absolute value of each of the calculated differences between the frames with a predetermined threshold value and makes a correction by changing any difference that is larger than the predetermined threshold value to "0". In this manner, with respect to each of the differences calculated between the frames contained in the time period of the predetermined length, the calculating unit 152 calculates a time series of accumulated values of the differences between the frames obtained by changing any difference of which the absolute value is larger than the predetermined threshold value to "0", as a series of average luminance values (a green signal) of the skin region. As a result, drastic changes in bias components that were contained in the time series of average luminance values prior to the correction are cancelled. It is therefore possible to suppress transient responses of low frequency components, which are difficult to eliminate even by using a band-pass filter. This example represents a mode of "ε-filter", which is a non-linear filter.

Figure 19:
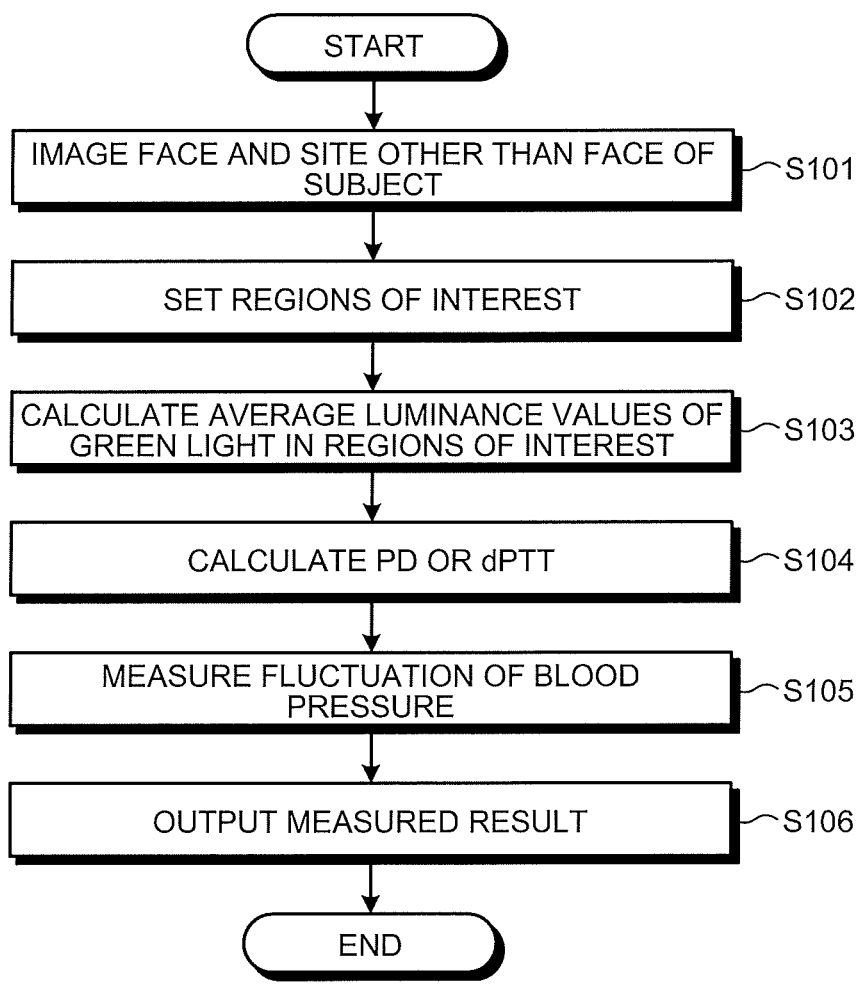
FIG. 19 is a flowchart of a processing procedure performed by a biological information measuring apparatus according to the first embodiment.

Next, a flow in a process performed by the biological information measuring apparatus 100 will be explained. FIG. 19 is a flowchart of a processing procedure performed by the biological information measuring apparatus 100 according to the first embodiment. As illustrated in FIG. 19, in the biological information measuring apparatus 100, either the picture obtaining unit 110a or the picture obtaining apparatus 110b images the face and a site other than the face (step S101).

After that, the skin region extracting unit 151 sets regions of interest (ROI) each in the face and in the site other than the face, by automatically extracting regions corresponding to the skin color or by having the operator manually set the ROIs (step S102). Subsequently, the calculating unit 152 calculates an average luminance value of the green light in each of the set regions of interest (step S103) and calculates either a "PD" or a "dPTT" from the calculated average luminance values (step S104).

After that, the measuring unit 153 measures the fluctuation of the blood pressure of the subject, by measuring a fluctuation of either the "PD" or the "dPTT" (step S105). Subsequently, either the output unit 120a or the output apparatus 120b outputs a measured result (step S106).

As explained above, according to the first embodiment, the calculating unit 152 is configured to calculate the difference between the luminance information of the picture signal of the face of the subject and the luminance information of the picture signal of the site other than the face taken at the same time as the picture signal of the face of the subject is taken. The measuring unit 153 is configured to measure the fluctuation of the blood pressure of the subject corresponding to the increase or the decrease in the difference. Consequently, the biological information measuring apparatus 100 according to the first embodiment is capable of measuring the fluctuation of the blood pressure of a human body in a simple and contactless manner.

Further, according to the first embodiment, the calculating unit 152 is configured to calculate the difference between the luminance information of the picture signal based on the light reflected by the epidermis of the face of the subject and the luminance information of the picture signal based on the light reflected by the epidermis of the site other than the face. In this situation, the site other than the face is a site in which, when the blood pressure increases, peripheral arterioles raise the peripheral blood vessel resistance under the control of sympathetic nerves. Further, the measuring unit 153 measures an increase in the difference as an increasing fluctuation of the blood pressure and measures a decrease in the difference as a decreasing fluctuation of the blood pressure. Further, the calculating unit 152 is configured to extract the luminance values of the green light contained in the picture signals of the face and the site other than the face of the subject and to calculate either the time difference between the predetermined feature points in the extracted luminance values of the green light in the picture signals or the phase difference between the luminance values of the green light in the picture signals. The measuring unit 153 is configured to measure the fluctuation of the blood pressure of the subject corresponding to the increase or the decrease in either the time difference or the phase difference. Consequently, the biological information measuring apparatus 100 according to the first embodiment is capable of measuring the fluctuation of the blood pressure by using the index value that has a positive correlation with, and is strongly related with, the fluctuation of the blood pressure.

Further, according to the first embodiment, on the basis of the difference, the measuring unit 153 is configured to measure at least one selected from among the following: a fluctuation of the blood pressure of the subject from the reference value; the difference between the reference value and a maximum value observed when the blood pressure increases; the difference between a maximum value observed when the blood pressure increases and a minimum value observed when the blood pressure decreases; and the time period from when the blood pressure starts fluctuating and when the blood pressure returns to the reference value. Consequently, the biological information measuring apparatus 100 according to the first embodiment is capable of providing the subject with the various types of information about the blood pressure.

Further, according to the first embodiment, by correcting the difference or the reference value calculated by the calculating unit 152 while using at least one selected from between the temperature and the humidity of the location where the subject was imaged, the measuring unit 153 is configured to measure at least one selected from among the following: a fluctuation of the blood pressure of the subject from the reference value; the difference between the reference value and a maximum value observed when the blood pressure increases; the difference between a maximum value observed when the blood pressure increases and a minimum value observed when the blood pressure decreases; and the time period from when the blood pressure starts fluctuating and when the blood pressure returns to the reference value. Consequently, the biological information measuring apparatus 100 according to the first embodiment is capable of measuring the fluctuation of the blood pressure corresponding to the environment.

Further, according to the first embodiment, the measuring unit 153 is configured to calculate the blood pressure value corresponding to the difference calculated by the calculating unit 152, on the basis of the correspondence information between the differences and the blood pressure values. Consequently, the biological information measuring apparatus 100 according to the first embodiment is capable of providing the information about the absolute value of the blood pressure in a contactless manner.

(Application Examples of the Biological Information Measuring Apparatus)

Figure 20:
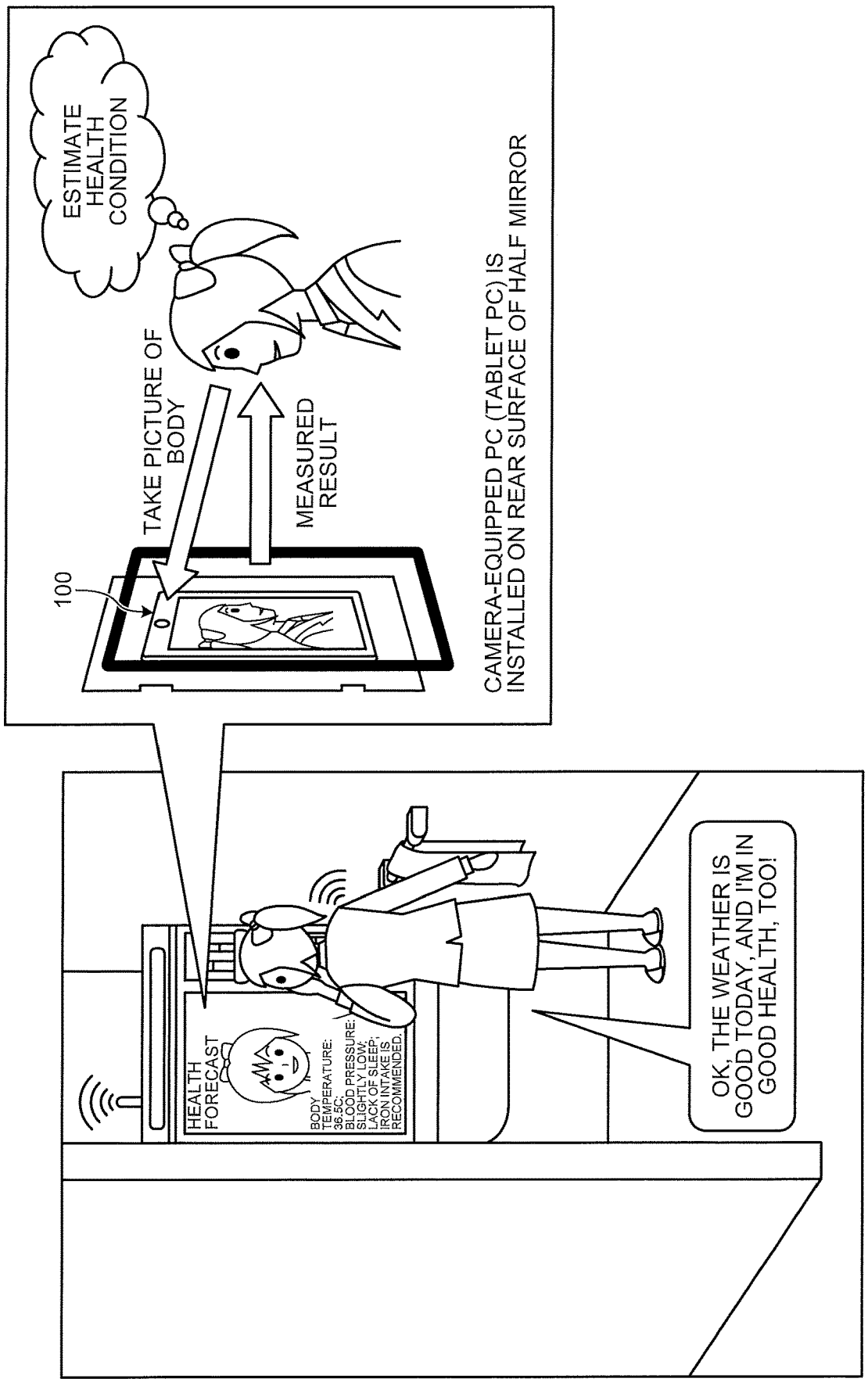
FIG. 20 is a drawing for explaining an example of an application of the biological information measuring apparatus according to the first embodiment.

Next, application examples of the biological information measuring apparatus 100 described above will be explained. As described above, the biological information measuring apparatus 100 according to the first embodiment is capable of measuring the fluctuation of the blood pressure of a human body in a simple and contactless manner. Accordingly, for example, it is possible to realize the daily-basis medical checkup system illustrated in FIG. 1. Next, an example for realizing the daily-basis medical checkup system illustrated in FIG. 1 will be explained, with reference to FIG. 20. FIG. 20 is a drawing for explaining an example of an application of the biological information measuring apparatus 100 according to the first embodiment.

For example, it is possible to realize the daily-basis medical checkup system illustrated in FIG. 1 capable of providing a health forecast when the subject only stands in front of a mirror in a washroom, by installing, for example, a camera-equipped Personal Computer (PC) (a tablet PC) serving as the biological information measuring apparatus 100 on the rear surface of a half mirror, as illustrated in FIG. 20. In other words, the biological information measuring apparatus 100 images the subject through the half mirror, measures a fluctuation of the blood pressure on the basis of picture signals that were taken, and outputs a measured result. For example, the picture obtaining unit 110a included in the biological information measuring apparatus 100 installed on the rear surface of the half mirror images the face and a site other than the face of the subject. After that, the skin region extracting unit 151 extracts the face region and the region of the site other than the face of the subject in the picture. The calculating unit 152 extracts an image-based photoplethysmogram of each of the regions and calculates either a "PD" or a "dPTT". The measuring unit 153 measures a fluctuation of the blood pressure of the subject on the basis of a fluctuation of either the "PD" or the "dPTT" calculated by the calculating unit 152, so that the output unit 120a outputs a measured result for the subject.

In this situation, to measure the fluctuation of the blood pressure from the picture signals, pictures of a certain length (moving images) are required. Thus, for example, information indicating that a fluctuation of the blood pressure is to be measured may be output. For example, under the control of the output controlling unit 154, the output apparatus 120b may output either audio information or display information indicating that "blood pressure is being measured". Further, because it is necessary to obtain the pictures of the face and the site other than the face of the subject, either audio information or display information may be output to suggest that the subject assume a posture that makes it possible to image the face and the site other than the face (e.g., a hand). In one example, the picture obtaining unit 110a images the washroom all the time so that, when the subject enters the washroom, either the audio information or the display information is output to prompt the subject to assume a posture that makes it possible to image the face and the site other than the face (e.g., a hand). After that, when the skin region extracting unit 151 has extracted the face and the site other than the face, the output apparatus 120b outputs either the audio information or the display information indicating that "blood pressure is being measured". With these arrangements, by only taking the action corresponding to the information output automatically, the subject is able to have the blood pressure information measured. In this situation, the blood pressure information measuring process may automatically be started as explained above, or alternatively, may be started by an operation performed by the subject.

Further, the face and the site other than the face of the subject may be imaged separately from each other. For example, mutually-different cameras may be used to take a picture of the face and a picture of the site other than the face separately from each other. In that situation, the pictures taken by the mutually-different cameras are kept in correspondence with each other by time information. In another example, a reflective photo sensor serving as the picture obtaining apparatus 110b may be provided in a position (e.g., a position where the subject places his/her hand or a position gripped by the subject) different from the rear surface of the half mirror, so that a signal of the green light reflected by the epidermis of the hand is obtained by the reflective photo sensor. In one example, a reflective photo sensor that uses a green-light LED as a light source is provided in a position where the subject places his/her hand, so as to obtain a photoplethysmogram of the green light (a green light PPG) by measuring the intensity of the green light reflected by the hand. After that, the calculating unit 152 calculates either a "dPTT" or a "PD" by using an iPPG extracted from the picture signal of the face and the green light PPG. In that situation, the green light PPG obtained by the reflective photo sensor and the picture obtained by the picture obtaining unit 110a are kept in correspondence with each other by time information. Accordingly, it is possible to obtain the pulse wave based on the light reflected by the epidermis of the site other than the face at the same time as the picture of the face is taken. It is also acceptable to cause the output unit 120a to output either audio information or display information suggesting that the subject brings a part of his/her body into contact with the reflective photo sensor. Alternatively, the picture signal of the site other than the face may be obtained by a wearable terminal. Further, the reflective photo sensor may obtain a green light PPG of the face.

Figure 21:
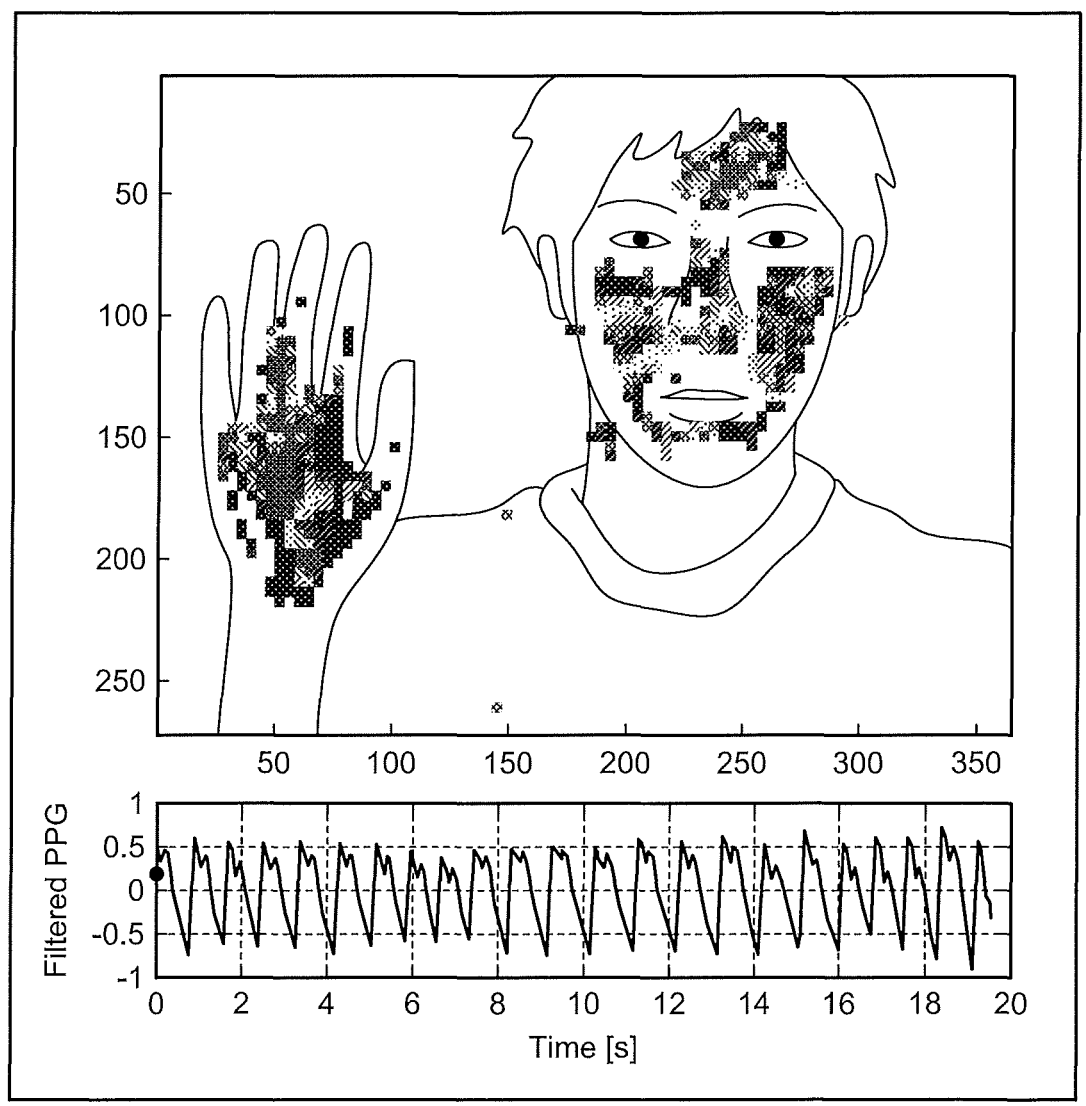
FIG. 21 is a drawing of an example of output information according to the first embodiment.

When the pictures of the subject have been obtained and the blood pressure information has been measured in this manner, the output unit 120a outputs the output information for the subject. For example, by using either display information or audio information, the output unit 120a outputs information about blood pressure such as whether the blood pressure has increased or not and, if the blood pressure has increased, how much from a baseline the blood pressure has increased. Further, the output unit 120a is able to output not only the output information related to the blood pressure, but also information about image-based photoplethysmograms. More specifically, the output unit 120a generates a hue moving image expressing the luminance information of the picture signals by using changes of hues and displays the generated hue moving image so as to be superimposed on a moving image of the subject. FIG. 21 is a drawing of an example of the output information according to the first embodiment. As illustrated in FIG. 21, the output unit 120a displays the hue moving image expressing the values related to the image-based photoplethysmograms calculated by the calculating unit 152 by using various hues, so as to be superimposed on a picture of the subject.

In that situation, the output controlling unit 154 generates the hue moving image and causes the output unit 120a to display the generated hue moving image so as to be superimposed on the moving image of the subject. For example, with respect to each of the pixels included in the skin regions (the ROIs) extracted by the skin region extracting unit 151, the calculating unit 152 extracts an image-based photoplethysmogram for the pixel. In other words, with respect to each of the frames structuring the picture, instead of extracting the luminance values of the green light of the pixels in the ROIs and averaging the luminance values for each ROI, the calculating unit 152 calculates an image-based photoplethysmogram for each of the pixels. By assigning a hue to each of the amplitude values of the pulse waves, the output controlling unit 154 generates a hue moving image in which each of the pixels in each of the frames is colored by using the hue corresponding to the amplitude value. For example, the output controlling unit 154 assigns hues in the range of "blue to red" for the amplitude in the range of "−0.1 to 0.1" of the image-based photoplethysmogram illustrated in FIG. 21. Further, the output controlling unit 154 generates the hue moving image in which the pixels in the ROIs in each of the frames of the picture of the subject are colored by using the hues in the range of "blue to red" in accordance with the amplitude values.

After that, the output controlling unit 154 causes either the output unit 120a or the output apparatus 120b to output the output information in which the hue moving image is superimposed on the moving image from which the image-based photoplethysmogram was extracted. As a result, it is possible to check the color of the face (the blood flow state) of the subject at a glance. For example, when evaluating the color of the face of a person, it would be difficult to make an objective evaluation by simply looking at the face; however, displaying the hue moving image so as to be superimposed on the picture makes it possible to easily evaluate the blood flow state by using the color information. For example, when it is possible to extract an image-based photoplethysmogram from the entire face and to have a hue moving image superimposed on almost the entire skin region of the face front part, it is understood at a glance that the blood circulation is good and that the person seems to be in good condition of health. On the contrary, when a hue moving image is not superimposed on much of the skin region of the face front part, it is understood at a glance that the blood circulation is not good and that the person does not seem to be in very good condition of health. Further, when the speed at which the colors change is extremely slow, it is understood that the blood circulation is not good. As explained above, by displaying not only the blood pressure information, but also the picture in which the image-based photoplethysmogram is colored, it is possible to check the condition of health of the user himself/herself or of someone else. Further, as illustrated in FIG. 21, the output controlling unit 154 is also capable of further displaying the image-based photoplethysmogram, in addition to the picture on which the hue moving image is superimposed.

Figure 22:
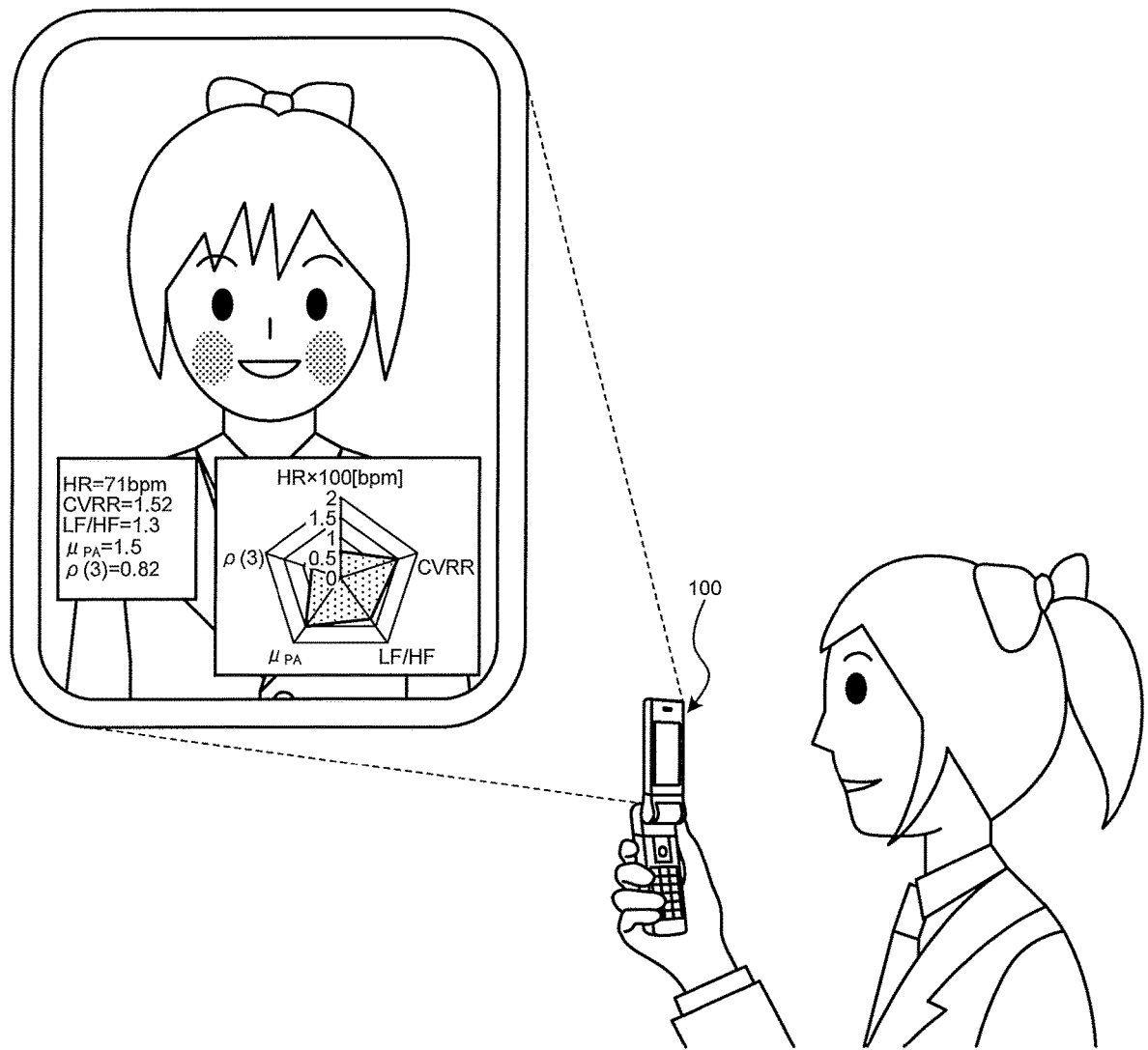
FIG. 22 is a drawing of another example of the output information according to the first embodiment.

Further, in addition to the blood pressure information, the output unit 120a is capable of further outputting an index value related to the heart rate and autonomic nerves. More specifically, on the basis of the luminance information of the picture signal of the face and the luminance information of the picture signal of the site other than the face, the calculating unit 152 calculates the index value related to the heart rate and the autonomic nerves of the subject. The output unit 120a further displays the index value related to the heart rate and the autonomic nerves calculated by the calculating unit 152. FIG. 22 is a drawing of another example of the output information according to the first embodiment. FIG. 22 illustrates an example in which the biological information measuring apparatus 100 is a mobile phone. For example, as illustrated in FIG. 22, the output unit 120a displays a heart rate "HR=71 bpm" and index values related to the autonomic nerves such as "CVRR=1.52", "LF/HF=1.3", "$\mu_{PA}$=1.5", and "$\rho(3)$=0.82", as well as charts based thereon.

In this situation, by considering the instantaneous phase difference as a PTT, the calculating unit 152 calculates a maximum value $\rho_{max}$ of a cross-correlation coefficient $\rho(\tau)$ between the PTT in a Mayer wave-band and the heart rate or an estimated value $\rho(3)$ corresponding to when the lag $\tau$ of $\rho(\tau)$ is three seconds. Further, the calculating unit 152 calculates $\rho_{max}$ by considering a single body-surface luminance time-series signal as a pulse wave signal. Further, the calculating unit 152 calculates a logarithm of a power ratio between two frequency regions with respect to the pulse wave amplitude expressed as $\mu_{PA}=\ln(MF_{PA}/HF_{PA})$, by considering a single body-surface luminance time-series signal as a pulse wave signal.

In the example above, the situations are explained in which the fluctuation of the blood pressure is measured in a current natural state of the subject. However, the biological information measuring apparatus 100 is also able to forcibly make blood pressure fluctuate and to provide measuring guidance for measuring a recovery from the forced fluctuation. More specifically, the output unit 120a further outputs instruction information instructing to take an action that makes the blood pressure of the subject fluctuate. FIG. 23 is a drawing of an example of the measuring guidance provided by the biological information measuring apparatus 100 according to the first embodiment. FIG. 23 illustrates an example in which the biological information measuring apparatus 100 is installed on the rear surface of a half mirror in a washroom. As apparent from the experiment described above, blood pressure rapidly increases when one's breath is held. For this reason, as illustrated in the left section of FIG. 23, when a measuring process is started, the output unit 120a outputs audio information saying "Start holding your breath" for the subject. In this situation, as illustrated in FIG. 23, the output unit 120a also displays similar display information reading "Measuring process in progress . . . . Start holding your breath.".

After that, the biological information measuring apparatus 100 calculates "PD6" of the subject holding her/breath, whereas the measuring unit 153 monitors fluctuations of "PD6". In this situation, as illustrated in the right section of FIG. 23, when "PD6" has increased to a predetermined level, the output unit 120a outputs audio information saying "Resume breathing" for the subject. In this situation, as illustrated in FIG. 23, the output unit 120a displays similar display information reading "Measuring process in progress . . . Resume breathing.". The biological information measuring apparatus 100 continuously monitors fluctuations of "PD6" of the subject who has resumed breathing and measures the time period it takes for the blood pressure to return to a normal level.

The guidance provided by the biological information measuring apparatus 100 is not limited to the example described above. For instance, the biological information measuring apparatus 100 is able to provide guidance about timing with which the subject should end taking a deep breath, by using either audio information or display information. For example, a patient having a disorder in autonomic nerves may take a deep breath in order to stabilize the blood pressure. In this situation, the patient would not be able to find out when the blood pressure is stabilized unless the blood pressure was measured. To cope with this situation, the biological information measuring apparatus 100 monitors fluctuations of the blood pressure of the subject taking a deep breath and outputs guidance to suggest that taking a deep breath should be ended when the blood pressure has been stabilized. For example, when the measuring unit 153 has determined that either a "PD" value or a "dPTT" value of the subject has reached a reference value, the output unit 120a outputs either audio information or display information such as "Stop taking a deep breath".

Further, the biological information measuring apparatus 100 is also able to monitor the blood pressure of the subject and, when the blood pressure fluctuates significantly, to output information that stabilizes the blood pressure. More specifically, the measuring unit 153 monitors either a "PD" value or a "dPTT" value of the subject, and when the "PD" value or the "dPTT" value has exceeded a predetermined threshold value, the output unit 120a outputs information such as music or the like to stabilize the blood pressure. After that, the measuring unit 153 may continuously monitor the "PD" value or the "dPTT" value of the subject, so that when the "PD" value or the "dPTT" value has become smaller than the predetermined threshold value, the output unit 120a finishes outputting the information such as music.

Figure 24:
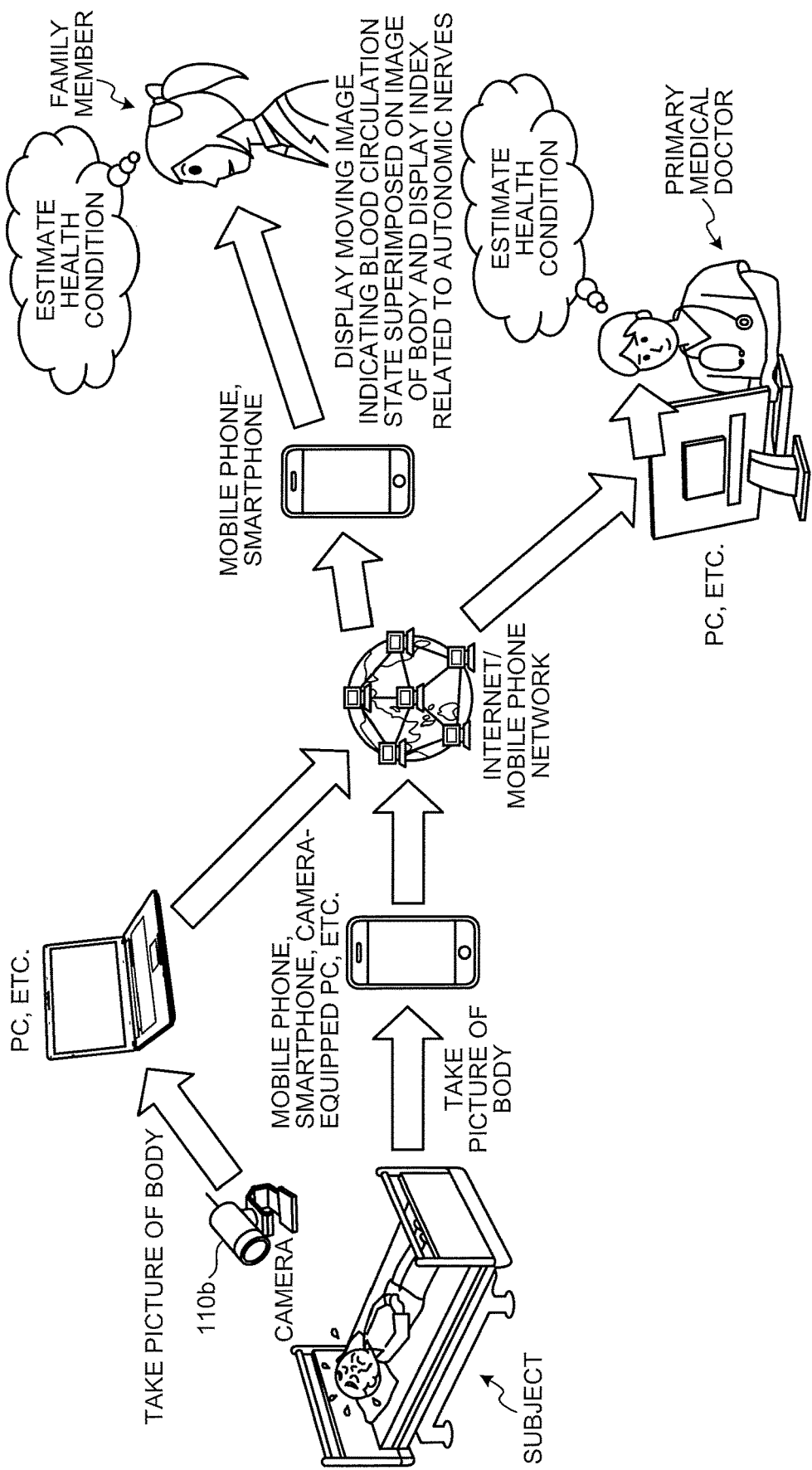
FIG. 24 is a drawing for explaining examples of applications of the biological information measuring apparatus according to the first embodiment.

In the example described above, the situation is explained in which the subject checks his/her own blood pressure information. Next, another example will be explained in which the subject's family member or primary medical doctor who is in a location distant from the subject checks the state of the blood pressure of the subject. FIG. 24 is a drawing for explaining examples of applications of the biological information measuring apparatus according to the first embodiment. For example, as illustrated in FIG. 24, a camera serving as the picture obtaining apparatus 110b is installed in the residence in which the subject lives, so that the installed camera takes pictures of the face and a site other than the face of the subject. Further, the pictures of the face and the site other than the face taken by the camera are sent to a PC serving as the biological information measuring apparatus 100. The PC receives the pictures of the face and the site other than the face, extracts image-based photoplethysmograms, performs the process of measuring the blood pressure as described above, generates the hue moving image, and calculates the index related to the autonomic nerves.

After that, the PC transmits the measured result, the hue moving image, and the index related to the autonomic nerves to the subject's family member or primary medical doctor via the Internet. The subject's family member or primary medical doctor views the measured result, the hue moving image, and the index related to the autonomic nerves sent from the PC and estimates the subject's health condition. In the explanation above, the example is explained in which the blood pressure measuring process that uses the pictures taken by the camera is performed by the PC that receives the pictures. However, possible embodiments are not limited to this example. Another arrangement is acceptable in which the pictures of the subject are sent to a mobile phone or a smartphone of the family member or a PC used by the primary medical doctor, so that the blood pressure measuring process that uses the pictures is performed by the receiving device. The pictures of the subject may be obtained not only by a camera serving as the picture obtaining apparatus 110b, but also by a camera built in a mobile phone or a smartphone of the subject. In that situation, the obtained picture may be sent to the subject's family member or primary medical doctor by the mobile phone or the smartphone that has obtained the picture, and the picture of the subject may be sent to a mobile phone or a smartphone of the family member or to a PC used by the primary medical doctor. With these arrangements, for example, it is possible to check how one's family member is doing in a distant location or how a patient is doing on a daily basis.

Figure 25:
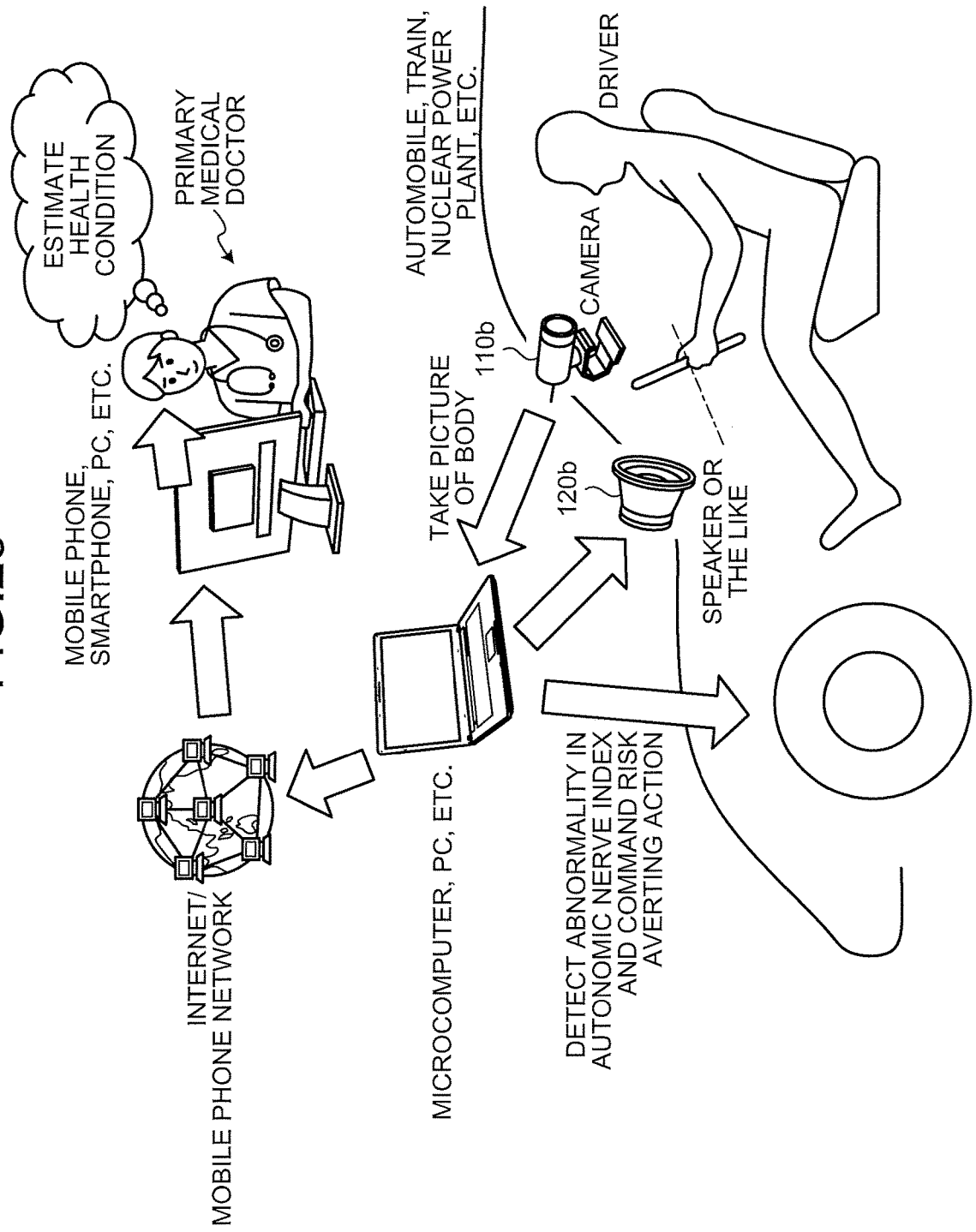
FIG. 25 is a drawing for explaining another example of applications of the biological information measuring apparatus according to the first embodiment.

Further, the biological information measuring apparatus 100 may also be used for monitoring the blood pressure of a subject who is operating machinery. More specifically, the calculating unit 152 calculates the difference by using picture signals obtained by imaging the subject who is operating the machinery. The measuring unit 153 measures a fluctuation of the blood pressure of the subject who is operating the machinery. Either the output unit 120a or the output apparatus 120b outputs the output information related to the subject operating the machinery for the subject operating the machinery. FIG. 25 is a drawing for explaining another example of applications of the biological information measuring apparatus according to the first embodiment. FIG. 25 illustrates an example in which fluctuations of the blood pressure are monitored with respect to a subject who is a driven car driving an automobile.

For example, when an operator who is engaged in the operation of an automobile, a train, a nuclear power plant, or the like is in bad condition of health due to some illness, a huge accident may be caused. To cope with this situation, by monitoring the state of blood pressure of the operator with the use of the biological information measuring apparatus 100 according to the first embodiment, it is possible to prevent accidents beforehand. For example, as illustrated in FIG. 25, a camera serving as the picture obtaining apparatus 110b images the face and a site other than the face of the driver of an automobile and sends the pictures to a microcomputer or a PC serving as the biological information measuring apparatus 100. The microcomputer or the PC extracts image-based photoplethysmograms from the picture signals of the face and the site other than the face received from the camera and performs the blood pressure measuring process, the hue moving image generating process, and the calculation of the index related to the autonomic nerves described above.

In this situation, when having detected an abnormality in the measured result of the blood pressure or the index related to the autonomic nerves of the driver, the microcomputer or the PC outputs an alert to the driver via a speaker or the like serving as the output apparatus 120b. For example, audio information may be output from the speaker to issue an alert saying "Your health condition changed rapidly. Please quit the driving operation immediately". Alternatively, the microcomputer or the PC may command a risk-averting action such as automatically braking the automobile, by transmitting a signal to a controlling device of the automobile. Further, the microcomputer or the PC transmits information about the measured result of the blood pressure or the index related to the autonomic nerves that exhibited the abnormality, to the driver's primary medical doctor via a network. The microcomputer and the PC illustrated in FIG. 25 may be installed in the automobile or may be provided on the network.

Figure 26:
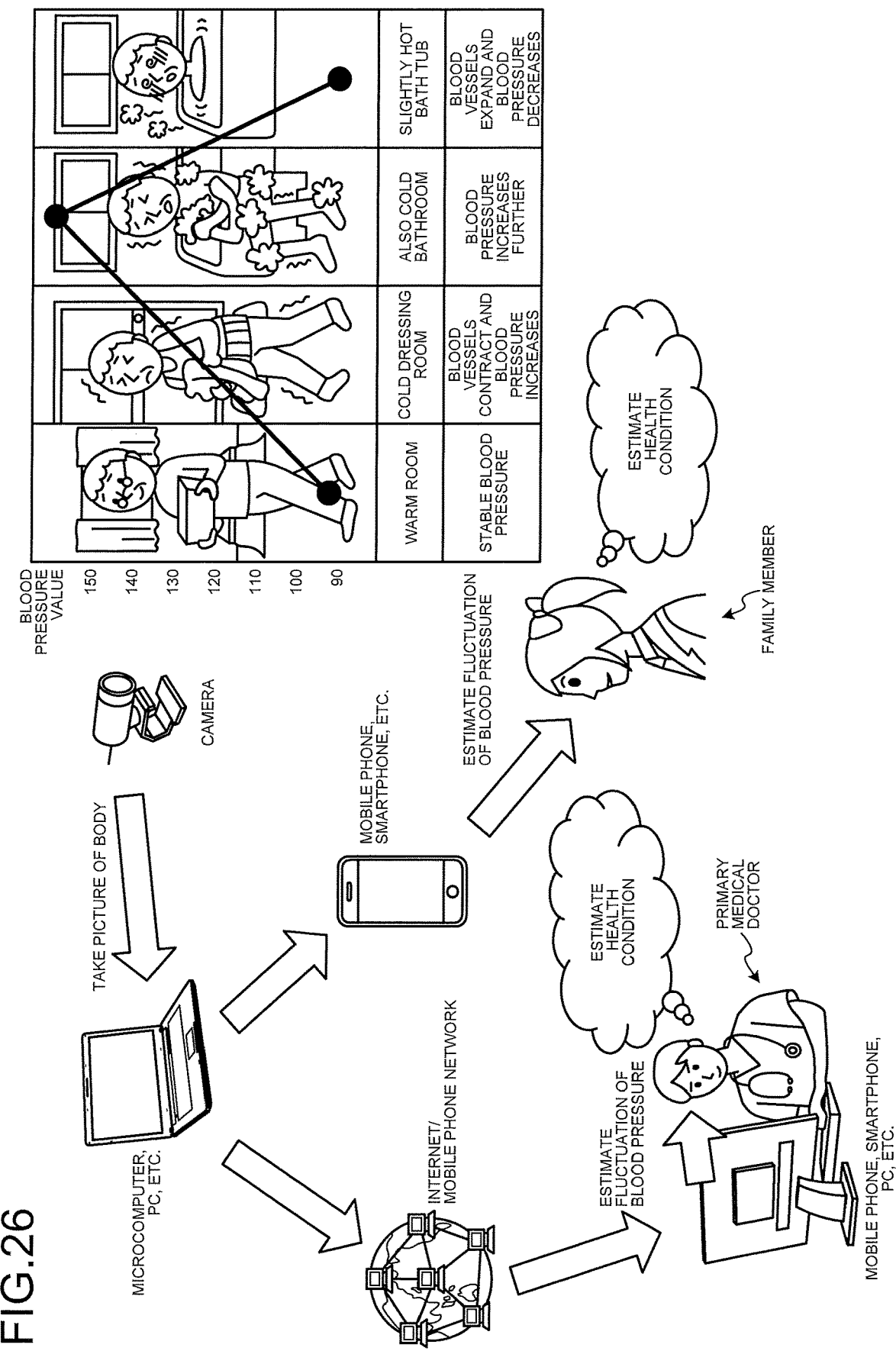
FIG. 26 is a drawing for explaining yet another example of applications of the biological information measuring apparatus according to the first embodiment.

Next, an example in which fluctuations of blood pressure caused by taking a bath are monitored will be explained. As explained above, the impacts on human bodies made by changes in the environment temperature when people take a bath are recognized as a major problem. To cope with this problem, for the purpose of reducing the number of deaths during a bath related to a heat shock, fluctuations of blood pressure before and after taking a bath can be monitored so as to call for attention when a dangerous situation arises. FIG. 26 is a drawing for explaining yet another example of applications of the biological information measuring apparatus according to the first embodiment. In this situation, FIG. 26 illustrates an example in which fluctuations of blood pressure before and after taking a bath are monitored. As illustrated in FIG. 26, a major cause of the fluctuations of blood pressure during a bath is drastic temperature changes in a short period of time such as moving from a warm room to a cold dressing room, further moving to the inside of a cold bathroom, and moving to the inside of a relatively hot bath tub. For this reason, estimating the subject's health condition is made possible by monitoring the blood pressure of the subject before and after he/she takes a bath and calling for his/her attention or transmitting information about the state of the fluctuation of the blood pressure to a mobile phone or a smartphone of his/her family member or to a PC used by his/her primary medical doctor.

For example, pictures of the subject before and after taking a bath are obtained by a camera, so that a microcomputer or a PC serving as the biological information measuring apparatus 100 performs the process of measuring the fluctuation of the blood pressure and the process of calculating the index related to the autonomic nerves. After that, the measured result of the fluctuation of the blood pressure and the index related to the autonomic nerves are provided for the subject, his/her family member, his/her primary medical doctor, or the like. As a result, the subject himself/herself, his/her family member, and his/her primary medical doctor are able to pay attention to the blood pressure and the index value related to the autonomic nerves of the subject.

Figure 27:
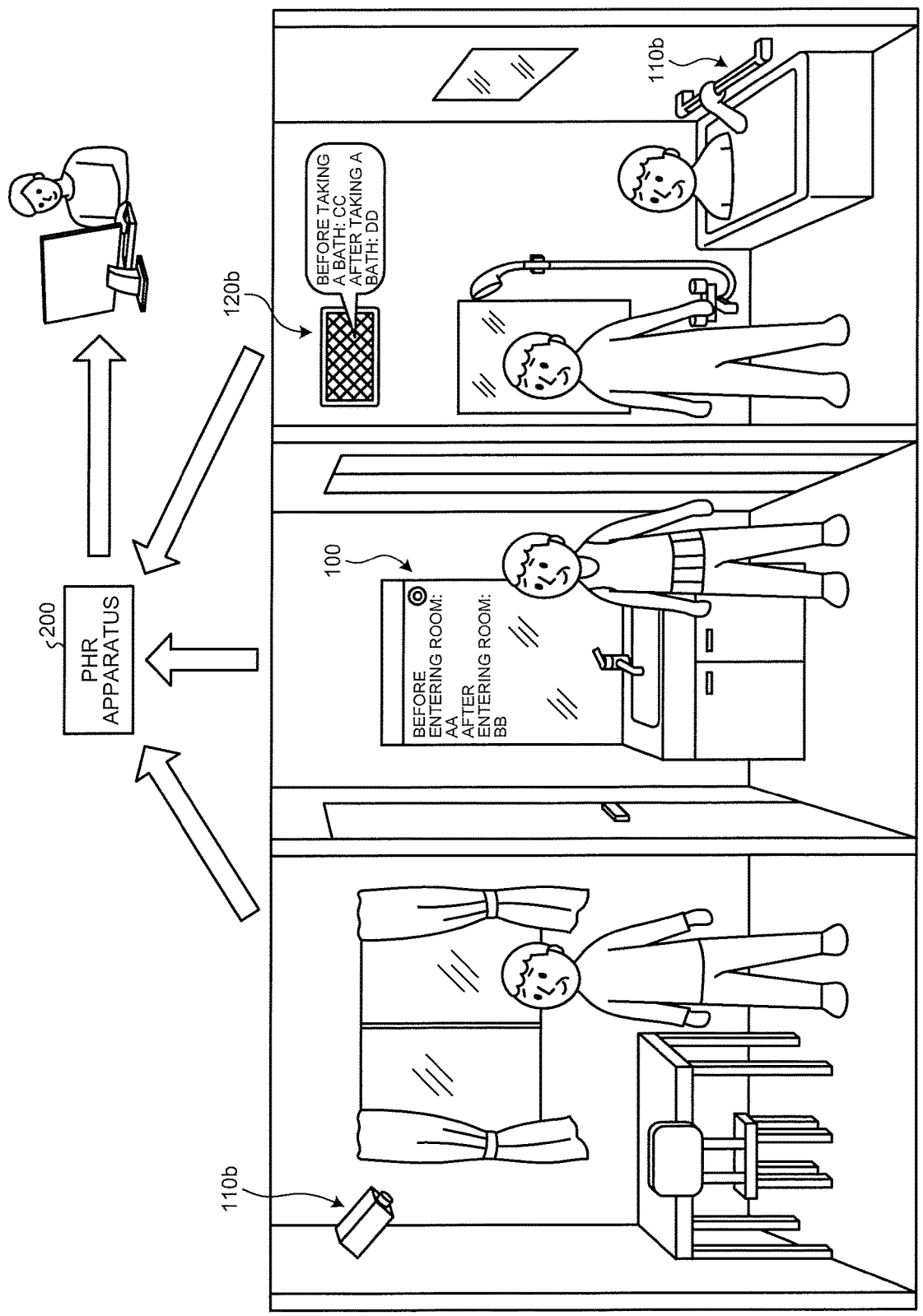
FIG. 27 is a drawing for explaining an example of a blood pressure monitoring process before and after taking a bath according to the first embodiment.

FIG. 27 is a drawing for explaining an example of the blood pressure monitoring process before and after taking a bath according to the first embodiment. FIG. 27 illustrates an example in which the blood pressure is monitored in a living room, a dressing room, and a bathroom. For example, to monitor the blood pressure before and after the subject takes a bath, the blood pressure is monitored especially before and after the subject moving from one place to another, which involves a drastic change in the temperature. In other words, the biological information measuring apparatus 100 the blood pressure monitoring process before and after the moving from the living room to the dressing room, the moving from the dressing room to the bathroom, and the beginning of the bathing. FIG. 27 illustrates an example in which the biological information measuring apparatus 100 is installed on the rear surface of a half mirror in the dressing room and is configured to receive picture signals from each of the rooms and to output the output information to each of the rooms.

For example, the biological information measuring apparatus 100 receives pictures of the face and a site other than the face of the subject who is in the living room, from a camera being installed in the living room and serving as the picture obtaining apparatus 110b and measures the state of the subject's blood pressure while the subject is in the living room. In this situation, the biological information measuring apparatus 100 continuously measures blood pressure information while the subject is in the living room. After that, when the subject moves from the living room to the dressing room, the biological information measuring apparatus 100 measures the blood pressure information by using the pictures of the face and the site other than the face of the subject obtained by the picture obtaining unit 110a. In this situation, as illustrated in FIG. 27, the output unit 120a outputs the blood pressure value in the living room such as "before entering room: AA" and the blood pressure value in the dressing room such as "after entering room: BB", for the subject. By viewing the information that is output, the subject is able to check the fluctuations of his/her own blood pressure. In this situation, for example, another arrangement is also possible in which alert information is displayed if the blood pressure increases significantly after the subject enters the dressing room.

After that, when the subject moves from the dressing room to the bathroom, the biological information measuring apparatus 100 measures blood pressure information by using the pictures of the face and the site other than the face of the subject obtained by the picture obtaining apparatus 110b such as a camera installed in the bathroom, as blood pressure information observed before taking a bath. Subsequently, when the subjects starts taking a bath, the biological information measuring apparatus 100 measures blood pressure information of the subject during the bathing by using the picture of the face obtained by the picture obtaining apparatus 110b such as a camera and the picture signal of the site other than the face obtained by the picture obtaining apparatus 110b such as a reflective photo sensor installed on a handrail in the bathroom. In this situation, as illustrated in FIG. 27, the output apparatus 120b such as a speaker installed in the bathroom provides audio information indicating blood pressure information observed before taking a bath such as "before taking a bath: CC" and blood pressure information during the bathing such as "after taking a bath: DD" measured by the biological information measuring apparatus 100. With these arrangements, the subject is able to check the fluctuations of the blood pressure before and after taking a bath. In this situation, for example, if the blood pressure starts decreasing significantly after the subject takes a bath, alert information may be output in the form of audio. In the description above, the example is explained in which the blood pressure information observed before and after entering the dressing room and before and after taking a bath is output. However, possible embodiments are not limited to this example. It is acceptable to output blood pressure information observed at any arbitrary point in time. For example, it is possible to output fluctuations of the blood pressure observed before and after the subject moving from the dressing room to the bathroom.

Another arrangement is also possible in which the picture signals obtained in the living room, the dressing room, and the bathroom are transmitted to the PHR apparatus 200 via a network, so that the PHR apparatus 200 measures blood pressure information and outputs the blood pressure information to the subject's family member or primary medical doctor who is in a distant location.

Figure 28:
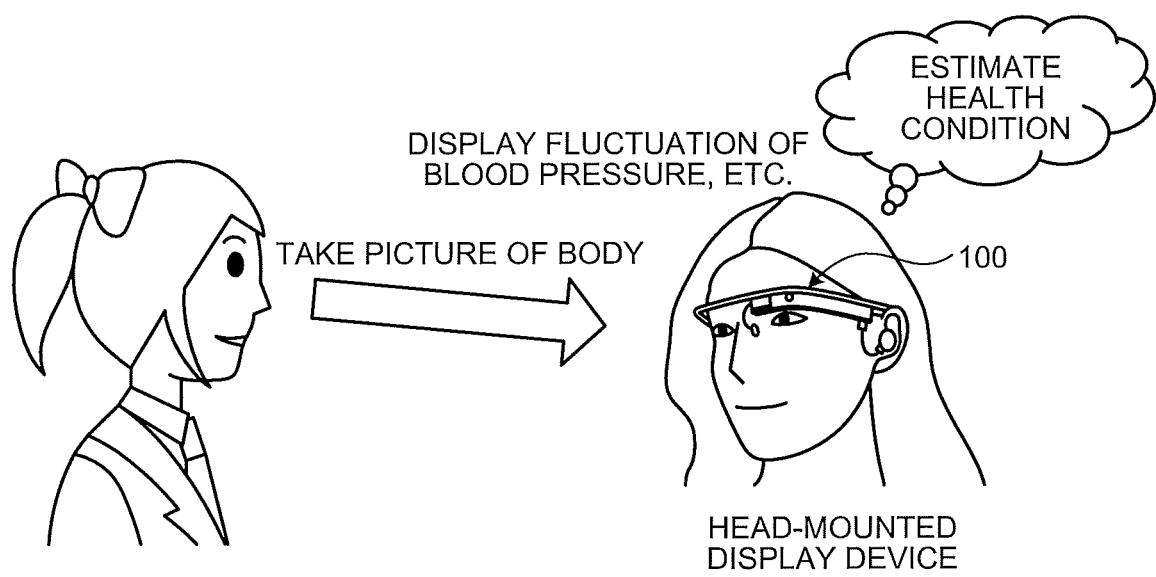
FIG. 28 is a drawing of an example of the biological information measuring apparatus according to the first embodiment.

In the first embodiment above, the example is explained in which the biological information measuring apparatus 100 is a tablet terminal or a PC; however, possible embodiments are not limited to this example. The biological information measuring apparatus 100 may be realized by using any of various apparatuses. For example, the biological information measuring apparatus 100 may be realized by using a display device mounted on the head (a Head Mounted Display [HMD]). FIG. 28 is a drawing of an example of the biological information measuring apparatus 100 according to the first embodiment. As illustrated in FIG. 28, for example, it is possible to realize the biological information measuring apparatus 100 as a spectacle-type wearable device used as an HMD. In that situation, the biological information measuring apparatus 100 takes the pictures of the subject by using a camera attached to the spectacle-type wearable device and displays the output information on a monitor provided on the spectacles. With this arrangement, for example, by viewing someone whose health condition the viewer wishes to estimate, the viewer is able to observe a hue moving image and to estimate a fluctuation of the blood pressure. For example, when a large number of people are injured, it is possible to understand the state of each of the injured people at a glance and to efficiently carry out triage.

Figure 29:
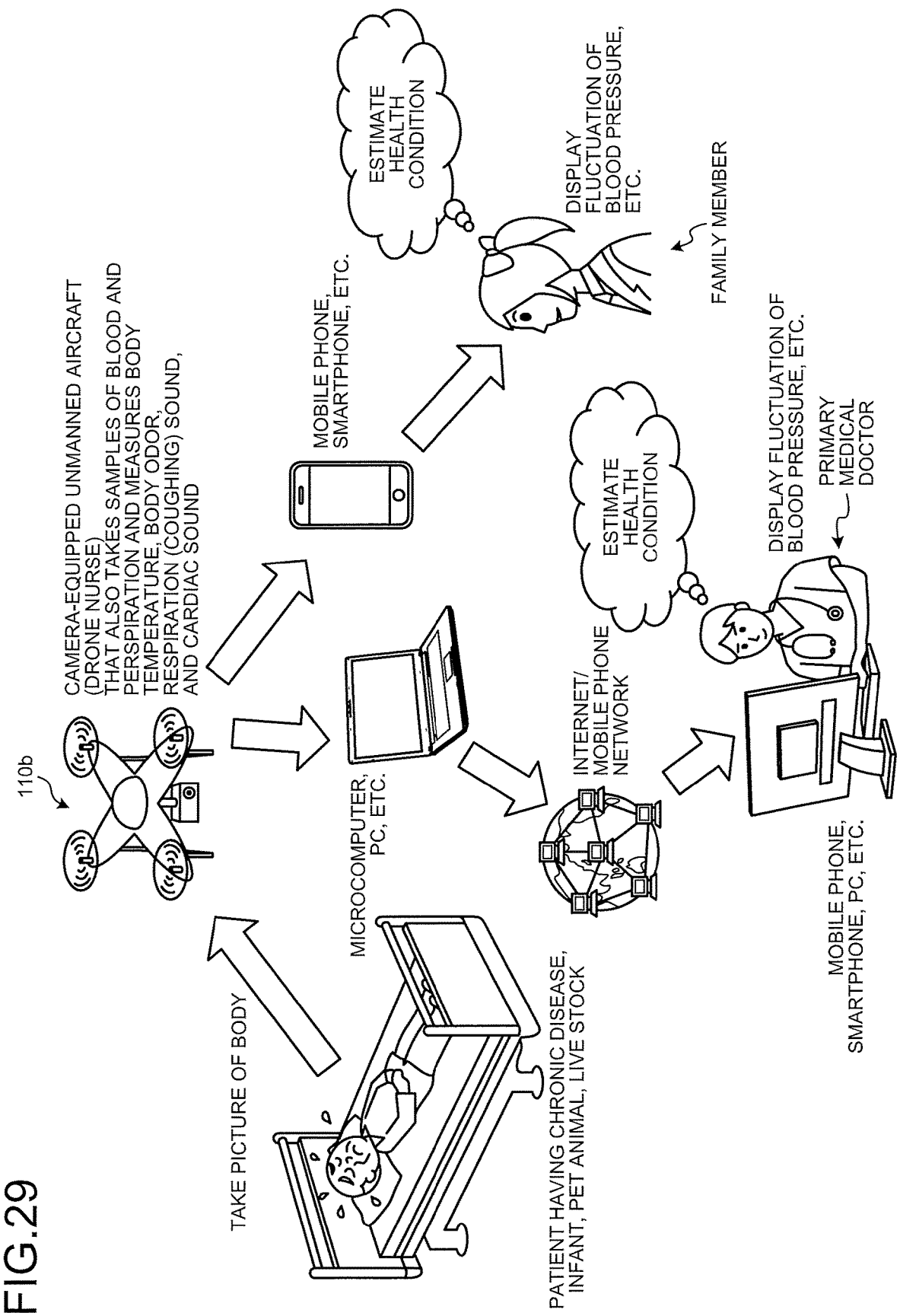
FIG. 29 is a drawing for explaining an example of a picture obtaining apparatus according to the first embodiment.

Further, in the first embodiment described above, the example is explained in which the picture obtaining apparatus 110b is a fixed-type camera. However, possible embodiments are not limited to this example. For instance, a camera-equipped unmanned aircraft (drone) may be used as the picture obtaining apparatus 110b. FIG. 29 is a drawing for explaining an example of the picture obtaining apparatus according to the first embodiment. For example, as illustrated in FIG. 29, a drone serving as the picture obtaining apparatus 110b obtains pictures of a patient having a chronic disease, an infant, a pet animal, livestock, or the like and transmits the picture signals to a microcomputer, a PC, a mobile phone, or a smartphone. After that, the subject's family member or primary medical doctor estimates the subject's health condition on the basis of the blood pressure information output by the mobile phone, the PC, or the like. With this arrangement, it is possible to address the situations in which fixed-type cameras would not be able to perform the imaging processes.

Second Embodiment

In the first embodiment described above, the example is explained in which the difference is calculated between the luminance information of the picture signal obtained by imaging the face of the subject and the luminance information of the picture signal obtained by imaging the site other than the face, so that the fluctuation of the blood pressure is estimated in accordance with an increase or a decrease in the difference. In other words, in the first embodiment, the example is explained in which either the "dPTT" or the "PD" is calculated from the picture signals so as to estimate the fluctuation of the blood pressure on the basis of the positive correlation thereof with the blood pressure, by using the blood flow that is affected by the delay in the arrival of the pulse wave caused by an increase in the peripheral blood vessel resistance and the blood flow that is not affected by the delay in the arrival of the pulse wave caused by the increase in the peripheral blood vessel resistance. In a second embodiment, an example will be explained in which a "dPTT" is calculated from picture signals by using a method different from the method used in the first embodiment, and a fluctuation of the blood pressure is estimated on the basis of the calculated "dPTT". The biological information measuring apparatus 100 according to the second embodiment is different from the biological information measuring apparatus 100 according to the first embodiment for processes performed by the skin region extracting unit 151, processes performed by the calculating unit 152, and processes performed by the measuring unit 153. The second embodiment will be explained below while a focus is placed on the differences.

According to a method explained in the second embodiment, any blood flow may be used as the processing target. In other words, according to the method explained below, it is possible to estimate a fluctuation of the blood pressure by using an arbitrary combination made up of a picture signal based on a blood flow affected by the delay in the arrival of the pulse wave caused by an increase in the peripheral blood vessel resistance and a picture signal based on a blood flow that is not affected by the delay in the arrival of the pulse wave caused by the increase in the peripheral blood vessel resistance. For example, it is possible to estimate a fluctuation of the blood pressure by using a picture signal of the face (cheek) and a picture signal of the face (forehead). Further, for example, it is also possible to estimate a fluctuation of the blood pressure by using a picture signal of the face and a picture signal of a site other than the face (e.g., a hand). Alternatively, it is also possible to estimate a fluctuation of the blood pressure by using picture signals of two sites other than the face.

Figure 30:
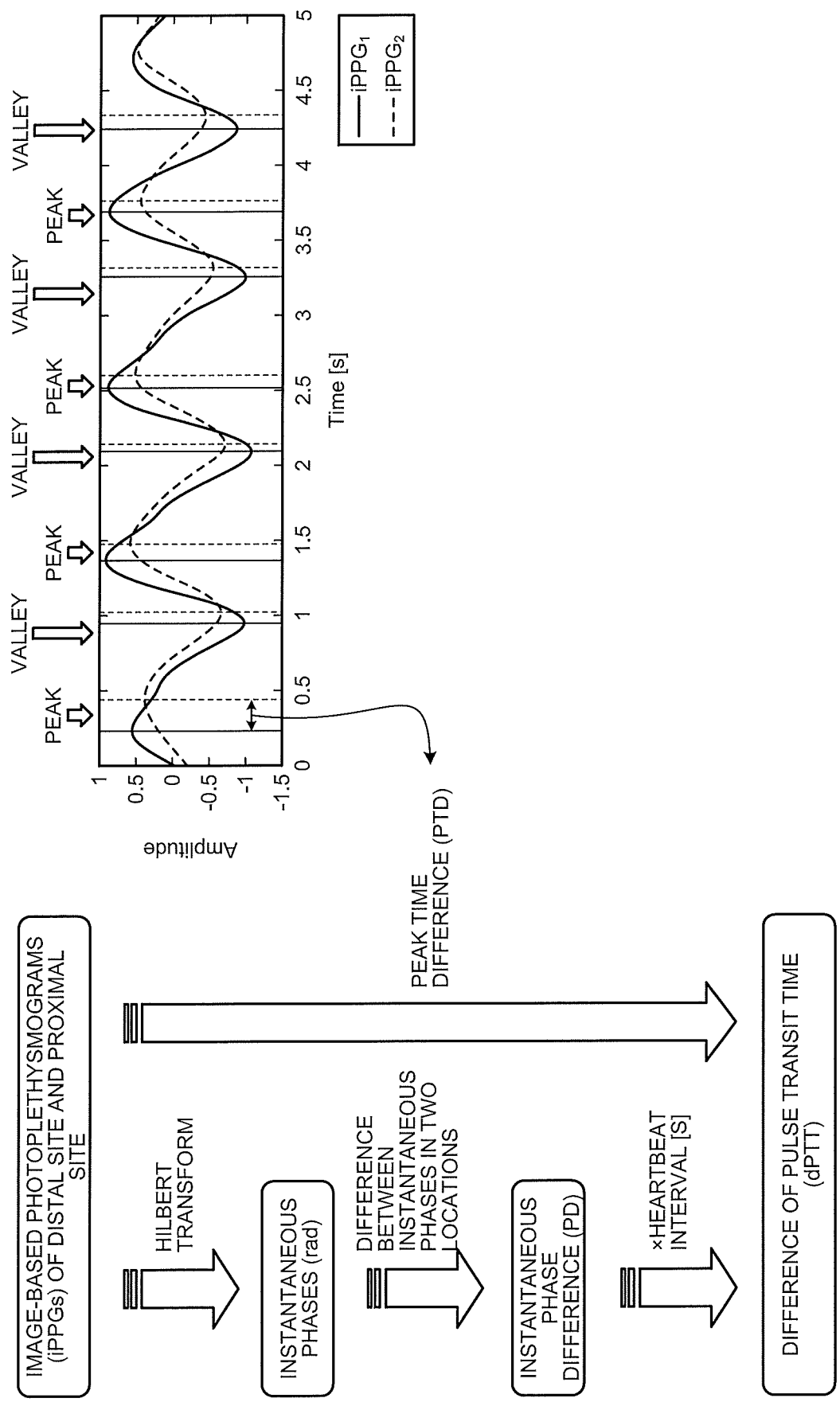
FIG. 30 is a drawing illustrating an outline of a process to calculate a difference of pulse transit time performed by a biological information measuring apparatus according to a second embodiment.

In the first embodiment described above, the fluctuation of the blood pressure is estimated by calculating the instantaneous phases of the picture signal of the face and the picture signal of the site other than the face and further calculating the instantaneous phase difference "PD" from the difference between the calculated instantaneous phases. In contrast, in a method according to the second embodiment, without calculating the instantaneous phases, a fluctuation of the blood pressure is estimated by directly calculating a "dPTT" from an image-based photoplethysmogram "iPPG". FIG. 30 is a drawing illustrating an outline of a process to calculate a difference of pulse transit time "dPTT" performed by the biological information measuring apparatus 100 according to the second embodiment. FIG. 30 illustrates an example of the "dPTT" calculating process performed by the biological information measuring apparatus 100 according to the second embodiment, together with a comparison to the "dPTT" calculating process performed by the biological information measuring apparatus 100 according to the first embodiment.

As illustrated in FIG. 30, the biological information measuring apparatus 100 according to the first embodiment calculates instantaneous phases "rad" by applying a Hilbert transform to an image-based photoplethysmogram of a "distal site" to which the propagation distance of the pulse wave is longer and to an image-based photoplethysmogram of a "proximal site" to which the propagation distance of the pulse wave is shorter. After that, the biological information measuring apparatus 100 according to the first embodiment calculates an instantaneous phase difference "PD" by calculating the difference between the instantaneous phases of the two locations calculated by performing the Hilbert transform. Further, the biological information measuring apparatus 100 according to the first embodiment calculates a difference of pulse transit time "dPTT" by multiplying the calculated "PD" by a "heartbeat interval [S]". The biological information measuring apparatus 100 according to the first embodiment estimates the fluctuation of the blood pressure by using the fluctuation of the "PD" or the difference of pulse transit time "dPTT", on the basis of the positive correlation.

In contrast, the biological information measuring apparatus 100 according to the second embodiment calculates a difference of pulse transit time "dPTT" from an image-based photoplethysmogram of a "distal site" and an image-based photoplethysmogram of a "proximal site", without calculating the instantaneous phases. In the present example, the biological information measuring apparatus 100 according to the second embodiment calculates the "dPTT" from a time difference between feature regions in the image-based photoplethysmograms "iPPGs" of the two locations. For example, as illustrated in FIG. 30, the biological information measuring apparatus 100 according to the second embodiment calculates the difference of pulse transit time (dPTT) by using "peak time differences (PTDs)" each indicating a time difference between peaks (i.e., parts forming a peak in the image-based photoplethysmograms) in two "iPPG charts" or a time difference between valleys (i.e., parts forming valleys in the image-based photoplethysmograms) in two "iPPG" charts.

In one example, as illustrated in FIG. 30, the biological information measuring apparatus 100 according to the second embodiment extracts corresponding peaking times (a peak time and a valley time) with respect to an image-based photoplethysmogram of a proximal site "iPPG$_1$" and an image-based photoplethysmogram of a distal site "iPPG$_2$". After that, the biological information measuring apparatus 100 calculates a peak time difference for each pair of corresponding peaking values (i.e., extreme values such as a peak value and a valley value) and further calculates a difference of pulse transit time by using the calculated peak time differences. In the second embodiment, an example will be explained in which the peaking values are used as feature regions of the image-based photoplethysmograms. However, possible embodiments are not limited to this example. Any arbitrary regions in the image-based photoplethysmograms may be used as the feature regions. In other words, any regions that correspond to each other between the two image-based photoplethysmograms may be used as feature regions. For example, it is acceptable to use a region (or a certain point) ranging from a valley to a peak or a region (or a certain point) ranging from a peak to a valley in the image-based photoplethysmograms. In that situation, the biological information measuring apparatus 100 extracts the regions corresponding to each other in the two image-based photoplethysmogram and further calculates the difference of pulse transit time by using the time difference between the extracted regions.

Next, details of a process performed by the biological information measuring apparatus 100 according to the second embodiment will be explained. As for the biological information measuring apparatus 100 according to the second embodiment, an example will be explained in which a "dPTT" is calculated from a picture signal of the face and a picture signal of a site other than the face, so as to estimate a fluctuation of the blood pressure on the basis of the calculated "dPTT". The skin region extracting unit 151 according to the second embodiment extracts a face region of the subject from a picture taken of the subject. For example, the skin region extracting unit 151 extracts coordinates of the pixels in the face region of the subject, by performing a face recognition process on the taken picture. In this situation, the skin region extracting unit 151 sets a plurality of regions in predetermined positions within the extracted face region. More specifically, within the extracted face region, the skin region extracting unit 151 sets a ROI in a "distant site" to which the propagation distance of the pulse wave is longer and a ROI in a "proximal site" to which the propagation distance of the pulse wave is shorter.

Figure 31A:
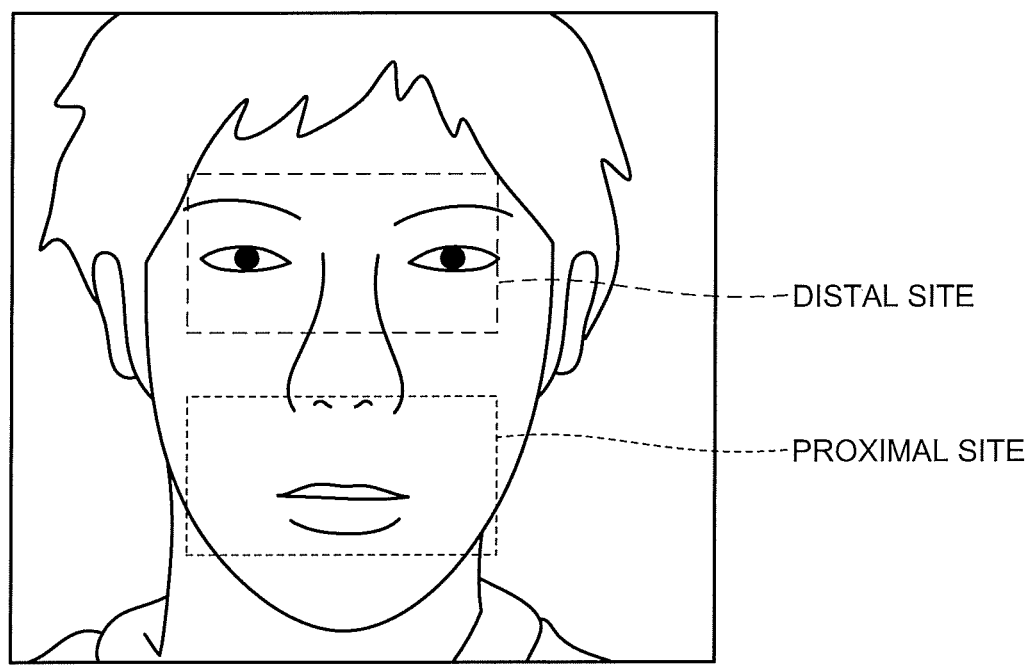
FIG. 31A is a drawing of an example of a process of setting a distal site and a proximal site performed by a skin region extracting unit according to the second embodiment.

FIG. 31A is a drawing of an example of a process of setting a distal site and a proximal site performed by the skin region extracting unit 151 according to the second embodiment. For example, the skin region extracting unit 151 extracts a face region of the subject by performing a face authentication process, from the picture taken of the subject. After that, as illustrated in FIG. 31A, the skin region extracting unit 151 sets a distal site and a proximal site in the extracted face region. For example, as illustrated in FIG. 31A, on the basis of the positions of different sites of the face included in the face region, the skin region extracting unit 151 sets a region enclosing the eyes and the eyebrows therein as a ROI in the distal site. Further, the skin region extracting unit 151 sets a region enclosing the mouth and a part of the nose therein, as a ROI in the proximal site. The distal site and the proximal site illustrated in FIG. 31A are merely examples. In other words, the skin region extracting unit 151 is able to set the distal site and the proximal site on the basis of an arbitrary setting designated by the operator.

In this situation, the skin region extracting unit 151 may exclude such a region (e.g., a region over which hair is present, a region of the eyes, a region of the eyebrows, a region of the lips, and a background part) from which it is difficult to obtain changes in the luminance information of green based on the blood flows, from the regions serving as the distal site and the proximal site. In one example, the skin region extracting unit 151 excludes the eyebrow regions and the eye regions from the distal site illustrated in FIG. 31A on the basis of information about feature points of the face and the pixel values. Further, the skin region extracting unit 151 excludes the lip region from the proximal site illustrated in FIG. 31A. When having set the ROI in the distal region and the ROI in the proximal region in this manner, the skin region extracting unit 151 transmits the coordinates of the ROIs that were set to the calculating unit 152. For example, from among the coordinates contained in the ROIs, the skin region extracting unit 151 transmits the coordinates corresponding to such a region from which it is possible to obtain changes in the luminance information of green based on the blood flows, to the calculating unit 152.

In the description above, the example is explained in which the skin region extracting unit 151 automatically sets the distal site and the proximal site. However, another arrangement is acceptable in which the operator sets a distal site and a proximal site. In that situation, the operator sets a ROI in the distal site and a ROI in the proximal site by operating an input unit such as a mouse and/or a touch panel while viewing the picture. When the ROI in the distal site and the ROI in the proximal site have been set via the input unit, the skin region extracting unit 151 transmits the coordinates of the ROIs that were set, to the calculating unit 152. Even when the ROI in the distal site and the ROI in the proximal site are manually set by the operator, the skin region extracting unit 151 is able to exclude, as explained above, such a region from which it is difficult to obtain changes in the luminance information of green based on the blood flows, from the regions serving the distal site and the proximal site. In other words, from among the coordinates contained in the ROIs, the skin region extracting unit 151 transmits the coordinates corresponding to such a region from which it is possible to obtain changes in the luminance information of green based on the blood flows, to the calculating unit 152.

With respect to each of the frames structuring the picture, the skin region extracting unit 151 performs the process of extracting the face region and the process of setting a ROI in a distal site and a ROI in a proximal site within the face region as described above and sequentially transmits the coordinates of the ROI in the distal site and the coordinates of the ROI in the proximal site in each of the frames, to the calculating unit 152. For example, with respect to the frame in which the ROIs are set and the frames following thereafter, the skin region extracting unit 151 tracks the coordinates of the ROIs in each frame by performing a tracking process that uses feature points in the picture and sequentially transmits the coordinates in the result of the tracking process, to the calculating unit 152.

The calculating unit 152 according to the second embodiment is configured to extract luminance values of green light contained in picture signals of a plurality of regions of the subject. More specifically, the calculating unit 152 extracts the luminance values of the green light in the ROI in the distal site and the ROI in the proximal site set by the skin region extracting unit 151. In this situation, similarly to the first embodiment, the calculating unit 152 according to the second embodiment performs a smoothing process on the images before extracting the green light from the picture signals. After that, the calculating unit 152 extracts the luminance values of the green light in the ROI in the distal site and the ROI in the proximal site. Further, with respect to each of the ROIs, the calculating unit 152 extracts a green signal expressed in a temporal-change curve obtained by calculating an average luminance value of the green light for each of the frames.

Figure 31B:
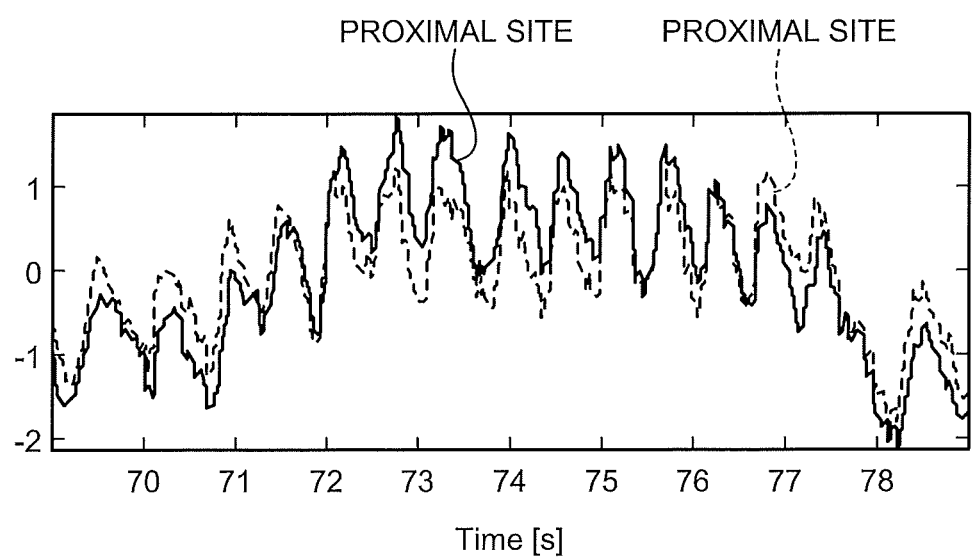
FIG. 31B is a chart for explaining an extraction of a luminance values of green light according to the second embodiment.

FIG. 31B is a chart for explaining the extraction of the luminance values of the green light according to the second embodiment. FIG. 31B illustrates a chart of an average luminance value of green light in which the vertical axis expresses "values based on the average luminance value", whereas the horizontal axis expresses "time [s]". For example, the calculating unit 152 extracts luminance values of the green light in each of the ROIs, from each of the plurality of frames structuring the picture. Further, as illustrated in FIG. 31B, by calculating an average value of the extracted luminance values of the green light for each of the ROIs in each of the frames, the calculating unit 152 extracts charts of the average luminance value of green, each for the ROI in the distal site and for the ROI in the proximal site. In this situation, FIG. 31B illustrates the charts obtained by multiplying the green signal by "−1" so as to reverse the positive and negative signs, for the purpose of arranging an increase or a decrease of the blood flow to match an increase or a decrease of the green signal.

Figure 31C:
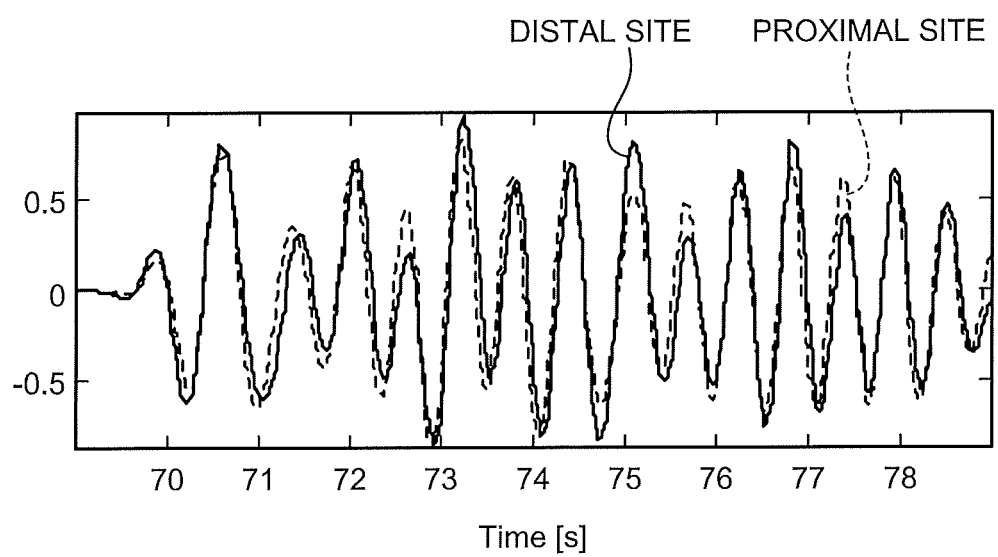
FIG. 31C is a chart for explaining an extraction of a pulse wave signal according to the second embodiment.

Subsequently, the calculating unit 152 extracts a pulse wave signal for each of the ROIs, by applying a filtering process to each of the extracted "green signals" of the ROIs. For example, the calculating unit 152 eliminates signal components other than heartbeat components by employing a fifth (5th)-degree Butterworth filter that passes the frequency band of "0.5 to 2.0 Hz". FIG. 31C is a chart for explaining the extraction of the pulse wave signal according to the second embodiment. FIG. 31C illustrates an example of extracting a pulse wave from the "green signal" illustrated in FIG. 31B. Further, FIG. 31C illustrates the pulse wave signal while the vertical axis expresses "amplitude", whereas the horizontal axis expresses "time [s]". For example, as illustrated in FIG. 31C, the calculating unit 152 extracts "image-based photoplethysmograms (iPPGs)" each corresponding to the distal site and to the proximal site, by applying the filtering process to the "green signal" of each of the ROIs. As illustrated in FIG. 31C, each of the extracted "image-based photoplethysmograms" exhibits a periodic sinusoidal waveform in which a pulse wave generated by one heartbeat corresponds to one crest in the waveform resulting from the filtering process.

As explained above, the calculating unit 152 extracts the image-based photoplethysmograms, each for the ROI in the distal site and for the ROI in the proximal site. After that, the calculating unit 152 calculates a difference of pulse transit time (dPTT) by using the calculated image-based photoplethysmograms. More specifically, the calculating unit 152 calculates a time difference between predetermined feature points in the luminance values of the green light in the picture signals, as the difference of pulse transit time. For example, the calculating unit 152 calculates peak time differences (PTDs) (the time difference between peak values and the time difference between valley values) in the image-based photoplethysmograms of the ROIs as the "dPTT".

In this situation, to enhance the level of precision for the calculation of the peak time differences (PTDs), the calculating unit 152 calculates a trimmed mean value of the time differences between the feature points during a predetermined time period, as the difference of pulse transit time. The propagation velocity of a pulse wave is "approximately 1.0 m/s". Accordingly, for example, when the distance between the distal site and the proximal site as illustrated in FIG. 31A is approximately "10 cm", the time period it takes for a pulse wave to propagate from the proximal site to the distal site is "approximately 100 milliseconds (ms)". In other words, the peak time differences in the image-based photoplethysmograms between the ROIs fluctuate with a time length of approximately "100 ms" due to fluctuations of the blood pressure. While the calculating unit 152 according to the second embodiment calculates the fluctuation of the time difference, the level of precision for the calculation of the time difference varies depending on the framerate of the pictures obtained by the picture obtaining unit 110a.

For example, when the picture is obtained at a high framerate such as approximately "140 fps", because the chart of the average luminance value is extracted on the basis of dense sampling points, it is possible to extract the times of the peaking values in the ROIs more accurately. As a result, the calculating unit 152 is able to calculate the fluctuation of the peak time differences more accurately, which fluctuate with a time length of approximately "100 ms". In contrast, when the framerate is approximately "30 fps" such as those of pictures taken by commonly-used cameras, because the chart of the average luminance value is extracted on the basis of sparse sampling points, the level of precision for extracting the times of the peaking values in the ROIs is lower than that in the example with the framerate of "140 fps". As a result, the level of precision for the fluctuation of the peak time differences calculated by the calculating unit 152 is lower than that in the example with the framerate of "140 fps".

Figure 32A:
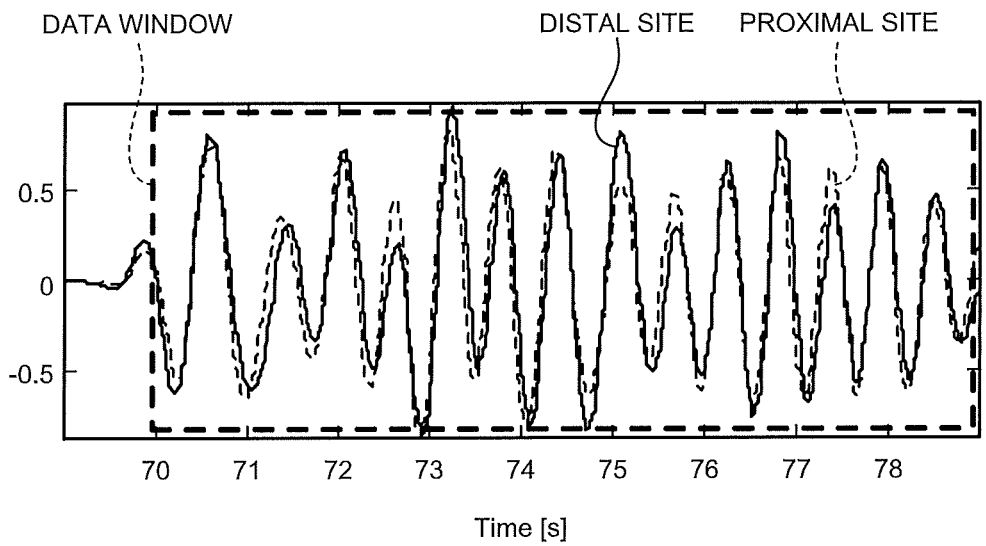
FIG. 32A is a chart for explaining an example of a trimmed mean value of peak time differences obtained by a calculating unit according to the second embodiment.
Figure 32B:
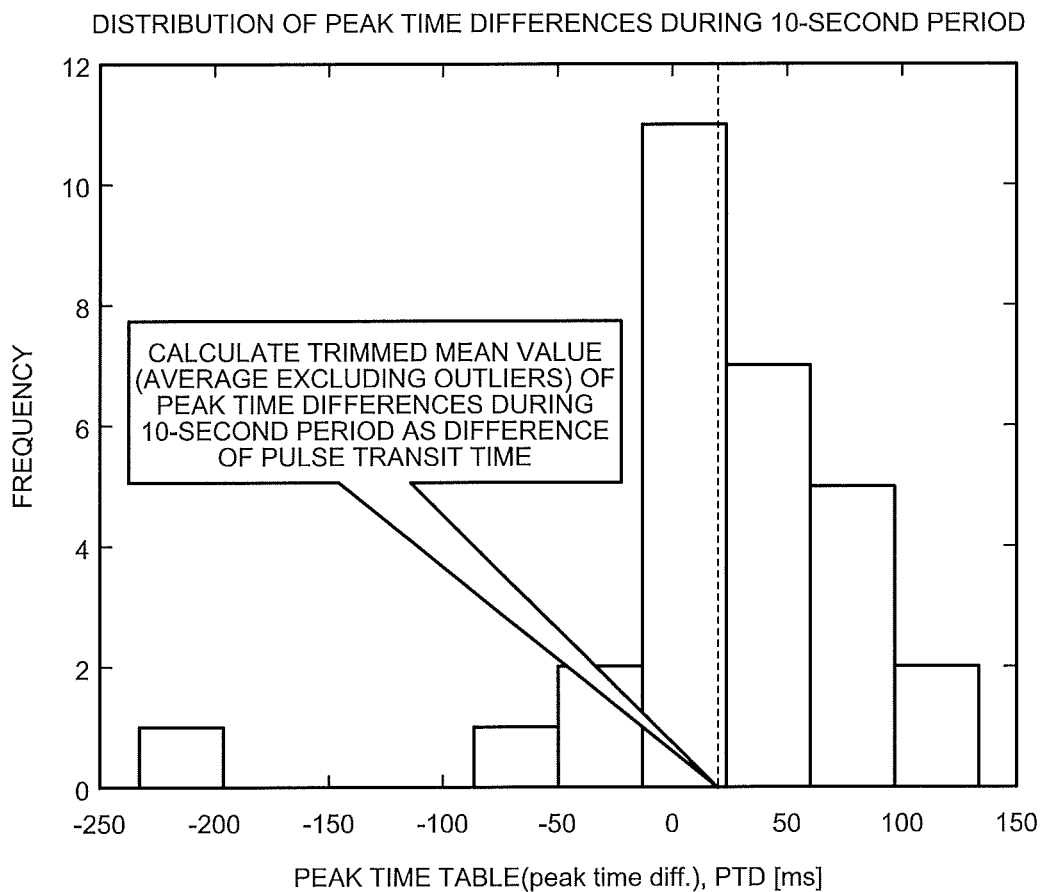
FIG. 32B is a chart for explaining another example of a trimmed mean value of peak time differences obtained by the calculating unit according to the second embodiment.

To cope with this situation, the calculating unit 152 according to the second embodiment calculates the trimmed mean value of the peak time differences in the predetermined time period, as the difference of pulse transit time. FIGS. 32A and 32B are charts for explaining examples of the trimmed mean value of the peak time differences obtained by the calculating unit 152 according to the second embodiment. FIG. 32A illustrates an example in which a trimmed mean value process is performed on the image-based photoplethysmograms illustrated in FIG. 31C. For example, the calculating unit 152 calculates a trimmed mean value of the peak time differences, by using "10 seconds" as the predetermined time period. In one example, as illustrated in FIG. 32A, the calculating unit 152 performs the trimmed mean value process by using a data window of "10 seconds" on the image-based photoplethysmograms of the distal site and the proximal site. In other words, the calculating unit 152 calculates time differences of the peaking times contained in the data window within the image-based photoplethysmogram of each of the ROIs and calculates an average value of certain values remaining after excluding outliers from the calculated peak time differences.

For example, with respect to the peaking values (the peak values and the valley values) contained in the data window of "10 seconds", the calculating unit 152 calculates a peak time difference for each pair. Further, the calculating unit 152 extracts outliers on the basis of a frequency distribution of the calculated peak time differences and calculates an average value while excluding the extracted outliers. FIG. 32B illustrates a frequency distribution of the peak time differences for the peaking values contained in the data window of "10 seconds". In FIG. 32B, the vertical axis expresses frequency, whereas the horizontal axis expresses peak time differences. For example, while excluding the outliers (e.g., the value of the peak time difference near −200) from the peak time differences illustrated in FIG. 32B, the calculating unit 152 calculates an average value of the other values as the difference of pulse transit time.

In this situation, for example, the calculating unit 152 extracts the outliers by applying a predetermined threshold value to the frequency distribution of the peak time differences, so as to exclude the extracted outliers. In one example, from the distribution of the peak time differences, the calculating unit 152 excludes such peak time difference values corresponding to the top "30%" and the bottom "30%" as the outliers, so as to calculate an average value of the remaining peak time difference values as the difference of pulse transit time. In this situation, the threshold value used for extracting the outliers for the trimmed mean value may arbitrarily set by the operator.

Figure 33:
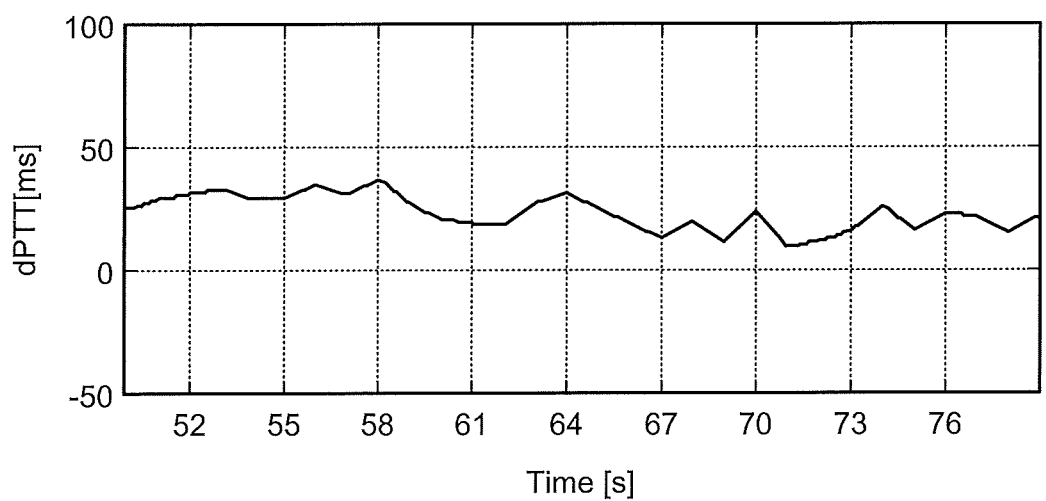
FIG. 33 is a chart illustrating an example of a difference of pulse transit time calculated by the calculating unit according to the second embodiment.

While sliding the data window used for calculating a trimmed mean value by a certain length of time, the calculating unit 152 calculates a trimmed mean value in each of the positions, so as to calculate changes of the difference of pulse transit time "dPTT" over time. For example, the calculating unit 152 calculates difference of pulse transit time values over time, by calculating a trimmed mean value in the positions obtained by sliding the data window of "10 seconds" illustrated in FIG. 32A by "1 second" at a time. FIG. 33 is a chart illustrating an example of the difference of pulse transit time calculated by the calculating unit 152 according to the second embodiment. FIG. 33 illustrates the chart of the difference of pulse transit time in which the vertical axis expresses difference of pulse transit time (dPTT [ms]), whereas the horizontal axis expresses "time[s]". For example, by sliding the data window by "1 second" at a time, the calculating unit 152 calculates the chart indicating the changes in the difference of pulse transit time over time as illustrated in FIG. 33, by plotting, in the chart, the trimmed mean values (the difference of pulse transit time values) calculated in the positions of the data window corresponding to the "1-second" sliding and by connecting the values to one another with straight lines.

The example described above is merely an example, and possible embodiments are not limited to this example. For instance, the time width of the data window used for calculating the trimmed mean value is not limited to "10 seconds" and may arbitrarily set. In other words, the operator is able to arbitrarily set the time width of the data window and may, for example, set the time width in accordance with the framerate of the picture signal obtained by the picture obtaining unit 110a. In one example, the time width may be set in such a manner that the time width of the data window is shorter when the framerate is higher and that the time width of the data window is longer when the framerate is lower. Further, for example, the time length by which the data window is slid is not limited to "1 second" and may arbitrarily be set. In other words, the operator is able to arbitrarily set the time length by which the data window is slid.

The measuring unit 153 according to the second embodiment is configured to measure a fluctuation of the blood pressure of the subject, on the basis of an increase or a decrease in the difference of pulse transit time. More specifically, when the picture signals from which the difference of pulse transit time is calculated are obtained from the face of the subject, the measuring unit 153 measures an increase in the difference of pulse transit time as a decreasing fluctuation of the blood pressure and measures a decrease in the difference of pulse transit time as an increasing fluctuation of the blood pressure. For example, when the ROI in the distant site and the ROI in the proximal site are set in the face region of the subject so as to calculate the difference of pulse transit time by using the image-based photoplethysmograms of the ROIs as explained above, the measuring unit 153 measures the blood pressure on the basis of a negative correlation between difference of pulse transit time values and blood pressure values.

As explained in the first embodiment, when the ROIs used for calculating a difference of pulse transit time are the face and a site other than the face, because the image-based photoplethysmograms are extracted on the basis of a blood flow not affected by the delay in the arrival of the pulse wave caused by an increase in the peripheral blood vessel resistance and a blood flow affected by the delay in the arrival of the pulse wave caused by the increase in the peripheral blood vessel resistance, the fluctuation of the blood pressure is measured on the basis of the positive correlation. In contrast, according to the second embodiment, the difference of pulse transit time is calculated on the basis of the image-based photoplethysmograms of the two ROIs set in the face region. In other words, from both the ROI in the distant site and the ROI in the proximal site set in the face region, the image-based photoplethysmograms based on blood flows that are not affected by the delay in the arrival of the pulse wave caused by an increase in the peripheral blood vessel resistance are extracted. Accordingly, on the basis of a negative correlation between difference of pulse transit time values and blood pressure values, the measuring unit 153 measures an increase in the difference of pulse transit time as a decreasing fluctuation of the blood pressure and measures a decrease in the difference of pulse transit time as an increasing fluctuation of the blood pressure. It should be noted that, however, when a difference of pulse transit time is calculated from image-based photoplethysmograms of the face and a site other than the face by implementing the abovementioned method, the measuring unit 153 according to the second embodiment measures a fluctuation of the blood pressure on the basis of the positive correlation like in the first embodiment.

Next, examples of image-based photoplethysmogram analyses performed by the biological information measuring apparatus 100 according to the second embodiment will be explained, with reference to FIGS. 34A to 34J. FIGS. 34A to 34J are drawings for explaining examples of the image-based photoplethysmogram analyses performed by the biological information measuring apparatus 100 according to the second embodiment. FIGS. 34A to 34J illustrate examples of display screens that are output and displayed by the output unit 120a or the output apparatus 120b for the purpose of performing the image-based photoplethysmogram analyses. First, when the biological information measuring apparatus 100 receives an operation to start an image-based photoplethysmogram analysis, the output controlling unit 154 causes the output unit 120a or the output apparatus 120b to output and display a setting screen for the analysis.

For example, as illustrated in FIG. 34A, the output controlling unit 154 causes a setting screen to be displayed, the setting screen including setting items such as "the input source of the picture signals", "setting analysis target regions", "type of the filter", "mosaic display", and "skin color region tracking". In this situation, "the input source of the picture signals" illustrated in FIG. 34A denotes an item for setting the input source of the pictures serving as an analysis target. For example, when "From a camera" is selected, a picture obtained by the picture obtaining unit 110a or the picture obtaining apparatus 110b serves as an analysis target. In contrast, when "From a file" is selected, a picture stored in the picture storage unit 141 serves as an analysis target. In other words, the operator selects the picture serving as the analysis target by performing a selecting operation to select "the input source of the picture signals". When "From a file" is selected, the output controlling unit 154 further displays a selection screen used for selecting a file.

Further, the "setting analysis target regions" illustrated in FIG. 34A denotes an item for setting ROIs in the picture. For example, when "top and bottom" is selected, ROIs are set in top and bottom sections of a skin region. For example, ROIs are set in top and bottom sections of a face region. In another example, when "left and right" is selected, ROIs are set in left and right sections of a skin region. For example, ROIs are set in left and right sections of a face region. In yet another example, when "manual" is selected, the operator sets ROIs in a skin region. In other words, when "manual" is selected, the output controlling unit 154 displays the picture, whereas the input unit receives the operation to set the ROIs. In this situation, each of the ROIs that are set as the analysis target regions may further be divided into sections in a mosaic formation. For example, each of the ROIs may be divided into regions in a predetermined quantity, so that each of the regions serves as an analysis target region. The dividing of the ROIs will be explained in detail later.

The "type of the filter" illustrated in FIG. 34A denotes an item for setting the type of the filter used for extracting the image-based photoplethysmograms from the green signals. For example, when the "band pass filter" is selected, the image-based photoplethysmograms are extracted by using a band-pass filter. In contrast, when the "comb filter" is selected, the image-based photoplethysmograms are extracted by using a comb filter. In this situation, the "comb filter" is a filter that eliminates components other than the fundamental component and the harmonic component, by using a combination of a Fast Fourier Transform (FFT) and an inverse FFT, while utilizing the characteristic where a pulse wave is structured with periodic triangular waves. Accordingly, by using this type of filter, the positions of the peaks (parts forming peaks) and the valleys (parts forming valleys) in the image-based photoplethysmograms are accurately defined, and it is therefore possible to enhance the level of precision of the difference of pulse transit time. Further, the "mosaic display" illustrated in FIG. 34A denotes an item for setting whether a mosaic display is to be realized or not when the area inside each of the ROIs is divided into sections in a mosaic formation. For example, when "Yes" is selected, the area inside each of the ROIs is divided into sections in a mosaic formation, so as to be displayed while being superimposed on the picture. In contrast, when "No" is selected, the ROIs are displayed while being superimposed on the picture, without the area inside each of the ROIs being divided into sections in a mosaic formation.

The "skin color region tracking" illustrated in FIG. 34A denotes an item for setting whether a skin color region tracking process is to be performed or not in each of the frames of the picture. For example, when "Yes" is selected, the process of extracting a skin region of the subject by extracting a region in the skin color is performed for each of the frames. On the contrary, when "No" is selected, the process of extracting a skin region of the subject is not performed. The setting items illustrated in FIG. 34A are merely examples and may arbitrarily be added or deleted.

When the setting items illustrated in FIG. 34A have been selected and the "OK" button is clicked, the output controlling unit 154 causes the output unit 120a or the output apparatus 120b to output and display a setting screen used for making detailed settings. For example, as illustrated in FIG. 34B, the output controlling unit 154 further causes another setting screen to be displayed, the setting screen including items such as "frame frequency [fps]", "calculation display cycle [s]", "length [s] of the input data window", "length [s] of the output display", "length [s] of the data to be stored on a disk", "cycle [s] for tracking the skin color region", "[lower limit frequency and upper limit frequency] [Hz] of the band-pass filter", "the number [quantity] of sections into which the screen is divided [columns, rows]", "degree (3 or larger for applications) of the median filter for luminance signals", and "threshold value [%] for trimmed mean values (0-50%)".

In this situation, the "frame frequency [fps]" illustrated in FIG. 34B denotes an item for setting the framerate of the picture. For example, as illustrated in FIG. 34B, by inputting the numerical value "40" under the item "frame frequency [fps]", the operator is able to set the framerate of a picture that will be taken to "40 fps" or to lower the framerate of a picture that has already been taken to "40 fps". Further, the "calculation display cycle [s]" illustrated in FIG. 34B denotes an item for setting the cycle with which the green signals or the image-based photoplethysmograms are displayed. For example, as illustrated in FIG. 34B, by inputting the numerical value "10" under the "calculation display cycle [s]", the operator is able to set the display cycle of the green signals or the image-based photoplethysmograms to "10 s".

Further, the "length [s] of the input data window" illustrated in FIG. 34B denotes an item for setting the time width of the data window used for performing the trimmed mean value process. For example, as illustrated in FIG. 34B, by inputting the numerical value "10" under the "length [s] of the input data window", the operator is able to set the time width of the data window to "10 s". Further, the "length [s] of the output display" illustrated in FIG. 34B denotes an item for setting the cycle with which the heartbeat or the difference of pulse transit time is displayed. For example, as illustrated in FIG. 34B, by inputting the numerical value "100" under the "length [s] of the output display", the operator is able to set the display cycle of the heartbeats or the difference of pulse transit time to "100 s".

Further, the "length [s] of the data to be stored on a disk" illustrated in FIG. 34B denotes an item for setting the time period of the data to be stored. For example, as illustrated in FIG. 34B, by inputting the numerical value "120" under the "length [s] of the data to be stored on a disk", the operator is able to have data of "120 s" stored. Further, the "cycle [s] for tracking the skin color region" illustrated in FIG. 34B denotes an item for setting the cycle for the process of extracting the skin region of the subject. For example, as illustrated in FIG. 34B, by inputting the numerical value "1" under the "cycle [s] for tracking the skin color region", the operator is able to cause the skin region extracting process to be performed once every "1 second" period.

The "[lower limit frequency and upper limit frequency] [Hz] of the band-pass filter" illustrated in FIG. 34B denotes an item for setting the band of the band-pass filter used for extracting the image-based photoplethysmograms. For example, as illustrated in FIG. 34B, by inputting the numerical values [0.5, 2] under the "[lower limit frequency and upper limit frequency] [Hz] of the band-pass filter", the operator is able to set the band of the band-pass filter to "0.5 Hz to 2.0 Hz". Further, "the number [quantity] of sections into which the screen is divided [columns, rows]" illustrated in FIG. 34B denotes an item for setting the number of sections into which the area inside each of the ROIs is divided in a mosaic formation. For example, as illustrated in FIG. 34B, by inputting the numerical values "[10, 10]" under "the number [quantity] of sections into which the screen is divided [columns, rows]", the operator is able to arrange the area inside each of the ROIs to be divided into sections of "10 (columns) by 10 (rows)" in a mosaic formation.

The "degree (3 or larger for applications) of the median filter for luminance signals" illustrated in FIG. 34B denotes an item for setting the degree of the median filter used for extracting the green signals. In this situation, as for the setting of the degree of the median filter, an arrangement is acceptable as illustrated in FIG. 34B where the median filter is not applied when the degree is smaller than three, as indicated by the wording "3 or larger for applications". For example, as illustrated in FIG. 34B, by inputting the numerical value "0" under the "degree (3 or larger for applications) of the median filter for luminance signals", the operator is able to make a setting so that the median filter is not applied. Further, the "threshold value [%] for trimmed mean values (0-50%)" illustrated in FIG. 34B denotes an item for setting a threshold value for the trimmed mean value process. For example, as illustrated in FIG. 34B, by inputting the numerical value "30" under the "threshold value [%] for trimmed mean values (0-50%)", the operator is able to make a setting so as to exclude any difference of pulse transit time values in the top "30%" and the bottom "30%" during the trimmed mean value process. The setting items illustrated in FIG. 34B are merely examples and may arbitrarily be added or deleted.

Figure 34C:
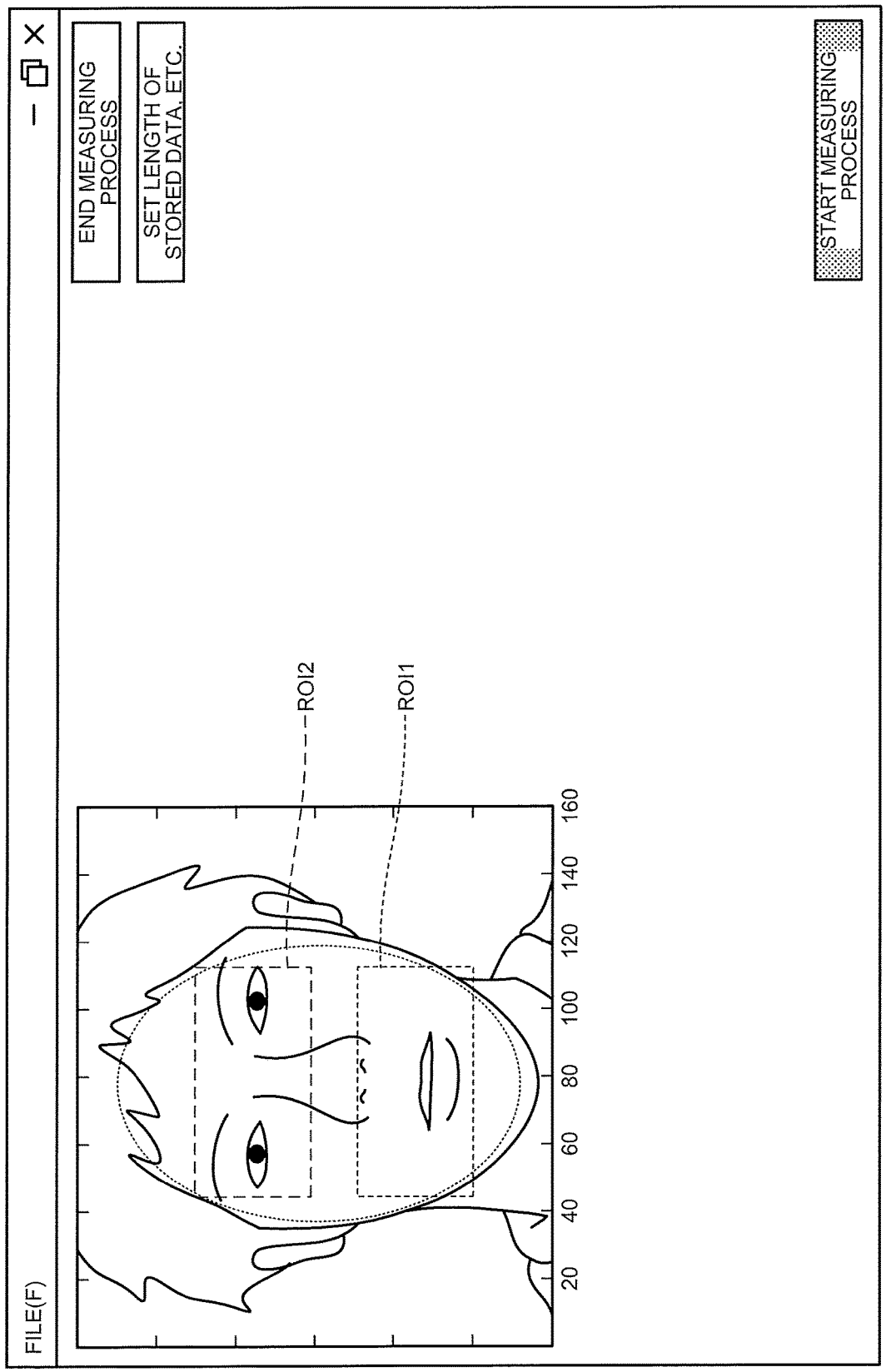
FIG. 34C is a drawing for explaining yet another example of the image-based photoplethysmogram analysis performed by the biological information measuring apparatus according to the second embodiment.

When the setting items illustrated in FIG. 34B have been input, and the "OK" button is clicked, the output controlling unit 154 causes the output unit 120a or the output apparatus 120b to output and display a screen for starting the analysis. For example, as illustrated in FIG. 34C, the output controlling unit 154 causes a measuring screen containing a picture of the subject to be displayed. In this situation, the output controlling unit 154 is also able to present to the operator whether the analysis result from the analysis to be performed is to be saved or not. For example, the output controlling unit 154 may present options as to whether the analysis result is to be saved or not. When "Yes" is selected, the output controlling unit 154 exercises control so that the analysis result is stored into the measured result storage unit 142. On the contrary, when "No" is selected, the output controlling unit 154 exercises control so that the analysis result is not saved.

Figure 34D:
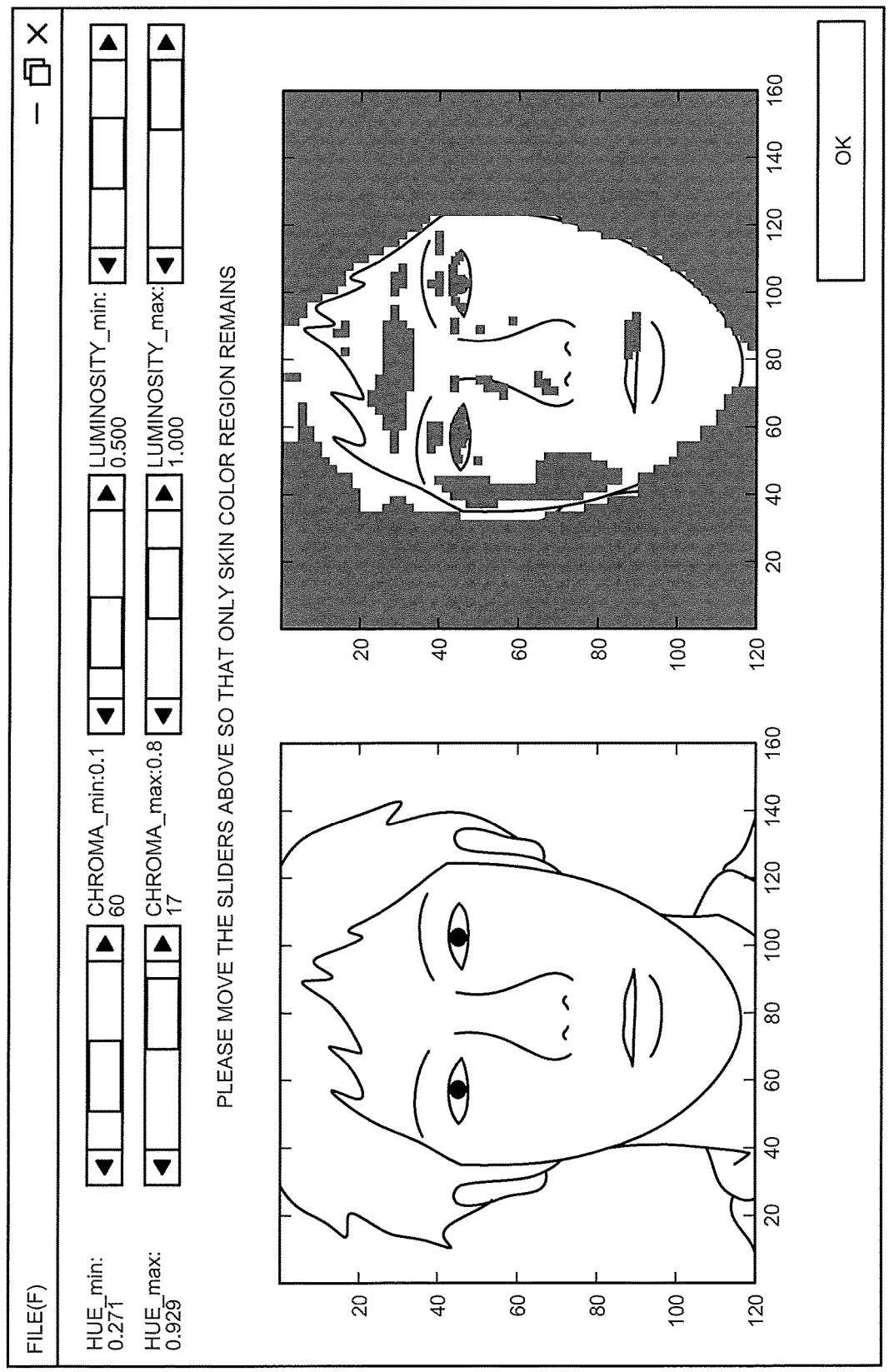
FIG. 34D is a drawing for explaining yet another example of the image-based photoplethysmogram analysis performed by the biological information measuring apparatus according to the second embodiment.

When the output controlling unit 154 causes the screen illustrated in FIG. 34C to be displayed, the ROIs are set so as to start a measuring process. For example, as illustrated in FIG. 34C, ROI 1 and ROI 2 are set in the upper and lower sections of the face region of the subject. In this situation, the ROIs set with the subject are set either automatically or manually, in accordance with the abovementioned setting of the analysis target region. When the manual setting is selected, for example, the ROIs are set in the picture illustrated in FIG. 34C. When the ROIs have been set and the "Start measuring process" button is clicked, the output controlling unit 154 causes a setting screen used for extracting the skin color region to be displayed. For example, as illustrated in FIG. 34D, the output controlling unit 154 causes a setting screen to be displayed to receive settings of maximum values and minimum values for the "hue", the "chroma", and the "luminosity" of the picture and to limit the picture only to the region in the skin color. For example, by adjusting the settings of the maximum values and the minimum values for the "hue", the "chroma", and the "luminosity" via the input unit, the operator is able to perform the process of changing the image displayed in the left section of FIG. 34D into the image displayed in the right section rendering only the region in the skin color. By using the picture processed as displayed in the right section of FIG. 34D as a processing target, the skin region extracting unit 151 is able to easily identify the pixels corresponding to the skin color in the ROIs in each of the frames.

Figure 34E:
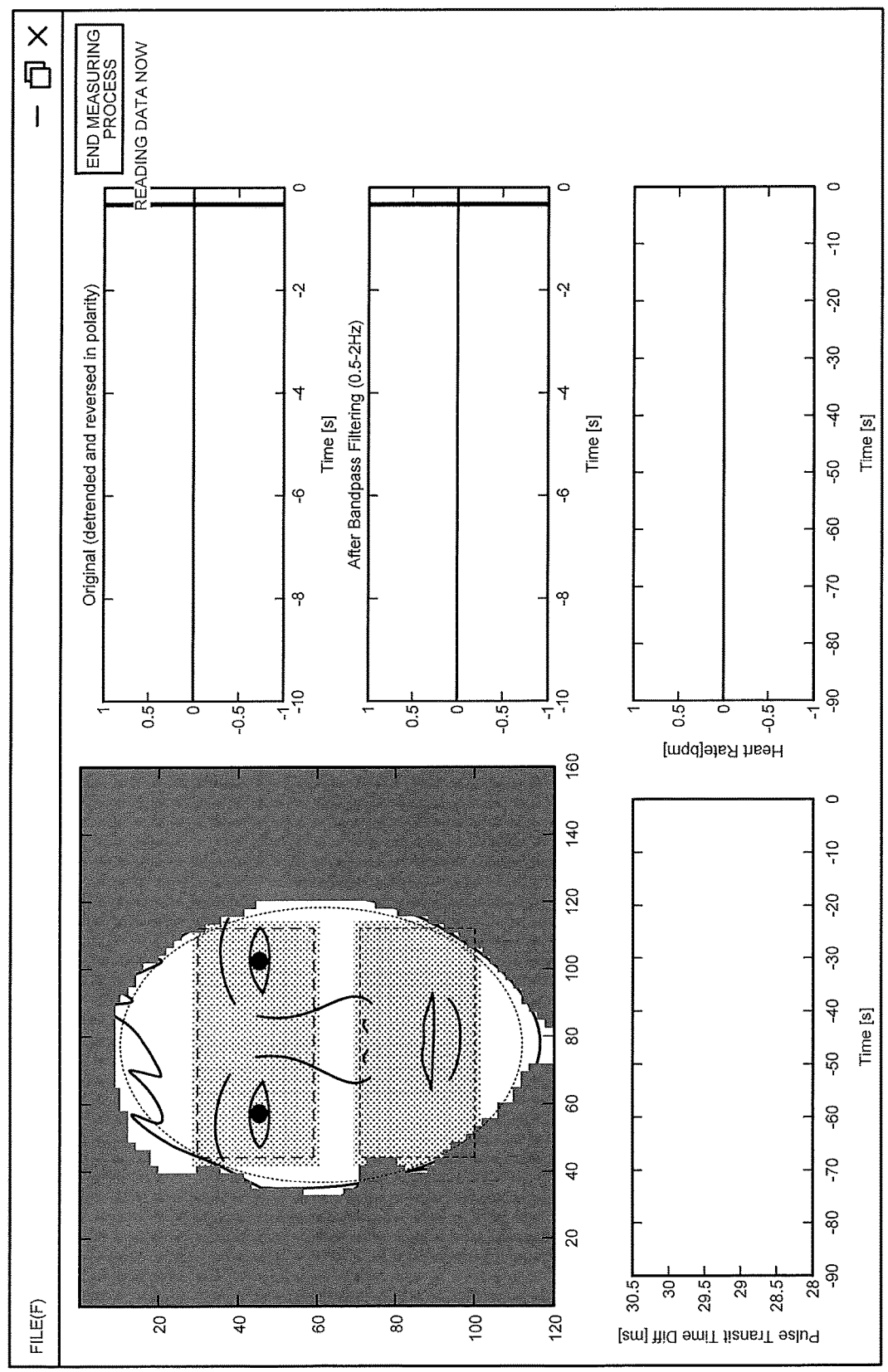
FIG. 34E is a drawing for explaining yet another example of the image-based photoplethysmogram analysis performed by the biological information measuring apparatus according to the second embodiment.

When the settings illustrated in FIG. 34D are completed and the "OK" button is clicked, the output controlling unit 154 displays an analysis screen. For example, as illustrated in FIG. 34E, the output controlling unit 154 causes an analysis screen to be displayed, the analysis screen containing information such as a picture of the subject, green signals (original), the image-based photoplethysmograms (after band-pass filtering), the heart rate, and the pulse transit time difference ("diff."). The output controlling unit 154 arranges the picture of the subject to be displayed after the process of extracting the skin color region is performed thereon, as illustrated in FIG. 34E, so that the ROIs are displayed so as to be superimposed thereon. In this situation, in the setting of the number of sections into which the screen is divided illustrated in FIG. 34B, when the setting to divide each of the ROIs into sections in a mosaic formation has been selected, each of the ROIs illustrated in FIG. 34E is analyzed while being divided into sections in a mosaic formation according to the setting. For example, in the setting illustrated in FIG. 34B, because the numerical values "[10, 10]" are input under "the number [quantity] of sections into which the screen is divided [columns, rows]", the area inside each of the ROIs is divided into sections in a mosaic information of 10 columns by 10 rows, so as to perform an analysis by using the average luminance value of each of the regions resulting from the dividing.

In this situation, when each of the ROIs is divided into sections in a mosaic formation as described above, the calculating unit 152 is able to judge whether or not the picture signal (the average luminance value) obtained from each of the regions in the mosaic formation contains information about the pulse wave or not. More specifically, the calculating unit 152 judges whether the information about the pulse wave is contained or not, by analyzing the frequency components contained in the picture signal obtained from each of the regions. A pulse wave is a signal indicating the propagation of arterial pressure wave motion generated by the contraction of the heart and reflects the state of heartbeats. For this reason, for example, the calculating unit 152 judges whether each of the picture signals contains the information about the pulse wave, by judging whether or not the picture signal obtained from each of the regions contains a frequency component of the heartbeat.

In this situation, the interval of heartbeats (e.g., RR intervals) varies slightly due to various factors. For example, when a frequency analysis is performed on the variance in the heartbeat interval, a number of frequency components are extracted. Accordingly, by judging whether each of the picture signals contains these frequency components, it is possible to judge whether or not each of the picture signals contains a pulse wave component. Thus, for example, the calculating unit 152 performs the judging process by using a standard deviation of the heartbeat frequency in the picture signals, on the basis of the notion that the heartbeat contains a number of frequency components.

Figure 34F:
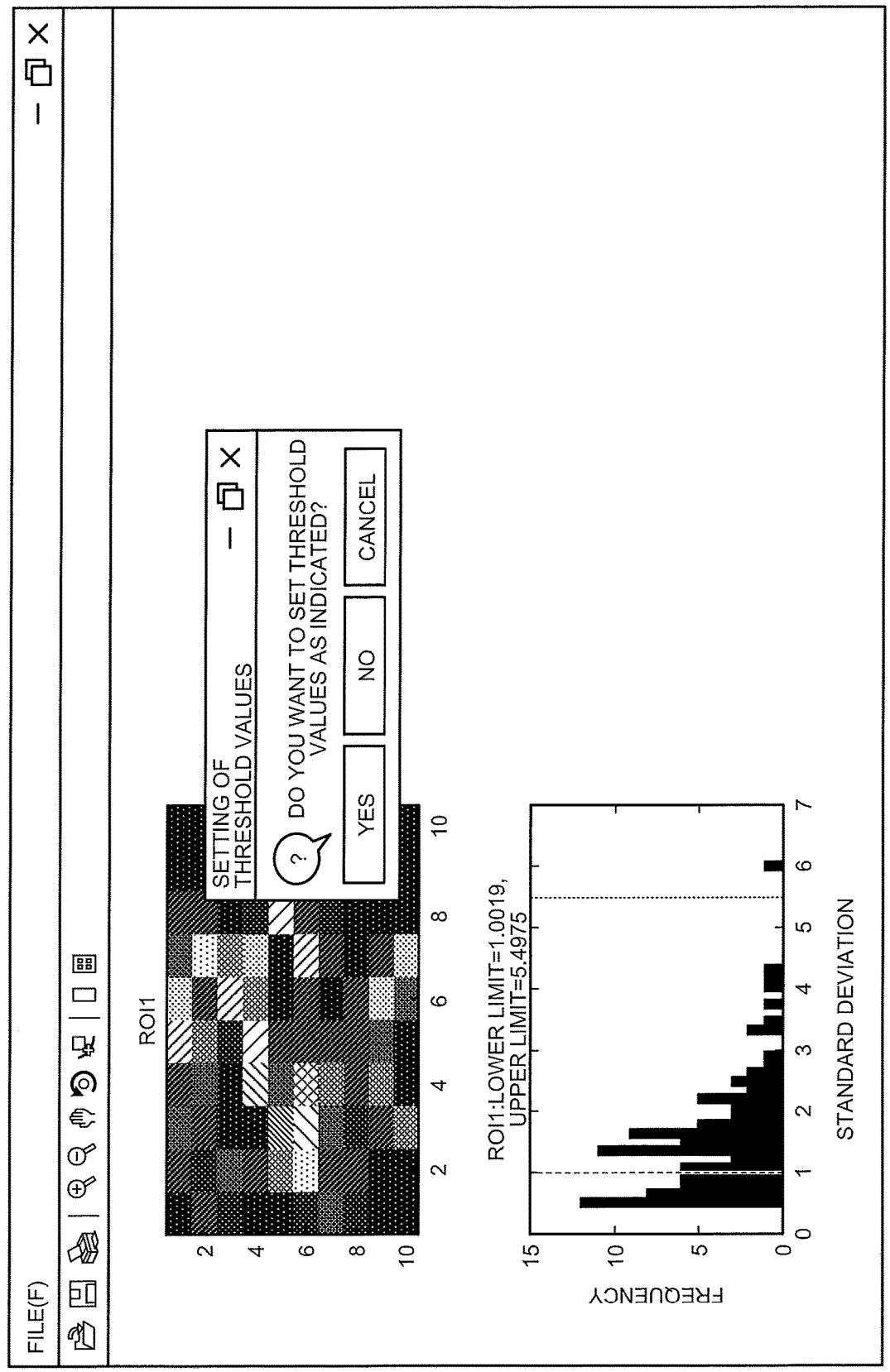
FIG. 34F is a drawing for explaining yet another example of the image-based photoplethysmogram analysis performed by the biological information measuring apparatus according to the second embodiment.

Next, an example of the judging process will be explained, with reference to FIG. 34F. FIG. 34F illustrates a drawing indicating the state of the green signal in each of the regions in ROI 1 (the ROI in the lower section of the face of the subject) divided into sections of "10 columns by 10 rows" as well as a histogram of a standard deviation of the heartbeat frequency components in the picture signal (the average luminance value) obtained from each of the regions. Although FIG. 34F illustrates the state of the green signals at one point in time, a moving image is displayed in actuality so as to display the changes in the state of the green signal in each of the regions. For example, as illustrated in FIG. 34F, the calculating unit 152 performs a frequency analysis on the picture signal obtained from each of the regions in the ROI divided into the sections in the mosaic formation and extracts a heartbeat frequency component for each region. After that, the calculating unit 152 calculates a standard deviation of the frequency components for each of the regions and performs the judging process on the basis of the calculated standard deviations.

As explained above, because heartbeats contain a number of frequency components, the standard deviation of heartbeat frequency components is large to a certain extent. For this reason, the calculating unit 152 extracts a region from which a picture signal containing the pulse wave component is obtained, by excluding the frequency components of which the standard deviation is low (in the left section of the histogram) and frequency components of which the standard deviation is too high (in the right section of the histogram), from the histogram of the standard deviation of the heartbeat frequency components. For example, as illustrated in FIG. 34F, the calculating unit 152 sets threshold values used for extracting the region to "lower limit=1.0019" and "upper limit=5.4975" so as to extract the region in which the standard deviation of the heartbeat frequency components falls within the range. With this arrangement, the calculating unit 152 makes it possible to perform the analysis with a high level of precision, by excluding the regions where the pulse wave component is weak (e.g., the region not representing the face) and the regions where the pulse wave component is too strong (e.g., a region where unexpected noise occurred) from the analysis target.

Figure 34G:
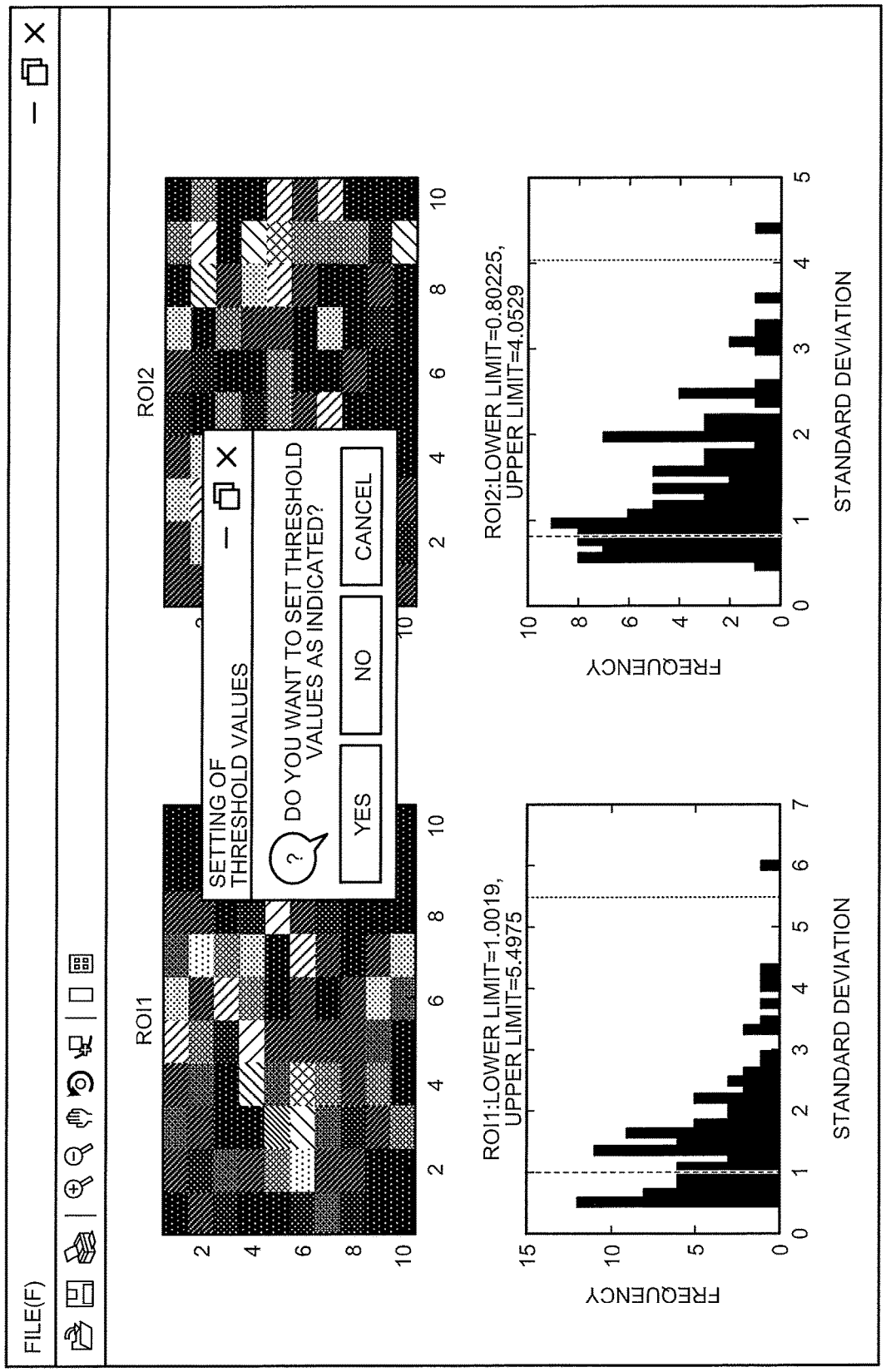
FIG. 34G is a drawing for explaining yet another example of the image-based photoplethysmogram analysis performed by the biological information measuring apparatus according to the second embodiment.

As explained above, when the calculating unit 152 has set the threshold values used for extracting the region serving as an analysis target with respect to ROI 1, the output controlling unit 154 displays, as illustrated in FIG. 34F, a window (the window saying "Do you want to set the threshold values as indicated?") to check the setting with the operator. In this situation, if the operator clicks "YES", the output controlling unit 154 causes a window to be displayed as illustrated in FIG. 34G, the window being used for performing a judging process regarding ROI 2 (the region in the upper section of the face of the subject). In the same manner as with ROI 1, the calculating unit 152 sets threshold values for the regions contained in ROI 2. In the same manner as with ROI 1, the output controlling unit 154 causes a window to be displayed so as to have the operator confirm the setting.

Figure 34H:
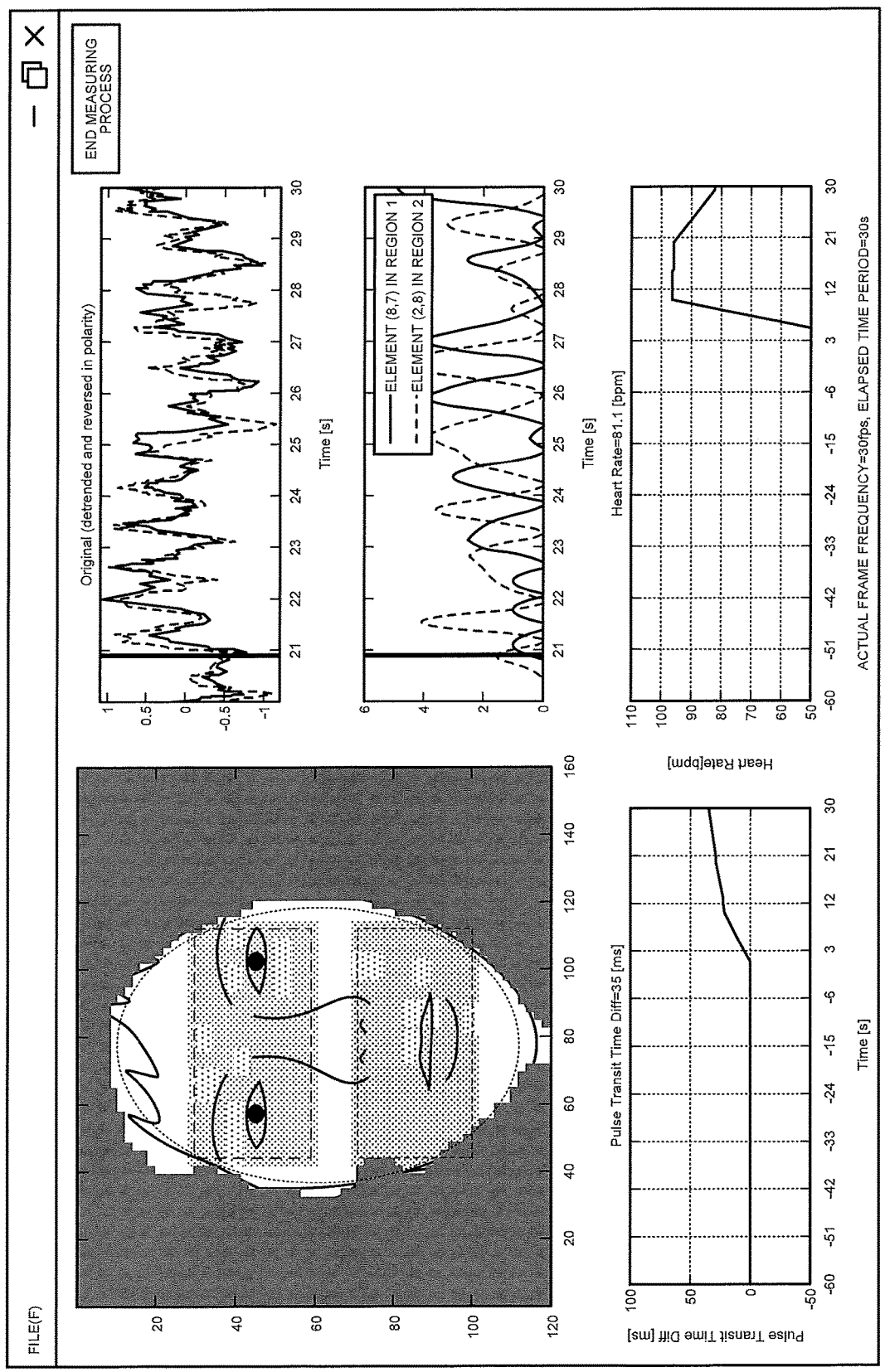
FIG. 34H is a drawing for explaining yet another example of the image-based photoplethysmogram analysis performed by the biological information measuring apparatus according to the second embodiment.

Further, when the various types of settings have been made as explained above, the analysis is started, and the analysis screen illustrated in FIG. 34E is sequentially updated. For example, as illustrated in FIG. 34H, the output controlling unit 154 causes an analysis screen to be displayed in which the following pieces of information are occasionally updated: the picture of the subject, the green signals (original), the information related to image-based photoplethysmograms of predetermined regions, the heart rate, the pulse transit time difference, and the like. In this situation, as illustrated in FIG. 34H, the output controlling unit 154 divides each of the ROIs into the sections in a mosaic formation and displays pulse wave information indicating the state of the image-based photoplethysmogram of each of the regions so as to be superimposed on the picture of the subject. In other words, with respect to each of the regions in the mosaic formation, the output controlling unit 154 generates a hue moving image expressing the luminance information of the picture signal (the green signal) in the region by using changes of hues and further displays the generated hue moving image so as to be superimposed on a moving image of the subject. As a result, it is possible to visually recognize the propagation of the pulse wave for each of the ROIs and to visually understand the state of the blood circulation.

Further, the output controlling unit 154 causes the analysis screen to display the green signals of ROI 1 and ROI 2 (the upper right section of FIG. 34H) and the information related to image-based photoplethysmograms of predetermined regions (the middle right section of FIG. 34H). In this situation, as the information related to the image-based photoplethysmograms of the predetermined regions, the output controlling unit 154 displays image-based photoplethysmograms of such regions that are extracted on the basis of the heartbeat frequency component. For example, the output controlling unit 154 calculates an average value of the standard deviations of the heartbeat frequency components for each of the ROIs. After that, the output controlling unit 154 extracts the standard deviation that is closest to the calculated average value, from among the standard deviations of the heartbeat frequency components of the regions represented by the sections in the mosaic formation. After that, the output controlling unit 154 causes the analysis screen to display the image-based photoplethysmograms of the regions from which the extracted standard deviation was calculated. The output controlling unit 154 extracts a region from each of the ROIs and causes the analysis screen to display the image-based photoplethysmograms of the extracted regions. In this situation, the image-based photoplethysmograms illustrated in the middle right section FIG. 34H are a result of a conversion that makes the minimum value "0". For example, as illustrated in FIG. 34H, the output controlling unit 154 extracts the region corresponding to "column: 8; row: 7" in ROI 1 (Region 1) and the region corresponding to "column: 2; row: 8" in ROI 2 (Region 2) by performing the process described above and causes the analysis screen to display the image-based photoplethysmogram of each of the regions.

Further, as illustrated in FIG. 34H, the output controlling unit 154 causes the analysis screen to display, with occasional updates, the state of the heart rate and the pulse transit time difference calculated by the calculating unit 152. For example, as illustrated in the lower right section of FIG. 34H, the output controlling unit 154 displays the heart rate calculated from the image-based photoplethysmogram of ROI 1. In this situation, the heart rate is calculated as a transition of the trimmed mean value in the data window in the image-based photoplethysmogram of ROI 1. Further, as illustrated in the lower left section of FIG. 34H, the output controlling unit 154 displays a difference of pulse transit time (dPTT) calculated by using the average luminance value of ROI 1 and the average luminance value of ROI 2.

In this situation, the difference of pulse transit time may be calculated by using the average luminance values of the ROIs as illustrated in FIG. 34H or may be calculated by using average luminance values of regions within the ROIs. For example, the calculating unit 152 is able to calculate a difference of pulse transit time by using an image-based photoplethysmogram of the region corresponding to "column: 8; row: 7" in ROI 1 (Region 1) and an image-based photoplethysmogram of the region corresponding to "column: 2; row: 8" in ROI 2 (Region 2). As explained above, the calculating unit 152 according to the second embodiment is configured to calculate a difference of pulse transit time on the basis of the peak time differences between the image-based photoplethysmograms of two regions. In other words, the calculating unit 152 is able to use any regions as long as it is possible to calculate the difference in the time periods required by the propagations of the pulse waves from the picture signals of the regions. That is to say, the calculating unit 152 may calculate a difference of pulse transit time by using the average luminance value of ROI 1 and the average luminance value of ROI 2.

Alternatively, the calculating unit 152 may calculate a difference of pulse transit time by using the average luminance value of one region within ROI 1 and the average luminance value of one region within ROI 2, the regions being represented by the sections into which the ROIs are divided in a mosaic formation.

Further, the calculating unit 152 also may calculate a difference of pulse transit time by using two regions in a single ROI. For example, the calculating unit 152 may calculate a difference of pulse transit time, by extracting two regions from ROI 1 divided into the sections in a mosaic formation and by using the average luminance values of the extracted two regions. Accordingly, it is not necessary to set a plurality of ROIs. For example, it is acceptable to calculate a difference of pulse transit time by setting one ROI in the entire face and dividing the set ROI into sections in a mosaic formation. By setting the ROI in this manner, it is also possible to check the state of blood pressure by measuring a fluctuation of the blood pressure on the basis of a fluctuation of the difference of pulse transit time, while observing the state of blood circulation from the hue moving image rendering the entire face. In this situation, when the picture of the face of the subject is used as an analysis target, and if "left and right" is selected in the setting of the analysis target in FIG. 34A, two regions in the single ROI are used for calculating the difference of pulse transit time.

Figure 34I:
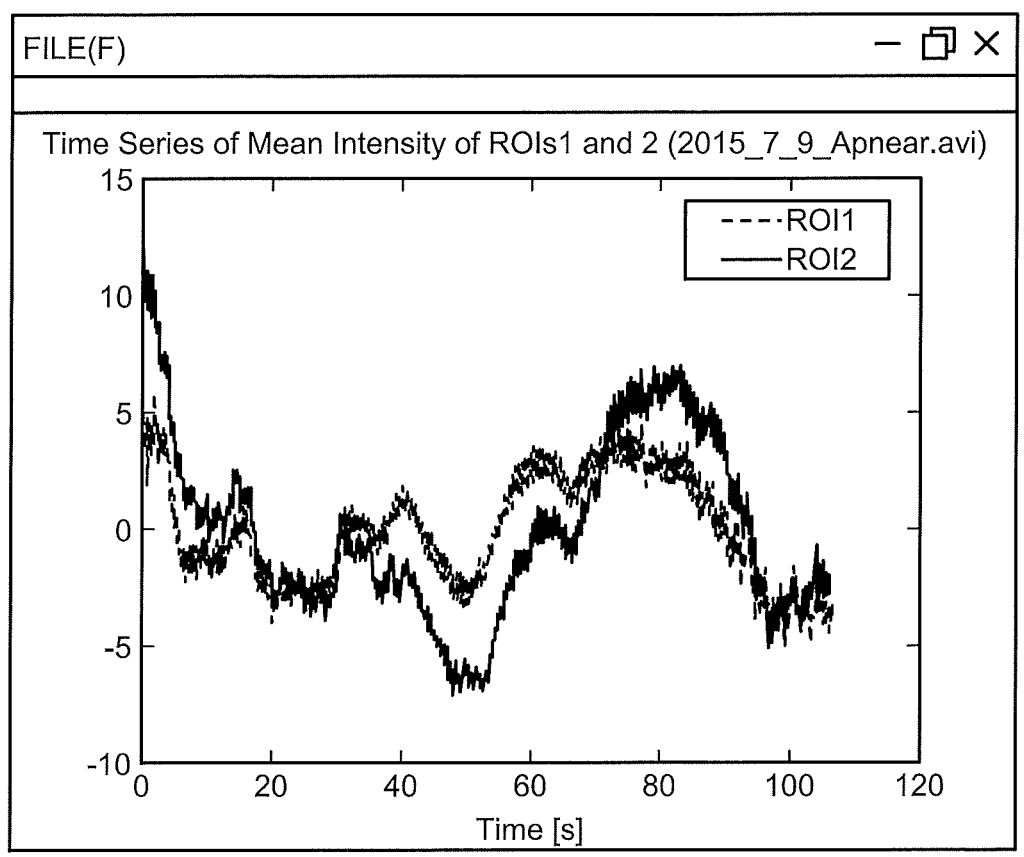
FIG. 34I is a drawing for explaining yet another example of the image-based photoplethysmogram analysis performed by the biological information measuring apparatus according to the second embodiment.
Figure 34J:
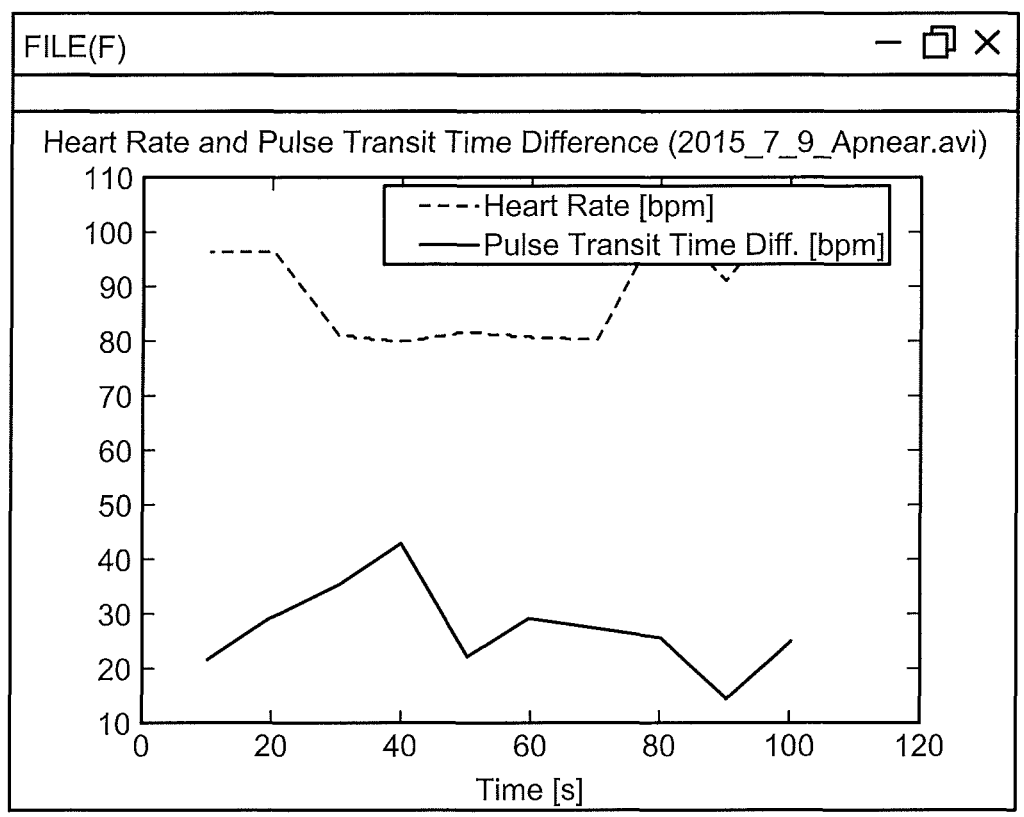
FIG. 34J is a drawing for explaining yet another example of the image-based photoplethysmogram analysis performed by the biological information measuring apparatus according to the second embodiment.

When the analysis has been performed as described above, and "End measuring process" is clicked on the analysis screen, the output controlling unit 154 causes the output unit 120*a* or the output apparatus 120*b* to output various types of information resulting from the analysis. For example, as illustrated in FIG. 34I, the output controlling unit 154 displays transitions of image-based photoplethysmograms (the average luminance values) of the ROIs. Further, as illustrated in FIG. 34J, the output controlling unit 154 displays transitions of the difference of pulse transit time and the heart rate.

When the analysis has been performed with respect to the picture signals of the subject as explained above, the measuring unit 153 measures a fluctuation of the blood pressure, on the basis of the fluctuation of the difference of pulse transit time resulting from the analysis. Further, the output controlling unit 154 causes the output unit 120*a* or the output apparatus 120*b* to output the fluctuation of the blood pressure measured by the measuring unit 153. In this situation, because the difference of pulse transit time in the above example is calculated from the two regions in the face of the subject, the measuring unit 153 measures the fluctuation of the blood pressure on the basis of the negative correlation. In other words, when the "dPTT" calculated by the calculating unit 152 increases over time, the measuring unit 153 according to the second embodiment determines that the blood pressure of the subject decreases during the time period. On the contrary, for example, when the "dPTT" calculated by the calculating unit 152 decreases over time, the measuring unit 153 determines that the blood pressure of the subject increases during the time period. In these situations, the measuring unit 153 may determine that the blood pressure decreases or increases when the amount of increase or decrease from the beginning of the measuring process has reached a predetermined percentage. Further, the measuring unit 153 according to the second embodiment is capable of performing the same process as performed by the measuring unit 153 according to the first embodiment, on the basis of the negative correlation between "dPTT" values and blood pressure values. In other words, the measuring unit 153 according to the second embodiment is capable of performing the same process as in the first embodiment, except that the correlation used as the criterion of the judgment is the negative correlation.

An example of the analyzing process according to the second embodiment has thus been explained. In the example described above, the situation is explained in which the difference of pulse transit time is calculated by using the image-based photoplethysmograms of the two ROIs set in the face of the subject (or the two regions among the sections in the mosaic formation into which the ROI is divided). However, possible embodiments are not limited to this example. It is acceptable to set ROIs in the face and in a site other than the face. In that situation, the calculating unit 152 calculates a difference of pulse transit time (dPTT) by calculating peak time differences between image-based photoplethysmograms of the face and the site other than the face. After that, the measuring unit 153 measures a fluctuation of the blood pressure of the subject, on the basis of a fluctuation of the calculated "dPTT". In this situation, when the ROIs are set in the face and a site other than the face, the measuring unit 153 measures the blood pressure, on the basis of the positive correlation between "dPTT" values and blood pressure values. In other words, as explained in the first embodiment, the measuring unit 153 determines an increase in the "dPTT" value to be an increase of the blood pressure and determines a decrease in the "dPTT" value to be a decrease of the blood pressure. When the ROIs are set in the face and a site other than the face, the calculating unit 152 may use either of the methods explained in the first and the second embodiments.

Further, it is also acceptable to set two ROIs in one or two sites other than the face. In that situation, the calculating unit 152 calculates a difference of pulse transit time (dPTT) by calculating peak time differences in image-based photoplethysmograms of the sites other than the face. After that, the measuring unit 153 measures a fluctuation of the blood pressure of the subject, on the basis of a fluctuation of the calculated "dPTT". In this situation, when two ROIs are set in one or more sites other than the face, the measuring unit 153 measures the blood pressure, on the basis of the negative correlation between "dPTT" values and blood pressure values. In other words, the measuring unit 153 determines an increase in the "dPTT" value to be a decrease of the blood pressure and determines a decrease in the "dPTT" value to be an increase of the blood pressure.

As explained above, the biological information measuring apparatus 100 according to the second embodiment measures the fluctuation of the blood pressure on the basis of the positive correlation, when using the picture signal based on the blood flow that is affected by the delay in the arrival of the pulse wave caused by an increase in the peripheral blood vessel resistance and the picture signal based on the blood flow that is not affected by the delay in the arrival of the pulse wave caused by an increase in the peripheral blood vessel resistance. Further, the biological information measuring apparatus 100 measures the fluctuation of the blood pressure on the basis of the negative correlation, when using only picture signals based on the blood flows that are not affected by the delay in the arrival of the pulse wave caused by an increase in the peripheral blood vessel resistance or only picture signals based on the blood flows that are affected by the delay in the arrival of the pulse wave caused by an increase in the peripheral blood vessel resistance. In other words, the biological information measuring apparatus 100 varies the measuring process in accordance with the sites from which the image-based photoplethysmograms are extracted.

For example, the skin region extracting unit 151 judges in which site of the subject the set ROIs are located, so that the measuring unit 153 is able to determine whether the positive correlation should be used or the negative correlation should be used on the basis of the judgment result. In one example, the skin region extracting unit 151 may identify the sites of the subject in the picture so as to judge to which sites the set ROIs correspond. Alternatively, the skin region extracting unit 151 may judge which sites are used on the basis of site information input by the operator. In that situation, for example, the output controlling unit 154 causes the setting screen illustrated in FIG. 34A to display an item used for inputting the site information, so that the input unit receives an input of the site information from the operator.

Further, when the ROIs are set in the face and a site other than the face, the biological information measuring apparatus 100 according to the second embodiment is able to use the method described in the first embodiment, besides the method explained above by which the peak time differences are calculated. Accordingly, for example, the output controlling unit 154 may cause the setting screen illustrated in FIG. 34A to display an item used for setting a blood pressure measuring method, so that the input unit receives an input of the site information from the operator.

Further, the biological information measuring apparatus 100 according to the second embodiment is applicable to other various usages, besides the usages explained with reference to FIGS. 34A to 34J. In other words, the biological information measuring apparatus 100 according to the second embodiment is applicable to the various usages explained in the first embodiment. For example, the biological information measuring apparatus 100 is capable of analyzing the picture signals obtained by imaging the subject reflected on the mirror and outputting an analysis result for the subject reflected on the mirror. Further, for example, the biological information measuring apparatus 100 is capable of analyzing the picture signals of the subject taken by a camera provided for a mobile terminal and outputting an analysis result to a display unit of the mobile terminal.

Further, for example, the biological information measuring apparatus 100 is capable of analyzing the picture signals obtained by imaging the subject who is operating machinery and outputting an analysis result for the subject operating the machinery. Further, for example, the biological information measuring apparatus 100 is capable of analyzing the picture signals obtained by imaging the subject who is observed via a head-mounted display device and outputting an analysis result for an observer who is wearing the display device. Further, for example, the biological information measuring apparatus 100 is capable of outputting an analysis result related to the subject for an observer who is observing the subject. Further, for example, the biological information measuring apparatus 100 is capable of analyzing the picture signals of the subject taken by a camera installed on an unmanned aircraft and outputting an analysis result for an observer who is observing the subject.

Figure 35:
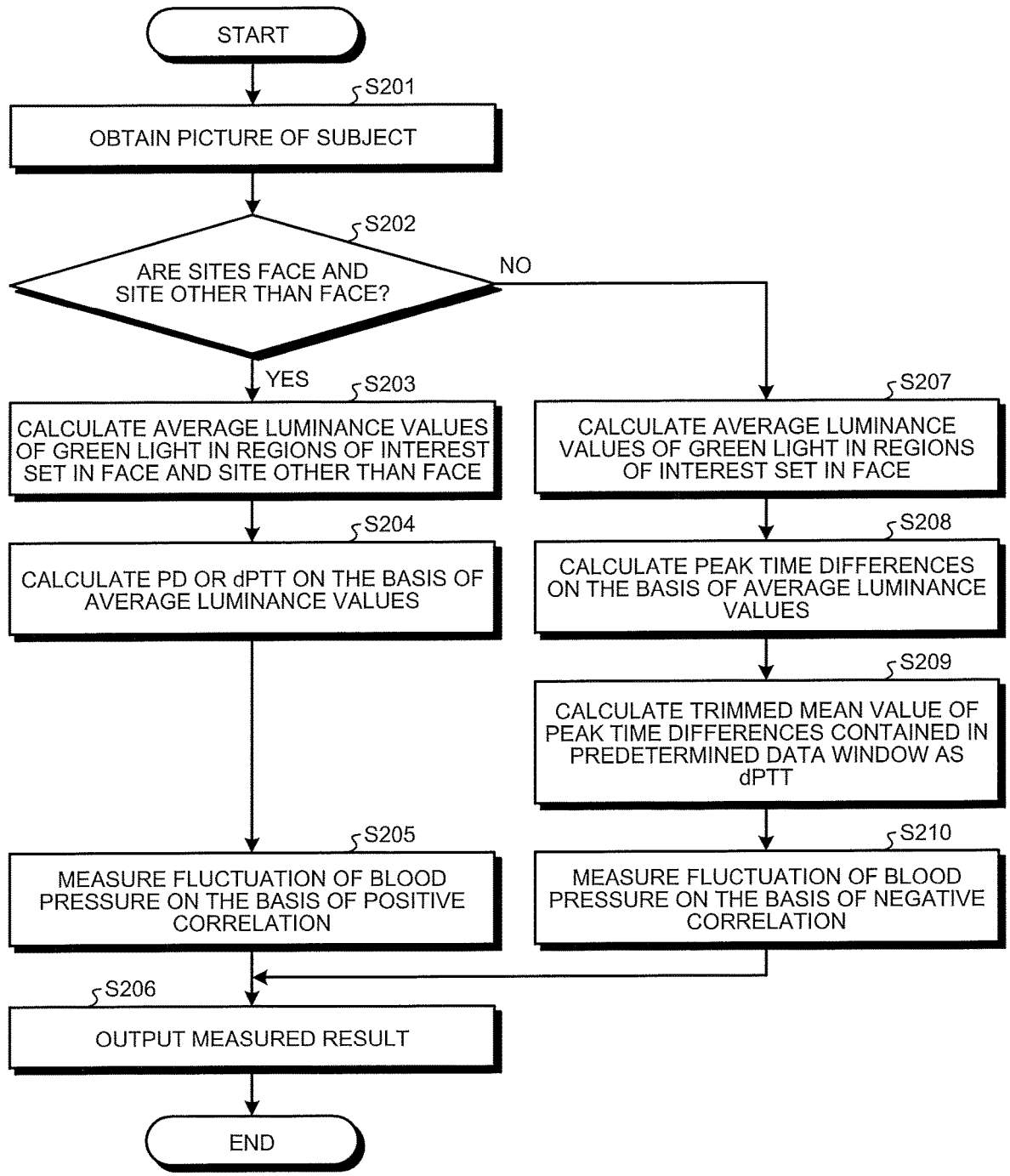
FIG. 35 is a flowchart of a processing procedure performed by the biological information measuring apparatus according to the second embodiment.

Next, a flow in a process performed by the biological information measuring apparatus 100 according to the second embodiment will be explained. FIG. 35 is a flowchart of a processing procedure performed by the biological information measuring apparatus 100 according to the second embodiment. As illustrated in FIG. 35, in the biological information measuring apparatus 100, either the picture obtaining unit 110a or the picture obtaining apparatus 110b obtains a picture of the subject (step S201). Further, the skin region extracting unit 151 judges whether the sites in which ROIs are set are the face and a site other than the face (step S202). When the sites in which the ROIs are set are the face and a site other than the face (step S202: Yes), the biological information measuring apparatus 100 proceeds to the process at steps S203 to S205. On the contrary, when the sites in which the ROIs are set are not the face and a site other than the face (step S202: No), the biological information measuring apparatus 100 proceeds to the process at steps S207 to S210.

At steps S203 to S205, the calculating unit 152 calculates average luminance values of the green light in the ROIs set in the face and the site other than the face (step S203) and further calculates either an instantaneous phase difference "PD" or a difference of pulse transit time "dPTT", on the basis of the average luminance values (step S204). After that, the measuring unit 153 measures a fluctuation of the blood pressure on the basis of the positive correlation (step S205).

At steps S207 to S210, the calculating unit 152 calculates average luminance values of the green light in the ROIs set in the face (step S207) and further calculates peak time differences on the basis of the average luminance values (step S208). After that, the calculating unit 153 calculates a trimmed mean value of the peak time differences contained in a predetermined data window as a difference of pulse transit time "dPTT" (step S209). Subsequently, the measuring unit 153 measures a fluctuation of the blood pressure on the basis of the negative correlation (step S210).

When either the process at steps S203 to S205 or the process at steps S207 to S210 is completed, the output controlling unit 154 causes either the output unit 120a or the output apparatus 120b to output a measured result (step S206).

As explained above, according to the second embodiment, the calculating unit 152 calculates the information related to the pulse wave of the subject, on the basis of the luminance information of the picture signals of the subject. The measuring unit 153 measures the fluctuation of the blood pressure of the subject based on the increase or the decrease in the information related to the pulse wave, in accordance with the sites of the subject from which the picture signals were obtained. Consequently, the biological information measuring apparatus 100 according to the second embodiment makes it possible to measure the fluctuation of the blood pressure in accordance with the characteristics of the blood flows.

Further, according to the second embodiment, the skin region extracting unit 151 extracts the luminance values of the green light contained in the picture signals of the plurality of regions of the subject. The calculating unit 152 calculates the time difference between the predetermined feature points in the extracted luminance values of the green light in the picture signals, as the difference of pulse transit time. The measuring unit 153 measures the fluctuation of the blood pressure of the subject on the basis of the increase or the decrease in the difference of pulse transit time. Consequently, the biological information measuring apparatus 100 according to the second embodiment makes it possible to measure the fluctuation of the blood pressure by using the various sites.

Further, according to the second embodiment, the calculating unit 152 calculates the trimmed mean value of the time differences between the predetermined feature points during the predetermined time period, as the difference of pulse transit time. Consequently, the biological information measuring apparatus 100 according to the second embodiment makes it possible to calculate the difference of pulse transit time with a high level of precision, even when the distance between the ROIs is short.

Further, according to the second embodiment, when the picture signals from which the difference of pulse transit time is calculated are obtained from the face of the subject, the measuring unit 153 measures an increase in the difference of pulse transit time as a decreasing fluctuation of the blood pressure and measures a decrease in the difference of pulse transit time as an increasing fluctuation of the blood pressure. Consequently, the biological information measuring apparatus 100 according to the second embodiment makes it possible to measure the fluctuation of the blood pressure while the characteristics of the blood flows are taken into consideration.

Further, according to the second embodiment, the output controlling unit 154 generates the hue moving image expressing the luminance information of the picture signals of the plurality of regions of the subject by using the changes of hues and further displays the generated hue moving image so as to be superimposed on a moving image of the subject. Consequently, the biological information measuring apparatus 100 according to the second embodiment makes it possible to easily understand the state of the blood circulation of the subject visually.

Third Embodiment

Figure 36:
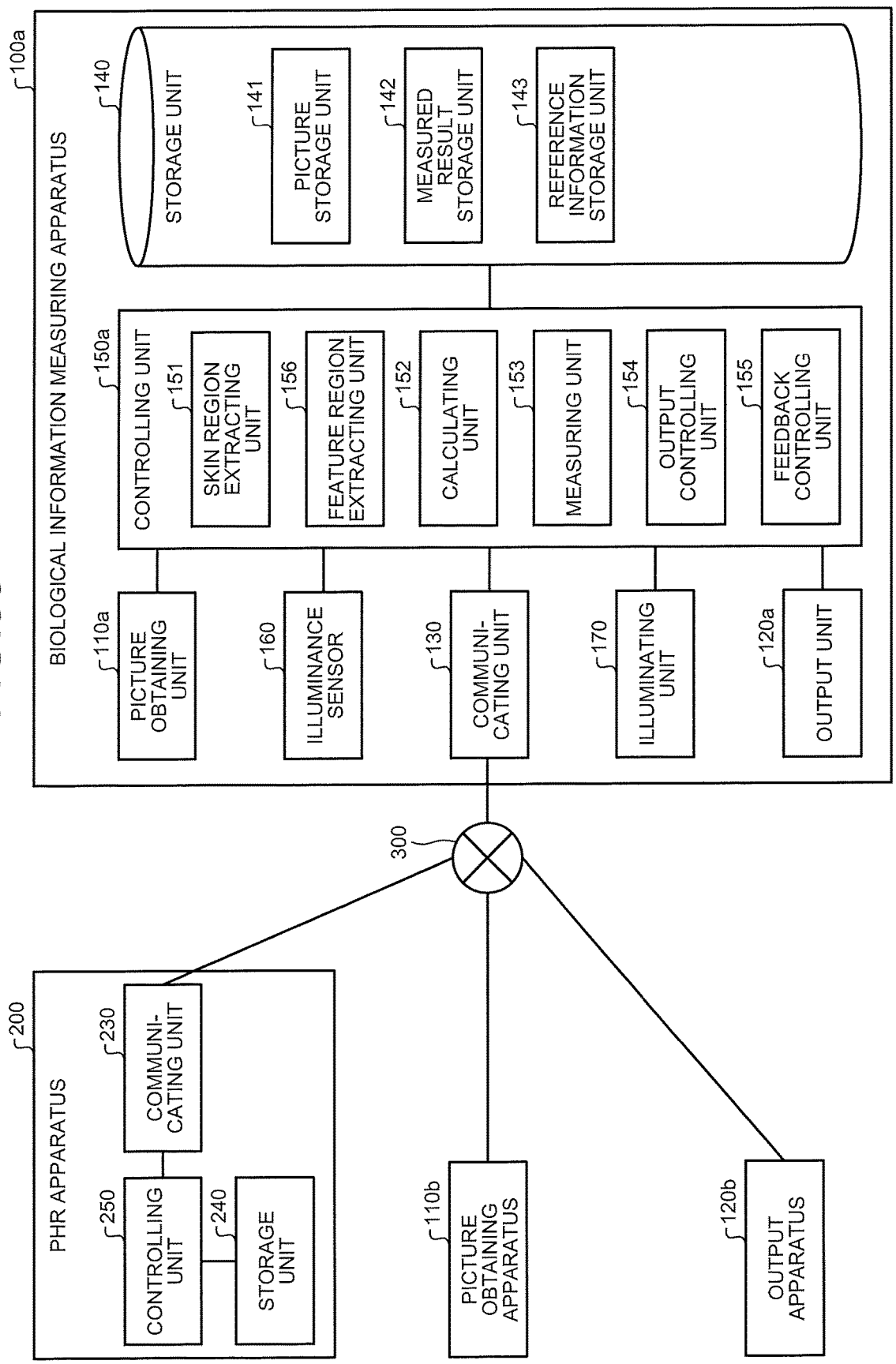
FIG. 36 is a functional block diagram of an exemplary configuration of a biological information measuring apparatus according to a third embodiment.

In the first and the second embodiments described above, the example is explained in which the fluctuation of the blood pressure is measured by setting the plurality of ROIs (or the plurality of regions) and extracting the image-based photoplethysmogram from each of the picture signals. In a third embodiment, an example will be explained in which the moving (the propagation) of a pulse wave is detected from a picture of the subject, so as to calculate a difference of pulse transit time from the detected pulse wave. FIG. 36 is a functional block diagram of an exemplary configuration of a biological information measuring apparatus 100a according to the third embodiment. The biological information measuring apparatus 100a according to the third embodiment is different from the biological information measuring apparatus 100 according to the second embodiment for newly having a feature region extracting unit 156 included in a controlling unit 150a and for the contents of processes performed by the calculating unit 152. The third embodiment will be explained below, while a focus is placed on the differences.

The feature region extracting unit 156 is configured to extract a feature region in a picture of the subject, on the basis of luminance information of a picture signal of the subject. More specifically, the feature region extracting unit 156 extracts a region exhibiting predetermined luminance information in the picture of the subject, as the feature region. For example, the feature region extracting unit 156 extracts a region in which the image-based photoplethysmogram is in a predetermined state (e.g., a region in which the image-based photoplethysmogram has an extreme value (i.e., a peaking value)) in the picture of the subject. In this situation, the feature region extracting unit 156 extracts the feature region from at least two frames in the picture of the subject. In other words, with respect to the plurality of frames contained in the picture, the feature region extracting unit 156 extracts an image-based photoplethysmogram from each of the frames. After that, the feature region extracting unit 156 extracts two or more frames each containing the region in which the image-based photoplethysmogram is in the predetermined state (e.g., a region in which the image-based photoplethysmogram has a peaking value).

The calculating unit 152 according to the third embodiment is configured to calculate a difference of pulse transit time, on the basis of a result of a tracking process performed on the feature region. More specifically, the calculating unit 152 calculates a moving amount per unit time period with respect to the region exhibiting the predetermined luminance information in the picture of the subject, as the difference of pulse transit time. In other words, the calculating unit 152 calculates the moving amount per unit time period with respect to the region extracted by the feature region extracting unit 156, as the difference of pulse transit time. For example, the calculating unit 152 calculates the moving amount per unit time period with respect to the region in which the image-based photoplethysmogram has a peaking value.

Figure 37:
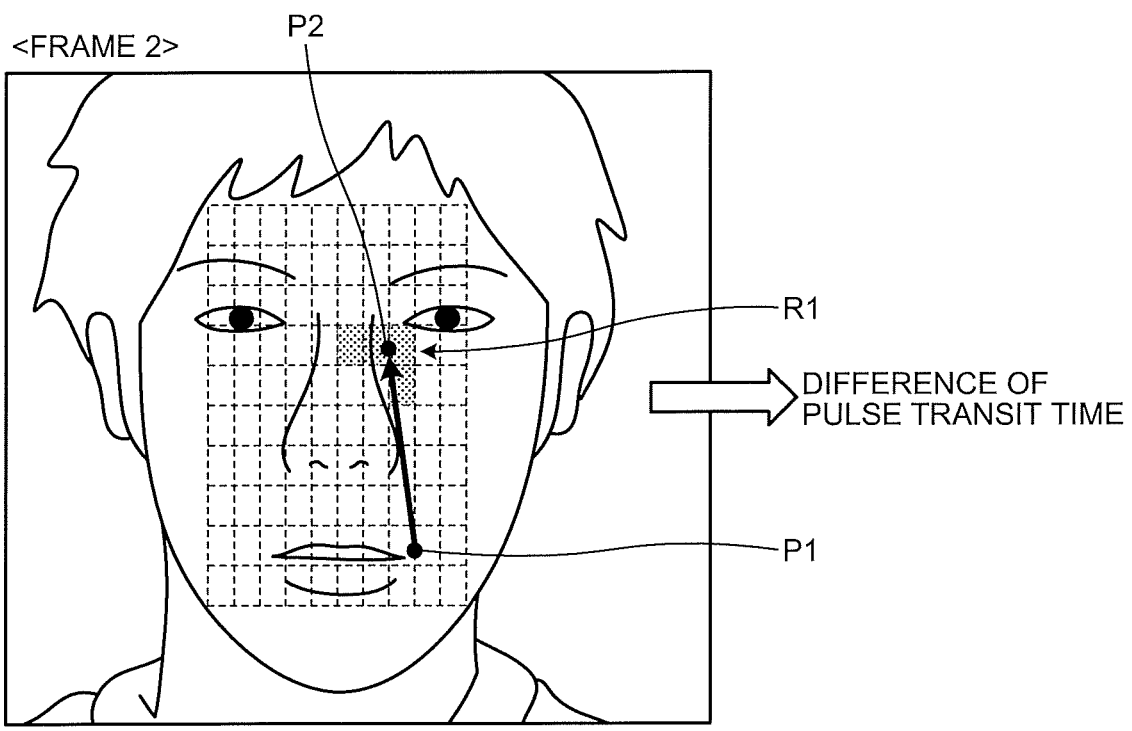
FIG. 37 is a drawing for explaining an example of a calculation of a difference of pulse transit time performed by the biological information measuring apparatus according to the third embodiment.

FIG. 37 is a drawing for explaining an example of the calculation of the difference of pulse transit time performed by the biological information measuring apparatus 100a according to the third embodiment. For example, as illustrated in FIG. 37, the feature region extracting unit 156 extracts a region R1 where the image-based photoplethysmogram has a peak in the picture of the subject. In this situation, as illustrated in FIG. 37, the feature region extracting unit 156 divides the face region in the picture of the subject into regions in a mosaic formation. After that, the feature region extracting unit 156 extracts an image-based photoplethysmogram (an average luminance value) for each of the regions. Further, the feature region extracting unit 156 extracts two or more frames each containing a region in which the image-based photoplethysmogram has a peak, from among the plurality of frames contained in the picture. For example, as illustrated in FIG. 37, the feature region extracting unit 156 extracts "frame 1" and "frame 2" each including the region R1 in which the image-based photoplethysmogram has a peak, from among the plurality of frames structuring the picture of the subject.

The calculating unit 152 calculates a moving amount per unit time period with respect to the region R1 extracted by the feature region extracting unit 156. For example, as illustrated in FIG. 37, the calculating unit 152 calculates the moving amount per unit time period with respect to the region R1 by using frame 1 and frame 2. In this situation, the calculating unit 152 calculates a position corresponding to the average luminance value in the region R1 and further calculates the moving amount of the calculated position. In other words, the calculating unit 152 sets an average position in the region R1 exhibiting a peak of the image-based photoplethysmogram. In one example, as illustrated in FIG. 37, the calculating unit 152 calculates a gravity point P1 of the region R1 in frame 1 and a gravity point P2 of the region R1 in frame 2 and further calculates the moving amount of the calculated gravity points between the frames. Further, the calculating unit 152 calculates the time difference between frame 1 and frame 2 on the basis of the framerate of the picture and calculates the moving amount of the gravity point per unit time period by using the calculated time difference and the moving amount of the gravity point. In other words, the calculating unit 152 calculates a propagation velocity of the pulse wave.

As explained above, a difference of pulse transit time (dPTT) between regions that have mutually-the-same blood flow characteristics has a negative correlation with blood pressure values. In other words, when the blood pressure increases, the propagation velocity of the pulse wave increases (i.e., the difference of pulse transit time decreases). On the contrary, when the blood pressure decreases, the propagation velocity of the pulse wave decreases (i.e., the difference of pulse transit time increases). As explained herein, the propagation velocity of a pulse wave can express a difference of pulse transit time. Accordingly, the measuring unit 153 is capable of measuring a fluctuation of the blood pressure, on the basis of the propagation velocity of the pulse wave calculated by the calculating unit 152. For example, when the propagation velocity of a pulse wave has increased, the measuring unit 153 determines that the blood pressure has increased. On the contrary, when the propagation velocity of a pulse wave has decreased, the measuring unit 153 determines that the blood pressure has decreased.

For example, from the plurality of frames structuring the picture of the subject, the feature region extracting unit 156 sequentially extracts a pair made up of a frame containing a pre-moving feature region and a frame containing a post-moving feature region. As explained above, because the propagation velocity of a pulse wave in general is "approximately 1 m/s", when a framerate is given, it is possible to predict how much a pulse wave propagates per frame. On the basis of the framerate of the picture, the feature region extracting unit 156 extracts the pair made up of the frame containing the pre-moving feature region and the frame containing the post-moving feature region, from among the plurality of frames arranged in a time series. The feature region extracting unit 156 sequentially extracts pairs of frames as described above, from among the plurality of frames structuring the picture and sequentially transmits the extracted pairs of frames to the calculating unit 152.

From the pairs of frames sequentially received from the feature region extracting unit 156, the calculating unit 152 sequentially calculates propagation velocity values of the pulse wave. The measuring unit 153 measures a fluctuation of the blood pressure on the basis of a fluctuation of the propagation velocity values of the pulse wave sequentially calculated by the calculating unit 152. For example, when the propagation velocity has increased, the measuring unit 153 determines that the blood pressure has increased. On the contrary, when the propagation velocity has decreased, the measuring unit 153 determines that the blood pressure has decreased.

Further, the measuring unit 153 is capable of not only measuring the blood pressure on the basis of the fluctuation of the propagation velocity values calculated from the pairs of frames, but also measuring a fluctuation of the blood pressure on the basis of a comparison with a predetermined value. In other words, the measuring unit 153 is also capable of measuring the fluctuation of the blood pressure by comparing the propagation velocity of the pulse wave calculated by the calculating unit 152, with a velocity that is set in advance. In one example, the propagation velocity of the pulse wave is calculated as described above, on the basis of the picture signal taken while the blood pressure is being measured. In addition, correspondence information is generated and stored into the reference information storage unit 143, the correspondence information keeping calculated propagation velocity values of the pulse wave in correspondence with actual blood pressure values measured. By referring to the correspondence information stored in the reference information storage unit 143, the measuring unit 153 measures the fluctuation of the blood pressure on the basis of the propagation velocity of the pulse wave calculated by the calculating unit 152. In this situation, the correspondence information may be generated in advance for each subject.

The example described above is merely an example, and possible embodiments are not limited to this example. For example, the feature region does not necessarily have to be a region in which the image-based photoplethysmogram has a peak, but may be a region in which the image-based photoplethysmogram has a valley. Further, for example, the feature region does not necessarily have to be a region exhibiting a peak or a valley. The feature region may be a region in which the luminance value is equal to or larger than a first threshold value or is equal to or smaller than a second threshold value. Further, the picture serving as the processing target does not necessarily have to be a picture of the face of the subject. It is acceptable to use a picture taken of another site. For example, it is acceptable to use a picture of an arm of the subject. Further, in the description above, the example is explained in which the gravity point of the feature region is calculated, so as to calculate the moving amount of the extracted gravity point. However, possible embodiments are not limited to this example. It is acceptable to calculate a moving amount on the basis of a predetermined position in the region.

When the measuring unit 153 has measured the fluctuation of the blood pressure as explained above, the output controlling unit 154 according to the third embodiment causes the output unit 120a or the output apparatus 120b to output the measured result. Further, the output controlling unit 154 is capable of causing the output unit 120a or the output apparatus 120b to output not only the measured result of the blood pressure, but also various analysis results. In other words, the output controlling unit 154 is configured to cause various types of analysis results to be displayed, in the same manner as in the first and the second embodiments. In this situation, as illustrated in FIG. 37, when a ROI is set in the entire face region of the subject, and the ROI is divided into regions in a mosaic formation, the output controlling unit 154 is capable of displaying a hue moving image expressing the luminance information of the picture signal (the green signal) of each of the regions by using changes of hues in a superimposed manner. Further, the output controlling unit 154 is also capable of displaying a hue moving image in which only the feature region of the image-based photoplethysmogram is rendered in a predetermined color. In one example, the output controlling unit 154 is capable of displaying a hue moving image indicating only such regions that exhibit a peak of the image-based photoplethysmogram, only such regions that exhibit a valley, only such regions at a stage of transitioning from a valley to a peak, or only such regions at a stage of transitioning from a peak to a valley.

Figure 38:
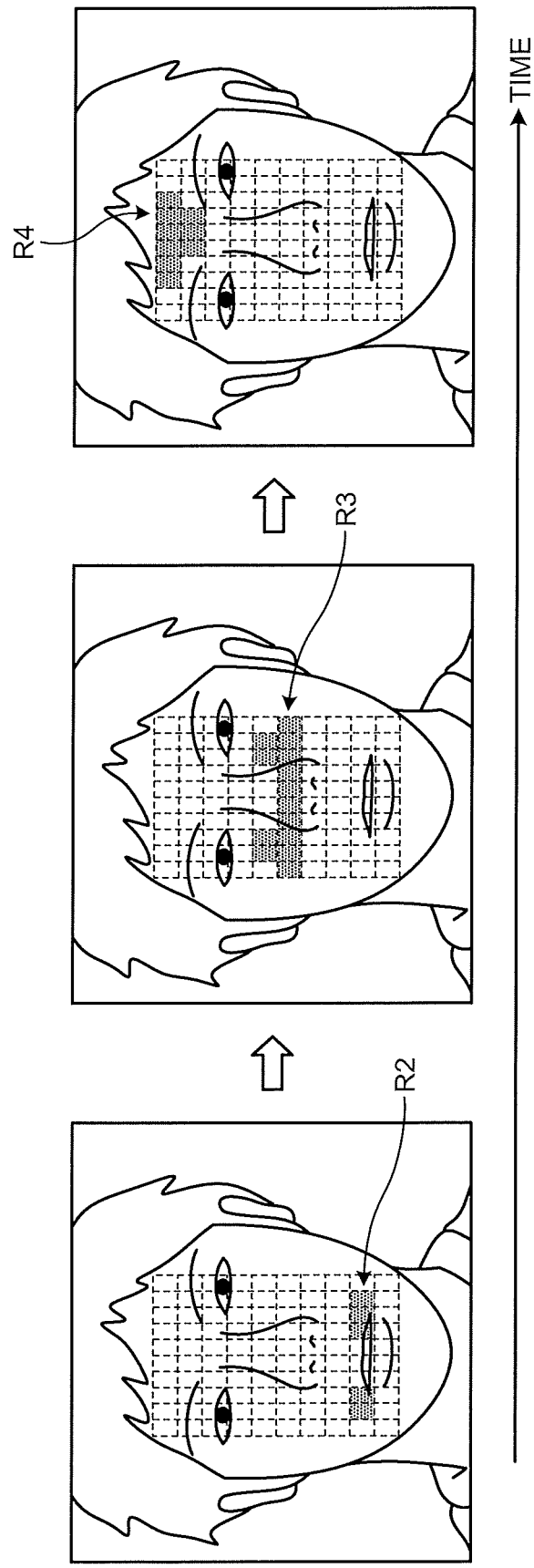
FIG. 38 is a drawing of examples of a hue moving image according to the third embodiment.

FIG. 38 is a drawing of examples of a hue moving image according to the third embodiment. For example, the output controlling unit 154 extracts regions each exhibiting a peak of the image-based photoplethysmogram from the frames structuring the picture. For example, as illustrated in FIG. 38, the output controlling unit 154 extracts regions R2, R3, and R4 each exhibiting a peak, from among the frames of the picture. Further, the output controlling unit 154 displays a hue moving image in which these regions are rendered in mutually-the-same hue, so as to be superimposed on the picture of the subject. As a result, as illustrated in FIG. 38, the observer is able to observe the manner in which the regions each exhibiting a peak move across the face of the subject as time elapses. In other words, the observer is able to observe the manner in which the pulse wave propagates in the image-based photoplethysmogram in an easy-to-understand manner and is thus able to easily understand the state of the blood circulation of the subject.

The biological information measuring apparatus 100a according to the third embodiment has thus been explained. The biological information measuring apparatus 100a according to the third embodiment is applicable to the various usages explained in the first and the second embodiments. For example, it is possible to cause the biological information measuring apparatus 100a to similarly perform the analyzing process by using the various windows explained in the second embodiment. In other words, the third embodiment may be carried out as being incorporated into the setting screens or the analysis screens explained in the second embodiment. Further, the biological information measuring apparatus 100a is capable of analyzing the picture signal obtained by imaging the subject who is reflected on a mirror and outputting an analysis result for the subject reflected on the mirror. Further, for example, the biological information measuring apparatus 100a is capable of analyzing the picture signal of the subject taken by a camera provided for a mobile terminal and outputting an analysis result to a display unit of the mobile terminal.

Further, for example, the biological information measuring apparatus 100a is capable of analyzing the picture signal obtained by imaging the subject who is operating machinery and outputting an analysis result for the subject operating the machinery. Further, for example, the biological information measuring apparatus 100a is capable of analyzing the picture signal obtained by imaging the subject who is observed via a head-mounted display device and outputting an analysis result for the observer who is wearing the display device. Further, for example, the biological information measuring apparatus 100a is capable of outputting an analysis result related to the subject for an observer who is observing the subject. Further, for example, the biological information measuring apparatus 100a is capable of analyzing the picture signal of the subject taken by a camera installed on an unmanned aircraft and outputting an analysis result for an observer who is observing the subject.

Figure 39:
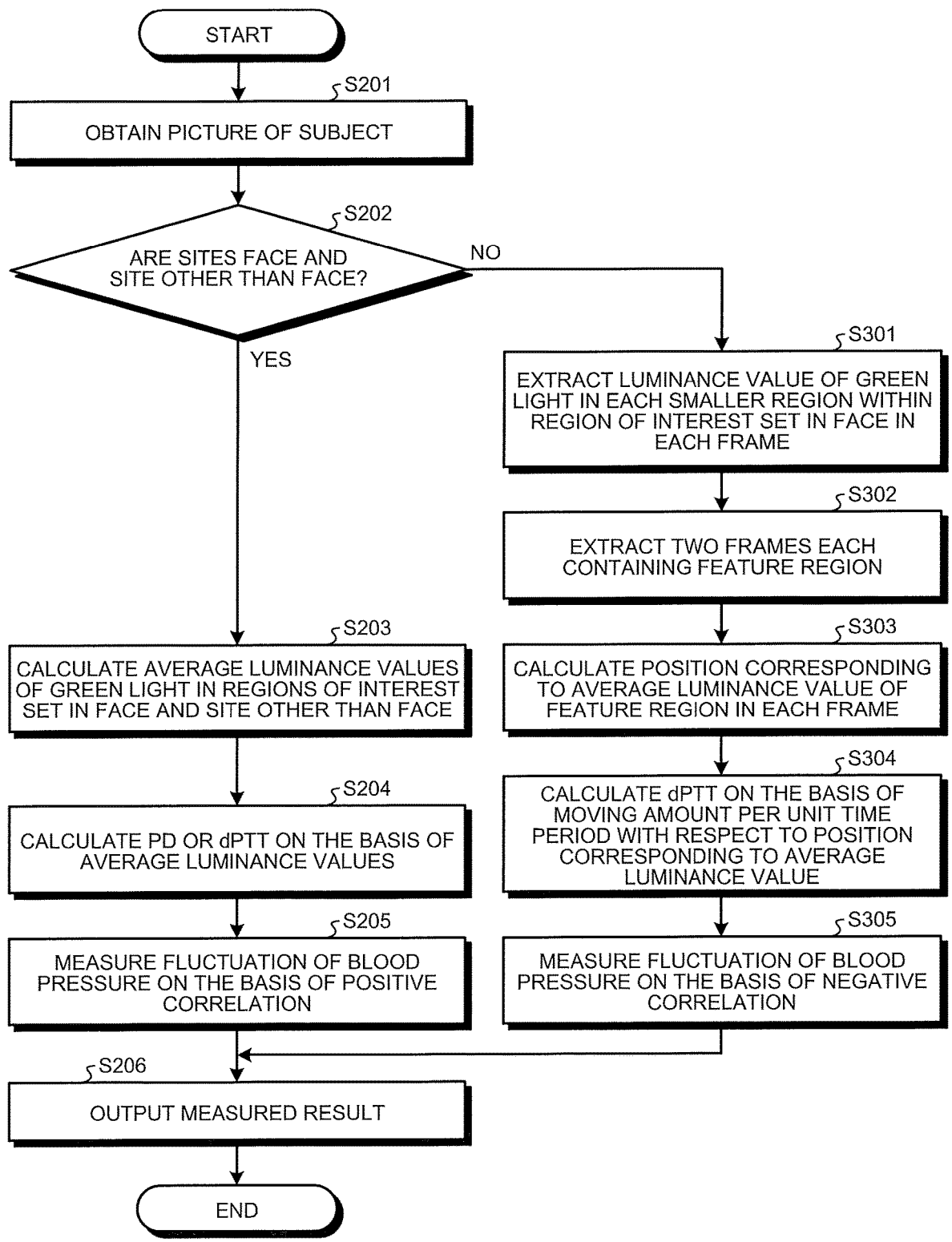
FIG. 39 is a flowchart of a processing procedure performed by the biological information measuring apparatus according to the third embodiment.

Next, a flow in a process performed by the biological information measuring apparatus 100a according to the third embodiment will be explained. FIG. 39 is a flowchart of a processing procedure performed by the biological information measuring apparatus 100a according to the third embodiment. As illustrated in FIG. 39, in the biological information measuring apparatus 100a, either the picture obtaining unit 110a or the picture obtaining apparatus 110b obtains a picture of the subject (step S201). Further, the skin region extracting unit 151 judges whether the sites in which ROIs are set are the face and a site other than the face (step S202). When the sites in which the ROIs are set are the face and a site other than the face (step S202: Yes), the biological information measuring apparatus 100*a* proceeds to the process at steps S203 to S205. On the contrary, when the sites in which the ROIs are set are not the face and a site other than the face (step S202: No), the biological information measuring apparatus 100*a* proceeds to the process at steps S301 to S305. The process at steps S202 to S205 is the same as that explained in the second embodiment.

At steps S301 to S305, in each of the frames structuring the picture, the feature region extracting unit 156 extracts the luminance value of the green light in each of the smaller regions in the ROI set in the face (step S301). Further, the feature region extracting unit 156 extracts two frames each containing a feature region (step S302). After that, the calculating unit 152 calculates a position corresponding to the average luminance value of the feature region in each of the frames (step S303) and calculates a dPTT on the basis of a moving amount per unit time period with respect to the position corresponding to the average luminance value (step S304). Subsequently, the measuring unit 153 measures a fluctuation of the blood pressure on the basis of the negative correlation (step S305).

When either the process at steps S203 to S205 or the process at steps S301 to S305 is completed, the output controlling unit 154 causes either the output unit 120*a* or the output apparatus 120*b* to output a measured result (step S206).

As explained above, according to the third embodiment, the feature region extracting unit 156 extracts the feature region in the picture of the subject, on the basis of the luminance information of the picture signal of the subject. The calculating unit 152 calculates the difference of pulse transit time, on the basis of the result of the tracking process performed on the feature region. The measuring unit 153 measures the fluctuation of the blood pressure of the subject, on the basis of the increase or the decrease in the difference of pulse transit time. Consequently, the biological information measuring apparatus 100*a* according to third embodiment makes it possible to measure the fluctuation of the blood pressure, without setting a plurality of ROIs.

Further, according to the third embodiment, the feature region extracting unit 156 extracts the region exhibiting the predetermined luminance information in the picture of the subject, as the feature region. The calculating unit 152 calculates the moving amount per unit time period with respect to the region exhibiting the predetermined luminance information in the picture of the subject, as the difference of pulse transit time. Consequently, the biological information measuring apparatus 100*a* according to the third embodiment is capable of calculating the propagation velocity of the pulse wave by using the image-based photoplethysmogram and thus makes it possible to measure the fluctuation of the blood pressure on the basis of the propagation velocity of the pulse wave.

Further, according to the third embodiment, the feature region extracting unit 156 extracts the luminance values of the green light contained in the picture signal based on the light reflected by the epidermis of the subject and further extracts the region exhibiting the predetermined luminance value in the extracted luminance values of the green light. The calculating unit 152 calculates the moving amount per unit time period, with respect to the region exhibiting the predetermined luminance value in the picture of the subject. Consequently, the biological information measuring apparatus 100*a* according to the third embodiment makes it possible to accurately calculate the propagation velocity of the pulse wave by using the image-based photoplethysmogram.

Further, according to the third embodiment, the feature region extracting unit 156 extracts each of the regions exhibiting the predetermined luminance values from a different one of the two frames in the picture of the subject. The calculating unit 152 calculates the moving amount per unit time period between the two frames, with respect to the region exhibiting the predetermined luminance value, on the basis of the framerate of the picture of the subject. Consequently, the biological information measuring apparatus 100*a* according to the third embodiment makes it possible to easily calculate the propagation velocity of the pulse wave.

Further, according to the third embodiment, the feature region extracting unit 156 extracts the two frames each containing the region exhibiting the predetermined luminance value, from among the plurality of frames contained in the predetermined time period, in the picture of the subject. Consequently, the biological information measuring apparatus 100*a* according to the third embodiment makes it possible to extract the frames from which it is possible to calculate the propagation velocity of the pulse wave.

Further, according to the third embodiment, the feature region extracting unit 156 extracts, as the region exhibiting the predetermined luminance value, at least one selected from between: the region in which the luminance value of the green light is equal to or larger than the first threshold value; and the region in which the luminance value of the green light is equal to or smaller than the second threshold value. The calculating unit 152 calculates the moving amount per unit time period, with respect to at least one selected from between: the region in which the luminance value of the green light is equal to or larger than the first threshold value; and the region in which the luminance value of the green light is equal to or smaller than the second threshold value. Consequently, the biological information measuring apparatus 100*a* according to the third embodiment makes it possible to easily extract the region exhibiting a peak or the region exhibiting a valley from each of the frames.

According to the third embodiment, the calculating unit 152 calculates the moving amount per unit time period, with respect to the position corresponding to the average luminance value in the feature region extracted by the feature region extracting unit 156. Consequently, the biological information measuring apparatus 100*a* according to the third embodiment makes it possible to accurately calculate the moving amount of the feature region.

Further, according to the third embodiment, the calculating unit 152 uses the gravity point of the feature region, as the position corresponding to the average luminance value. Consequently, the biological information measuring apparatus 100*a* according to the third embodiment makes it possible to easily identify the position of the feature region.

Next, exemplary embodiments of a biological information displaying apparatus and a biological information displaying method of the present disclosure will be explained in detail, with reference to the accompanying drawings. In the embodiments below, details of the biological information displaying apparatus will be explained by using an example of the "daily-basis medical checkup system" realized by a "health monitoring process" employing a biological information displaying apparatus according to a fourth embodiment. The embodiments described below are merely examples and possible embodiments are not limited to the

Fourth Embodiment

With reference to FIGS. 40 to 52 and so on, an embodiment (hereinafter, "the fourth embodiment") to carry out the biological information displaying apparatus and the biological information displaying method of the present disclosure will be explained in detail, while referring to the drawings. The embodiment described below is merely an example, and the fourth embodiment is not limited to the contents of the explanation below. Further, some of the constituent elements that are the same as those in the first to the third embodiments will be referred to by using the reference numerals in which the digit on the far left is replaced by "5" (e.g., "5") or by using the same reference characters, and duplicate explanations will be omitted. As mentioned above, in a "modern society", it would be ideal for everyone to be able to live a healthy and active life while working or enjoying hobbies with his/her family in the society. For this purpose, for example, the "daily-basis medical checkup system" illustrated in FIG. 1** acquires blood flow information by using unconscious sensing technology and feeds back the subject's daily-basis health condition based on the acquired blood flow information, to the subject (which hereinafter may be referred to as "user").

More specifically, the biological information displaying apparatus employed by the "daily-basis medical checkup system" according to the fourth embodiment is configured to acquire blood flow information of the user by analyzing a picture signal of the user from whom the blood flow information is acquired and to provide the user with information about his/her health condition on the basis of the acquired blood flow information. More specifically, the biological information displaying apparatus is configured to generate blood circulation information indicating a fluctuation of the blood flow of the user by analyzing the picture signal that varies according to the fluctuation of the blood flow between before and after a predetermined user action (which hereinafter may simply be referred to as "user action") and to provide the user with the information about his/her health condition on the basis of the generated blood circulation information. Even more specifically, the biological information displaying apparatus extracts a piece of pulse wave information from each of the picture signals taken of a predetermined reference position (e.g., the face) of the user and of a body position of the user other than the reference position and further generates the blood circulation information on the basis of a fluctuation of the difference between the extracted pieces of pulse wave information. Further, in this situation, the reference position denotes a region having a predetermined area including the reference position. Further, in this situation, the body position denotes a region having a predetermined area including the body position. In the following explanation, the face is used as the reference position. When a difference in the blood flow volume between before and after a user action observed in a body position is used as the blood flow information, instead of the difference between the pieces of pulse wave information, it is not necessary to set the reference position.

Figure 40:
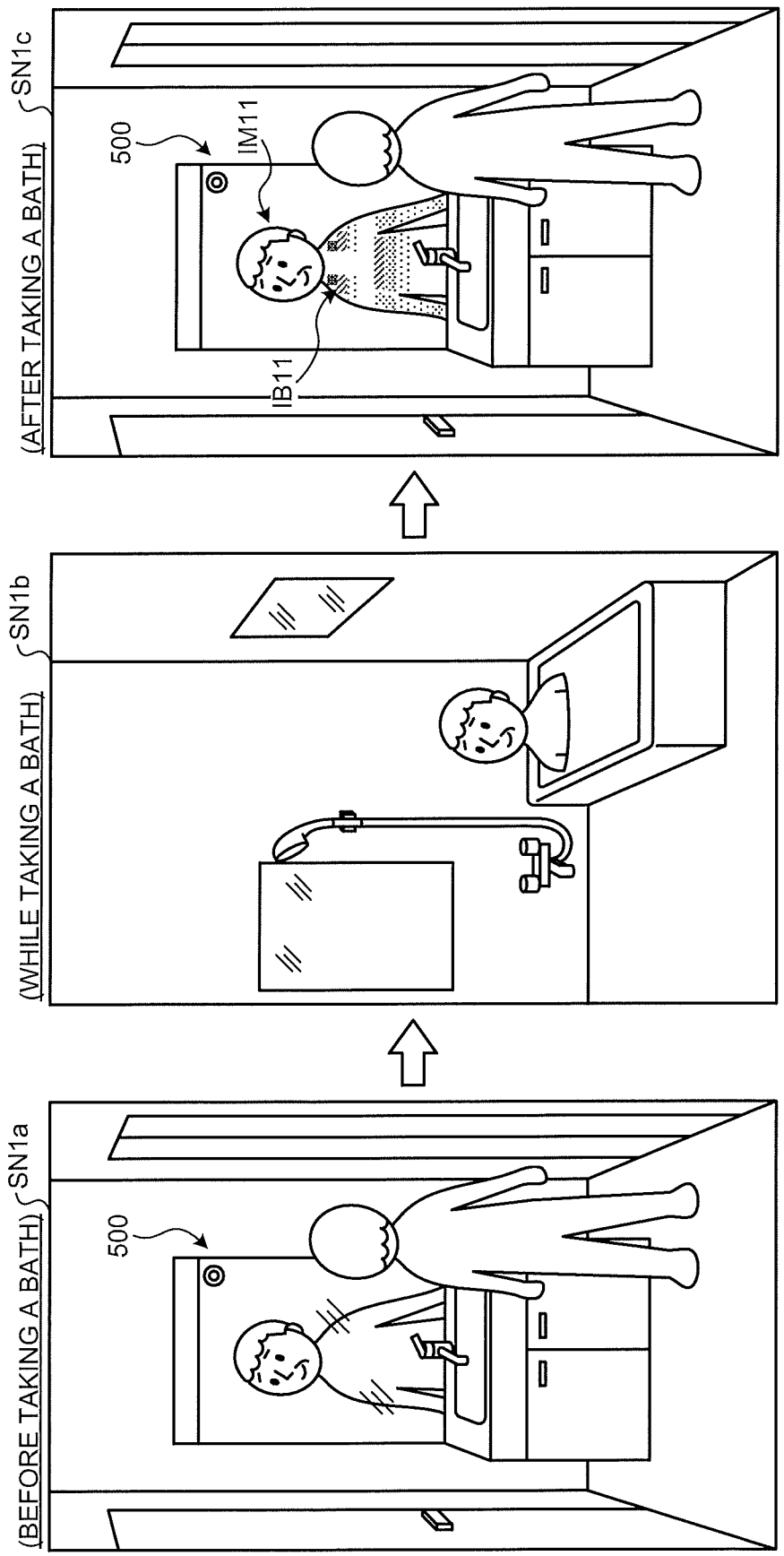
FIG. 40 is a drawing of an example of a display of a blood flow fluctuation observed between before and after taking a bath according to a fourth embodiment.

The "user action" in the present example may be any action as long as the action causes a fluctuation related to the blood flow in the body of the user, between before and after the action. In other words, as long as the action causes a fluctuation related to the blood flow in the body of the user between before and after the action, the user action may be an action that does not involve physical movements of the user and may be a psychological action (e.g., thinking). Further, for example, FIG. 40 illustrates an example in which the user action is the user's taking a bath. Further, in the following sections, the blood flow information in a body position of the user observed before the user action will be referred to as "first blood flow information", whereas the blood flow information in the body position of the user observed after the user action will be referred to as "second blood flow information".

In the present example, the pulse wave denotes a propagation of arterial pressure wave motion generated by the pump action of the heart. In the following sections, an example will be explained in which the blood circulation information is generated on the basis of a Pulse Transit Time (PTT) defined as a time period it takes for a pulse wave to propagate through blood vessels. More specifically, in the following sections, the example is explained in which the blood circulation information is generated on the basis of the first blood flow information based on the pulse transit time of the user observed before the user action and the second blood flow information based on the pulse transit time of the user observed after the user action. For example, the first blood flow information and the second blood flow information are extracted from luminance information of the picture signals of the body of the user.

Next, a principle used for extracting the pulse wave information from the picture signals will be explained. For example, image taking apparatuses such as video cameras are configured to record the light reflected by a subject as a picture that has passed through filters corresponding to different wavelengths while using the light in the three colors of red (R), green (G), and blue (B) as primary colors and to express various colors in accordance with the luminance values thereof. As a focus is placed on the optical absorption characteristics of bloodstream hemoglobin for visible light, a high peak is exhibited at the wavelength band of 520 nm to 600 nm and substantially overlaps the wavelength band of 500 nm to 570 nm where a green filter of a camera is highly sensitive. While the pulse wave propagates through the whole body due to the pulsation of the heart, the blood flow volume in the whole body including the body surface cyclically increases and decreases. When the blood flow volume in peripheral sites increases as the heart contracts, because a relative amount of bloodstream hemoglobin also increases, the absorption amount for green light on the surface of the skin also increases. Because the camera receives the light reflected by the surface of the skin, the luminance value of the green in the picture becomes smaller when the relative amount of bloodstream hemoglobin increases. On the contrary, when the heart expands, because the blood flow volume in peripheral sites decreases, a relative amount of bloodstream hemoglobin also decreases. Thus, the absorption amount for green light on the surface of the skin also decreases. The fluctuation in the luminance values of the green light is extremely small and is not visually recognizable for human eyes. However, it is possible to detect the fluctuation by using a commercially-available video camera or the like.

The biological information displaying apparatus is configured to extract the luminance value of the green light explained above as the pulse wave information and to generate the blood circulation information indicating a fluctuation of the blood flow. For example, when the blood flow information is acquired by using a wearable terminal, the blood flow information is acquired when the user consciously attaches a wearable device or the like to his/her own body. Thus, according to conventional acquiring methods, it is not easy to continuously acquire the blood flow information on a daily basis, due to the trouble of attaching the wearable device and the cost of the wearable device. Further, if a wearable device were used for acquiring the blood flow information of the user before and after the user takes a bath, the user would need to attach the wearable device to his/her body immediately after the input, which would impose a large psychological burden on the user and would not be practical. Further, if the blood flow information were acquired by a wearable device, it would be difficult to acquire the blood flow information from locations other than where the wearable device is attached.

In contrast, the daily-basis medical checkup system realized in the fourth embodiment is configured to acquire the blood flow information by analyzing the picture signals of the user. Accordingly, as illustrated in FIG. 1, for example, the user simply standing in front of a mirror makes it possible to feedback a "health forecast" that indicates the condition of health of the day to the user, by acquiring the blood flow information of the user in a contactless manner and analyzing the acquired blood flow information. In other words, without the user being particularly conscious about the process, it is possible to acquire the blood flow information in his/her daily life unconsciously and to feedback the condition of health to the user. Further, because the blood flow information is acquired by analyzing the picture signals of the user, it is possible to acquire the blood flow information and to feedback the information about the condition of health to the user no matter where the body position is, as long as the body position belongs to the user being imaged.

In this situation, the "health forecast" illustrated in FIG. 1 is configured to provide information about the condition of health analyzed on the basis of the fluctuation of the blood flow of the user. For example, the "health forecast" is provided on the basis of how much the blood flow fluctuates between before and after a user action when the first blood flow information is compared with the second blood flow information, and further, on the basis of an evaluation made on a significant fluctuation of the blood flow.

With these arrangements, it is possible to casually carry out the health monitoring process regarding the blood circulation in the user's daily life so as to make it possible for the user to understand his/her own health condition on a daily basis. For example, as illustrated in FIG. 1, the user is able to understand the current condition of his/her own, by being provided with the "health forecast" indicating "body temperature: 36.5° C., blood pressure: slightly low; lack of sleep; iron intake is recommended". In this situation, the information about the condition of the user's health can not only be fed back to the user, but also be offered to his/her family member or primary medical doctor via a network. For example, every time blood flow information of the user is acquired, an analysis result may be transmitted to a mobile phone, a smartphone, or a tablet terminal of the family member or to a terminal operated by the primary medical doctor. With this arrangement, not only the user himself/herself, but also the family member and the primary medical doctor are able to understand the user's health condition.

As explained above, by using the biological information displaying apparatus according to the fourth embodiment, it is possible to measure the fluctuation of the blood flow in a simple and contactless manner. In this situation, not only the biological information displaying apparatus according to the fourth embodiment can be installed in a residence, but also the same process may be performed in a server apparatus provided in a network outside the residence. For example, a picture signal taken by a camera installed in a residence may be transmitted to a server apparatus via a network, so that the server apparatus receives the picture signal and calculates a fluctuation of the blood flow of the user corresponding to the picture signal. Further, a server apparatus provided in a network may acquire pieces of blood flow information of individual people from biological information displaying apparatuses installed in the residences thereof and may manage the acquired pieces of blood flow information in a centrally-controlled manner. In that situation, the server apparatus may acquire and store, as life log information, the blood flow information of the individual people so as to be kept in association with action information. Further, the server apparatus may manage big data in a cloud in a centrally-controller manner, the big data integrating together a large volume of biological information and life log information that are acquired in a time series with respect to a plurality of users.

Further, by analyzing the big data, the server apparatus may analyze potential risks of illnesses in the future and responsive reactions of the human bodies to amounts of food, amounts of exercise, or exercise loads in a sophisticated and detailed manner. Accordingly, the users become able to plan day-to-day life while pursuing the ideals, by selecting meals, exercises, life styles, medications, and supplements that are suitable for the potential risks of illnesses, signs of seizures, their own physical tendencies, and life styles. Further, the server apparatus is able to feedback the information not only to the users, but also to medical institutions. Medical doctors are able to, for example, recognize a group of people having a high risk of developing illnesses on the basis of the results of the analyses provided by the server apparatus as a feedback and to proactively contact those people, if necessary. In addition, the blood flow information transmitted from each of the users is also useful in detecting abnormalities in the body of the user. For example, the server apparatus may constantly monitor the blood flow information transmitted daily from the users who are in the group having a high risk of developing illnesses, and when an abnormality is detected, the server apparatus may immediately feedback the detection result to a medical institution or the like. By configuring the server apparatus to provide medical institutions and various corporations with results of the analyses performed on the big data, the system may be used in various services and may contribute to creation of new industries.

(An Example of the Display of the Blood Circulation Information According to the Fourth Embodiment)

Next, an example of the display of the blood circulation information realized by a biological information displaying apparatus 500 according to the fourth embodiment will be explained. FIG. 40 is a drawing of an example of the display of a blood flow fluctuation observed between before and after taking a bath according to the fourth embodiment. More specifically, FIG. 40 illustrates an example in which the biological information displaying apparatus 500 displays the blood circulation information on the basis of the fluctuation of the blood flow of the user observed between before and after taking a bath. The example in FIG. 40 illustrates a situation where the biological information displaying apparatus 500 is installed in the dressing room of the bath.

The scene SN1*a* in the left section of FIG. 40 illustrates the situation where the user is in the dressing room of the bath before taking a bath. In the scene SN1*a*, the image of the user reflected on the washstand in the dressing room may be an image of the user reflected on the mirror or may be an image of the user taken by a picture obtaining unit 510a included in the biological information displaying apparatus 500 and displayed by a display unit 520. Although FIG. 40 illustrates the example in which the image of the user above the waist reflected on the washstand in the dressing room is used as the image of the user, the image of the user may be that of his entire body. Further, details of the picture obtaining unit 510a will be explained later. Further, in the scene SN1a, the biological information displaying apparatus 500 images the user before the user takes a bath. After that, the biological information displaying apparatus 500 calculates first blood flow information that is the blood flow information in body positions of the user observed before the user takes a bath, on the basis of the luminance information of picture signals of the body of the user. Details of the process of calculating the first blood flow information will be explained later.

In FIG. 40, the biological information displaying apparatus 500 installed at the washstand in the dressing room is configured to image the user from the front by employing the picture obtaining unit 510a. Thus, the biological information displaying apparatus 500 calculates the first blood flow information that is the blood flow information in one or more body positions of the user observed before the user takes a bath, on the basis of the luminance information of picture signals of the body obtained by imaging the user from the front. In FIG. 40, the biological information displaying apparatus 500 calculates first blood flow information in a plurality of body positions of the user. For example, the biological information displaying apparatus 500 calculates the first blood flow information in the plurality of body positions such as both shoulders, both arms, and the abdomen of the user. For example, by dividing the image taken of the body of the user into a plurality of regions, the biological information displaying apparatus 500 may calculate the first blood flow information in the plurality of body positions corresponding to the regions.

Further, the biological information displaying apparatus 500 may start the image taking process when a predetermined condition is satisfied. For example, the biological information displaying apparatus 500 may start the image taking process by using the user's entering the dressing room as a trigger. As another example, the biological information displaying apparatus 500 may start the image taking process by using the user's being reflected on the predetermined mirror as a trigger.

After that, the user moves from the dressing room to the bathroom and takes a bath. In that situation, the biological information displaying apparatus 500 may stop the image taking process. For example, the biological information displaying apparatus 500 may stop the image taking process by using the user's moving from the dressing room into the bathroom as a trigger. As another example, the biological information displaying apparatus 500 may stop the image taking process by using the user's stopping being reflected on the predetermined mirror, as a trigger. Further, the biological information displaying apparatus 500 may inform the user that the information required by the calculation of the first blood flow information has been obtained. With this arrangement, the biological information displaying apparatus 500 is able to inform the user of the timing with which the user can go into the bathroom and is able to obtain the information required by the display of the blood circulation information observed before and after taking a bath.

The scene SN1b in the middle section of FIG. 40 illustrates the situation where the user is taking a bath. In the scene SN1b, the user takes a bath for a certain period of time (e.g., 30 minutes). For example, when the user takes a bath at an appropriate temperature (e.g., 38° C. to 40° C.), the capillary vessels of the skin and the subcutaneous blood vessels of the user expand, and the blood flow becomes better. Accordingly, the second blood flow information calculated by the biological information displaying apparatus 500 exhibits a value that fluctuated from the first blood flow information. For example, the second blood flow information calculated by the biological information displaying apparatus 500 has a value larger than that of the first blood flow information. In this situation, the biological information displaying apparatus 500 may obtain the temperature of the bath during the user's bathing period by using an appropriate means. For example, the biological information obtaining apparatus 500 may obtain information about the temperature of the bath during the user's bathing period, by using a predetermined thermometer configured to measure the temperature of the bath. In that situation, the biological information displaying apparatus 500 may correct the first blood flow information and the second blood flow information in accordance with the obtained information about the temperature of the bath.

After having taken a bath as illustrated in SN1b in FIG. 40, the user moves from the bathroom to the dressing room. In that situation, the biological information displaying apparatus 500 may start an image taking process. For example, the biological information displaying apparatus 500 may start the image taking process, by using the user's moving from the bathroom to the dressing room as a trigger. As another example, the biological information displaying apparatus 500 may start the image taking process by using the user's being reflected on the predetermined mirror as a trigger. The scene SN1c in the right section of FIG. 40 illustrates the situation where the user is in the dressing room of the bath after taking a bath. In the scene SN1c in FIG. 40, the biological information displaying apparatus 500 calculates second blood flow information that is the blood flow information in the body positions of the user observed after the user takes a bath, on the basis of the luminance information of picture signals of the body obtained by imaging the user from the front. In FIG. 40, the biological information displaying apparatus 500 calculates the second blood flow information in a plurality of body positions of the user. For example, the biological information displaying apparatus 500 calculates the second blood flow information in the plurality of body positions such as both shoulders, both arms, and the abdomen of the user. For example, by dividing the image taken of the body of the user into a plurality of regions, the biological information displaying apparatus 500 may calculate the second blood flow information in the plurality of body positions corresponding to the regions.

Further, the biological information displaying apparatus 500 calculates the difference (which hereinafter may be referred to as "blood flow difference") between the first blood flow information and the second blood flow information in the body positions. In this situation, the blood flow difference in each of the body positions denotes a fluctuation of the blood flow observed between before taking a bath and after taking a bath in the body position. The relationship between the magnitude of the blood flow difference and whether the blood flow is good or bad may vary depending on the first blood flow information and the second blood flow information used as the bases of the blood flow difference. For example, in some situations, the relationship may be such that the larger the blood flow difference is, the better the blood flow is. In other situations, for example, the relationship may be such that the smaller the blood flow difference is, the better the blood flow is. In other words, the evaluation of the blood flow difference may vary depending on the first blood flow information and the second blood flow information used as the basis of the blood flow difference.

For example, when "the larger the blood flow difference is, the better the blood flow is" is true, the biological information displaying apparatus 500 may determine that, when the blood flow difference is equal to or larger than a predetermined threshold value, the blood flow in the corresponding body position has become better. Also, when "the larger the blood flow difference is, the better the blood flow is" is true, for example, the biological information displaying apparatus 500 may determine that, when the blood flow difference is smaller than a predetermined threshold value, the blood flow in the corresponding body position has become worse. On the contrary, when "the smaller the blood flow difference is, the better the blood flow is" is true, for example, the biological information displaying apparatus 500 may determine that, when the blood flow difference is equal to or larger a predetermined threshold value, the blood flow in the corresponding body position has become worse. Also, when "the smaller the blood flow difference is, the better the blood flow is" is true, for example, the biological information displaying apparatus 500 may determine that, when the blood flow difference is smaller than a predetermined threshold value, the blood flow in the corresponding body position has become better. FIG. 40 illustrates an example in which "the larger the blood flow difference is, the better the blood flow is" is true.

In FIG. 40, by dividing the image taken of the body of the user including both shoulders, both arms, and the abdomen of the user into a plurality of regions, the biological information displaying apparatus 500 calculates the blood flow difference in each of the plurality of body positions corresponding to the regions. For example, the biological information displaying apparatus 500 calculates a blood flow difference with respect to each of a plurality of body positions near the right shoulder of the user. Further, for example, the biological information displaying apparatus 500 calculates a blood flow difference with respect to each of a plurality of body positions near the abdomen of the user.

Further, the biological information displaying apparatus 500 generates blood circulation information indicating a blood flow state in each of the body positions, on the basis of the blood flow differences. In FIG. 40, as blood circulation information IB11, the biological information displaying apparatus 500 generates an image in which the larger the blood flow difference in each of the body positions is, the darker the hatching is. Further, in FIG. 40, as the blood circulation information IB11, the biological information displaying apparatus 500 generates the image in which the smaller the blood flow difference in each of the body positions is, the lighter the hatching is.

After that, the biological information displaying apparatus 500 displays the generated blood circulation information IB11 together with a body image IM11 of the user. More specifically, the biological information displaying apparatus 500 displays the generated blood circulation information IB11 so as to be superimposed on the corresponding body position in the body image IM11 of the user. For example, the biological information displaying apparatus 500 displays the blood circulation information IB11 of the right shoulder so as to be superimposed on the right shoulder in the body image IM11 of the user. In FIG. 40, of the displayed blood circulation information IB11, an image having the darkest hatching is superimposed on the body position near the neck on the right shoulder, the user is able to intuitively recognize that the body position near the neck on the right shoulder has the best blood circulation. As a result, the user is able to remotely compare the changes in the blood circulation state in a quantitative and intuitive manner, without the need to attach any sensor to the body. The user is thus able to manage health on a daily basis, to assess the effect of physical exercises, and to intuitively understand the intensity of psychological stress.

In the explanation above, the example is explained in which the blood circulation information is displayed by using the level of darkness/lightness of the hatching. However, in another example, the biological information displaying apparatus 500 may display a hue image, such as what is called a heat map, expressing the blood flow differences by using changes of hues. More specifically, the biological information displaying apparatus 500 may display an image in which the larger the blood flow difference is, the warmer the color is (e.g., red), so as to be superimposed on a corresponding body position and may display an image in which the smaller the blood flow difference is, the colder the color is (e.g., blue), so as to be superimposed on a corresponding body position. In other words, the biological information displaying apparatus 500 displays a body position on which an image in a warm color is superimposed, as a position where the body circulation has become better and displays a body position on which an image in a cold color is superimposed, as a position where the body circulation has become worse. With these arrangements, the biological information displaying apparatus 500 makes it possible for the user to intuitively recognize the changes in the blood circulation of his/her own.

Next, details of the biological information displaying apparatus according to the fourth embodiment will be explained. In the embodiment below, an example will be explained in which the biological information displaying apparatus installed in a residence is connected via a network to a Personal Health Record (PHR) apparatus, which serves as the server apparatus described above; however possible embodiments are not limited to this example. The biological information displaying apparatus may be used without being connected to any network.

(A Configuration of the Biological Information Displaying Apparatus According to the Fourth Embodiment)

Figure 41:
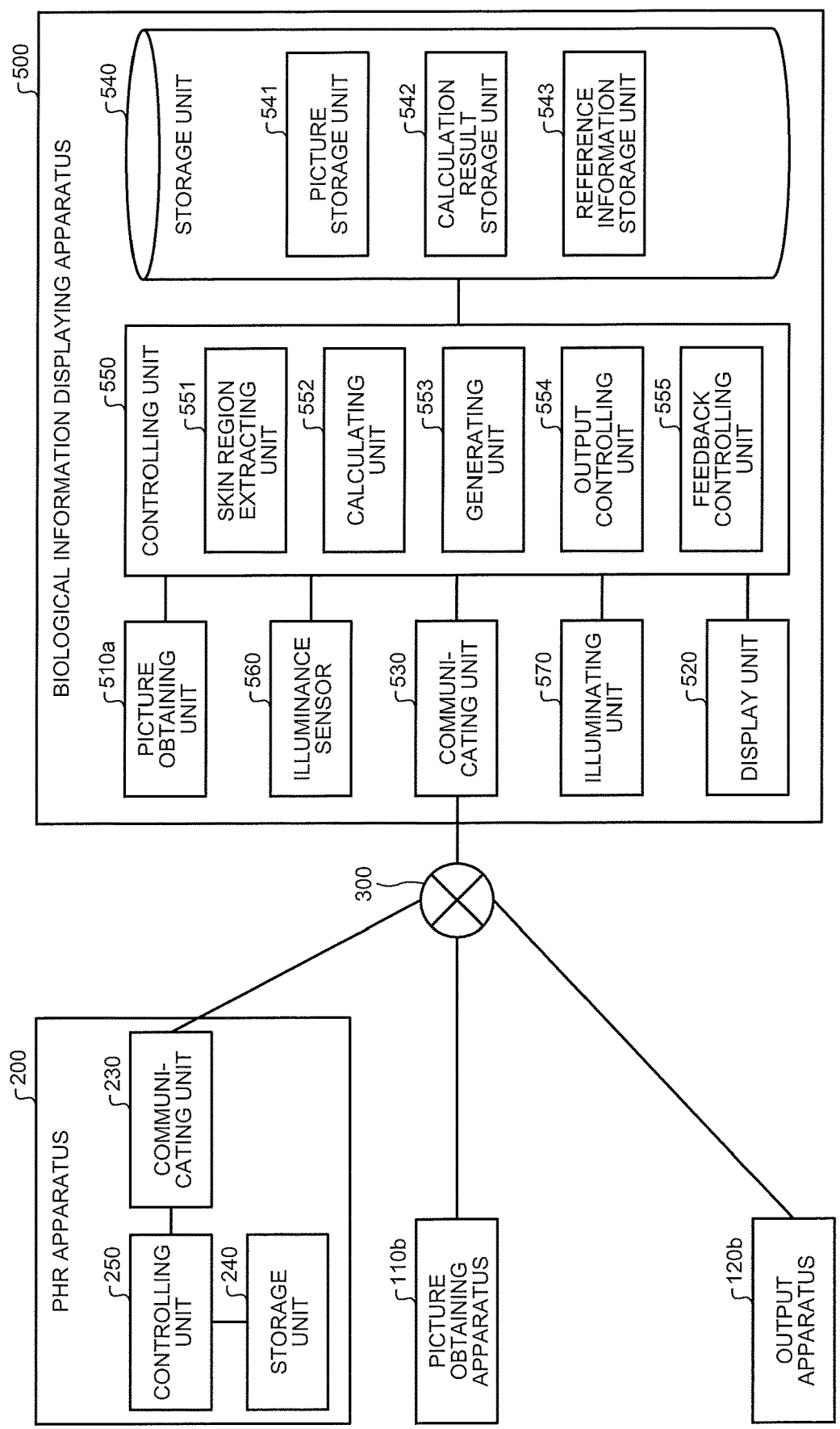
FIG. 41 is a functional block diagram of an exemplary configuration of a biological information displaying apparatus according to the fourth embodiment.

The biological information displaying apparatus according to the fourth embodiment used for realizing the "daily-basis medical checkup system" described above will be explained. FIG. 41 is a functional block diagram of an exemplary configuration of the biological information displaying apparatus 500 according to the fourth embodiment. As illustrated in FIG. 41, the biological information displaying apparatus 500 includes the picture obtaining unit 510*a*, the display unit 520, a communicating unit 530, a storage unit 540, a controlling unit 550, an illuminance sensor 560, and an illuminating unit 570. The biological information displaying apparatus 500 is connected to the PHR apparatus 200, the picture obtaining apparatus 110*b*, and the output apparatus 120*b*, via the network 300. In FIG. 41, one biological information displaying apparatus 500, one PHR apparatus 200, one picture obtaining apparatus 110*b*, and one output apparatus 120*b* are provided; however, two or more of each type of apparatus may be connected together.

The network 300 is a Local Area Network (LAN), a Wide Area Network (WAN), or the like. As illustrated in FIG. 41, the PHR apparatus 200 is a server apparatus that includes the communicating unit 230, the storage unit 240, and the controlling unit 250 and is configured to manage PHR data (e.g., the blood flow information) unconsciously acquired on a daily basis, in a health care cloud in a centrally-controlled manner. In this situation, the PHR data is information in which sensing data (e.g., the blood flow information) acquired from each individual person is kept in correspondence with the individual person. In other words, the PHR apparatus 200 obtains and manages the blood flow information of the individual people from a plurality of biological information displaying apparatuses 500 via the network 300. Further, the health care cloud is a cloud that is structured by the one or more PHR apparatuses 200, the one or more biological information displaying apparatuses 500, the network 300, and the like and is configured to provide various users with the service of the "daily-basis medical checkup system".

The communicating unit 230 included in the PHR apparatus 200 is configured to communicate, via the network 300, with the biological information displaying apparatus 500, the picture obtaining apparatus 110b, and the output apparatus 120b in a wired or wireless manner, to receive blood flow information acquired by the biological information displaying apparatus 500, to receive picture signals obtained by the picture obtaining apparatus 110h, and to transmit output information to the output apparatus 120b. The storage unit 240 is configured to store therein various types of information such as the PHR data. For example, the storage unit 240 stores therein the blood flow information acquired by the biological information displaying apparatus 500 so as to be kept in correspondence with the user. Further, the storage unit 240 stores therein the picture signals taken by the biological information displaying apparatus 500 so as to be kept in correspondence with the user. In other words, the storage unit 240 stores the big data therein and is also able to store therein the same information as stored in the storage unit 540 of the biological information displaying apparatus 500.

In this situation, the PHR apparatus 200 is able to not only manage the information acquired by the biological information displaying apparatus 500, but also perform the same processes as those performed by the biological information displaying apparatus 500 described below. In other words, the PHR apparatus 200 is able to measure the blood flow information of the user by receiving the picture signals of the user obtained by either the biological information displaying apparatus 500 or the picture obtaining apparatus 110b and analyzing the received picture signals. More specifically, the controlling unit 250 included in the PHR apparatus 200 measures the fluctuation of the blood flow on the basis of the picture signals by performing the same processes as those performed by the controlling unit 550 included in the biological information displaying apparatus 500 described below. The storage unit 240 stores therein the blood flow information or the like measured by the controlling unit 250 so as to be kept in correspondence with the user. Further, in response to a request from the biological information displaying apparatus 500 or the output apparatus 120b for output information, the controlling unit 250 exercises control so that information is read from the storage unit 240 and the read information is transmitted to the biological information displaying apparatus 500 or the output apparatus 120b.

The picture obtaining apparatus 110b is a camera that has installed therein an imaging device such as a Charge Coupled Device (CCD) or a Complementary Metal Oxide Semiconductor (CMOS) and may have installed therein three or more types of light receiving elements corresponding to, for example, red (R), green (G), and blue (B). Further, the picture obtaining apparatus 110b may be, for example, a reflective photo sensor that has installed therein a green LED. Further, the picture obtaining apparatus 110b can be provided in any of various places where the user spends time in life. For example, the picture obtaining apparatus 110b is provided in a predetermined area (e.g., a dressing room of a bath or a changing room) and is configured to obtain picture signals of the user and to transmit the obtained picture signals to the biological information displaying apparatus 500 or the PHR apparatus 200 via the network 300. For example, the picture obtaining apparatus 110b obtains a picture signal of the face of the user and a picture signal of a body position other than the face taken at the same time as the picture signal of the face of the user is taken and transmits the obtained picture signals to the biological information displaying apparatus 500 or the PHR apparatus 200. For example, the body position is a position from which the user wishes to obtain a fluctuation of the blood flow, i.e., the position for which blood circulation information is generated. Further, the picture obtaining apparatus 110b may be a camera configured to image the face and the body position other than the face of the user in a single picture. Alternatively, the picture obtaining apparatus 110b may be configured with two separate cameras that image the face and the body position other than the face of the user, respectively.

The output apparatus 120b is a display device such as a monitor and/or an audio output device such as a speaker. Further, the output apparatus 120b may be installed in any of various places where the user spends time in life or a place where information can be output for the user's family member or primary medical doctor who observes the blood flow information of the user. The output apparatus 120b is configured to receive the output information such as picture information and/or audio information from the biological information displaying apparatus 500 or the PHR apparatus 200 and to output the received output information. Alternatively, the output apparatus 120b may be configured by using a display device such as a liquid crystal panel and may be configured by being combined with an input unit so as to be able to display a Graphical User Interface (GUI) to receive an input operation through the input unit.

The biological information displaying apparatus 500 is an information processing apparatus installed in a predetermined area and is configured to generate the blood circulation information on the basis of the fluctuation of the blood flow, by analyzing the picture signals of the user. For example, FIG. 40 illustrates an example in which the biological information displaying apparatus 500 is incorporated into the washstand provided in the dressing room of the bath. Alternatively, the biological information displaying apparatus 500 may be configured by using a camera-equipped mobile phone, a smartphone, a tablet terminal, a camera-equipped Personal Computer (PC), or the like. Although FIG. 41 illustrates the example in which the biological information displaying apparatus 500 includes the picture obtaining unit 510a, possible embodiments are not limited to this example. For instance, the biological information displaying apparatus 500 may be configured to analyze the picture signals received from the picture obtaining apparatus 110b, without including the picture obtaining unit 510a.

The picture obtaining unit 510a may be configured by using a camera that has installed therein an imaging device such as a CCD or a CMOS and may have installed therein three or more types of light receiving elements corresponding to, for example, R, G, and B. Further, the picture obtaining unit 510a is configured to obtain the picture signals of the user and to transmit the obtained picture signals to the controlling unit 550. For example, the picture obtaining unit 510a obtains the picture signal of the face of the user and the picture signal of a site other than the face taken at the same time as the picture signal of the face of the user is taken and transmits the obtained picture signals to the controlling unit 550. Further, the picture obtaining unit 510a may be a camera configured to image the face and the body position other than the face of the user in a single picture. Alternatively, the picture obtaining unit 510a may be configured with two separate cameras that image the face and the body position other than the face of the user, respectively.

The display unit 520 is a display device such as a monitor realized by, for example, a liquid crystal display, an organic Electro-Luminescence (EL) display, or the like. For example, the display unit 520 may be configured by being combined with an input unit so as to be able to display a Graphical User Interface (GUI) used for receiving an input operation through the input unit. For example, the display unit 520 is configured to display the blood circulation information generated by a generating unit 553, together with a body image of the user. More specifically, the display unit 520 displays the blood circulation information so as to be superimposed on the body position within the body image of the user. Further, for example, the display unit 520 displays image information as the blood circulation information.

In FIG. 40, for example, the display unit 520 displays a hue image in which the difference between the first blood flow information and the second blood flow information in the body positions is expressed by using a change of the hue, as the blood circulation information. Further, for example, the display unit 520 displays text information as the blood circulation information. Further, for example, the display unit 520 displays a numerical value related to the difference between the first blood flow information and the second blood flow information, as the blood circulation information. Further, for example, the display unit displays blood circulation information of another user, together with the body image of the user. Further, for example, the display unit 520 displays an average of blood circulation information of another user, as the blood circulation information of the other user. Further, for example, the display unit 520 displays the blood circulation information on a display surface provided in a predetermined area, together with the body image of the user. Further, for example, the display unit 520 displays the blood circulation information on a mirror together with the body image of the user. Examples of the display of the blood circulation information will be explained later.

The communicating unit 530 is configured to communicate, via the network 300, with the picture obtaining apparatus 110b, the output apparatus 120b, and the PHR apparatus 200, in a wired or wireless manner. For example, the communicating unit 530 receives the picture signals of the user from the picture obtaining apparatus 110b and transmits the received picture signals to the controlling unit 550. Further, the communicating unit 530 transmits the output information to the output apparatus 120b. Further, the communicating unit 530 transmits the picture signals and a measured result to the PHR apparatus 200 and transmits and receives the output information to and from the PHR apparatus 200.

The illuminance sensor 560 is a sensor configured to measure illuminance in the vicinity of the skin of the subject. For example, the illuminance sensor measures levels of illuminance of the face and the site other than the face of the subject from which the picture signals are obtained and transmits the measured results to the controlling unit 550. The illuminating unit 570 is configured to irradiate the subject with light. For example, the illuminating unit 570 may be an illumination device employing one or more light emitting diodes (LEDs) and is configured to irradiate the subject with the light under the control of the controlling unit 550. The irradiation of the subject with the light will be explained in detail later.

As illustrated in FIG. 41, the storage unit 540 includes a picture storage unit 541, a calculation result storage unit 542, and a reference information storage unit 543. The storage unit 540 may be, for example, a storage device such as a hard disk, an optical disk, or the like or a semiconductor memory device such as a Random Access Memory (RAM), a flash memory, or the like. The storage unit 540 is configured to store therein various types of computer programs executed by the biological information displaying apparatus 500, and the like.

The picture storage unit 541 is configured to store therein the picture signals of the user. More specifically, the picture storage unit 541 stores therein the picture signals of the user obtained by the picture obtaining unit 510a and the picture obtaining apparatus 110b. For example, the picture storage unit 541 stores therein the picture signal of the face of the user and the picture signal of a body position other than the face taken at the same time as the picture signal of the face of the user is taken. In this situation, the picture storage unit 541 may store therein a picture containing the picture signals of the face and the body position other than the face in the single picture. Alternatively, the picture storage unit 541 may store therein a picture of the face and a picture of the body position other than the face, as separate pictures. When the picture of the face and the picture of the body position other than the face are separate from each other, in order to make it possible to compare pieces of luminance information belonging to the separate pictures and corresponding to mutually the same time, the picture storage unit 541 stores the pictures therein so as to be kept in correspondence with time information.

The calculation result storage unit 542 is configured to store therein a result of a blood flow fluctuation calculating process performed by the controlling unit 550 explained later. More specifically, the calculation result storage unit 542 stores therein information related to the fluctuation of the blood flow of the user calculated by a calculating unit 552 included in the controlling unit 550. For example, the calculation result storage unit 542 stores therein a calculation result of the fluctuation of the blood flow calculated by using an index value corresponding to a PTT and being calculated from the picture signals. FIG. 42A is a table of examples of calculation results according to the fourth embodiment. For example, as illustrated in FIG. 42A, the calculation result storage unit 542 stores therein calculation information that keeps calculation dates/times and calculation results in correspondence with one another for each of the users. In this situation, the "calculation date/time" illustrated in FIG. 42A denotes the dates/times at each of which the face and a body position other than the face of the user were imaged and a fluctuation of the blood flow was calculated on the basis of the picture signals taken. Further, the "calculation results" illustrated in FIG. 42A denote results of the items calculated at each of the calculation dates/times.

In this situation, as illustrated in FIG. 42A, examples of the calculated items include "first blood flow information", "second blood flow information", and "difference". The first blood flow information and the second blood flow information described above each do not have to represent an absolute value of the blood flow volume and may each be a relative value based on a relationship with a predetermined blood flow amount used as a reference. In other words, the first blood flow information and the second blood flow information described above may each be an index value corresponding to a blood flow volume used as a reference. For example, as illustrated in FIG. 42A, the calculation result storage unit 542 stores therein "first blood flow information: FV11; second blood flow information SV11; difference: ΔV11" as a calculation result corresponding to the "calculation date/time 201501010715". In other words, in the above information, the result calculated at "7:15 a.m. on the first of January in the year 2015" indicates that the first blood flow information is "FV11", that the second blood flow information is "SV11", and that the difference is "ΔV11". Although FIG. 42A illustrates the example in which the pieces of information corresponding to the items are conceptually expressed as FV11, SV11, and ΔV11, the pieces of information corresponding to the items may be specific numerical values.

Similarly, the calculation result storage unit 542 stores therein "first blood flow information: FV12; second blood flow information SV12; difference: ΔV12" as a calculation result of the same user corresponding to the "calculation date/time 201501011026". The calculation result storage unit 542 stores therein a result of calculated index values in this manner, every time a fluctuation of the blood flow is calculated. The information stored in the calculation result storage unit 542 is not limited to the examples described above. Various types of information may be stored in accordance with purposes. For example, the calculation result storage unit 542 may store therein information related to the body positions for which the first blood flow information, the second blood flow information, and the difference were calculated. For example, when the body position for which the first blood flow information "FV11", the second blood flow information "SV11", and the difference "ΔV11" were calculate is a "shoulder", the calculation result storage unit 542 may store therein information indicating the body position "shoulder".

Returning to the description of FIG. 41, the reference information storage unit 543 is configured to store therein reference information referenced during a calculating process performed by the controlling unit 550 (explained later). More specifically, the reference information storage unit 543 stores therein the reference information referenced when the calculating unit 552 calculates the information related to the fluctuation of the blood flow of the user. FIG. 42B is a table illustrating examples of the reference information according to the fourth embodiment. For example, as illustrated in FIG. 42B, the reference information storage unit 543 stores therein information in which "reference information" is kept in correspondence with "dPTT" values and "PD" values. In this situation, the "reference information" denotes the information referenced when the calculating unit 552 calculates the fluctuation of the blood flow. For example, as illustrated in FIG. 42B, the "reference information" includes "blood flow value conversion information (updated on 20150101)", "correction information (temperature)", and "correction information (humidity)". Further, the "dPTT" denotes a difference of pulse transit time, which is the time difference between predetermined feature points in the luminance values of the green light in the picture signals of the face and a site other than the face. Further, the "PD" denotes an instantaneous phase difference (or simply, "phase difference") indicating a phase difference between the luminance values of the green light in the picture signals of the face and the site other than the face. The "blood flow value conversion information" is information used for correcting the first blood flow information and the second blood flow information. Further, the "correction information (temperature)" is information used for correcting the first blood flow information or the second blood flow information in accordance with temperatures. The "correction information (humidity)" is information used for correcting the first blood flow information or the second blood flow information in accordance with humidity levels. The first blood flow information and the second blood flow information may be corrected in this manner.

Further, the "dPTT" and the "PD" illustrated in FIG. 42B each denote an index value corresponding to a PTT and being calculated from the picture signals. The biological information displaying apparatus 500 according to the fourth embodiment calculates the fluctuation of the blood flow of the user by using either the "dPTT" or the "PD" described above. In this situation, by referencing the reference information corresponding to each index value, the biological information displaying apparatus 500 is able to calculate the first blood flow information and the second blood flow information and to make corrections in accordance with temperatures and humidity levels. The process of calculating the fluctuation of the blood flow of the user by using the "dPTT" or the "PD" will be explained in detail later.

Returning to the description of FIG. 41, the controlling unit 550 includes a skin region extracting unit 551, the calculating unit 552, the generating unit 553, an output controlling unit 554, and a feedback controlling unit 555. The controlling unit 550 may be, for example, an electronic circuit such as a Central Processing Unit (CPU), a Micro Processing Unit (MPU), or the like, or an integrated circuit such as an Application Specific Integrated Circuit (ASIC), a Field Programmable Gate Array (FPGA), or the like and is configured to exercise overall control of the biological information displaying apparatus 500.

As a result of the processes performed by the functional units described above, the controlling unit 550 is configured to calculate the index value corresponding to a PTT by extracting the pulse wave information from the picture signals of the face and the body position other than the face of the user and to calculate the first blood flow information and the second blood flow information on the basis of a fluctuation of the calculated index value. Next, at first, a principle and a definition of the pulse transit time (PTT) will be explained. A PTT value denotes the time period it takes for a pulse wave propagating from an aorta toward peripheral regions to travel from a certain reference point and reach a separate measurement point. The definition of the pulse transit time according to the fourth embodiment is the same as the definition of the pulse transit time illustrated in FIG. 5. For example, in the chart illustrated in FIG. 5, the vertical axis expresses "amplitude", whereas the horizontal axis expresses "time", so as to indicate waveforms of an electrocardiogram (ECG) and photoplethysmography (PPG) data.

For example, as illustrated in FIG. 5, a PTT is defined, in general, as the time difference up to a feature point in a pulse wave waveform measured on the peripheral side while using an "R-wave Peak" in an electrocardiogram as a reference point. For example, the velocity "v" with which a pulse wave propagates through a blood vessel is dependent on the inside diameter of the blood vessel and stiffness of the vascular wall. An analytical relational expression may be a "Moens-Korteweg" equation presented above as Expression (1).

As explained above, Expressions (4) and (5) above are obtained by assigning Expressions (1) and (2) to Expression (3) and squaring both sides of the equation. Further, by calculating the logarithm of Expression (5), it is possible to obtain Expression (6) above indicating the blood pressure "P". Further, with respect to changes in the blood pressure "P" expressed by Expression (6), when changes in the thickness "h" of the vascular wall and the diameter "d" of the blood vessel are small while changes in "$E_0$" is sufficiently slow, the first term on the right-hand side of Expression (6) is negligible. Thus, by taking the derivative of Expression (6) with respect to the pulse transit time "T", Expression (7) presented above is obtained. In other words, as explained above, Expression (7) is obtained in which the fluctuation amount "$\Delta P$" of the blood pressure "P" is expressed by using the fluctuation amount "$\Delta T$" of the pulse transit time. Because the fluctuation amount "$\Delta P$" of the blood pressure "P" is expressed by using the fluctuation amount "$\Delta T$" of the pulse transit time in this manner, it is understood that it is possible to estimate the fluctuation of the blood pressure (the blood circulation) by using the pulse transit time "T".

According to the principle explained above, the biological information displaying apparatus 500 according to the fourth embodiment measures the fluctuation of the blood pressure (the blood circulation) by considering the luminance value of the green light in the picture signal as the pulse wave and measuring the fluctuation of the pulse transit time "PTT". In this situation, as explained above, the "PTT" denotes the time period it takes to travel from a certain reference point and reach a separate measurement point. In general, a "PTT" value is defined as the time difference up to a feature point in a pulse wave waveform measured on the peripheral side while using an "R-wave" in an electrocardiogram as a reference point. However, because it is necessary to use an apparatus to obtain the electrocardiogram, if the fluctuation of the blood flow were to be measured on the basis of a "PTT" value using an electrocardiogram, it would be impossible to measure the fluctuation of the blood flow in a contactless manner. To cope with this situation, according to the fourth embodiment, the fluctuation of the blood flow is measured by using the aforementioned index value corresponding to a "PTT" without using any electrocardiograms, so that it is possible to measure the fluctuation of the blood pressure in a simple and contactless manner.

More specifically, the biological information displaying apparatus 500 according to the fourth embodiment measures the fluctuation of the blood flow by measuring the fluctuation of either the "PD" indicating the phase difference between the luminance values of the green light in the picture signals of the face and the site other than the face of the user or the "dPTT" indicating the time difference between the predetermined feature points in the luminance values of the green light in the picture signals of the face and the site other than the face of the user. In the following sections, processes performed by the biological information displaying apparatus 500 will sequentially be explained in the order of: a process of extracting pulse wave information from the picture signals and a process of calculating the "PD" and the "dPTT" from the extracted pulse wave information.

Returning to the description of FIG. 41, the skin region extracting unit 551 included in the controlling unit 550 is configured to extract one or more skin region of the user contained in the picture obtained by either the picture obtaining unit 510*a* or the picture obtaining apparatus 110*b*. More specifically, the skin region extracting unit 551 automatically extracts the skin regions on the basis of color information in the picture. Alternatively, the skin region extracting unit 551 may extract one or more regions designated by an operator via an input unit (not illustrated) as the skin regions. In the following sections, these processes will sequentially be explained in detail. In this situation, the picture serving as a processing target of the skin region extracting unit 551 may be a real-time picture obtained by either the picture obtaining unit 510*a* or the picture obtaining apparatus 110*b* or may be a picture from the past stored in the picture storage unit 541.

Figure 43:
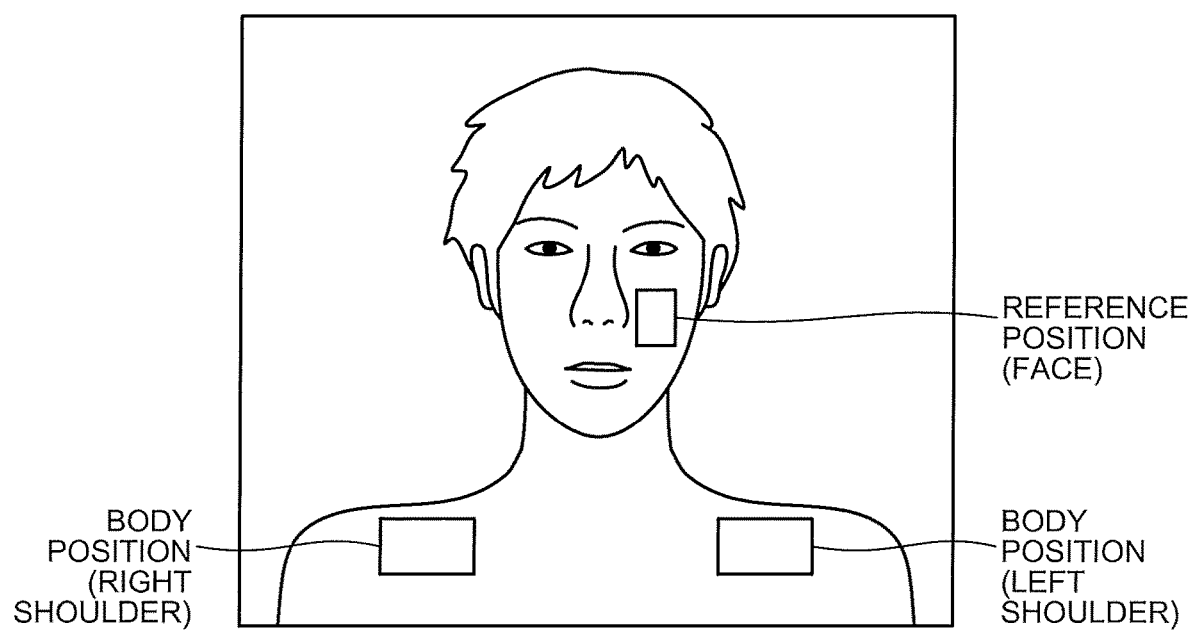
FIG. 43 is a drawing for explaining an automatic extracting process of skin regions according to the fourth embodiment.

First, an example in which skin regions are automatically extracted on the basis of the color information in the picture will be explained, with reference to FIG. 43. FIG. 43 is a drawing for explaining the automatic extracting process of the skin regions according to the fourth embodiment. For example, as illustrated in FIG. 43, the skin region extracting unit 551 extracts the skin regions of the user by extracting regions exhibiting a skin color from the picture. In other words, the skin region extracting unit 551 extracts all the coordinates (coordinates of the pixels) exhibiting colors (luminance values) corresponding to the skin color from the two-dimensional coordinates of the picture and extracts one or more regions obtained by putting together such pixels that have continuous coordinates among the extracted coordinates, as the skin regions. In this situation, by putting together such pixels of which the coordinates are not continuous, as the coordinates of mutually-different regions, the skin region extracting unit 551 is able to extract the skin regions corresponding to a plurality of sites (body positions).

In one example, the skin region extracting unit 551 extracts coordinates of a shoulder section and the coordinates of a face section exhibiting the skin color (luminance values) in the picture illustrated in FIG. 43. Further, the skin region extracting unit 551 puts together such pixels that have continuous coordinates among the extracted coordinates as skin regions. In this situation, because the coordinates of the shoulder section and the coordinates of the face section are not continuous with each other, the skin region extracting unit 551 puts together and extracts the coordinates extracted from the shoulder section separately from the coordinates extracted from the face section, as two sets of coordinates of the skin regions of the mutually-different sites. Further, by performing a face recognition process on the picture illustrated in FIG. 43, for example, the skin region extracting unit 551 extracts the coordinates of the pixels of the face region of the user. After that, the skin region extracting unit 551 determines the region containing the extracted coordinates of the face region within the extracted skin regions, as a face skin region.

As explained above, the skin region extracting unit 551 extracts the coordinates of the skin region of the face of the user and the coordinates of the skin region of the site other than the face contained in the picture and transmits the extracted sets of coordinates of the skin regions to the calculating unit 552. In this situation, the colors (the luminance values) corresponding to the skin color may arbitrarily be set. For example, it is possible to set luminance values in a predetermined range for each of different human races, so that such coordinates that exhibit luminance values included in the set range in the picture are extracted as the coordinates corresponding to the skin color.

Further, for example, within the picture, the skin region extracting unit 551 may automatically set a face region serving as a "reference position" and a region (e.g., the shoulder in FIG. 43) serving as a "body position" of which a fluctuation of the blood flow is to be calculated, as Regions Of Interest (ROIs). Alternatively, the user may set the ROIs by operating an input unit configured with a mouse and/or a touch panel. For example, when the regions of interest have been set, the skin region extracting unit 551 extracts the coordinates of the set regions and transmits the coordinates of the regions to the calculating unit 552. In this situation, whether each of the regions is a face region serving as a reference position or a region serving as a body position other than the face may be designated by the operator or may be determined by performing the face recognition process described above.

For example, from among three regions of interest that are set, the operator designates the region of the "left cheek of the face" as a region serving as a reference position and designates the region of the "right shoulder" and the region of the "left shoulder" as regions serving as body positions. As a result, the skin region extracting unit 551 is able to recognize whether each of the regions of interest is a region serving as a reference position or a region serving as a body position. Alternatively, when the abovementioned designation is not made, the skin region extracting unit 551 may, as described above, extract the coordinates of the face region of the user by performing the face recognition process on the picture and extract such a region that contains the extracted coordinates of the face region from within the set regions of interest, as the skin region serving as the reference position.

The skin region extracting unit 551 performs the skin region extracting process described above on each of the frames structuring the picture and sequentially transmits the coordinates of the skin regions in each of the frames to the calculating unit 552. In this situation, when the regions of interest are set, the skin region extracting unit 551 tracks the coordinates of the regions of interest in each of the frames by performing a tracking process while using feature points in the picture, with respect to the frame in which the regions of interest are set and the frames following thereafter, so as to sequentially transmit the coordinates in the results of the tracking process to the calculating unit 552.

When the regions of interest are manually set, it is desirable to arrange the skin region to occupy a large area of each of the ROIs while including as little as possible of the eyes, the nose, and the hair and to avoid any part that has a shadow. Further, the skin region extracting unit 551 is able to extract such pixels that have luminance values corresponding to the skin color from each of the ROIs that are manually set and to set the region obtained by putting together the extracted pixels as a region of interest. In other words, when the ROIs are manually set, even if the set ROIs include the eyes or the hair, the skin region extracting unit 551 is able to set a region excluding the pixels corresponding to such parts, as a skin region.

Returning to the description of FIG. 41, the calculating unit 552 is configured to calculate the difference between luminance information of the picture signal of the face of the user and luminance information of the picture signal of the site other than the face taken at the same time as the picture signal of the face of the user is taken. More specifically, the calculating unit 552 extracts the luminance values of the green light contained in the picture signals of the face and the site other than the face of the user and calculates either a time difference (dPTT) between predetermined feature points in the extracted luminance values of the green light in the picture signals or a phase difference (PD) of the luminance values of the green light in the picture signals.

In this situation, before extracting the green light from the picture signals, the calculating unit 552 at first eliminates artificial impulse noise occurring in the camera itself serving as the picture obtaining unit 510*a* or the picture obtaining apparatus 110*b*, by performing an image smoothing process. For example, the calculating unit 552 applies a median filter of 5-by-5 pixels to the entire image in each of the frames. After that, the calculating unit 552 extracts the green light in the skin regions extracted by the skin region extracting unit 551, with respect to each of the frames to which the median filter has been applied.

As explained above, each of the pixels in each of the frames of the picture stores therein luminance values corresponding to the three colors of "R", "G" and "B". The color of each pixel is expressed by a combination of such luminance values. Accordingly, the calculating unit 552 extracts only the luminance value of green light having strong optical absorption characteristics for bloodstream hemoglobin, by applying a green filter to the skin regions (i.e., the skin region of the face and the skin region of the site other than the face) in each of the frames. After that, the calculating unit 552 extracts a green signal expressed in a temporal-change curve obtained by calculating an average luminance value of the green light for each of the frames, with respect to the skin region of the face and the skin region of the site other than the face. FIG. 44 is a drawing for explaining the extraction of the green signal according to the fourth embodiment. In FIG. 44, the upper section illustrates a schematic drawing of a plurality of frames contained in the picture; the middle section illustrates a chart of the average luminance value of the green light in which the vertical axis expresses "average luminance value (Average Luminance)", whereas the horizontal axis expresses "frame numbers (Frame No.)". Further, the lower section of FIG. 44 illustrates an example of the green signal while the vertical axis expresses "average luminance value of green (Average Green Luminance)", whereas the horizontal axis expresses "time [s]".

For example, as illustrated in the upper section of FIG. 44, the calculating unit 552 extracts the luminance values of the green light in the skin regions, by applying a green filter to each of the plurality of frames structuring the picture. After that, the calculating unit 552 extracts a chart indicating the average luminance values of the green as illustrated in the middle section of FIG. 44, by calculating an average value of the extracted luminance values of the green light for each of the frames. By performing the abovementioned process on each of the frames in the picture, the calculating unit 552 extracts a "green signal" as illustrated in the lower section of FIG. 44. The calculating unit 552 extracts a "green signal" for each of the skin regions extracted by the skin region extracting unit 551. More specifically, the calculating unit 552 extracts the "green signal" for the skin region of the face (i.e., the region of interest set in the face) and for the skin region of the site other than the face (i.e., the region of interest set in the site other than the face).

Subsequently, the calculating unit 552 extracts a pulse wave signal for each of the skin regions, by applying a filtering process to each of the extracted "green signals" of the skin regions. In other words, because the green signals include body motions and respiratory fluctuations, the calculating unit 552 performs the filtering process to eliminate the body motions and the respiratory fluctuations. For example, the calculating unit 552 eliminates signal components other than heartbeat components by employing a fifth (5th)-degree Butterworth filter that passes the frequency band of "0.7 Hz to 2.0 Hz". This arrangement corresponds to the component of "40 bpm to 120 bpm", which is a range of fluctuations of a heart rate of a healthy person. In the fourth embodiment, the example is explained in which the Butterworth filter is used as the band-pass filter that passes only the heartbeat frequency band; however, possible embodiments are not limited to this example. It is acceptable to use any band-pass filter as long as the filter is capable of passing only the heartbeat frequency band.

The extraction of the pulse wave signal according to the fourth embodiment is the same as the extraction of the pulse wave illustrated in FIG. 8. For example, when a pulse wave is extracted from the "green signal" indicated in the lower section of FIG. 44, the extracting process is the same as that illustrated in FIG. 8. Further, the lower section of FIG. 8 illustrates a pulse wave signal, while the vertical axis expresses "amplitude", whereas the horizontal axis expresses "time [s]". In the fourth embodiment, to make a distinction from a pulse wave in a "photoplethysmogram (PPG)" measured by an apparatus such as a photoplethysmograph, the pulse wave extracted from the picture signal will be referred to as image-based photoplethysmography (iPPG), as indicated in FIG. 8. For example, as illustrated in FIG. 8, the calculating unit 552 extracts an "image-based photoplethysmogram (iPPG)" by applying a filtering process to the "green signal". As illustrated in FIG. 8, the extracted "image-based photoplethysmogram" exhibits a periodic sinusoidal waveform in which a pulse wave generated by one heartbeat corresponds to one crest in the waveform resulting from the filtering process.

In the fourth embodiment, in principle, the green signal decreases when the blood flow increases. For this reason, for the purpose of arranging an increase or a decrease of the blood flow to match an increase or a decrease of the green signal, the calculating unit 552 may perform the abovementioned filtering process after multiplying the green signal by "−1" so as to reverse the positive and negative signs. For example, the image-based photoplethysmogram illustrated in FIG. 8 is a waveform obtained by reversing the positive and negative signs of the example in the fourth embodiment.

As explained above, the calculating unit 552 extracts the image-based photoplethysmogram of the face from the luminance information of the green light in the picture signal of the face and extracts the image-based photoplethysmogram of the site other than the face from the luminance information of the green light in the picture signal of the site other than the face. Further, by using the extracted image-based photoplethysmograms, the calculating unit 552 calculates the index values "dPTT" and "PD" corresponding to a "PTT" that uses an R-wave in an ECG. In the following sections, the calculation of the "dPTT" will be explained first, and subsequently, the calculation of the "PD" will be explained.

Generally speaking, a "PTT" can be defined as the time difference between an R-wave in an ECG and a feature point in a PPG. However, because a "PTT" is the propagation time period of a pulse wave pumped out from the heart, it is also possible to define a "PTT" by using a pulse wave waveform measured in two locations such as a site positioned close to the heart and a site positioned distant from the heart on a blood vessel serving as a propagation path. In other words, it is possible to define the difference in the propagation time period between the pulse wave waveform measured in the site positioned close to the heart and the pulse wave waveform measured in the site positioned distant from the heart, as the propagation time period of the pulse wave. Accordingly, in the fourth embodiment, the time difference between a feature point in a pulse wave waveform (iPPG) extracted from the picture signal of the face serving as a reference position and a feature point in a pulse wave waveform (iPPG) extracted from the picture signal of a body position will be used as an index value "dPTT: a difference of pulse transit time" corresponding to a "PTT".

As for the feature points in the pulse wave waveforms, there is no definite definitions and a plurality of determining methods are available. Examples of the determining methods include: the "bottom method" by which a point at which the "PPG" is at a minimum within a heartbeat is used as a feature point; the "top method" by which a point at which the "PPG" is at a maximum within a heartbeat is used as a feature point; the "first derivative method" by which a point at which a velocity pulse wave (a waveform from the first-order derivative of a PPG) is at a maximum within a heartbeat is used as a feature point; and the "second derivative method" by which a point at which an acceleration pulse wave (a waveform from the second-order derivative of a PPG) is at a maximum within a heartbeat is used as a feature point. The calculating unit 552 is able to determine the feature points by using any method arbitrarily selected from among various methods including these methods. Among the methods listed above, because the "second derivative method" tends to have a higher tolerance against noise than the other methods, the "second derivative method" may be set as a default method.

By determining the feature points in the pulse wave waveforms by implementing the method described above, the calculating unit 552 is able to define a "dPTT" and to calculate the "dPTT" from the image-based photoplethysmograms extracted from the picture signals, as illustrated in FIG. 9, for example. The definition of a difference of pulse transit time according to the fourth embodiment is the same as the definition of a difference of pulse transit time illustrated in FIG. 9. The left section of FIG. 9 illustrates the definition of a Pulse Transit Time (PTT), whereas the right section of FIG. 9 illustrates the definition of a difference of Pulse Transit Time (dPTT). In other words, in the fourth embodiment, as an index value corresponding to a "PTT" indicating the time period from an R-wave in an electrocardiogram to a feature point in a pulse wave A, the time difference between a feature point in the pulse wave A and the same feature point in a pulse wave B will be used as a "dPTT".

For example, by implementing the second derivative method, the calculating unit 552 detects feature points from the image-based photoplethysmogram "iPPG" extracted from the picture signal of the face serving as a reference position and the image-based photoplethysmogram "iPPG" extracted from the picture signal of the body position other than the face and further calculates the time difference "dPTT" between the detected feature points. The calculating unit 552 calculates "dPTT" values over time by calculating a "dPTT" value for each of the crests that each correspond to one heartbeat, by using the image-based photoplethysmograms each exhibiting a periodic sinusoidal waveform.

Next, the calculation of a "PD" will be explained. In the present example, the "PD" corresponding to a "PTT" is calculated from a phase difference between "iPPGs" in two mutually-different ROIs.

In the present example, to calculate the phase difference between the two pulse wave signals (the image-based photoplethysmographic signal extracted from the picture signal of the face serving as the reference position and the image-based photoplethysmographic signal extracted from the picture signal of the body position other than the face), the calculating unit 552 first calculates an instantaneous phase by using a Hilbert transform explained below. A Hilbert transform on "iPPG" at a time "t" (i.e., "H[iPPG(t)]") can be expressed on a time axis by using Expression (8) above.

Further, in Expression (8), "*" denotes a convolution operation. When "1/πt" in Expression (8) is Fourier-transformed, "−i sgn(f)" is obtained. Thus, it is possible to express the result (i.e., "F[H[iPPG(t)]]") of a Fourier transform on "H[iPPG(t)]" by using Expression (9) above. In other words, the Hilbert transform is an operation to either delay or advance the positive and negative frequency components of "iPPG(t)" by "90 degree". As a result, a "cos" component becomes "−sin" component, whereas a "sin" component becomes a "cos" component. Further, as for the result (i.e., "H[iPPG(t)]") of the Hilbert transform on "iPPG(t)", because the phase thereof is advanced from that of "iPPG(t)" by "90 degrees", it is possible to express the instantaneous phase "θW" as indicated in Expression (10) above.

The calculating unit 552 calculates an instantaneous phase of each of the two pulse wave signals by performing the Hilbert transform described above and further calculates the difference between the two instantaneous phases as the index value "PD" corresponding to a "PTT". For example, when the "iPPGs" obtained from two mutually-different regions (a region serving as the reference position and a region serving as the body position) are expressed as "iPPG$_1$(t)" and "iPPG$_2$(t)", it is possible to obtain instantaneous phases "θ$_1$(t)" and "θ$_2$(t)" of the "iPPGs" by using Expression (10) above. In this situation, when the iPPG measured from a position closer to the heart is assumed to be "iPPG$_1$(t)", because the pulse wave sequentially propagates starting from positions close to the heart, the instantaneous phase "θ$_1$(t)" is considered to be more advanced than the instantaneous phase "θ$_2$(t)". Accordingly, because the difference "PD" between the two instantaneous phases is considered to reflect the time difference in the propagations of the pulse waves of the two mutually-different ROIs, it is possible to assume the "PD" to be substantially equivalent to a "PTT". It is possible to calculate the instantaneous phase difference PD by using Expression (11) above. As explained herein, by using the instantaneous phases of the pulse waves, the calculating unit 552 calculates the phase difference while using the information in the entirety of the waveform corresponding to one heartbeat, instead of using the phase information of one point per heartbeat. In this situation, the calculating unit 552 calculates an instantaneous phase difference as illustrated in FIG. 10.

For example, as illustrated in FIG. 10, the calculating unit 552 calculates instantaneous phase$_1$ "θ$_1$" and instantaneous phase$_2$ "θ$_2$" from the image-based photoplethysmogram "iPPG$_1$" extracted from the picture signal of the face serving as the reference position and the image-based photoplethysmogram "iPPG$_2$" extracted from the picture signal of the body position (e.g., a shoulder). The instantaneous phases illustrated in the middle section of FIG. 10 are results of folding back the data in the range of (−π,π). Further, the calculating unit 552 calculates the instantaneous phase difference "PD" as illustrated in FIG. 10, by calculating the difference by subtracting instantaneous phase$_2$ "θ$_2$" from instantaneous phase difference$_1$ "θ$_1$" while using Expression (11) presented above.

Further, the calculating unit 552 calculates first blood circulation information and second blood circulation information by using either the calculated difference of pulse transit time "dPTT" or the calculated instantaneous phase difference "PD". For example, the calculating unit 552 calculates, as the first blood circulation information, a pulse wave propagation velocity based on the difference of pulse transit time "dPTT" observed before the predetermined user action between the face serving as the reference position and the body position and the distance between the reference position and the body position. In this situation, the calculating unit 552 may use the difference of pulse transit time "dPTT" observed before the predetermined user action between the face serving as the reference position and the body position, as the first blood circulation information. Alternatively, the calculating unit 552 may use the instantaneous phase difference "PD" observed before the predetermined user action between the face serving as the reference position and the body position, as the first blood circulation information. The calculation of the difference of pulse transit time described above is merely an example. The calculating unit 552 may calculate the difference of pulse transit time by using any of various methods as appropriate. For example, the calculating unit 552 may calculate the difference of pulse transit time by using any of the methods for calculating a difference of pulse transit time described in the first to the third embodiments.

Further, for example, the calculating unit 552 calculates, as the second blood circulation information, a pulse wave propagation velocity based on the difference of pulse transit time "dPTT" observed after the predetermined user action between the face serving as the reference position and the body position and the distance between the reference position and the body position. In this situation, the calculating unit 552 may use the difference of pulse transit time "dPTT" observed after the predetermined user action between the face serving as the reference position and the body position, as the second blood circulation information. Alternatively, the calculating unit 552 may use the instantaneous phase difference "PD" observed after the predetermined user action between the face serving as the reference position and the body position, as the second blood circulation information.

For instance, in FIG. 40, as first blood circulation information related to the right shoulder, the calculating unit 552 calculates a pulse wave propagation velocity based on a difference of pulse transit time "dPTT" observed before the user takes a bath between the face and the right shoulder and the distance between the face and the right shoulder. Further, for instance, in FIG. 40, as second blood circulation information related to the right shoulder, the calculating unit 552 calculates a pulse wave propagation velocity based on a difference of pulse transit time "dPTT" observed after the user takes a bath between the face and the right shoulder and the distance between the face and the right shoulder.

Further, for instance, in FIG. 40, as first blood circulation information related to the left shoulder, the calculating unit 552 calculates a pulse wave propagation velocity based on a difference of pulse transit time "dPTT" observed before the user takes a bath between the face and the left shoulder and the distance between the face and the left shoulder. Further, for instance, in FIG. 40, as second blood circulation information related to the left shoulder, the calculating unit 552 calculates a pulse wave propagation velocity based on a difference of pulse transit time "dPTT" observed after the user takes a bath between the face and the left shoulder and the distance between the face and the left shoulder.

Further, the calculating unit 552 calculates the difference between the first blood circulation information and the second blood circulation information. For instance, in FIG. 40, the calculating unit 552 calculates the difference between the first blood circulation information related to the right shoulder and the second blood circulation information related to the right shoulder. Further, for instance, in FIG. 40, the calculating unit 552 calculates the difference between the first blood circulation information related to the left shoulder and the second blood circulation information related to the left shoulder. Further, the calculating unit 552 may store the results of the abovementioned various types of calculations into the calculation result storage unit 542.

The generating unit 553 generates blood circulation information indicating a blood flow state in any of the body positions, in accordance with the differences calculated by the calculating unit 552. More specifically, the generating unit 553 generates the blood circulation information to be displayed on the display unit 520. For example, the generating unit 553 generates image information as the blood circulation information. More specifically, the generating unit 553 generates, as the blood circulation information, a hue image in which the difference between the first blood flow information and the second blood flow information in any of the body positions is expressed by using a change of the hue. In FIG. 40, the generating unit 553 generates a hue image in which the difference between the first blood flow information of the right shoulder and the second blood flow information of the right shoulder is expressed by using a change of the hue, as the blood circulation information of the right shoulder. Further, in FIG. 40, the generating unit 553 generates a hue image in which the difference between the first blood flow information of the left shoulder and the second blood flow information of the left shoulder is expressed by using a change of the hue, as the blood circulation information of the left shoulder. Further, for example, the generating unit 553 displays text information as blood circulation information.

The output controlling unit 554 controls the display by the display unit 520. For example, the output controlling unit 554 exercises control so that the blood circulation information generated by the generating unit 553 is displayed by the display unit 520. For example, the output controlling unit 554 controls the display by the display unit 520 so as to display the hue image expressing the difference between the first blood flow information and the second blood flow information in any of the body positions by using a change of the hue, so as to be superimposed on the corresponding body position. For instance, in FIG. 40, the output controlling unit 554 controls the display by the display unit 520 so as to display the hue image expressing the difference between the first blood flow information of the right shoulder and the second blood flow information of the right shoulder by using a change of the hue, so as to be superimposed on the right shoulder in the corresponding body image of the user. The output controlling unit 554 may control the output of the output apparatus 120b.

As explained above, the biological information displaying apparatus 500 performs the process on the basis of the change in the luminance value (the change in the green signal) in the picture signals of the subject. In this situation, if the subject or the camera moves while the subject is being imaged, the skin regions of the subject in the picture may move (make a translation movement or a rotation movement). Further, while the subject is being imaged, the intensity of the ambient light with which the skin is irradiated may change. Such a change in the luminance value due to the movement of the skin regions and such a temporal change in the intensity of the ambient light have a possibility of causing a noise component that does not directly reflect an actual change in the volume of blood. To cope with this situation, the biological information displaying apparatus 500 of the present disclosure performs a process while taking the abovementioned circumstances into consideration.

As for the noise caused by the translation movement and/or the rotation movement of the skin regions, the biological information displaying apparatus 500 makes a correction by performing a sequential tracking process on the skin color parts. For example, by sequentially tracking how each of the skin regions changes in the following frames, the skin region extracting unit 551 extracts the skin region from each of the frames. In one example, the skin region extracting unit 551 extracts the skin region from each of the frames by varying (updating) the positions of the feature points in the picture and a mutual positional relationship between the plurality of feature points. The sequential tracking process is not limited to the example explained herein. It is acceptable to use any other method to perform the sequential tracking process.

As for the temporal change in the intensity of the ambient light, the biological information displaying apparatus 500 adjusts the intensity of the light in the vicinity of the skin of the subject, by controlling the illuminating unit 570 in accordance with the level of illuminance measured by the illuminance sensor 560. More specifically, the feedback controlling unit 555 varies the intensity of the light radiated from the illuminating unit 570, on the basis of the level of illuminance received from the illuminance sensor 560. In other words, the feedback controlling unit 555 varies the intensity of the light radiated from the illuminating unit 570 in such a manner that the level of illuminance measured by the illuminance sensor 560 is kept at a certain value. With this arrangement, for example, even in an environment where there is a high possibility that the intensity of the ambient light may temporally change (e.g., inside an automobile), it is possible to perform the process with a high level of precision.

The feedback controlling unit 555 is also capable of exercising feedback control that is different from that in the process described above. For example, the feedback controlling unit 555 is capable of correcting temporal changes in the intensity of the ambient light, by exercising feedback control based on changes in the luminance values of the picture signals, without using the measured result obtained by the illuminance sensor 560. In one example, the feedback controlling unit 555 varies the intensity of the light radiated by the illuminating unit 570 in such a manner that, with respect to an average luminance of the skin region, frequency components in direct-current components and the alternating-current components that are lower than the heartbeat frequency band are kept at a certain value.

Although FIG. 41 illustrates the example in which the biological information displaying apparatus 500 includes the illuminance sensor 560 and the illuminating unit 570, possible embodiments are not limited to this example. The illuminance sensor 560 and the illuminating unit 570 provided on the outside of the biological information displaying apparatus 500 may be connected to the biological information displaying apparatus 500. Further, another arrangement is also acceptable in which the illuminance sensor 560 and the illuminating unit 570 are included in the picture obtaining apparatus 110*b*, so that the feedback controlling unit 555 included in the biological information displaying apparatus 500 controls the illuminating unit 570 via the network 300.

In the description above, the example is explained in which the correction is made by using the illuminating unit 570 in response to the temporal changes in the intensity of the ambient light. However, the biological information displaying apparatus 500 is also capable of making a correction in response to the temporal changes in the intensity of the ambient light, without using the illuminance sensor 560 or the illuminating unit 570. For example, the calculating unit 552 calculates the difference in the average luminance value in the skin region between frames, with respect to the frames contained in a time period of a predetermined length within the picture signals of the subject. After that, the calculating unit 552 compares the absolute value of each of the calculated differences between the frames with a predetermined threshold value and makes a correction by changing any difference that is larger than the predetermined threshold value to "0". In this manner, with respect to each of the differences calculated between the frames contained in the time period of the predetermined length, the calculating unit 552 calculates a time series of accumulated values of the differences between the frames obtained by changing any difference of which the absolute value is larger than the predetermined threshold value to "0", as a series of average luminance values (a green signal) of the skin region. As a result, drastic changes in bias components that were contained in the time series of average luminance values prior to the correction are cancelled. It is therefore possible to suppress transient responses of low frequency components, which are difficult to eliminate even by using a band-pass filter. This example represents a mode of "ε-filter", which is a non-linear filter.

(An Example of the Display of the Blood Circulation Information on the Dorsal Side)

Figure 45:
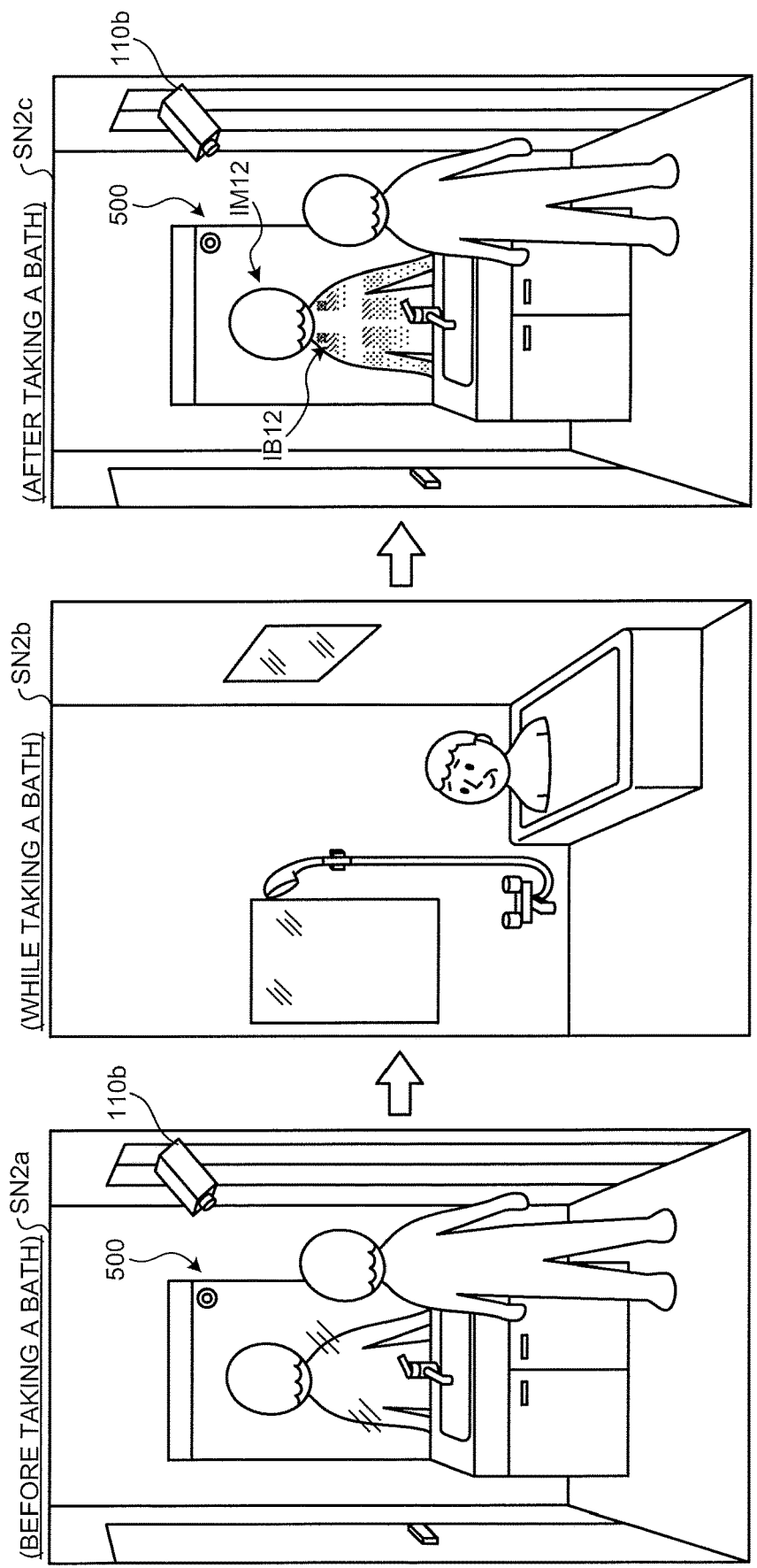
FIG. 45 is a drawing of an example of a display of a blood flow fluctuation observed between before and after taking a bath according to the fourth embodiment.

The example in FIG. 40 illustrates the situation where the blood circulation information on the front side of the user is displayed. However, the blood circulation information may be blood circulation information of any position of the body of the user. Thus, an example will be explained in which the biological information displaying apparatus 500 according to the fourth embodiment displays blood circulation information on the dorsal side of the user, with reference to FIG. 45. FIG. 45 is a drawing of an example of the display of a blood flow fluctuation observed between before and after taking a bath according to the fourth embodiment. More specifically, FIG. 45 illustrates the example in which the biological information displaying apparatus 500 displays blood circulation information based on the fluctuation of the blood flow observed between before and after taking a bath. The example in FIG. 45 illustrates a situation where the biological information displaying apparatus 500 is installed in a dressing room of a bath, while the picture obtaining apparatus 110*b* is installed opposite the washstand. The same explanations as those with FIG. 40 will be omitted as appropriate.

The scene SN2*a* in the left section of FIG. 45 illustrates the situation where the user is in the dressing room of the bath before taking a bath. In the scene SN2*a*, the image of the user reflected on the washstand in the dressing room is an image of the user taken by the picture obtaining apparatus 110*b* and displayed by the display unit 520. More specifically, the image of the user reflected on the washstand in the dressing room is a dorsal image of the user taken by the picture obtaining apparatus 110*b* from the back of the user and displayed by the display unit 520. Although FIG. 45 illustrates the example in which the image of the user above the waist reflected on the washstand in the dressing room is used as the image of the user, the image of the user may be that of his entire body. Further, in the scene SN2*a*, the biological information displaying apparatus 500 images the user before the user takes a bath. After that, the biological information displaying apparatus 500 calculates first blood flow information in body positions of the user observed before the user takes a bath, on the basis of luminance information of picture signals of the body of the user.

As explained above, in FIG. 45, the biological information displaying apparatus 500 installed at the washstand in the dressing room is configured to image the user from the dorsal side by employing the picture obtaining apparatus 110*b*. Thus, the biological information displaying apparatus 500 calculates the first blood flow information that is the blood flow information in one or more body positions of the user observed before the user takes a bath, on the basis of the luminance information of picture signals of the body obtained by imaging the user from the dorsal side. In FIG. 45, the biological information displaying apparatus 500 calculates first blood flow information in a plurality of body positions of the user. For example, the biological information displaying apparatus 500 calculates the first blood flow information in the plurality of body positions such as both shoulders, both arms, and a lumbar part of the user. For example, by dividing the image taken of the body of the user into a plurality of regions, the biological information displaying apparatus 500 may calculate the first blood flow information in the plurality of body positions corresponding to the regions.

The scene SN2*b* in the middle section of FIG. 45 illustrates the situation where the user is taking a bath. After having taken a bath as illustrated in SN2*b* in FIG. 45, the user moves from the bathroom to the dressing room. The scene SN2*c* in the right section of FIG. 45 illustrates the situation where the user is in the dressing room of the bath after taking a bath. In the scene SN2*c* in FIG. 45, the biological information displaying apparatus 500 calculates second blood flow information that is the blood flow information in the body positions of the user observed after the user takes a bath, on the basis of the luminance information of the picture signals of the body obtained by imaging the user from the dorsal side. In FIG. 45, the biological information displaying apparatus 500 calculates the second blood flow information in a plurality of body positions of the user. For example, the biological information displaying apparatus 500 calculates the second blood flow information in the plurality of body positions such as both shoulders, both arms, and a lumbar part of the user. For example, by dividing the image taken of the body of the user into a plurality of regions, the biological information displaying apparatus 500 may calculate the second blood flow information in the plurality of body positions corresponding to the regions.

Further, the biological information displaying apparatus 500 calculates a blood flow difference in each of the body positions. FIG. 45 illustrates the situation where the larger the blood flow difference is, the better the blood circulation is. In FIG. 45, by dividing the image taken of the body of the user including both shoulders, both arms, and the lumbar part of the user into a plurality of regions, the biological information displaying apparatus 500 calculates the blood flow difference in each of the plurality of body positions corresponding to the regions. For example, the biological information displaying apparatus 500 calculates a blood flow difference with respect to each of the plurality of body positions near the right shoulder of the user. Further, for example, the biological information displaying apparatus 500 calculates a blood flow difference with respect to each of a plurality of body positions near the lumbar part of the user.

Further, the biological information displaying apparatus 500 generates blood circulation information indicating a blood flow state in each of the body positions, on the basis of the blood flow differences. In FIG. 45, as blood circulation information IB12, the biological information displaying apparatus 500 generates an image in which the larger the blood flow difference in each of the body positions is, the darker the hatching is. Further, in FIG. 45, as the blood circulation information IB12, the biological information displaying apparatus 500 generates the image in which the smaller the blood flow difference in each of the body positions is, the lighter the hatching is.

After that, the biological information displaying apparatus 500 displays the generated blood circulation information IB12 together with a body image IM12 of the user. More specifically, the biological information displaying apparatus 500 displays the generated blood circulation information IB12 so as to be superimposed on the corresponding body position in the body image IM12 of the user. For example, the biological information displaying apparatus 500 displays the blood circulation information IB12 of the lumbar part so as to be superimposed on the lumbar part in the body image IM12 of the user. In FIG. 45, because the image with the hatching is superimposed on the entire lumbar part, the user is able to intuitively recognize that the blood circulation in the entire lumbar part has become better.

(Examples of Installation of the Biological Information Displaying Apparatus)

In the examples illustrated in FIGS. 40 and 45, the situation is explained in which the user action is the user's taking a bath. However, the user action may be any action as long as a fluctuation related to the blood flow is caused in the body of the user between before and after the action. Further, in the examples illustrated in FIGS. 40 and 45, the situation is explained in which the biological information displaying apparatus 500 is installed in the dressing room of the bath. However, the biological information displaying apparatus 500 may be installed in any location. Thus, examples will be explained in which the biological information displaying apparatus 500 according to the fourth embodiment is installed in locker rooms, with reference to FIGS. 46 and 47.

Figure 46:
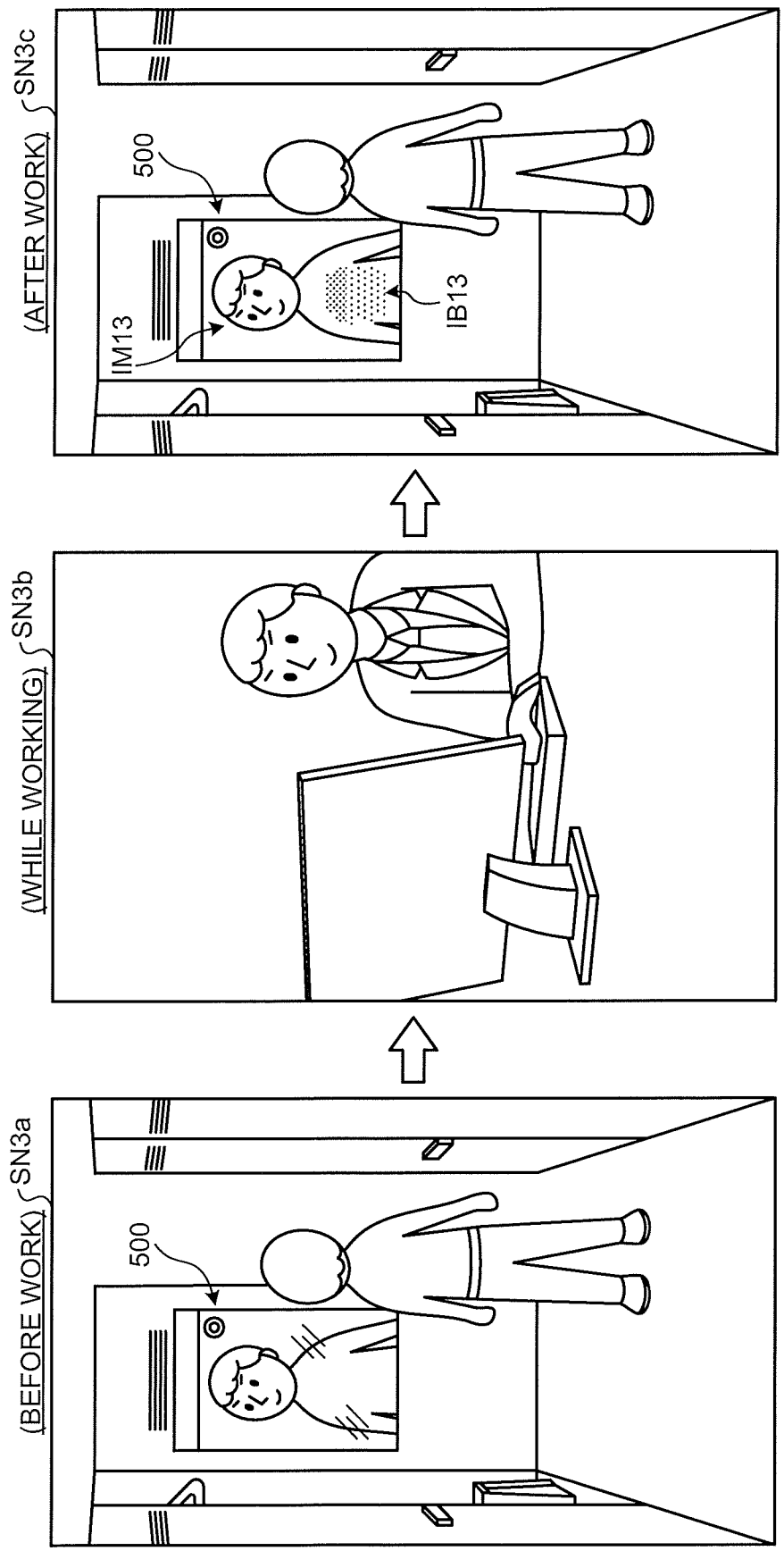
FIG. 46 is a drawing of an example of a display of a blood flow fluctuation observed between before and after work according to the fourth embodiment.

First, with reference to FIG. 46, an example will be explained in which the biological information displaying apparatus 500 according to the fourth embodiment is installed in a locker room in a workplace, while the user action is the user's work. FIG. 46 is a drawing of an example of the display of a blood flow fluctuation observed between before and after work according to the fourth embodiment. More specifically, FIG. 46 illustrates an example in which the biological information displaying apparatus 500 displays blood circulation information based on the fluctuation of the blood flow observed between before and after the user's work.

The scene SN3a in the left section of FIG. 46 illustrates the situation where the user is in the locker room before work. In the scene SN3a, the image of the user reflected on the door of the locker in the locker room may be an image of the user reflected on the mirror or may be an image of the user taken by the picture obtaining unit 510a included in the biological information displaying apparatus 500 and displayed by the display unit 520. Further, in the scene SN3a, the biological information displaying apparatus 500 images the user before work. After that, the biological information displaying apparatus 500 calculates first blood flow information that is the blood flow information in body positions of the user observed before work, on the basis of the luminance information of picture signals of the body of the user.

In FIG. 46, the biological information displaying apparatus 500 installed on the door of the locker in the locker room images the user from the front, by employing the picture obtaining unit 510a. Thus, the biological information displaying apparatus 500 calculates the first blood flow information that is the blood flow information in one or more body positions of the user observed before work, on the basis of the luminance information of picture signals of the body obtained by imaging the user from the front. In FIG. 46, the biological information displaying apparatus 500 calculates the first blood flow information in a plurality of body positions of the user. For example, the biological information displaying apparatus 500 calculates the first blood flow information in the plurality of body positions such as both shoulders, both arms, and the abdomen of the user. For example, by dividing the image taken of the body of the user into a plurality of regions, the biological information displaying apparatus 500 may calculate the first blood flow information in the plurality of body positions corresponding to the regions.

Further, the biological information displaying apparatus 500 may start the image taking process when a predetermined condition is satisfied. For example, the biological information displaying apparatus 500 may start the image taking process by using the user's opening the door of the locker as a trigger. As another example, the biological information displaying apparatus 500 may start the image taking process by using the user's being reflected on the predetermined mirror as a trigger.

After that, the user moves from the locker room to his own desk, or the like and works. In that situation, the biological information displaying apparatus 500 may stop the image taking process. For example, the biological information displaying apparatus 500 may stop the image taking process, by using the user's closing the door of the locker as a trigger. As another example, the biological information displaying apparatus 500 may stop the image taking process by using the user's stopping being reflected on the predetermined mirror as a trigger. Further, the biological information displaying apparatus 500 may inform the user that information required by the calculation of the first blood flow information has been obtained. With this arrangement, the biological information displaying apparatus 500 is able to inform the user of the timing with which the user can leave the locker room and is able to obtain the information required by the display of the blood circulation information observed before and after the work.

The scene SN3b in the middle section of FIG. 46 illustrates the situation where the user is working. In the scene SN3b, the user works for a certain time period (e.g., eight hours). For example, the blood flow of the user becomes worse because the capillary vessels in the skin and the subcutaneous blood vessels of the user contract due to stress from the user's work or the like. For this reason, the second blood flow information calculated by the biological information displaying apparatus 500 has a value that fluctuated from the first blood flow information. For example, the second blood flow information calculated by the biological information displaying apparatus 500 has a value smaller than that of the first blood flow information. In this situation, the biological information displaying apparatus 500 may obtain the ambient temperature and/or the ambient humidity during the user's work by using an appropriate means. For example, the biological information displaying apparatus 500 may obtain information about the ambient temperature and/or the ambient humidity during the user's work by using a predetermined thermometer and/or a hygrometer configured to measure the ambient temperature and/or the ambient humidity during the user's work. In that situation, the biological information displaying apparatus 500 may correct the first blood flow information and the second blood flow information in accordance with the obtained information about the ambient temperature and/or the ambient humidity during the user's work.

After the work illustrated in the scene SN3*b* in FIG. 46, the user moves to the locker room. In that situation, the biological information displaying apparatus 500 may start an image taking process. For example, the biological information displaying apparatus 500 may start the image taking process by using the user's opening the door of the locker as a trigger. As another example, the biological information displaying apparatus 500 may start the image taking process by using the user's being reflected on the predetermined mirror as a trigger. The scene SN3*c* in the right section of FIG. 46 illustrates the situation where the user is in the locker room after the work. In the scene SN3*c* in FIG. 46, the biological information displaying apparatus 500 calculates second blood flow information that is the blood flow information in the body positions of the user observed after work, on the basis of the luminance information of picture signals of the body obtained by imaging the user from the front. In FIG. 46, the biological information displaying apparatus 500 calculates the second blood flow information in a plurality of positions of the user. For example, the biological information displaying apparatus 500 calculates the second blood flow information in the plurality of body positions such as both shoulders, both arms, and the abdomen of the user. For example, by dividing the image taken of the body of the user into a plurality of regions, the biological information displaying apparatus 500 may calculate the second blood flow information in the plurality of body positions corresponding to the regions.

Further, the biological information displaying apparatus 500 calculates a blood flow difference in each of the body positions. In this situation, the blood flow difference in each of the body positions denotes a fluctuation of the blood flow observed between before and after the work in the body position. FIG. 46 illustrates an example in which the larger the blood flow difference is, the better the blood flow is.

In FIG. 46, by dividing the image taken of the body of the user including both shoulders, both arms, and the abdomen of the user into a plurality of regions, the biological information displaying apparatus 500 calculates the blood flow difference in each of the plurality of body positions corresponding to the regions. For example, the biological information displaying apparatus 500 calculates a blood flow difference with respect to each of the plurality of body positions near the right shoulder of the user. Further, for example, the biological information displaying apparatus 500 calculates a blood flow difference with respect to each of a plurality of body positions near the abdomen of the user.

Further, the biological information displaying apparatus 500 generates blood circulation information indicating a blood flow state in each of the body positions, on the basis of the blood flow differences. In FIG. 46, as blood flow information IB13, the biological information displaying apparatus 500 generates an image in which the larger the blood flow difference in each of the body positions is, the darker the hatching is. Further, in FIG. 46, as the blood circulation information IB13, the biological information displaying apparatus 500 generates the image in which the smaller the blood flow difference in each of the body positions is, the lighter the hatching is. After that, the biological information displaying apparatus 500 displays the generated blood circulation information IB13 together with a body image IM13 of the user. More specifically, the biological information displaying apparatus 500 displays the generated blood circulation information IB13 so as to be superimposed on the corresponding body position in the body image IM13 of the user. For example, the biological information displaying apparatus 500 displays the blood circulation information IB13 of the abdomen so as to be superimposed on the abdomen in the body image IM13 of the user. In FIG. 46, because the displayed blood circulation information IB13 is superimposed on the entire abdomen, the user is able to intuitively recognize that the blood circulation in the entire abdomen has become better. Further, in FIG. 46, because the blood circulation information IB13 is not superimposed on the two shoulders or the two arms, the user is able to intuitively recognize that the blood circulation at the two shoulders and the two arms has not become better (has become worse).

Figure 47:
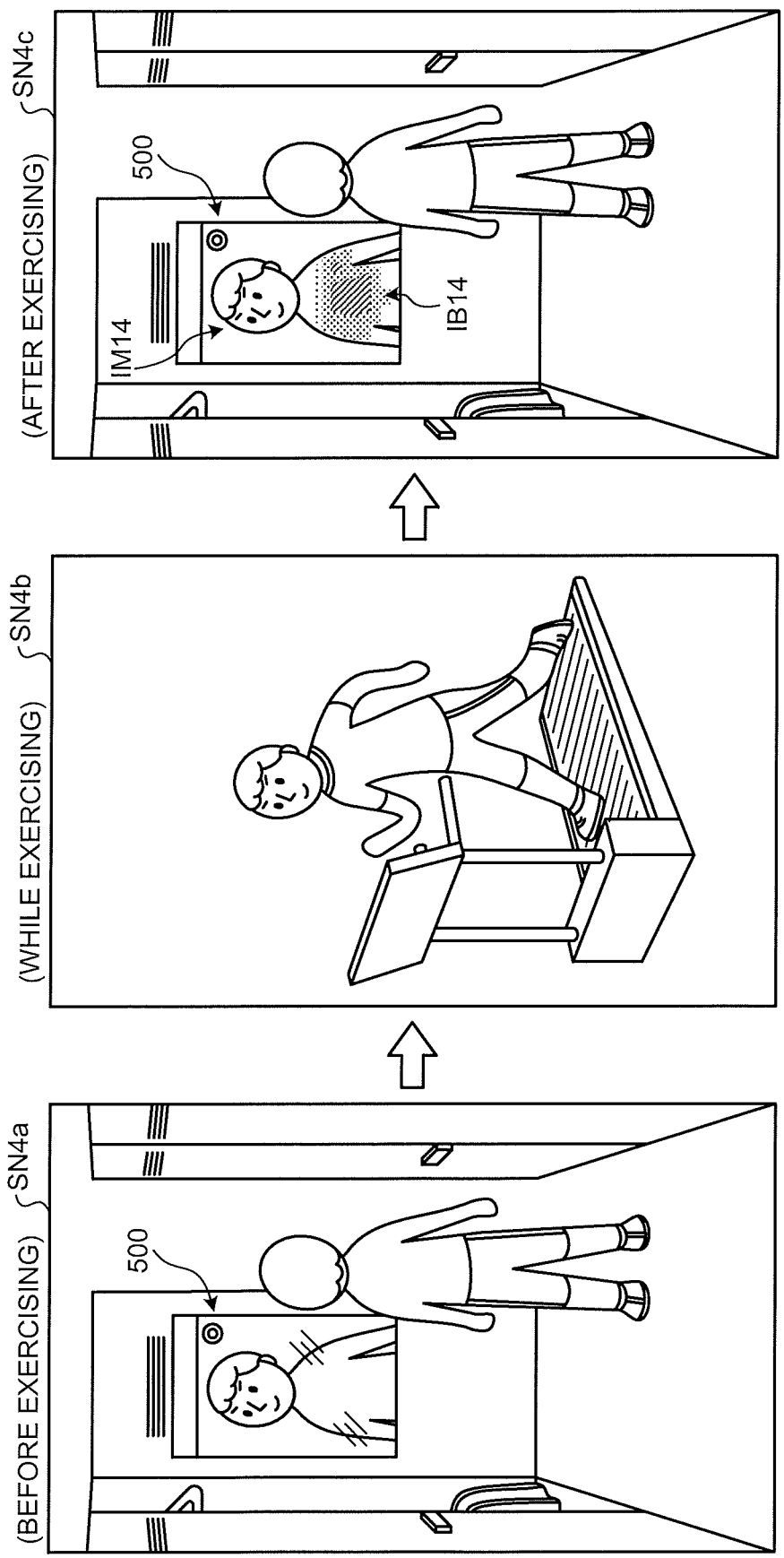
FIG. 47 is a drawing of an example of a display of a blood flow fluctuation observed between before and after exercise according to the fourth embodiment.

Next, with reference to FIG. 47, an example will be explained in which the biological information displaying apparatus 500 according to the fourth embodiment is installed in a locker room of a sports gym, while the user action is the user's exercise. FIG. 47 is a drawing of an example of a display of a blood flow fluctuation observed between before and after exercise according to the fourth embodiment. More specifically, FIG. 47 illustrates the example in which the biological information displaying apparatus 500 displays blood circulation information based on the fluctuation of the blood flow observed between before and after the user exercises.

First, the scene SN4*a* in the left section of FIG. 47 illustrates the situation where the user is in the locker room before exercising. In the scene SN4*a*, the image of the user reflected on the door of the locker in the locker room may be an image of the user reflected on the mirror or may be an image of the user taken by the picture obtaining unit 510*a* included in the biological information displaying apparatus 500 and displayed by the display unit 520. Further, in the scene SN4*a*, the biological information displaying apparatus 500 images the user before the exercise. After that, the biological information displaying apparatus 500 calculates first blood flow information that is blood flow information in body positions of the user observed before the exercise, on the basis of the luminance information of picture signals of the body of the user.

In FIG. 47, the biological information displaying apparatus 500 installed on the door of the locker in the locker room images the user from the front, by employing the picture obtaining unit 510*a*. Thus, the biological information displaying apparatus 500 calculates the first blood flow information that is the blood flow information in one or more body positions of the user observed before the exercise, on the basis of the luminance information of picture signals of the body obtained by imaging the user from the front. In FIG. 47, the biological information displaying apparatus 500 calculates the first blood flow information in a plurality of body positions of the user. For example, the biological information displaying apparatus 500 calculates the first blood flow information in the plurality of body positions such as both shoulders, both arms, and the chest of the user. For example, by dividing the image taken of the body of the user into a plurality of regions, the biological information displaying apparatus 500 may calculate the first blood flow information in the plurality of body positions corresponding to the regions.

After that, the user moves from the locker room to the inside of the gym and exercises. The scene SN4*b* in the middle section of FIG. 47 illustrates the situation where the user is exercising. In the scene SN4*b*, the user exercises for a certain time period (e.g., two hours). For example, the blood flow of the user becomes better because the capillary vessels in the skin and the subcutaneous blood vessels of the user expand due to the user's exercising. For this reason, the second blood flow information calculated by the biological information displaying apparatus 500 has a value that fluctuated from the first blood flow information. For example, the second blood flow information calculated by the biological information displaying apparatus 500 has a value larger than that of the first blood flow information.

After the exercise illustrated in the scene SN4*b* in FIG. 47, the user moves to the locker room. In that situation, the biological information displaying apparatus 500 may start an image taking process. The scene SN4*c* in the right section of FIG. 47 illustrates the situation where the user is in the locker room after exercising. In the scene SN4*c* in FIG. 47, the biological information displaying apparatus 500 calculates second blood flow information that is the blood flow information in the body positions of the user observed after the exercise, on the basis of the luminance information of picture signals of the body obtained by imaging the user from the front. In FIG. 47, the biological information displaying apparatus 500 calculates the second blood flow information in a plurality of positions of the user. For example, the biological information displaying apparatus 500 calculates the second blood flow information in the plurality of body positions such as both shoulders, both arms, and the chest of the user. For example, by dividing the image taken of the body of the user into a plurality of regions, the biological information displaying apparatus 500 may calculate the second blood flow information in the plurality of body positions corresponding to the regions. Further, the biological information displaying apparatus 500 calculates a blood flow difference in each of the body positions. In this situation, the blood flow difference in each of the body positions denotes a fluctuation of the blood flow observed between before and after the exercise in the body position. FIG. 47 illustrates an example in which the larger the blood flow difference is, the better the blood flow is.

In FIG. 47, by dividing the image taken of the body of the user including both shoulders, both arms, and the chest of the user into a plurality of regions, the biological information displaying apparatus 500 calculates the blood flow difference in each of the plurality of body positions corresponding to the regions. For example, the biological information displaying apparatus 500 calculates a blood flow difference with respect to each of the plurality of body positions near the chest of the user.

Further, the biological information displaying apparatus 500 generates blood circulation information indicating a blood flow state in each of the body positions, on the basis of the blood flow differences. In FIG. 47, as blood circulation information IB14, the biological information displaying apparatus 500 generates an image in which the larger the blood flow difference in each of the body positions is, the darker the hatching is. Further, in FIG. 47, as the blood circulation information IB14, the biological information displaying apparatus 500 generates the image in which the smaller the blood flow difference in each of the body positions is, the lighter the hatching is.

After that, the biological information displaying apparatus 500 displays the generated blood circulation information IB14 together with a body image IM14 of the user. More specifically, the biological information displaying apparatus 500 displays the generated blood circulation information IB14 so as to be superimposed on the corresponding body position in the body image IM14 of the user. For example, the biological information displaying apparatus 500 displays the blood circulation information IB14 of the chest so as to be superimposed on the chest in the body image IM14 of the user. In FIG. 47, because the displayed blood circulation information IB14 is superimposed on the entire chest, the user is able to intuitively recognize that the blood circulation in the entire chest has become better.

(An Example of Installation of the Biological Information Displaying Apparatus)

Next, a specific example of installation of the biological information displaying apparatus 500 described above will be explained. As described above, the biological information displaying apparatus 500 according to the fourth embodiment is capable of measuring the fluctuations of the blood pressure of the human body in a simple and contactless manner. As a result, for example, it is possible to make the fluctuations of the blood pressure of the human body visible in the daily-basis medical checkup system illustrated in FIG. 1. As explained below, it is possible to make the fluctuations of the blood pressure of the human body visible in the daily-basis medical checkup system illustrated in FIG. 1, by using the configuration illustrated in FIG. 20, for example. In this situation, the biological information measuring apparatus 100 illustrated in FIG. 20 is replaced with the biological information displaying apparatus 500.

For example, it is possible to realize the daily-basis medical checkup system illustrated in FIG. 1 capable of providing a health forecast when the subject only stands in front of a mirror in a washroom, by installing, for example, a camera-equipped PC (a tablet PC) serving as the biological information displaying apparatus 500 on the rear surface of a half mirror, as illustrated in FIG. 20. In other words, the biological information displaying apparatus 500 images the subject through the half mirror, calculates a blood flow difference on the basis of picture signals that were taken, and displays generated blood circulation information. For example, the picture obtaining unit 510*a* included in the biological information displaying apparatus 500 installed on the rear surface of the half mirror images the body of the user. After that, the skin region extracting unit 551 extracts the regions corresponding to the face serving as the reference position and the body positions such as the shoulders of the user in the picture, so that the calculating unit 552 extracts an image-based photoplethysmogram of each of the regions and calculates either a "PD" or a "dPTT". Further, the calculating unit 552 calculates a blood flow difference from the first blood flow information and the second blood flow information calculated on the basis of the "PD" or the "dPTT". The generating unit 553 generates blood circulation information on the basis of the blood flow difference calculated by the calculating unit 552, so that the display unit 520 displays the blood circulation information.

(An Example of the Display of the Blood Circulation Information)

Figure 48:
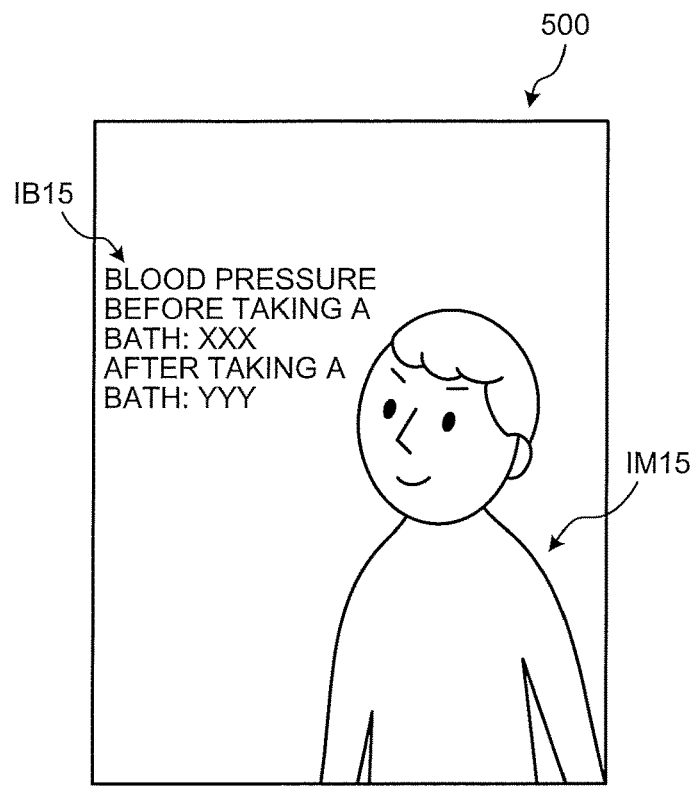
FIG. 48 is a drawing of an example of displayed information according to the fourth embodiment.
Figure 49:
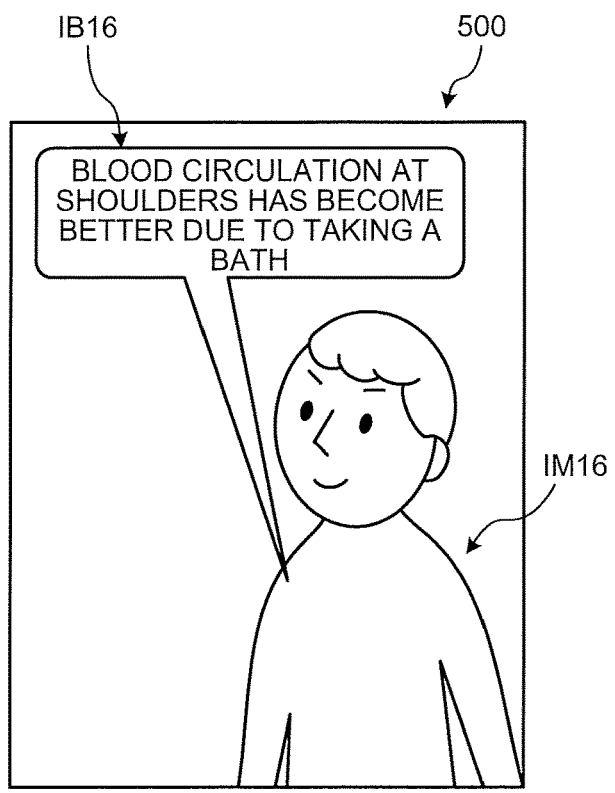
FIG. 49 is a drawing of another example of displayed information according to the fourth embodiment.
Figure 50:
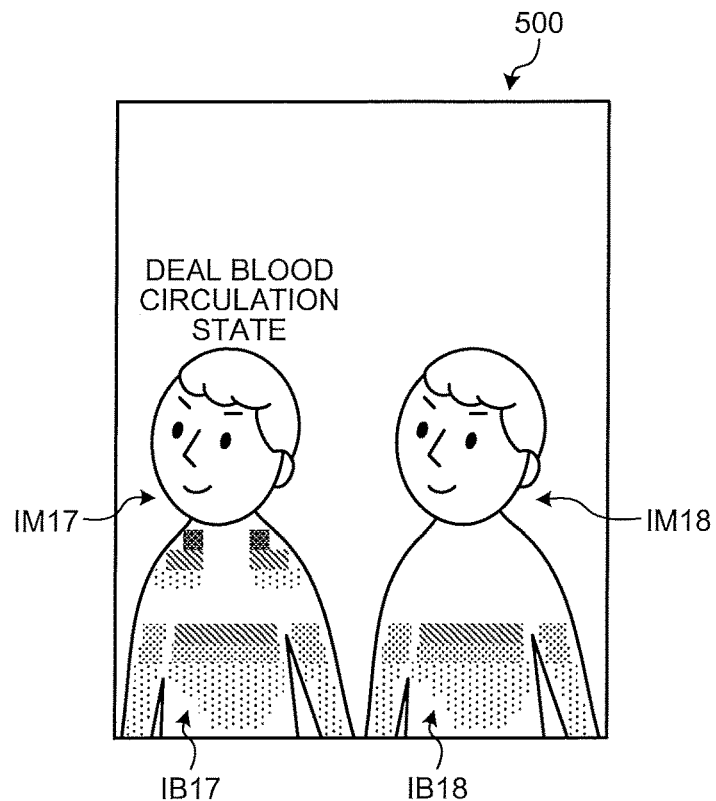
FIG. 50 is a drawing of yet another example of displayed information according to the fourth embodiment.

In the description above, the example is explained in which, as the blood circulation information, the image based on the blood flow difference is displayed so as to be superimposed on the body image of the user; however, the blood circulation information does not necessarily have to be an image and may be any of various types of information. This point will be explained with reference to FIGS. 48 to 50. FIGS. 48 to 50 are drawings of examples of displayed information according to the fourth embodiment. More specifically, FIGS. 48 and 49 each illustrate an example in which text information is displayed as the blood circulation information. FIG. 50 illustrates an example in which information that makes it possible to make a comparison with another user is displayed as the blood circulation information.

First, FIG. 48 illustrate an example in which the biological information displaying apparatus 500 displays blood circulation information IB15 that is text information, together with a body image IM15 of the user. More specifically, FIG. 48 illustrates an example in which the biological information displaying apparatus 500 displays the blood circulation information IB15 related to the blood pressure of the user observed before and after the user takes a bath, together with the body image IM15 of the user. With this arrangement, the biological information displaying apparatus 500 makes it possible for the user to logically recognize the changes in the blood circulation of his own, by using the text information. In this situation, in addition to the blood circulation information IB15 that is the text information, the biological information displaying apparatus 500 may also display the blood circulation information IB11 that is an image as illustrated in FIG. 40, so as to be superimposed on the body image IM15 of the user. With this arrangement, the biological information displaying apparatus 500 makes it possible for the user to intuitively recognize the changes in the blood circulation of his own by using the image and to logically recognize the same by using the text information. It is therefore possible to communicate with the user about the blood circulation information appropriately.

Next, FIG. 49 illustrates an example in which the biological information displaying apparatus 500 displays blood circulation information IB16 that is text information, together with a body image IM16 of the user. More specifically, FIG. 49 illustrates the example in which the biological information displaying apparatus 500 displays the blood circulation information IB16 related to a change in the blood flow observed between before and after the user takes a bath, together with the body image IM16 of the user. In FIG. 49, the blood circulation information IB16 is information indicated by the sentence "The blood circulation at the shoulders has become better due to taking a bath". With this arrangement, the biological information displaying apparatus 500 makes it possible for the user to more easily recognize the change in the blood circulation of his own, by displaying the blood circulation information by using the simple sentence. In this situation, in addition to the blood circulation information IB16 that is the text information, the biological information displaying apparatus 500 may display the blood circulation information IB11 that is an image as illustrated in FIG. 40, so as to be superimposed on the body image IM16 of the user.

Next, FIG. 50 illustrates an example in which the biological information displaying apparatus 500 displays blood circulation information IB17 of another user. More specifically, FIG. 50 illustrates the example in which the biological information displaying apparatus 500 displays the blood circulation information IB17 related to a change in the blood flow observed between before and after the other user takes a bath, together with a body image IM17 of the other user. In this situation, the body image IM17 of the other user may be any body image such as a body image IM18 of the user himself, for example. Further, the blood circulation information IB17 of the other user may be an average of blood circulation information of a plurality of other users. In FIG. 50, the blood circulation information IB17 of the other user illustrates a situation where the blood circulation on the two shoulders has become better and indicates the state that is desirable as a change in the blood flow observed between before and after taking a bath.

Further, FIG. 50 illustrates the example in which the biological information displaying apparatus 500 displays the body image IM18 of the user on which the blood circulation information IB18 is displayed in a superimposed manner, together with the body image IM17 of the other user on the blood circulation information IB17 is displayed in a superimposed manner. In FIG. 50, the blood circulation information IB18 of the user illustrates a situation where the blood circulation on the two shoulders has not become better and indicates the state that is not desirable as a change in the blood flow observed between before and after taking a bath. With this arrangement, the biological information displaying apparatus 500 makes it possible for the user to recognize the change in the blood circulation of his own in comparison with the other piece of information, by displaying the change in the user's blood circulation together with the change in the other user's blood circulation. It is therefore possible to communicate with the user about the blood circulation information appropriately. Further, because the user is able to recognize the ideal change in the blood circulation, the user is able to easily understand what he needs to improve.

(A Processing Flow)

Figure 51:
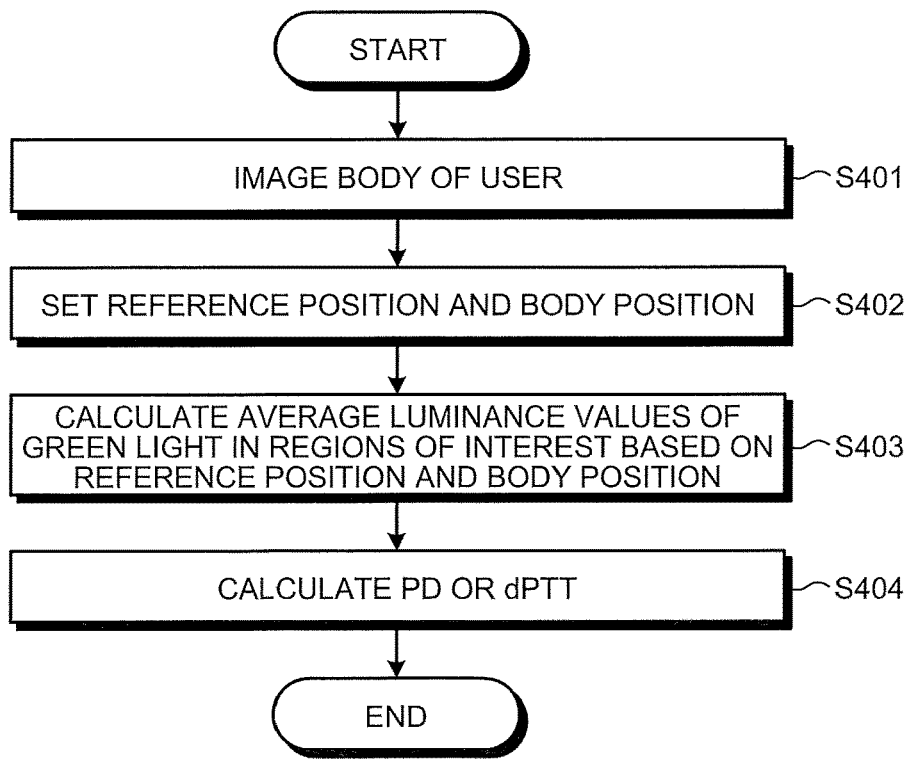
FIG. 51 is a flowchart of a processing procedure performed by the biological information displaying apparatus according to the fourth embodiment.
Figure 52:
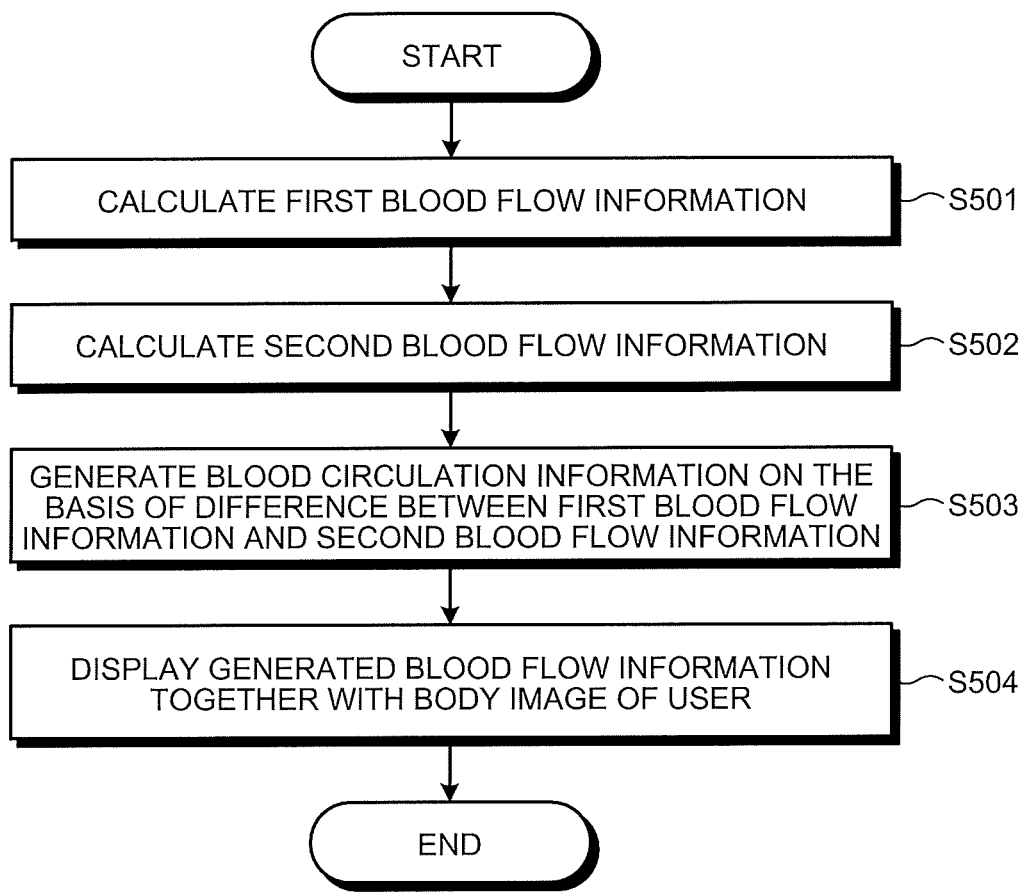
FIG. 52 is a flowchart of another processing procedure performed by the biological information displaying apparatus according to the fourth embodiment.

Next, a flow in a process performed by the biological information displaying apparatus 500 will be explained. FIGS. 51 and 52 are flowcharts illustrating processing procedures performed by the biological information displaying apparatus 500 according to the fourth embodiment. More specifically, FIG. 51 is a flowchart illustrating a processing procedure up to when the biological information displaying apparatus 500 calculates a "PD" or a "dPTT". Further, FIG. 52 is a flowchart illustrating a processing procedure up to when the biological information displaying apparatus 500 displays the blood circulation information.

First, as illustrated in FIG. 51, in the biological information displaying apparatus 500, either the picture obtaining unit 510a or the picture obtaining apparatus 110b images the body of the user (step S401).

After that, the skin region extracting unit 551 automatically extracts regions corresponding to the skin color. Alternatively, as a result of the operator manually setting Regions of Interest (ROIs), the ROIs are each set in a reference position and a body position (step S402). Subsequently, the calculating unit 552 calculates an average luminance value of the green light in each of the set regions of interest (step S403) and calculates either a "PD" or a "dPTT" from the calculated average luminance values (step S404).

Subsequently, as illustrated in FIG. 52, in the biological information displaying apparatus 500, the calculating unit 552 calculates the first blood flow information (step S501). For example, the calculating unit 552 calculates the first blood flow information on the basis of the calculated "PD" or "dPTT". After that, the calculating unit 552 calculates the second blood flow information (step S502). For example, the calculating unit 552 calculates the second blood flow information on the basis of the calculated "PD" or "dPTT".

Subsequently, the generating unit 553 generates the blood circulation information on the basis of the difference between the first blood flow information and the second blood flow information (step S503). After that, the display unit 520 displays the generated blood circulation information, together with the body image of the user (step S504).

(A Hardware Configuration)

Figure 53:
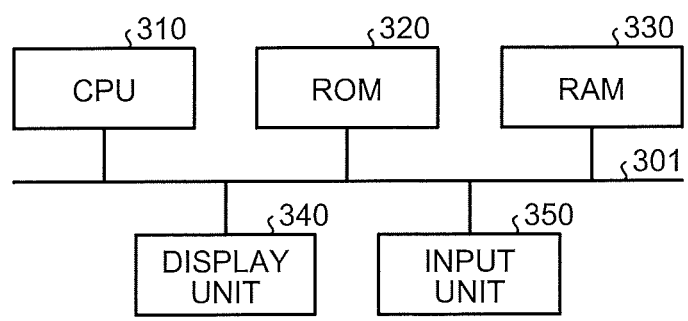
FIG. 53 is a diagram of a hardware configuration of a biological information measuring apparatus, the biological information displaying apparatus, or a Personal Health Record (PHR) apparatus according to the fourth embodiment.

FIG. 53 is a diagram of a hardware configuration of the biological information measuring apparatus 100 (the biological information measuring apparatus 100a, the biological information displaying apparatus 500, or the PHR apparatus 200) according to the present embodiments. The biological information measuring apparatus 100 (the biological information measuring apparatus 100a, the biological information displaying apparatus 500, or the PHR apparatus 200) includes a CPU 310, a Read-Only Memory (ROM) 320, a RAM 330, a display unit 340, and an input unit 350. Further, in the biological information measuring apparatus 100 (the biological information measuring apparatus 100a, the biological information displaying apparatus 500, or the PHR apparatus 200) the CPU 310, the ROM 320, the RAM 330, the display unit 340, and the input unit 350 are connected together via a bus line 301.

A biological information measuring computer program (hereinafter, "biological information measuring program") or a biological information displaying computer program (hereinafter, "biological information displaying program") configured to execute the various types of processes described in the embodiments above are stored in the ROM 320 and are loaded into the RAM 330 via the bus line 301. The CPU 310 executes the biological information measuring program or the biological information displaying program loaded into the RAM 330. For example, in the biological information measuring apparatus 100 (the biological information measuring apparatus 100a, the biological information displaying apparatus 500, or the PHR apparatus 200), according to an input of an instruction from the operator through the input unit 350, the CPU 310 reads the biological information measuring program from the ROM 320, loads the read program into a program storage region in the RAM 330, and execute the various types of processes. The CPU 310 temporarily stores various types of data generated as a result of the various types of processes, into a data storage region formed in the RAM 330.

The biological information measuring program or the biological information displaying program executed by the biological information measuring apparatus 100 (the biological information measuring apparatus 100a, the biological information displaying apparatus 500, or the PHR apparatus 200) has a module structure including the skin region extracting unit 151, the calculating unit 152, the measuring unit 153, the output controlling unit 154, and the feedback controlling unit 155, or a module structure including the skin region extracting unit 151, the calculating unit 152, the measuring unit 153, the output controlling unit 154, the feedback controlling unit 155, and the feature region extracting unit 156, or a module structure including the skin region extracting unit 551, the calculating unit 552, the generating unit 553, the output controlling unit 554, and the feedback controlling unit 555, so that these functional units are loaded into a main storage device and are generated in the main storage device.

Other Embodiments

Possible embodiments are not limited to the embodiments described above.

Further, the physical configurations described in the embodiments above are merely examples. It is possible to integrate or distribute, as appropriate, the functional units described as examples in the embodiments, in accordance with modes of operation and loads.

While certain embodiments of the present invention have been described, these embodiments have been presented by way of examples only, and are not intended to limit the scope of the invention. These exemplary embodiments may be embodied in a variety of other forms, and various omissions, substitutions, and changes may be made without departing from the spirit of the invention. Those embodiments and modification thereof are included in the invention set forth in the claims and the equivalents thereof, in the same manner as those embodiments and modifications would fall within the scope and spirits of the invention.

What is claimed is:

1. A biological information measuring apparatus comprising a processor configured to:

calculate a difference, at a mutually same time, between an image-based photoplethysmogram extracted from luminance information of a picture signal of a designated region of interest that is a skin region on a face, an arm or a hand of a subject included in a picture and an image-based photoplethysmogram extracted from luminance information of a picture signal of a further designated region of interest that is a skin region on the face, the arm or the hand of the subject other than the designated region of interest;

calculate at least one of a pulse transit time or an instantaneous phase difference from the difference calculated; and measure a fluctuation of a blood pressure of the subject on basis of the difference calculated, wherein the processor performs, in the measuring, a measuring process in accordance with a combination of the regions of interests from which the image-based photoplethysmograms are extracted and based on a correlation between the at least one of the pulse transit time or the instantaneous phase difference and the fluctuation of the blood pressure, the correlation being a positive correlation or a negative correlation, and, when a combination of the regions of interests from which the image-based photoplethysmograms are extracted, the correlation is either a combination of any of first regions of interest, in which, due to a peripheral arteriole being under control of a sympathetic nerve when the blood pressure increases, a first delay in an arrival of a first pulse wave is greater than a threshold, or, when a combination of any of second regions of interest from which the image-based photoplethysmograms are extracted, in which, due to a peripheral arteriole being under control of the sympathetic nerve and a parasympathetic nerve when the blood pressure increases, a second delay in an arrival of a second pulse wave is less than the first delay in the first regions of interest.

2. The biological information measuring apparatus according to claim 1, wherein the processor performs the measuring process including measuring the fluctuation of the blood pressure based on the positive correlation when the designated region of interest and the further designated region of interest from which the image-based photoplethysmograms are extracted are one of the first regions of interest and one of the second regions of interest, and measuring the fluctuation of the blood pressure based on the negative correlation when the designated region of interest and the further designated region of interest from which the image-based photoplethysmograms are extracted are both any of the first regions of interest or any two of the second regions of interest.

3. A biological information measuring method comprising:
- calculating a difference, at a mutually same time, between an image-based photoplethysmogram extracted from luminance information of a picture signal of a designated region of interest that is a skin region on a face, an arm or a hand of a subject included in a picture and an image-based photoplethysmogram extracted from luminance information of a picture signal of a further designated region of interest that is a skin region on the face, the arm or the hand of the subject other than the designated region of interest;
- calculating at least one of a pulse transit time or an instantaneous phase difference from the difference calculated; and
- measuring a fluctuation of a blood pressure of the subject on basis of the difference calculated, wherein
- the measuring includes performing a measuring process in accordance with a combination of the regions of interests from which the image-based photoplethysmograms are extracted and based on a correlation between the at least one of the pulse transit time or the instantaneous phase difference and the fluctuation of the blood pressure, the correlation being a positive correlation or a negative correlation, and, when a combination of the regions of interests from which the image-based photoplethysmograms are extracted, the correlation is either a combination of any of first regions of interest, in which, due to a peripheral arteriole being under control of a sympathetic nerve when the blood pressure increases, a first delay in an arrival of a first pulse wave is greater than a threshold, or, when a combination of any of second regions of interest from which the image-based photoplethysmograms are extracted, in which, due to a peripheral arteriole being under control of the sympathetic nerve and a parasympathetic nerve when the blood pressure increases, a second delay in an arrival of a second pulse wave is less than the first delay in the first regions of interest.

4. A computer program product having a non-transitory computer readable medium including a biological information measuring program, wherein the biological information measuring program, when executed by a computer, causes the computer to perform:
- calculating a difference, at a mutually same time, between an image-based photoplethysmogram extracted from luminance information of a picture signal of a designated region of interest that is a skin region on a face, an arm or a hand of a subject included in a picture and an image-based photoplethysmogram extracted from luminance information of a picture signal of a further designated region of interest that is a skin region on the face, the arm or the hand of the subject other than the designated region of interest;
- calculating at least one of a pulse transit time or an instantaneous phase difference from the difference calculated;
- performing a measuring process in accordance with a combination of the regions of interests from which the image-based photoplethysmograms are extracted and based on a correlation between the at least one of the pulse transit time or the instantaneous phase difference and the fluctuation of the blood pressure, the correlation being a positive correlation or a negative correlation, and when a combination of the regions of interests from which the image-based photoplethysmograms are extracted, the correlation is either a combination of any of first regions of interest in which, due to a peripheral arteriole being under control of a sympathetic nerve when the blood pressure increases, a first delay in an arrival of a first pulse wave is greater than a threshold, or, when a combination of any of second regions of interest from which the image-based photoplethysmograms are extracted, in which, due to a peripheral arteriole being under control of the sympathetic nerve and a parasympathetic nerve when the blood pressure increases, a second delay in an arrival of a second pulse wave is less than the first delay in the first regions of interest; and
- measuring the fluctuation of the blood pressure of the subject by processing the difference using the measuring process.

5. The biological information measuring method according to claim 3, wherein the measuring includes
- measuring the fluctuation of the blood pressure based on the positive correlation when the designated region of interest and the further designated region of interest from which the image-based photoplethysmograms are extracted are one of the first regions of interest and one of the second regions of interest, and
- measuring the fluctuation of the blood pressure based on the negative correlation when the designated region of interest and the further designated region of interest from which the image-based photoplethysmograms are extracted are both any of the first regions of interest or any two of the second regions of interest.

6. The computer program product according to claim 4, wherein performing the measuring process includes
- measuring the fluctuation of the blood pressure based on the positive correlation when the designated region of interest and the further designated region of interest from which the image-based photoplethysmograms are extracted are one of the first regions of interest and one of the second regions of interest, and
- measuring the fluctuation of the blood pressure based on the negative correlation when the designated region of interest and the further designated region of interest from which the image-based photoplethysmograms are extracted are both any of the first regions of interest or any two of the second regions of interest.

* * * * *